US008835137B2

(12) United States Patent
Roberts et al.

(10) Patent No.: US 8,835,137 B2
(45) Date of Patent: Sep. 16, 2014

(54) MODIFIED PHOTOSYNTHETIC MICROORGANISMS WITH REDUCED GLYCOGEN AND THEIR USE IN PRODUCING CARBON-BASED PRODUCTS

(75) Inventors: James Roberts, Seattle, WA (US); Fred Cross, Seattle, WA (US); Paul Warrener, Seattle, WA (US); Kimberly Marie Kotovic, Seattle, WA (US); Margaret Mary McCormick, Seattle, WA (US)

(73) Assignee: Matrix Genetics, LLC, Seattle, WA (US)

( * ) Notice: Subject to any disclaimer, the term of this patent is extended or adjusted under 35 U.S.C. 154(b) by 99 days.

(21) Appl. No.: 12/645,228

(22) Filed: Dec. 22, 2009

(65) Prior Publication Data

US 2010/0184169 A1 Jul. 22, 2010

Related U.S. Application Data

(60) Provisional application No. 61/140,545, filed on Dec. 23, 2008.

(51) Int. Cl.
| | |
|---|---|
| *C12N 1/21* | (2006.01) |
| *C12P 7/64* | (2006.01) |
| *C12N 9/90* | (2006.01) |
| *C12N 9/16* | (2006.01) |
| *C12N 9/10* | (2006.01) |
| *C12N 1/36* | (2006.01) |
| *C12N 1/20* | (2006.01) |
| *C12N 9/12* | (2006.01) |

(52) U.S. Cl.
CPC ............... *C12P 7/6409* (2013.01); *C12N 9/90* (2013.01); *C12N 9/16* (2013.01); *C12N 9/1029* (2013.01); *C12N 1/36* (2013.01); *C12N 9/1051* (2013.01); *C12P 7/6481* (2013.01); *C12N 1/20* (2013.01); *C12P 7/6463* (2013.01); *Y02E 50/13* (2013.01); *C12P 7/649* (2013.01); *C12N 9/1241* (2013.01)
USPC ......................... 435/134; 435/252.3; 435/471

(58) Field of Classification Search
None
See application file for complete search history.

(56) References Cited

U.S. PATENT DOCUMENTS

| | | | | |
|---|---|---|---|---|
| 6,306,639 | B1 | 10/2001 | Woods et al. | 435/252.3 |
| 7,118,896 | B2 | 10/2006 | Kalscheuer et al. | 435/134 |
| 7,157,619 | B1 | 1/2007 | Lassner et al. | 800/281 |
| 7,427,593 | B1 | 9/2008 | Dahlqvist et al. | 514/12 |
| 7,498,026 | B2 | 3/2009 | Dahlqvist et al. | 424/94.5 |
| 7,794,969 | B1 | 9/2010 | Reppas et al. | 435/41 |
| 2003/0233675 | A1 | 12/2003 | Cao et al. | 800/279 |
| 2006/0137043 | A1 | 6/2006 | Puzio et al. | 800/289 |
| 2007/0269859 | A1 | 11/2007 | Lassner et al. | 435/69.1 |
| 2008/0160592 | A1 | 7/2008 | Dahlqvist et al. | 435/134 |
| 2009/0035832 | A1 | 2/2009 | Koshland, Jr. | 435/167 |
| 2009/0155864 | A1 | 6/2009 | Bauer et al. | 435/134 |
| 2009/0215179 | A1 | 8/2009 | Gressel et al. | 435/471 |
| 2009/0298143 | A1 | 12/2009 | Roessler et al. | 435/134 |
| 2010/0081178 | A1 | 4/2010 | Roberts et al. | 435/134 |
| 2010/0251601 | A1 | 10/2010 | Hu et al. | 44/313 |
| 2010/0255551 | A1 | 10/2010 | Roberts et al. | 435/134 |

FOREIGN PATENT DOCUMENTS

| | | |
|---|---|---|
| WO | WO 98/39457 | 9/1998 |
| WO | WO2006078050 | 7/2006 |
| WO | WO 2007/136762 A2 | 11/2007 |
| WO | WO 2008/119082 A2 | 10/2008 |
| WO | WO 2008/130437 A2 | 10/2008 |
| WO | WO 2009/009391 A2 | 1/2009 |
| WO | WO 2009/036095 A1 | 3/2009 |
| WO | WO 2009/042950 A1 | 4/2009 |
| WO | WO 2009/062190 A2 | 5/2009 |
| WO | WO 2009/076559 A1 | 6/2009 |
| WO | WO 2009/089185 A1 | 7/2009 |
| WO | WO 2009/111513 A1 | 9/2009 |
| WO | WO 2010/006312 A2 | 1/2010 |
| WO | WO 2010/017245 A1 | 2/2010 |
| WO | WO 2010/019813 A2 | 2/2010 |
| WO | WO 2010/021711 A1 | 2/2010 |
| WO | WO 2010/022090 A1 | 2/2010 |
| WO | WO 2010/027516 A2 | 3/2010 |
| WO | WO 2010/033921 A2 | 3/2010 |
| WO | WO 2010/036951 A2 | 4/2010 |
| WO | WO 2010/042664 A2 | 4/2010 |
| WO | WO 2010/044960 A1 | 4/2010 |
| WO | WO 2010/048568 A1 | 4/2010 |
| WO | WO 2010/062480 A2 | 6/2010 |
| WO | WO 2010/062707 A1 | 6/2010 |

(Continued)

OTHER PUBLICATIONS

NCBI Gene ID 951909 "glgc glucose-1-phosphate adenylyltransferase [*Synechocystis* sp. PCC 6803]" Aug. 2003 downloaded from http://www.ncbi.nlm.nih.gov/gene on Jun. 2, 2011.*
GenBank Accession No. CP000100. *Synechococcus elongatus* PCC 7942, complete genome (Dec. 2007).*
Acreman, "Algae and cyanobacteria: isolation, culture and long-term maintenance," *Journal of Industrial Microbiology* 13:193-194, 1994.
Alvarez et al., "Triacylglycerols in prokaryotic microorganisms," *Appl. Microbiol. Biotechnol.* 60:367-376, 2002.

(Continued)

*Primary Examiner* — Rebecca Prouty
(74) *Attorney, Agent, or Firm* — Lee & Hayes, PLLC

(57) ABSTRACT

This disclosure describes genetically modified photosynthetic microorganisms, including Cyanobacteria, that contain one or more mutations or deletions in a glycogen biosynthesis or storage pathway, which accumulate a reduced amount of glycogen as compared to a wild type Cyanobacterium, and which are capable of producing an increased amount of lipids and/or fatty acids. In certain embodiments, the genetically modified photosynthetic microorganisms also contain one or more exogenous genes encoding a diacyglycerol acyltransferase, a phosphatidate phosphatase, and/or an acetyl-CoA carboxylase, and which are capable of producing increased amounts of lipids or fatty acids and/or synthesizing triglycerides.

12 Claims, 11 Drawing Sheets

(56) References Cited

FOREIGN PATENT DOCUMENTS

| | | |
|---|---|---|
| WO | WO 2010/075440 A1 | 7/2010 |
| WO | WO 2010/075483 A2 | 7/2010 |
| WO | WO 2010/078584 | 7/2010 |
| WO | WO 2010/104763 A1 | 9/2010 |
| WO | WO 2010/118410 A1 | 10/2010 |
| WO | WO 2010/126891 A1 | 11/2010 |
| WO | WO 2011/008535 A1 | 1/2011 |
| WO | WO 2011/008565 A1 | 1/2011 |
| WO | WO 2011/011568 A2 | 1/2011 |
| WO | WO 2011/029013 A2 | 3/2011 |
| WO | WO 2011/038132 A1 | 3/2011 |
| WO | WO 2011/038134 A1 | 3/2011 |
| WO | WO 2011/059745 A1 | 5/2011 |

OTHER PUBLICATIONS

Bagchi et al., "A *Synechococcus elongates* PCC 7942 mutant with a higher tolerance toward the herbicide bentazone also confers resistance to sodium chloride stress," *Photosynth. Res.* 92:87-101, 2007.

Christensen et al., "Lipid domains of mycobacteria studied with fluorescent molecular probes," *Molecular Microbiology* 31(5):1561-1572, 1999.

Chungjatupornchai et al., "Isolation and Characterization of *Synechococcus* PCC7942 Promoters: tRNA$^{pro}$ Gene Functions as a Promoter," *Current Microbiology* 38:210-216, 1999.

Coleman et al., "Physiological and Nutritional Regulation of Enzymes of Triacylglycerol Synthesis," *Annu. Rev. Nutr.* 20:77-103, 2000.

Dahlqvist et al., "Phospholipid: diacylglycerol acyltransferase: an enzyme that catalyzes the acyl-CoA-independent formation of triacylglycerol in yeast and plants," *Proc. Natl. Acad. Sci.* 97(12):6487-6492, 2000.

Daniel et al., "Induction of a Novel Class of Diacylglycerol Acyltransferases and Triacylglycerol Accumulation in *Mycobacterium tuberculosis* as It Goes into a Dormancy-Like State in Culture," *Journal of Bacteriology* 186(15):5017-5030, 2004.

Daum et al., "Biochemistry, Cell Biology and Molecular Biology of Lipids of *Saccharomyces cerevisiae*," *Yeast* 14:1471-1510, 1998.

Davis et al., "Overproduction of Acetyl-CoA Carboxylase Activity Increases the Rate of Fatty Acid Biosynthesis in *Escherichia coli*," *The Journal of Biological Chemistry* 275(37):28593-28598, 2000.

Han et al., "The Cellular Functions of the Yeast Lipin Homolog Pah1p Are Dependent on Its Phosphatidate Phosphatase Activity," *The Journal of Biological Chemistry* 282(51):37026-37035, 2007.

Han et al., "The *Saccharomyces cerevisiae* Lipin Homolog Is a Mg$^{2+}$-dependent Phosphatidate Phosphatase Enzyme," *The Journal of Biological Chemistry* 281(14):9210-9218, 2006.

Harwood, "Recent advances in the biosynthesis of plant fatty acids," *Biochimica et Biophysica Ata* 1301:7-56, 1996.

Hu et al., "Microalgal triaglycerols as feedstocks for biofuel production: perspectives and advances," *The Plant Journal* 54:621-639, 2008.

Imashimizu et al., "Thymine at -5 Is Crucial for *cpc* Promoter Activity of *Synechocystis* sp. Strain PCC 6714," *Journal of Bacteriology* 185(21):6477-6480, 2003.

Kalscheuer et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1," *The Journal of Biological Chemistry* 278(10):8075-8082, 2003.

Kalscheuer et al., "Neutral Lipid Biosynthesis in Engineered *Escherichia coli*: Jojoba Oil-Like Wax Esters and Fatty Acid Butyl Esters," *Applied and Environmental Microbiology* 72(2):1373-1379, 2006.

Koksharova et al., "Genetic tools for cyanobacteria," *Appl. Micrbiol. Biotechnol.* 58:123-137, 2002.

Maeda et al., "*cis*-Acting Sequences Required for NtcB-Dependent, Nitrite-Responsive Positive Regulation of the Nitrate Assimilation Operon in the Cynabacterium *Synechococcus* sp. Strain PCC-7942," *Journal of Bacteriology* 180(16):4080-4088, 1998.

Mermet-Bouvier et al., "Transfer and Replication of RSF1010-Derived Plasmids in Several Cyanobacteria of the Genera *Synechocystis* and *Synechococcus*," *Current Microbiology* 27:323-327, 1993.

Mermet-Bouvier et al., "A Conditional Expression Vector for the Cyanobacteria *Synechocystis* sp. Strains PCC6803 and PCC6714 or *Synechococcus* sp. Strains PCC7942 and PCC6301," *Current Microbiology* 28:145-148, 1994.

Nakamura et al., "Plastidic Phosphatidic Acid Phosphatases Identified in a Distinct Subfamily of Lipid Phosphate Phosphatases with Prokaryotic Origin," *The Journal of Biological Chemistry* 282(39):29013-29021, 2007.

Nedbal et al., "A Photobioreactor System for Precision Cultivation of Photoautotrophic Microorganisms and for High-Content Analysis of Suspension Dynamics," *Biotechnology and Bioengineering* 100(5):902-910, 2008.

Nishizuka, "Intracellular Signaling by Hydrolysis of Phospholipids and Activation of Protein Kinase C," *Science* 258:607-614, 1992.

Office Action mailed Sep. 17, 2010, U.S. Appl. No. 12/605,204, filed Oct. 23, 2009.

Qi et al., "Application of the *Synechoccus nirA* Promoter to Establish an Inducible Expression System for Engineering the *Synechocystis* Tocopherol Pathway," *Applied and Environmental Microbiology* 71(10):5678-5684, 2005.

Ronen-Tarazi et al., "The Genomic Region of *rbcLS* in *Synechococcus* sp. PCC 7942 Contains Genes Involved in the Ability to Grow under Low $CO_2$ Concentration and in Chlorophyll Biosynthesis," *Plant Physiol.* 108:1461-1469, 1995.

Saha et al., "Cytosolic Triacylglycerol Biosynthetic Pathway in Oilseeds. Molecular Cloning and Expression of Peanut Cytosolic Diacylglycerol Acyltransferase," *Plant Physiology* 141:1533-1543, 2006.

Singh et al., "Bioactive Compounds from Cyanobacteria and Microalgae: An Overview," *Critical Reviews in Biotechnology* 25:73-95, 2005.

Van Heeke et al., "The N-terminal Cysteine of Human Asparagine Synthetase Is Essential for Glutamine-dependent Activity," *The Journal of Biological Chemistry* 264(33):19475-19477, 1989.

Waditee et al., "Overexpression of a Na$^+$/H$^+$ antiporter confers salt tolerance on a freshwater cyanobacterium, making it capable of growth in sea water," *Proc. Natl. Acad. Sci.* 99(6):4109-4114, 2002.

Waltermann et al., "Mechanism of lipid-body formation in prokaryotes: how bacteria fatten up," *Molecular Microbiology* 55(3):750-763, 2005.

Waltermann et al., "Neutral Lipid Bodies in Prokaryotes: Recent Insights into Structure, Formation, and Relationship to Eukaryotic Lipid Depots," *Journal of Bacteriology* 187(11):3607-3619, 2005.

Wirth et al., "Transformation of various species of gram-negative bacteria belonging to 11 different genera by electroporation," *Mol. Gen. Genet.* 216:175-177, 1989.

Yu et al., "Production of Eicosapentaenoic Acid by a Recombinant Marine Cyanobacterium, *Synechococcus* sp.," *Lipids* 35(10):1061-1064, 2000.

Zhang et al., "Crystal Structure of the Carboxyltransferase Domain of Acetyl-Coenzyme A Carboxylase," *Science* 299:2064-2067, 2003.

Jiang et al., "Inhibition of Fatty Acid Synthesis in *Escherichia coli* in the Absence of Phospholipid Synthesis and Release of Inhibition by Thioesterase Action," *Journal of Bacteriology* 176(10):2814-2821, 1994.

Kalscheuer et al., "Microdiesel: *Escherichia coli* engineered for fuel production," *Microbiology* 152:2529-2536, 2006.

Liu et al., "$CO_2$-limitation-inducible Green Recovery of fatty acids from cyanobacterial biomass," *PNAS Early Edition*, www.pnas.org/cgi/doi/10.1073/pnas.1103016108, 2011. (4 pages).

Liu et al., "Fatty acid production in genetically modified cyanobacteria," *PNAS Early Edition*, www.pnas.org/cgi/doi/10.1073/pnas.1103014108, 2011. (6 pages).

Lykidis et al., "Genomic prospecting for microbial biodiesel production," U.S. Department of Energy Office of Science, Biological and Environmental Research Program and The University of California, Lawrence Berkeley National Laboratory, 2008. (39 pages).

Morgan-Kiss et al., "The *Escherichia coli fadK* (*ydiD*) Gene Encodes an Anerobically Regulated Short Chain Acyl-CoA Synthetase," *The Journal of Biological Chemistry* 279(36):37324-37333, 2004.

(56) References Cited

OTHER PUBLICATIONS

Qiu et al., "Metabolic engineering of *Aeromonas hydrophila* for the enhanced production of poly(3-hydroxybutyrate-*co*-3-hydroxyhexanoate)," *Appl. Mircobiol. Biotechnol.* 69:537-542, 2006.

Roberts et al., "Modified Photosynthetic Microorganisms for Producing Lipids," International application No. PCT/US2011/031273, filed Apr. 5, 2011, 306 pages.

Roberts et al., "Modified Photosynthetic Microorganisms for Producing Lipids," U.S. Appl. No. 13/080,496, filed Apr. 5, 2011, 149 pages.

Voelker et al., "Alteration of the Specificity and Regulation of Fatty Acid Synthesis of *Escherichia coli* by Expression of a Plant Medium-Chain Acyl-Acyl Carrier Protein Thioesterase," *Journal of Bacteriology* 176(23):7320-7327, 1994.

Zhang et al., "Molecular effect of FadD on the regulation and metabolism of fatty acid in *Escherichia coli*," *FEMS Microbiol. Lett.* 259:249-253, 2006.

European Office Action mailed Dec. 18, 2013 for European patent application No. 09795664.3, a counterpart foreign application of U.S. Appl. No. 12/645,228, 4 pages.

Akiyama, et al., "Nucleotide Sequence of Plasmid pAG1 of Marine Cyanobacterium *Synechococcus* sp. PCC7002", DNA Res., 1998, vol. 5, pp. 127-129.

Bouvier-Nave, et al., "Expression in yeast and tobacco of plant cDNAs encoding acyl CoA: diacylglycerol acyltransferase", Eur. J. Biochem, 2000, vol. 267, pp. 85-96.

Jako, et al., "Seed-Specific Over-Expression of an Arabidopsis cDNA Encoding a Diacylglycerol Acyltransferase Enhances Seed Oil Content and Seed Weight", Plant Physiol., 2001, vol. 126, pp. 861-874.

Japanese Office Action mailed May 27, 2014 for Japanese patent application No. 2011-542580, a counterpart foreign application of U.S. Appl. No. 12/645,228, 9 pages.

Wu, et al., "Modification of carbon partitioning to enhance PHB production in *Synechocystis sp.* PCC6803", Enzyme Microb. Technol., 2002, vol. 30, pp. 710-715.

\* cited by examiner

SEQUENCE LISTING

<160> NUMBER OF SEQ ID NOS: 84

<210> SEQ ID NO 1
<211> LENGTH: 458
<212> TYPE: PRT
<213> ORGANISM: Acinetobacter baylii sp.

<400> SEQUENCE: 1

```
Met Arg Pro Leu His Pro Ile Asp Phe Ile Phe Leu Ser Leu Glu Lys
  1               5                  10                  15

Arg Gln Gln Pro Met His Val Gly Gly Leu Phe Leu Phe Gln Ile Pro
             20                  25                  30

Asp Asn Ala Pro Asp Thr Phe Ile Gln Asp Leu Val Asn Asp Ile Arg
         35                  40                  45

Ile Ser Lys Ser Ile Pro Val Pro Pro Phe Asn Asn Lys Leu Asn Gly
     50                  55                  60

Leu Phe Trp Asp Glu Asp Glu Glu Phe Asp Leu Asp His His Phe Arg
 65                  70                  75                  80

His Ile Ala Leu Pro His Pro Gly Arg Ile Arg Glu Leu Leu Ile Tyr
                 85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240
```

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Ser Asp Val Ser Asn Arg Ile Thr
    290                 295                 300

Met Ile Leu Ala Asn Leu Ala Thr His Lys Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Ile Gln Leu Phe Glu Gly Val Ile
        435                 440                 445

Ala Lys Gln Glu Asp Ile Lys Thr Ala Asn
    450                 455

<210> SEQ ID NO 2
<211> LENGTH: 864
<212> TYPE: PRT
<213> ORGANISM: Saccharomyces cerevisiae

<400> SEQUENCE: 2

Met Glu Phe Gln Tyr Val Gly Arg Ala Leu Gly Ser Val Ser Lys Thr
1               5                   10                  15

Trp Ser Ser Ile Asn Pro Ala Thr Leu Ser Gly Ala Ile Asp Val Ile
                20                  25                  30

Val Val Glu His Pro Asp Gly Arg Leu Ser Cys Ser Pro Phe His Val
            35                  40                  45

Arg Phe Gly Lys Phe Gln Ile Leu Lys Pro Ser Gln Lys Lys Val Gln
        50                  55                  60

Val Phe Ile Asn Glu Lys Leu Ser Asn Met Pro Met Lys Leu Ser Asp
65                  70                  75                  80

Ser Gly Glu Ala Tyr Phe Val Phe Glu Met Gly Asp Gln Val Thr Asp
                85                  90                  95

Val Pro Asp Glu Leu Leu Val Ser Pro Val Met Ser Ala Thr Ser Ser
            100                 105                 110

Pro Pro Gln Ser Pro Gly Thr Ser Ile Leu Glu Gly Gly Thr Glu Gly
        115                 120                 125

Glu Gly Glu Gly Glu Asn Glu Asn Lys Lys Glu Lys Lys Val Leu
    130                 135                 140

Glu Glu Pro Asp Phe Leu Asp Ile Asn Asp Thr Gly Asp Ser Gly Ser
145                 150                 155                 160

-continued

```
Lys Asn Ser Glu Thr Thr Gly Ser Leu Ser Pro Thr Glu Ser Ser Thr
                165                 170                 175
Thr Thr Pro Pro Asp Ser Val Glu Glu Arg Lys Leu Val Glu Gln Arg
            180                 185                 190
Thr Lys Asn Phe Gln Gln Lys Leu Asn Lys Lys Leu Thr Glu Ile His
            195                 200                 205
Ile Pro Ser Lys Leu Asp Asn Asn Gly Asp Leu Leu Leu Asp Thr Glu
            210                 215                 220
Gly Tyr Lys Pro Asn Lys Asn Met Met His Asp Thr Asp Ile Gln Leu
225                 230                 235                 240
Lys Gln Leu Leu Lys Asp Glu Phe Gly Asn Asp Ser Asp Ile Ser Ser
                245                 250                 255
Phe Ile Lys Glu Asp Lys Asn Gly Asn Ile Lys Ile Val Asn Pro Tyr
                260                 265                 270
Glu His Leu Thr Asp Leu Ser Pro Pro Gly Thr Pro Pro Thr Met Ala
                275                 280                 285
Thr Ser Gly Ser Val Leu Gly Leu Asp Ala Met Glu Ser Gly Ser Thr
            290                 295                 300
Leu Asn Ser Leu Ser Ser Ser Pro Ser Gly Ser Asp Thr Glu Asp Glu
305                 310                 315                 320
Thr Ser Phe Ser Lys Glu Gln Ser Ser Lys Ser Glu Lys Thr Ser Lys
                325                 330                 335
Lys Gly Thr Ala Gly Ser Gly Glu Thr Glu Lys Arg Tyr Ile Arg Thr
                340                 345                 350
Ile Arg Leu Thr Asn Asp Gln Leu Lys Cys Leu Asn Leu Thr Tyr Gly
            355                 360                 365
Glu Asn Asp Leu Lys Phe Ser Val Asp His Gly Lys Ala Ile Val Thr
            370                 375                 380
Ser Lys Leu Phe Val Trp Arg Trp Asp Val Pro Ile Val Ile Ser Asp
385                 390                 395                 400
Ile Asp Gly Thr Ile Thr Lys Ser Asp Ala Leu Gly His Val Leu Ala
                405                 410                 415
Met Ile Gly Lys Asp Trp Thr His Leu Gly Val Ala Lys Leu Phe Ser
                420                 425                 430
Glu Ile Ser Arg Asn Gly Tyr Asn Ile Leu Tyr Leu Thr Ala Arg Ser
            435                 440                 445
Ala Gly Gln Ala Asp Ser Thr Arg Ser Tyr Leu Arg Ser Ile Glu Gln
            450                 455                 460
Asn Gly Ser Lys Leu Pro Asn Gly Pro Val Ile Leu Ser Pro Asp Arg
465                 470                 475                 480
Thr Met Ala Ala Leu Arg Arg Glu Val Ile Leu Lys Lys Pro Glu Val
                485                 490                 495
Phe Lys Ile Ala Cys Leu Asn Asp Ile Arg Ser Leu Tyr Phe Glu Asp
                500                 505                 510
Ser Asp Asn Glu Val Asp Thr Glu Glu Lys Ser Thr Pro Phe Phe Ala
            515                 520                 525
Gly Phe Gly Asn Arg Ile Thr Asp Ala Leu Ser Tyr Arg Thr Val Gly
            530                 535                 540
Ile Pro Ser Ser Arg Ile Phe Thr Ile Asn Thr Glu Gly Glu Val His
545                 550                 555                 560
Met Glu Leu Leu Glu Leu Ala Gly Tyr Arg Ser Ser Tyr Ile His Ile
                565                 570                 575
```

```
Asn Glu Leu Val Asp His Phe Phe Pro Pro Val Ser Leu Asp Ser Val
                580                 585                 590

Asp Leu Arg Thr Asn Thr Ser Met Val Pro Gly Ser Pro Pro Asn Arg
            595                 600                 605

Thr Leu Asp Asn Phe Asp Ser Glu Ile Thr Ser Gly Arg Lys Thr Leu
        610                 615                 620

Phe Arg Gly Asn Gln Glu Glu Lys Phe Thr Asp Val Asn Phe Trp Arg
625                 630                 635                 640

Asp Pro Leu Val Asp Ile Asp Asn Leu Ser Asp Ile Ser Asn Asp Asp
                645                 650                 655

Ser Asp Asn Ile Asp Glu Asp Thr Asp Val Ser Gln Gln Ser Asn Ile
            660                 665                 670

Ser Arg Asn Arg Ala Asn Ser Val Lys Thr Ala Lys Val Thr Lys Ala
        675                 680                 685

Pro Gln Arg Asn Val Ser Gly Ser Thr Asn Asn Glu Val Leu Ala
                690                 695                 700

Ala Ser Ser Asp Val Glu Asn Ala Ser Asp Leu Val Ser His Ser
705                 710                 715                 720

Ser Ser Gly Ser Thr Pro Asn Lys Ser Thr Met Ser Lys Gly Asp Ile
                725                 730                 735

Gly Lys Gln Ile Tyr Leu Glu Leu Gly Ser Pro Leu Ala Ser Pro Lys
            740                 745                 750

Leu Arg Tyr Leu Asp Asp Met Asp Glu Asp Ser Asn Tyr Asn Arg
        755                 760                 765

Thr Lys Ser Arg Arg Ala Ser Ser Ala Ala Thr Ser Ile Asp Lys
770                 775                 780

Glu Phe Lys Lys Leu Ser Val Ser Lys Ala Gly Ala Pro Thr Arg Ile
785                 790                 795                 800

Val Ser Lys Ile Asn Val Ser Asn Asp Val His Ser Leu Gly Asn Ser
                805                 810                 815

Asp Thr Glu Ser Arg Arg Glu Gln Ser Val Asn Glu Thr Gly Arg Asn
            820                 825                 830

Gln Leu Pro His Asn Ser Met Asp Asp Lys Asp Leu Asp Ser Arg Val
        835                 840                 845

Ser Asp Glu Phe Asp Asp Asp Glu Phe Asp Glu Asp Glu Phe Glu Asp
850                 855                 860

<210> SEQ ID NO 3
<211> LENGTH: 2235
<212> TYPE: PRT
<213> ORGANISM: Saccharomyces cerevisiae

<400> SEQUENCE: 3

Met Glu Phe Ser Glu Glu Ser Leu Phe Glu Ser Ser Pro Gln Lys Met
 1               5                  10                  15

Glu Tyr Glu Ile Thr Asn Tyr Ser Glu Arg His Thr Glu Leu Pro Gly
                20                  25                  30

His Phe Ile Gly Leu Asn Thr Val Asp Lys Leu Glu Glu Ser Pro Leu
            35                  40                  45

Arg Asp Phe Val Lys Ser His Gly Gly His Thr Val Ile Ser Lys Ile
        50                  55                  60

Leu Ile Ala Asn Asn Gly Ile Ala Ala Val Lys Glu Ile Arg Ser Val
65                  70                  75                  80

Arg Lys Trp Ala Tyr Glu Thr Phe Gly Asp Asp Arg Thr Val Gln Phe
                85                  90                  95
```

```
Val Ala Met Ala Thr Pro Glu Asp Leu Glu Ala Asn Ala Glu Tyr Ile
            100                 105                 110

Arg Met Ala Asp Gln Tyr Ile Glu Val Pro Gly Gly Thr Asn Asn Asn
            115                 120                 125

Asn Tyr Ala Asn Val Asp Leu Ile Val Asp Ile Ala Glu Arg Ala Asp
        130                 135                 140

Val Asp Ala Val Trp Ala Gly Trp Gly His Ala Ser Glu Asn Pro Leu
145                 150                 155                 160

Leu Pro Glu Lys Leu Ser Gln Ser Lys Arg Lys Val Ile Phe Ile Gly
                165                 170                 175

Pro Pro Gly Asn Ala Met Arg Ser Leu Gly Asp Lys Ile Ser Ser Thr
            180                 185                 190

Ile Val Ala Gln Ser Ala Lys Val Pro Cys Ile Pro Trp Ser Gly Thr
        195                 200                 205

Gly Val Asp Thr Val His Val Asp Glu Lys Thr Gly Leu Val Ser Val
        210                 215                 220

Asp Asp Asp Ile Tyr Gln Lys Gly Cys Cys Thr Ser Pro Glu Asp Gly
225                 230                 235                 240

Leu Gln Lys Ala Lys Arg Ile Gly Phe Pro Val Met Ile Lys Ala Ser
                245                 250                 255

Glu Gly Gly Gly Gly Lys Gly Ile Arg Gln Val Glu Arg Glu Glu Asp
            260                 265                 270

Phe Ile Ala Leu Tyr His Gln Ala Ala Asn Glu Ile Pro Gly Ser Pro
        275                 280                 285

Ile Phe Ile Met Lys Leu Ala Gly Arg Ala Arg His Leu Glu Val Gln
        290                 295                 300

Leu Leu Ala Asp Gln Tyr Gly Thr Asn Ile Ser Leu Phe Gly Arg Asp
305                 310                 315                 320

Cys Ser Val Gln Arg Arg His Gln Lys Ile Ile Glu Glu Ala Pro Val
                325                 330                 335

Thr Ile Ala Lys Ala Glu Thr Phe His Glu Met Glu Lys Ala Ala Val
            340                 345                 350

Arg Leu Gly Lys Leu Val Gly Tyr Val Ser Ala Gly Thr Val Glu Tyr
        355                 360                 365

Leu Tyr Ser His Asp Asp Gly Lys Phe Tyr Phe Leu Glu Leu Asn Pro
    370                 375                 380

Arg Leu Gln Val Glu His Pro Thr Thr Glu Met Val Ser Gly Val Asn
385                 390                 395                 400

Leu Pro Ala Ala Gln Leu Gln Ile Ala Met Gly Ile Pro Met His Arg
                405                 410                 415

Ile Ser Asp Ile Arg Thr Leu Tyr Gly Met Asn Pro His Ser Ala Ser
            420                 425                 430

Glu Ile Asp Phe Glu Phe Lys Thr Gln Asp Ala Thr Lys Lys Gln Arg
        435                 440                 445

Arg Pro Ile Pro Lys Gly His Cys Thr Ala Cys Arg Ile Thr Ser Glu
        450                 455                 460

Asp Pro Asn Asp Gly Phe Lys Pro Ser Gly Gly Thr Leu His Glu Leu
465                 470                 475                 480

Asn Phe Arg Ser Ser Ser Asn Val Trp Gly Tyr Phe Ser Val Gly Asn
                485                 490                 495

Asn Gly Asn Ile His Ser Phe Ser Asp Ser Gln Phe Gly His Ile Phe
            500                 505                 510
```

```
Ala Phe Gly Glu Asn Arg Gln Ala Ser Arg Lys His Met Val Val Ala
            515                 520                 525

Leu Lys Glu Leu Ser Ile Arg Gly Asp Phe Arg Thr Thr Val Glu Tyr
        530                 535                 540

Leu Ile Lys Leu Leu Glu Thr Glu Asp Phe Glu Asp Asn Thr Ile Thr
545                 550                 555                 560

Thr Gly Trp Leu Asp Asp Leu Ile Thr His Lys Met Thr Ala Glu Lys
                565                 570                 575

Pro Asp Pro Thr Leu Ala Val Ile Cys Gly Ala Ala Thr Lys Ala Phe
            580                 585                 590

Leu Ala Ser Glu Glu Ala Arg His Lys Tyr Ile Glu Ser Leu Gln Lys
        595                 600                 605

Gly Gln Val Leu Ser Lys Asp Leu Leu Gln Thr Met Phe Pro Val Asp
    610                 615                 620

Phe Ile His Glu Gly Lys Arg Tyr Lys Phe Thr Val Ala Lys Ser Gly
625                 630                 635                 640

Asn Asp Arg Tyr Thr Leu Phe Ile Asn Gly Ser Lys Cys Asp Ile Ile
                645                 650                 655

Leu Arg Gln Leu Ser Asp Gly Gly Leu Leu Ile Ala Ile Gly Gly Lys
            660                 665                 670

Ser His Thr Ile Tyr Trp Lys Glu Val Ala Ala Thr Arg Leu Ser
        675                 680                 685

Val Asp Ser Met Thr Thr Leu Leu Glu Val Glu Asn Asp Pro Thr Gln
    690                 695                 700

Leu Arg Thr Pro Ser Pro Gly Lys Leu Val Lys Phe Leu Val Glu Asn
705                 710                 715                 720

Gly Glu His Ile Ile Lys Gly Gln Pro Tyr Ala Glu Ile Glu Val Met
                725                 730                 735

Lys Met Gln Met Pro Leu Val Ser Gln Glu Asn Gly Ile Val Gln Leu
            740                 745                 750

Leu Lys Gln Pro Gly Ser Thr Ile Val Ala Gly Asp Ile Met Ala Ile
        755                 760                 765

Met Thr Leu Asp Asp Pro Ser Lys Val Lys His Ala Leu Pro Phe Glu
770                 775                 780

Gly Met Leu Pro Asp Phe Gly Ser Pro Val Ile Glu Gly Thr Lys Pro
785                 790                 795                 800

Ala Tyr Lys Phe Lys Ser Leu Val Ser Thr Leu Glu Asn Ile Leu Lys
                805                 810                 815

Gly Tyr Asp Asn Gln Val Ile Met Asn Ala Ser Leu Gln Gln Leu Ile
            820                 825                 830

Glu Val Leu Arg Asn Pro Lys Leu Pro Tyr Ser Glu Trp Lys Leu His
        835                 840                 845

Ile Ser Ala Leu His Ser Arg Leu Pro Ala Lys Leu Asp Glu Gln Met
    850                 855                 860

Glu Glu Leu Val Ala Arg Ser Leu Arg Arg Gly Ala Val Phe Pro Ala
865                 870                 875                 880

Arg Gln Leu Ser Lys Leu Ile Asp Met Ala Val Lys Asn Pro Glu Tyr
                885                 890                 895

Asn Pro Asp Lys Leu Leu Gly Ala Val Val Glu Pro Leu Ala Asp Ile
            900                 905                 910

Ala His Lys Tyr Ser Asn Gly Leu Glu Ala His Glu His Ser Ile Phe
        915                 920                 925

Val His Phe Leu Glu Glu Tyr Tyr Glu Val Glu Lys Leu Phe Asn Gly
```

```
            930             935             940
Pro Asn Val Arg Glu Glu Asn Ile Ile Leu Lys Leu Arg Asp Glu Asn
945                 950                 955                 960

Pro Lys Asp Leu Asp Lys Val Ala Leu Thr Val Leu Ser His Ser Lys
                965                 970                 975

Val Ser Ala Lys Asn Asn Leu Ile Leu Ala Ile Leu Lys His Tyr Gln
            980                 985                 990

Pro Leu Cys Lys Leu Ser Ser Lys Val Ser Ala Ile Phe Ser Thr Pro
            995                 1000                1005

Leu Gln His Ile Val Glu Leu Glu Ser Lys Ala Thr Ala Lys Val Ala
        1010                1015                1020

Leu Gln Ala Arg Glu Ile Leu Ile Gln Gly Ala Leu Pro Ser Val Lys
1025                1030                1035                1040

Glu Arg Thr Glu Gln Ile Glu His Ile Leu Lys Ser Ser Val Val Lys
                1045                1050                1055

Val Ala Tyr Gly Ser Ser Asn Pro Lys Arg Ser Glu Pro Asp Leu Asn
                1060                1065                1070

Ile Leu Lys Asp Leu Ile Asp Ser Asn Tyr Val Val Phe Asp Val Leu
            1075                1080                1085

Leu Gln Phe Leu Thr His Gln Asp Pro Val Val Thr Ala Ala Ala Ala
        1090                1095                1100

Gln Val Tyr Ile Arg Arg Ala Tyr Arg Ala Tyr Thr Ile Gly Asp Ile
1105                1110                1115                1120

Arg Val His Glu Gly Val Thr Val Pro Ile Val Glu Trp Lys Phe Gln
                1125                1130                1135

Leu Pro Ser Ala Ala Phe Ser Thr Phe Pro Thr Val Lys Ser Lys Met
            1140                1145                1150

Gly Met Asn Arg Ala Val Ser Val Ser Asp Leu Ser Tyr Val Ala Asn
            1155                1160                1165

Ser Gln Ser Ser Pro Leu Arg Glu Gly Ile Leu Met Ala Val Asp His
        1170                1175                1180

Leu Asp Asp Val Asp Glu Ile Leu Ser Gln Ser Leu Glu Val Ile Pro
1185                1190                1195                1200

Arg His Gln Ser Ser Ser Asn Gly Pro Ala Pro Asp Arg Ser Gly Ser
                1205                1210                1215

Ser Ala Ser Leu Ser Asn Val Ala Asn Val Cys Val Ala Ser Thr Glu
            1220                1225                1230

Gly Phe Glu Ser Glu Glu Glu Ile Leu Val Arg Leu Arg Glu Ile Leu
            1235                1240                1245

Asp Leu Asn Lys Gln Glu Leu Ile Asn Ala Ser Ile Arg Arg Ile Thr
        1250                1255                1260

Phe Met Phe Gly Phe Lys Asp Gly Ser Tyr Pro Lys Tyr Tyr Thr Phe
1265                1270                1275                1280

Asn Gly Pro Asn Tyr Asn Glu Asn Glu Thr Ile Arg His Ile Glu Pro
                1285                1290                1295

Ala Leu Ala Phe Gln Leu Glu Leu Gly Arg Leu Ser Asn Phe Asn Ile
            1300                1305                1310

Lys Pro Ile Phe Thr Asp Asn Arg Asn Ile His Val Tyr Glu Ala Val
            1315                1320                1325

Ser Lys Thr Ser Pro Leu Asp Lys Arg Phe Phe Thr Arg Gly Ile Ile
        1330                1335                1340

Arg Thr Gly His Ile Arg Asp Asp Ile Ser Ile Gln Glu Tyr Leu Thr
1345                1350                1355                1360
```

```
Ser Glu Ala Asn Arg Leu Met Ser Asp Ile Leu Asp Asn Leu Glu Val
            1365                1370                1375

Thr Asp Thr Ser Asn Ser Asp Leu Asn His Ile Phe Ile Asn Phe Ile
        1380                1385                1390

Ala Val Phe Asp Ile Ser Pro Glu Asp Val Glu Ala Phe Gly Gly
        1395                1400                1405

Phe Leu Glu Arg Phe Gly Lys Arg Leu Leu Arg Leu Arg Val Ser Ser
    1410                1415                1420

Ala Glu Ile Arg Ile Ile Ile Lys Asp Pro Gln Thr Gly Ala Pro Val
1425                1430                1435                1440

Pro Leu Arg Ala Leu Ile Asn Asn Val Ser Gly Tyr Val Ile Lys Thr
            1445                1450                1455

Glu Met Tyr Thr Glu Val Lys Asn Ala Lys Gly Glu Trp Val Phe Lys
            1460                1465                1470

Ser Leu Gly Lys Pro Gly Ser Met His Leu Arg Pro Ile Ala Thr Pro
        1475                1480                1485

Tyr Pro Val Lys Glu Trp Leu Gln Pro Lys Arg Tyr Lys Ala His Leu
        1490                1495                1500

Met Gly Thr Thr Tyr Val Tyr Asp Phe Pro Glu Leu Phe Arg Gln Ala
1505                1510                1515                1520

Ser Ser Ser Gln Trp Lys Asn Phe Ser Ala Asp Val Lys Leu Thr Asp
            1525                1530                1535

Asp Phe Phe Ile Ser Asn Glu Leu Ile Glu Asp Glu Asn Gly Glu Leu
            1540                1545                1550

Thr Glu Val Glu Arg Glu Pro Gly Ala Asn Ala Ile Gly Met Val Ala
        1555                1560                1565

Phe Lys Ile Thr Val Lys Thr Pro Glu Tyr Pro Arg Gly Arg Gln Phe
    1570                1575                1580

Val Val Val Ala Asn Asp Ile Thr Phe Lys Ile Gly Ser Phe Gly Pro
1585                1590                1595                1600

Gln Glu Asp Glu Phe Phe Asn Lys Val Thr Glu Tyr Ala Arg Lys Arg
            1605                1610                1615

Gly Ile Pro Arg Ile Tyr Leu Ala Ala Asn Ser Gly Ala Arg Ile Gly
        1620                1625                1630

Met Ala Glu Glu Ile Val Pro Leu Phe Gln Val Ala Trp Asn Asp Ala
        1635                1640                1645

Ala Asn Pro Asp Lys Gly Phe Gln Tyr Leu Tyr Leu Thr Ser Glu Gly
        1650                1655                1660

Met Glu Thr Leu Lys Lys Phe Asp Lys Glu Asn Ser Val Leu Thr Glu
1665                1670                1675                1680

Arg Thr Val Ile Asn Gly Glu Glu Arg Phe Val Ile Lys Thr Ile Ile
            1685                1690                1695

Gly Ser Glu Asp Gly Leu Gly Val Glu Cys Leu Arg Gly Ser Gly Leu
        1700                1705                1710

Ile Ala Gly Ala Thr Ser Arg Ala Tyr His Asp Ile Phe Thr Ile Thr
        1715                1720                1725

Leu Val Thr Cys Arg Ser Val Gly Ile Gly Ala Tyr Leu Val Arg Leu
        1730                1735                1740

Gly Gln Arg Ala Ile Gln Val Glu Gly Gln Pro Ile Ile Leu Thr Gly
1745                1750                1755                1760

Ala Pro Ala Ile Asn Lys Met Leu Gly Arg Glu Val Tyr Thr Ser Asn
            1765                1770                1775
```

```
Leu Gln Leu Gly Gly Thr Gln Ile Met Tyr Asn Asn Gly Val Ser His
            1780                1785                1790

Leu Thr Ala Val Asp Asp Leu Ala Gly Val Glu Lys Ile Val Glu Trp
    1795                1800                1805

Met Ser Tyr Val Pro Ala Lys Arg Asn Met Pro Val Pro Ile Leu Glu
    1810                1815                1820

Thr Lys Asp Thr Trp Asp Arg Pro Val Asp Phe Thr Pro Thr Asn Asp
1825                1830                1835                1840

Glu Thr Tyr Asp Val Arg Trp Met Ile Glu Gly Arg Glu Thr Glu Ser
                1845                1850                1855

Gly Phe Glu Tyr Gly Leu Phe Asp Lys Gly Ser Phe Phe Glu Thr Leu
            1860                1865                1870

Ser Gly Trp Ala Lys Gly Val Val Gly Arg Ala Arg Leu Gly Gly
            1875                1880                1885

Ile Pro Leu Gly Val Ile Gly Val Glu Thr Arg Thr Val Glu Asn Leu
            1890                1895                1900

Ile Pro Ala Asp Pro Ala Asn Pro Asn Ser Ala Glu Thr Leu Ile Gln
1905                1910                1915                1920

Glu Pro Gly Gln Val Trp His Pro Asn Ser Ala Phe Lys Thr Ala Gln
            1925                1930                1935

Ala Ile Asn Asp Phe Asn Asn Gly Glu Gln Leu Pro Met Met Ile Leu
            1940                1945                1950

Ala Asn Trp Arg Gly Phe Ser Gly Gly Gln Arg Asp Met Phe Asn Glu
            1955                1960                1965

Val Leu Lys Tyr Gly Ser Phe Ile Val Asp Ala Leu Val Asp Tyr Lys
            1970                1975                1980

Gln Pro Ile Ile Ile Tyr Ile Pro Pro Thr Gly Glu Leu Arg Gly Gly
1985                1990                1995                2000

Ser Trp Val Val Val Asp Pro Thr Ile Asn Ala Asp Gln Met Glu Met
                2005                2010                2015

Tyr Ala Asp Val Asn Ala Arg Ala Gly Val Leu Glu Pro Gln Gly Met
            2020                2025                2030

Val Gly Ile Lys Phe Arg Arg Glu Lys Leu Leu Asp Thr Met Asn Arg
            2035                2040                2045

Leu Asp Asp Lys Tyr Arg Glu Leu Arg Ser Gln Leu Ser Asn Lys Ser
    2050                2055                2060

Leu Ala Pro Glu Val His Gln Gln Ile Ser Lys Gln Leu Ala Asp Arg
2065                2070                2075                2080

Glu Arg Glu Leu Leu Pro Ile Tyr Gly Gln Ile Ser Leu Gln Phe Ala
            2085                2090                2095

Asp Leu His Asp Arg Ser Ser Arg Met Val Ala Lys Gly Val Ile Ser
            2100                2105                2110

Lys Glu Leu Glu Trp Thr Glu Ala Arg Arg Phe Phe Phe Trp Arg Leu
            2115                2120                2125

Arg Arg Arg Leu Asn Glu Glu Tyr Leu Ile Lys Arg Leu Ser His Gln
            2130                2135                2140

Val Gly Glu Ala Ser Arg Leu Glu Lys Ile Ala Arg Ile Arg Ser Trp
2145                2150                2155                2160

Tyr Pro Ala Ser Val Asp His Glu Asp Asp Arg Gln Val Ala Thr Trp
                2165                2170                2175

Ile Glu Glu Asn Tyr Lys Thr Leu Asp Asp Lys Leu Lys Gly Leu Lys
            2180                2185                2190

Leu Glu Ser Phe Ala Gln Asp Leu Ala Lys Lys Ile Arg Ser Asp His
```

Asp Asn Ala Ile Asp Gly Leu Ser Glu Val Ile Lys Met Leu Ser Thr
       2210            2215            2220

Asp Asp Lys Glu Lys Leu Leu Lys Thr Leu Lys
2225            2230            2235

<210> SEQ ID NO 4
<211> LENGTH: 1377
<212> TYPE: DNA
<213> ORGANISM: Artificial Sequence
<220> FEATURE:
<223> OTHER INFORMATION: Codon-optimized Acinetobacter baylii sp. atfA

<400> SEQUENCE: 4

```
atgcggccct tgcaccccat tgacttcatc tttctgagtt tggagaaacg gcaacagccc      60
atgcatgtcg gtggcttgtt tctcttccaa atccccgata cgccccgga caccttatt      120
caggatctgg tcaatgatat ccggatctcg aaatcgatcc ccgtgccgcc gtttaataat     180
aaactgaacg gcctcttttg ggacgaagac gaggaatttg atctggatca ccattttcgg     240
cacatcgctt tgccccaccc gggtcggatt cgcgaactcc tgatctatat agccaagaa      300
cacagcacgt tgttggaccg ggccaaaccg ctctggacgt gcaatatcat cgaaggcatc     360
gaaggcaacc gctttgcgat gtacttcaag attcatcacg cgatggttga cggtgtcgct     420
ggcatgcgcc tgatcgaaaa atcgctgagc catgatgtga ccgaaaagag tatcgtcccc     480
ccctggtgcg tggaaggtaa gcgcgccaag cgcctccgcg aaccgaaaac gggcaagatt     540
aagaaaatca tgagcggtat caagtcgcag ctgcaggcta ccccgaccgt gatccaggag     600
ctgtcgcaaa ccgtgtttaa ggatattggt cggaacccgg atcatgtcag tagtttccaa     660
gctccctgtt cgatcttgaa tcagcgcgtt agcagcagcc gccggttcgc tgctcaaagt     720
tttgatctcg atcggtttcg gaatattgcc aagtcgctga acgtcaccat caatgatgtg     780
gttctcgcgg tttgttcggg tgccctccgc gcgtatctga tgagccataa cagtctcccc     840
agtaagccgc tgattgctat ggttcccgcg tcgattcgga tgacgacag cgatgtgagc      900
aaccggatta ccatgatcct ggctaacctc gcgacccaca agatgatcc gttgcaacgc     960
ctggagatta tccgccgcag tgtgcagaac agtaaacagc gcttcaaacg gatgaccagt    1020
gatcaaattc tgaattacag cgctgtggtc tatggtcccg ccggcttgaa tattatcagt    1080
ggtatgatgc ccaaacgcca agcgtttaac ttggtgatca gtaatgtgcc gggtccgcgc    1140
gaacccttgt attggaacgg tgctaaactc gatgccctct accccgccag tatcgtgctc    1200
gatggccagg ctctcaatat taccatgacc agctatctcg ataaactcga ggtgggtttg    1260
attgcgtgcc gcaacgcgct gccccgcatg cagaacttgc tgacccacct ggaagaggaa    1320
atccagctct cgagggcgt gattgcgaag caggaagata ttaaaacggc caactag       1377
```

<210> SEQ ID NO 5
<211> LENGTH: 2595
<212> TYPE: DNA
<213> ORGANISM: Artificial Sequence
<220> FEATURE:
<223> OTHER INFORMATION: Codon-optimized S. cerevisiae phosphatidate
      phosphatase (PAH1)

<400> SEQUENCE: 5

```
atggaattcc aatatgttgg tcgggctttg ggtagtgtta gtaaaacgtg gtcgagtatc       60
aaccccgcca ccctgagcgg cgctatcgat gtcattgtcg tggaacaccc cgatggccgg     120
```

```
ctcagttgta gccccttcca tgtgcgcttt ggtaaattcc agattctgaa acccagccaa    180
aagaaagtcc aggtctttat taacgagaaa ctgtcgaata tgcccatgaa actctcggat    240
agcggcgagg cgtacttcgt ttttgagatg ggtgatcaag tgacggatgt cccggatgaa    300
ctgctcgtct cgccggtcat gagtgccacg agtagtccgc cccaatcgcc ggaaacctcg    360
attctcgaag gcggtaccga aggcgagggc gaaggtgaga atgaaaataa gaaaaaggaa    420
aagaaggtgt tggaggagcc cgactttctg gacattaatg acaccggtga cagcggcagc    480
aagaacagtg agacgacggg ttcgctctcg ccgaccgaaa gtagtacgac gacgccgccc    540
gatagcgtcg aggaacgcaa gttggtcgaa caacggacca agaatttca gcaaaagctg    600 aataagaaac tgaccgaaat ccatattccg agcaaattgg acaataacgg tgatttgctc    660
ctggacaccg agggttataa gccgaataaa aacatgatgc acgacacgga tattcagctg    720
aagcaattgc tcaaggatga gttcggtaac gatagcgata tttcgagctt catcaaagaa    780
gacaagaatg gcaacattaa aatcgtgaac ccctatgagc atttgaccga tttgagtccc    840
ccgggtacgc ccccgaccat ggccacgagt ggcagtgtcc tgggcttgga tgcgatggag    900
agtggttcga cgctgaacag cttgagcagc agcccgagcg gcagtgacac cgaggatgag    960
acgagcttta gcaaggaaca gtcgtcgaag agtgaaaaaa cgtcgaagaa aggcaccgcg   1020
ggttcgggtg aaacggagaa acgctacatc cgcacgatcc ggctcacgaa tgatcagctg   1080
aaatgcctca acttgacgta cggtgaaaat gacttgaaat ttagtgttga ccatggcaaa   1140
gccattgtga ccagcaaatt gtttgtctgg cgctgggacg tccccatcgt tatcagcgac   1200
attgacggta cgattacgaa aagtgatgcg ctgggccacg tcctcgccat gatcggcaaa   1260
gattggaccc atctcggcgt cgctaagctg ttcagtgaga tctcgcgcaa cggttacaat   1320
atcctgtacc tgaccgcgcg ctcggccggt caggctgaca gtacccgctc gtatctccgc   1380
agtattgagc agaacggtag caagctcccg aacggccccg tcattctgag ccccgatcgg   1440
accatggctg ccctgcgccg ggaggtgatt ctgaaaaagc ccgaagtctt taaaatcgct   1500
tgcttgaacg atatccgctc gctctatttc gaagactcgg ataacgaagt ggacacggag   1560
gaaaagagca cgccgttttt cgcgggcttt ggcaatcgga tcaccgatgc gctcagctat   1620
cggacggtcg gcatcccgag tagccgcatc ttcacgatta acacggaagg cgaggtgcac   1680
atggagctgc tcgagctcgc cggttaccgg agtagctata tccatatcaa cgaactggtc   1740
gatcacttct tcccgccggt gagcctggac tcggtcgatc tgcgcacgaa cacgagcatg   1800
gtcccgggca gccgccgaa ccgcaccctg gataactttg atagcgaaat caccagtggc   1860
cgcaagacgt tgtttcgcgg taatcaggag gaaaaattca cggacgtcaa cttttggcgc   1920
gatccgttgg tggacatcga caacctctcg gatatcagta acgatgattc ggacaatatt   1980
gatgaagaca ccgatgtgag ccaacagtcg aacatcagcc gcaaccgcgc taactcggtc   2040
aagacggcca aggtgaccaa ggctccgcag cggaatgtgt cggcagtac gaataacaat   2100 gaagttctgg ctgcgagtag tgatgttgaa aatgccagtg acttggttag cagccactcg   2160
agtagcggct cgaccccaa caagtcgacg atgagtaagg gtgatatcgg caaacaaatc   2220
tatctggaac tgggctcgcc cttggcgagt cccaaactcc ggtatctgga cgatatggat   2280
gatgaggact cgaactataa tcgcaccaag agccgccggg ctagtagcgc cgctgctacc   2340
agcatcgaca aggagtttaa aaagctcagt gtgagtaaag ctggcgctcc caccccgcatc   2400 gttagcaaga tcaacgtgtc gaatgatgtg cacagtttgg gcaacagtga taccgaaagc   2460
cggcgggaac agagcgtcaa tgaaaccggt cgcaatcagt tgccgcacaa tagtatggat   2520
```
gataaggatt tggattcgcg ggtgagtgac gagttcgatg acgatgagtt tgatgaagat    2580
gagtttgagg attag                                                    2595

<210> SEQ ID NO 6
<211> LENGTH: 6708
<212> TYPE: DNA
<213> ORGANISM: Artificial Sequence
<220> FEATURE:
<223> OTHER INFORMATION: Codon-optimized S. cerevisiae acetyl Coa
      carboxylase (ACC1)

<400> SEQUENCE: 6
atggaattct ccgaggaaag tttgttcgaa agcagtccgc agaaaatgga atatgaaatt      60
acgaattatt cggaacgcca cacggagctc cccgggcact tcatcggact caacaccgtg     120
gataagctcg aagaaagtcc cctccgcgat tttgtgaaaa gccacggcgg ccataccgtg     180
atctcgaaga ttctgattgc caataacgga attgccgctg tcaaggagat ccgcagcgtc     240
cggaagtggg cgtacgaaac ttttggcgat gaccgtacga tccagtttgt tgctatggcg     300
actccggaag acttggaggc gaatgcggaa tacattcgaa tggccgatca atacatcgaa     360
gtccccggag gaacgaacaa caacaattat gcgaacgtcg atttgatcgt ggatatcgca     420
gaacgcgcgg acgtggatgc tgtttgggcc ggatggggcc acgcttcgga aaaccctctg     480
ttgccggaaa aactcagcca gtctaaacgg aaagtcattt tcatcggccc tccgggcaac     540
gcaatgcgct cgttgggtga taagatcagc tcgaccattg tggctcagag cgctaaagtc     600
ccatgtattc cctggtcggg taccggcgtg atacggtcc atgttgatga aaaactgga      660 ctggtcagcg tcgatgatga tatctaccaa aagggctgtt gcaccagccc ggaagatggc     720
ctgcaaaagg cgaagcgcat cgggttccca gtcatgatca aggcatccga aggcggaggc     780
ggtaagggta tccgccaggt tgagcgtgaa aagattttta tcgcactgta tcatcaagcg     840
gctaacgaaa tcccgggctc gccaattttc attatgaaac tggctggtcg ggcgcgtcat     900
ctcgaagtgc aactcctcgc tgaccagtac ggtacgaaca tctctttgtt cggtcgggat     960
tgttcggtcc agcgtcgtca ccagaagatc attgaagaag ccctgttac catcgcaaag    1020 gccgagacgt tcatgagat ggagaaagcg gccgtccgcc tcggcaagct ggtcggttac    1080
gttagcgcag gcaccgtgga ataccctctat tcccacgacg atggtaagtt ttactttctc    1140
gaactgaatc ctcgcctgca ggttgaacac ccgaccacag agatggtgtc gggggtcaat    1200
ctgccggctg cgcagttgca gattgcaatg ggcattccga tgcatcgaat cagcgacatc    1260
cgaaccctgt acggcatgaa cccgcacagt gcgagcgaaa tcgactttga gttcaagacc    1320
caagacgcca cgaagaaaca gcgacgccca attccgaagg gccattgcac cgcgtgtcgc    1380
attacctcgg aggaccccaa tgatggtttt aagccctcgg gcggtactct gcacgagctc    1440
aacttccgct cctcctcgaa cgtctggggc tatttcagcg tcggaaataa tggtaacatt    1500
catagttttt ccgattccca atttggccat atcttcgcct ttggcgaaaa ccgacaagct    1560
agccgcaaac acatggtcgt ggcgttgaag gagctgagta ccgagggga ctttcgcacg    1620 acggtggaat atctgatcaa actgctcgaa acggaggact tgaggataa cacaattacc    1680 accggatggt tggacgacct gattacgcac aaaatgaccg ccgagaaacc cgaccccacc    1740
ttggcagtga tttgtggcgc ggcaacgaag gcctttttgg cctctgaaga ggcacgccac    1800
aagtacattg agagtctcca aagggtcag gtgctgagta agatctctgct gcaaaccatg    1860 tttcctgtcg actttattca tgaggggaaa cgctacaaat tcacggttgc taagtctggt    1920

```
aatgatcggt acacattgtt tatcaatgga tcgaagtgcg atattatctt gcgacaactc   1980
tccgacggcg gcctcctgat tgctatcggc gggaaaagtc ataccatcta ttggaaagaa   2040
gaggtcgccg ccacccgact gagcgttgat tcgatgacta ctctgctcga agttgaaaac   2100
gatccaacgc aactgcgcac tccctctccg ggtaagctcg tgaagtttct cgtcgagaat   2160
ggcgaacaca ttattaaggg ccagccgtat gcggaaatcg aggtgatgaa gatgcagatg   2220
cccctggtca gccaagagaa cggtattgtg caactgctga acagcccgg cagcaccatc    2280 gtcgctggcg atatcatggc tatcatgacc ctcgatgatc cttccaaagt caaacatgcc   2340
ctgcccttcg aaggcatgct ccccgatttt ggctcccccg tgattgaggg caccaaacca   2400
gcttacaagt ttaaatcgct ggtttccacc ctcgagaaca tcttgaaggg ctacgataat   2460
caggtcatta tgaatgccag cctccagcag ctcattgagg tcctccgtaa ccccaagctg   2520
ccctacagtg aatggaagct ccacatcagt gcgctccact cgcgactgcc cgcgaagctc   2580
gatgagcaga tggaagagct cgtcgctcgc agcctgcgtc gcggcgcagt ctttccggca   2640
cggcaactgt cgaagctcat cgatatggct gtcaaaaacc ccgaatacaa ccccgataaa   2700
ctcttgggtg ctgtcgttga gccgctcgcc gatatcgcgc acaagtacag taatggcctg   2760
gaggcgcacg aacacagtat ctttgttcac ttcctggaag aatactatga ggttgagaaa   2820
ctgttcaatg ggcctaatgt ccgggaagag aatattatcc tgaagctccg tgatgaaaat   2880
ccgaaagatt tggataaagt cgccttgacg gtgctcagtc atagcaaggt gagtgccaag   2940
aacaatctca tcctggcgat cttgaaacac taccaacctt tgtgcaagct gagttccaag   3000
gtgtcggcta ttttagtac gccctgcag cacatcgtgg aactcgaaag taaagccacc     3060
gccaaggtgg ctctgcaggc ccgggagatt ctgatccagg gtgctctgcc gagcgtgaaa   3120
gagcggacgg aacaaatcga acacatcctg aagagttcgg tcgtgaaggt tgcatatggc   3180
agcagtaacc ctaaacgctc ggaaccggac ctcaatatcc tgaaggatct gatcgatagt   3240
aattatgttg tttttgatgt cctgctccaa tttctgactc accaagatcc ggttgttact   3300
gcggctgccg cgcaagttta cattcgacgc gcctatcgcg cctacacaat cggcgatatt   3360
cgagtccatg agggcgtgac cgttccaatc gttgaatgga aattccagtt gccatcggcg   3420
gcttttccta cattcccaac agtcaagagt aagatgggca tgaatcgtgc cgtttcggtc   3480
agtgatttgt cctatgtcgc aaactcgcaa tctagtcctc tgcgagaggg catcctgatg   3540
gcagtggatc atttggatga tgtcgatgag atcctctcgc aaagtctcga ggtcattcct   3600
cgccaccaat cgtcgtccaa tggcccagct cccgatcgat ccggttcttc cgccagcttg   3660
tcgaatgtcg ccaacgtctg tgtggcgtcg actgaggggt tcgaaagcga agaagaaatt   3720
ttggtccgct tgcgggaaat tttggacctc aacaagcagg aactgattaa tgcctctatt   3780
cgccgcatta cgtttatgtt cggtttcaag gatggctcgt acccaaaata ctatacgttc   3840
aacggcccga actacaatga gaacgagact atccgacata ttgaacctgc cctcgctttc   3900
caactggaac tggggcggct ctcgaatttc aatattaagc ctatttttac cgacaaccgt   3960
aacatccacg tttacgaggc tgtcagcaaa acaagcccgc tggataagcg attcttcacc   4020
cggggcatta tccgcacagg ccacatccgt gacgatatca gtatccaaga atacctgact   4080
agcgaagcta accgcttgat gagcgacatt ttggataatc tggaagtgac tgatacttcc   4140
aacagcgact tgaatcacat tttttatcaac ttcattgccg tgttcgatat ctcgccggaa   4200
gatgtggaag ccgcgtttgg aggctttctg gaacggtttg gcaaacggct gctgcgcttg   4260
```

```
cgggtgtcta gcgcggagat tcggattatc atcaaagatc cgcaaacggg ggctcctgtg    4320
ccactgcgcg cgctgattaa taacgtctcg ggttacgtga tcaagaccga gatgtacaca    4380
gaggttaaaa acgctaaagg cgagtgggtc ttcaagagct tgggcaaacc cggcagcatg    4440
catctccgcc ccatcgccac gccgtatccg gtcaaggagt ggctgcagcc caagcgatac    4500
aaggcgcact tgatggggac gacatatgtt tacgattttc ctgaactgtt ccgtcaagca    4560
agcagctccc agtggaaaaa cttttccgca gatgtgaaat tgactgatga tttcttcatc    4620
tcgaatgagc tcatcgaaga tgagaatggc gagctgaccg aagttgagcg agaacctggt    4680
gccaatgcga ttgggatggt cgcctttaaa atcacggtca aaactcccga gtaccctcgg    4740
ggtcgccagt tcgtcgttgt ggctaacgat atcaccttta agattggatc gtttggcccg    4800
caggaggatg agttctttaa caaggtcact gaatacgccc gaaaacgagg cattccgcgg    4860
atttacttgg cagccaatag cggtgcgcgc atcggcatgg ctgaagaaat cgttccgctg    4920
tttcaggttg cctggaacga cgcggccaac cccgacaagg ggttccagta cttgtatctg    4980
acttccgaag gcatggagac gttgaagaaa tttgataagg agaatagtgt cttgactgag    5040
cggaccgtta ttaacggcga ggagcggttt gtcattaaga ctatcatcgg cagcgaagat    5100
ggcctcggcg tcgaatgttt gcgcgggtcc ggcctgatcg caggggcaac ctcgcgagcc    5160
tatcacgata tctttaccat tactttggtc acgtgtcgtt cggttggcat tggagcatac    5220
ctcgtgcgcc tcggtcagcg cgccatccaa gtggaaggcc aacctatcat tttgactggc    5280
gcgcctgcta tcaataagat gctgggccgt gaagtctaca catcgaacct ccaactgggc    5340
ggtacccaaa ttatgtataa caatggcgtc agccatctga cagccgtcga tgacctggct    5400
ggcgttgaaa agattgttga gtggatgagc tatgtgcccg ccaaacggaa catgccagtc    5460
cccattttgg aaaccaagga tacctgggat cgcccagtgg atttcactcc gactaatgat    5520
gaaacctacg atgtccgctg gatgatcgaa gggcgcgaaa ctgagtcggg cttcgagtac    5580
ggactgtttg ataagggtag tttctttgag actctcagtg gttgggccaa aggcgttgtc    5640
gtcggtcggg cacgtctggg cggcatcccg ctgggagtta ttggtgttga gacacgtacg    5700
gtggaaaatc tgatcccggc tgatccggcc aaccccaata gtgcggaaac gctgattcaa    5760
gagcccgggc aagtgtggca cccgaatagt gcctttaaga cggcgcaggc tattaatgat    5820
tttaacaacg gcgaacaact gcctatgatg attctggcga attggcgggg gtttagtggt    5880
gggcagcgcg acatgttcaa cgaagtgctc aagtacggct ccttcatcgt ggacgccctg    5940
gtcgactata acaaccaat tatcatctat attcccccta ccggcgagct gcgaggcggt    6000
agctgggtcg tggtggaccc tactattaat gcagatcaaa tggagatgta cgccgacgtg    6060
aatgctcgag cgggcgtgct ggaaccacaa gggatggttg gcatcaaatt ccgccgcgaa    6120
aaactgttgg atactatgaa tcgactggat gataaatatc gcgagctgcg cagccaactg    6180
tcgaacaagt ctctggcccc ggaagtccat caacagattt ctaaacagct ggcagatcgc    6240
gaacgtgaac tcttgccgat ctacggccaa atcagcctcc aatttgccga cctgcatgat    6300
cgcagcagcc gcatggttgc gaaaggtgtc atcagcaaag agctcgagtg gacggaagct    6360
cggcggtttt tcttttggcg gctgcgccga cgcctgaatg aagaatactt gattaagcgt    6420
ctgagccacc aggtcggcga ggctagtcgg ttggaaaaga tcgcccgcat tcggagttgg    6480
tatccggcat cggttgacca cgaggacgat cgccaggtcg ctacctggat cgaagagaac    6540
tacaaaacct tggatgataa gctgaaagga ctgaagctgg agtctttcgc ccaagatctc    6600
gccaagaaga tccgtagcga tcatgacaat gcaatcgacg gtttgagcga ggttatcaag    6660
```

```
atgttgtcta ccgacgacaa ggagaagctg ctcaaaacgc tgaagtag              6708
```

<210> SEQ ID NO 7
<211> LENGTH: 1376
<212> TYPE: DNA
<213> ORGANISM: Acinetobacter sp.

<400> SEQUENCE: 7

```
atgcgcccat acatccgat tgattttata ttcctgtcac tagaaaaaag acaacagcct    60
atgcatgtag gtggtttatt tttgtttcag attcctgata acgccccaga caccttatt   120
caagatctgg tgaatgatat ccggatatca aaatcaatcc ctgttccacc attcaacaat  180
aaactgaatg ggcttttttg ggatgaagat gaagagtttg atttagatca tcattttcgt  240
catattgcac tgcctcatcc tggtcgtatt cgtgaattgc ttatttatat ttcacaagag  300
cacagtacgc tgctagatcg ggcaaagccc ttgtggacct gcaatattat tgaaggaatt  360
gaaggcaatc gttttgccat gtacttcaaa attcaccatg cgatggtcga tggcgttgct  420
ggtatgcggt taattgaaaa atcactctcc catgatgtaa cagaaaaaag tatcgtgcca  480
ccttggtgtg ttgagggaaa acgtgcaaag cgcttaagag aacctaaaac aggtaaaatt  540
aagaaaatca tgtctggtat taagagtcag cttcaggcga cacccacagt cattcaagag  600
cttttctcaga cagtatttaa agatattgga cgtaatcctg atcatgtttc aagctttcag  660
gcgccttgtt ctattttgaa tcagcgtgtg agctcatcgc gacgttttgc agcacagtct  720
tttgacctag atcgttttcg taatattgcc aaatcgttga atgtgaccat taatgatgtt  780
gtactagcgg tatgttctgg tgcattacgt gcgtatttga tgagtcataa tagtttgcct  840
tcaaaaccat taattgccat ggttccagcc tctattcgca atgacgattc agatgtcagc  900
aaccgtatta cgatgattct ggcaaatttg gcaacccaca aagatgatcc tttacaacgt  960
cttgaaatta tccgccgtag tgttcaaaac tcaaagcaac gcttcaaacg tatgaccagc 1020
gatcagattc taaattatag tgctgtcgta tatggccctg caggactcaa cataatttct 1080
ggcatgatgc caaaacgcca agccttcaat ctggttattt ccaatgtgcc tggcccaaga 1140
gagccacttt actggaatgg tgccaaactt gatgcactct acccagcttc aattgtatta 1200
gacggtcaag cattgaatat tacaatgacc agttatttag ataaacttga agttggtttg 1260
attgcatgcc gtaatgcatt gccaagaatg cagaaatttac tgcacacattt agaagaagaa 1320
attcaactat ttgaaggcgt aattgcaaag caggaagata ttaaaacagc caatta      1376
```

<210> SEQ ID NO 8
<211> LENGTH: 2589
<212> TYPE: DNA
<213> ORGANISM: Artificial Sequence
<220> FEATURE:
<223> OTHER INFORMATION: Synthetic construct Saccharomyces cerevisiae
       clone FLH148377.01X SMP2 gene

<400> SEQUENCE: 8

```
atgcagtacg taggcagagc tcttgggtct gtgtctaaaa catggtcttc tatcaatccg   60
gctacgctat caggtgctat agatgtcatt gtagtggagc atccagacgg aaggctatca  120
tgttctccct tcatgtgag gttcggcaaa tttcaaattc taaagccatc tcaaaagaaa  180
gtccaagtgt ttataaatga gaaactgagt aatatgccaa tgaaactgag tgattctgga  240
gaagccatatt tcgttttcga gatgggtgac caggtcactg atgtccctga cgaattgctt  300
gtgtcgcccg tgatgagcgc cacatcaagc cccctcaat cacctgaaac atccatctta  360
```

```
gaaggaggaa ccgagggtga aggtgaaggt gaaaatgaaa ataagaagaa ggaaaagaaa      420
gtgctagagg aaccagattt tttagatatc aatgacactg gagattcagg cagtaaaaat      480
agtgaaacta cagggtcgct ttctcctact gaatcctcta caacgacacc accagattca      540
gttgaagaga ggaagcttgt tgagcagcgt acaaagaact ttcagcaaaa actaaacaaa      600
aaactcactg aaatccatat acccagtaaa cttgataaca atggcgactt actactagac      660
actgaaggtt acaagccaaa caagaatatg atgcatgaca cagacataca actgaagcag      720
ttgttaaagg acgaattcgg taatgattca gatatttcca gttttatcaa ggaggacaaa      780
aatggcaaca tcaagatcgt aaatccttac gagcacctta ctgatttatc tcctccaggt      840
acgcctccaa caatggccac aagcggatca gttttaggct tagatgcaat ggaatcagga      900
agtactttga attcgttatc ttcttcacct tctggttccg atactgagga cgaaacatca      960
tttagcaaag aacaaagcag taaagtgaaa aaactagcag agaaaggaac agcagggagc     1020
ggtgagaccg agaaaagata catacgaacg ataagattga ctaatgacca gttaaagtgc     1080
ctaaatttaa cttatggtga aaatgatctg aaattttccg tagatcacgg aaaagctatt     1140
gttacgtcaa aattattcgt ttggaggtgg atgttccaa ttgttatcag tgatattgat      1200
ggcaccatca caaaatcgga cgctttaggc catgttctgg caatgatagg aaaagactgg     1260
acgcacttgg gtgtagccaa gttatttagc gagatctcca ggaatggcta taatatactc     1320
tatctaactg caagaagtgc tggacaagct gattccacga ggagttattt gcgatcaatt     1380
gaacagaatg gcagcaaact accaaatggg cctgtgattt tatcacccga tagaacgatg     1440
gctgcgttaa ggcgggaagt aatactaaaa aaacctgaag tctttaaaat cgcgtgtcta     1500
aacgacataa gatccttgta ttttgaagac agtgataacg aagtggatac agaggaaaaa     1560
tcaacaccat tttttgccgg ctttggtaat aggattactg atgctttatc ttacagaact     1620
gtggggatac ctagttcaag aattttcaca ataaatacag agggtgaggt tcatatggaa     1680
ttattggagt tagcaggtta cagaagctcc tatattcata tcaatgagct tgtcgatcat     1740 ttcttttccac cagtcagcct tgatagtgtc gatctaagaa ctaatacttc catggttcct     1800 ggctccccc ctaatagaac gttggataac tttgactcag aaattacttc aggtcgcaaa     1860
acgctattta gaggcaatca ggaagagaaa ttcacagacg taaattttg gagagacccg      1920 ttagtcgaca tcgacaactt atcggatatt agcaatgatg attctgataa catcgatgaa     1980
gatactgacg tatcacaaca aagcaacatt agtagaaata gggcaaattc agtcaaaacc     2040
gccaaggtca ctaaagcccc gcaaagaaat gtgagcggca gcacaaataa caacgaagtt     2100
ttagccgctt cgtctgatgt agaaaatgcg tctgacctgg tgagttccca tagtagctca     2160
ggatccacgc ccaataaatc tacaatgtcc aaaggggaca ttggaaaaca atatatttg      2220 gagctaggtt ctccacttgc atcgccaaaa ctaagatatt tagacgatat ggatgatgaa     2280
gactccaatt acaatagaac taaatcaagg agagcatctt ctgcagccgc gactagtatc     2340
gataaagagt tcaaaaagct ctctgtgtca aaggccggcg ctccaacaag aattgtttca     2400
aagatcaacg tttcaaatga cgtacattca cttgggaatt cagataccga atcacgaagg     2460
gagcaaagtg ttaatgaaac agggcgcaat cagctacccc acaactcaat ggacgataaa     2520
gatttggatt caagagtaag cgatgaattc gatgacgatg aattcgacga agatgaattc     2580
gaagattag                                                             2589
```

<210> SEQ ID NO 9

<211> LENGTH: 6702
<212> TYPE: DNA
<213> ORGANISM: Artificial Sequence
<220> FEATURE:
<223> OTHER INFORMATION: Synthetic construct Saccharomyces cerevisiae clone FLH148869.01X ACC1

<400> SEQUENCE: 9

| | | | | | |
|---|---|---|---|---|---|
| atgagcgaag | aaagcttatt | cgagtcttct | ccacagaaga | tggagtacga | aattacaaac | 60 |
| tactcagaaa | gacatacaga | acttccaggt | catttcattg | gcctcaatac | agtagataaa | 120 |
| ctagaggagt | ccccgttaag | ggactttgtt | aagagtcacg | gtggtcacac | ggtcatatcc | 180 |
| aagatcctga | tagcaaataa | tggtattgcc | gccgtgaaag | aaattagatc | cgtcagaaaa | 240 |
| tgggcatacg | agacgttcgg | cgatgacaga | accgtccaat | tcgtcgccat | ggccacccca | 300 |
| gaagatctgg | aggccaacgc | agaatatatc | cgtatggccg | atcaatacat | tgaagtgcca | 360 |
| ggtggtacta | ataataacaa | ctacgctaac | gtagacttga | tcgtagacat | cgccgaaaga | 420 |
| gcagacgtag | acgccgtatg | ggctggctgg | ggtcacgcct | ccgagaatcc | actattgcct | 480 |
| gaaaaattgt | cccagtctaa | gaggaaagtc | atctttattg | ggcctccagg | taacgccatg | 540 |
| aggtctttag | gtgataaaat | ctcctctacc | attgtcgctc | aaagtgctaa | agtcccatgt | 600 |
| attccatggt | ctggtaccgg | tgttgacacc | gttcacgtgg | acgagaaaac | cggtctggtc | 660 |
| tctgtcgacg | atgacatcta | tcaaaagggt | tgttgtacct | ctcctgaaga | tggtttacaa | 720 |
| aaggccaagc | gtattggttt | tcctgtcatg | attaaggcat | ccgaaggtgg | tggtggtaaa | 780 |
| ggtatcagac | aagttgaacg | tgaagaagat | ttcatcgctt | tataccacca | ggcagccaac | 840 |
| gaaattccag | gctcccccat | tttcatcatg | aagttggccg | gtagagcgcg | tcacttggaa | 900 |
| gttcaactgc | tagcagatca | gtacggtaca | aatatttcct | tgttcggtag | agactgttcc | 960 |
| gttcagagac | gtcatcaaaa | aattatcgaa | gaagcaccag | ttacaattgc | caaggctgaa | 1020 |
| acatttcacg | agatggaaaa | ggctgccgtc | agactgggga | aactagtcgg | ttatgtctct | 1080 |
| gccggtaccg | tggagtatct | atattctcat | gatgatggaa | aattctactt | tttagaattg | 1140 |
| aacccaagat | acaagtcga | gcatccaaca | acggaaatgg | tctccggtgt | taacttacct | 1200 |
| gcagctcaat | tacaaatcgc | tatgggtatc | cctatgcata | gaataagtga | cattagaact | 1260 |
| ttatatggta | tgaatcctca | ttctgcctca | gaaatcgatt | tcgaattcaa | aactcaagat | 1320 |
| gccaccaaga | aacaaagaag | acctattcca | aagggtcatt | gtaccgcttg | tcgtatcaca | 1380 |
| tcagaagatc | caaacgatgg | attcaagcca | tcgggtggta | ctttgcatga | actaaacttc | 1440 |
| cgttcttcct | ctaatgtttg | gggttacttc | tccgtgggta | acaatggtaa | tattcactcc | 1500 |
| tttcggact | ctcagttcgg | ccatatttt | gcttttggtg | aaaatagaca | agcttccagg | 1560 |
| aaacacatgg | ttgttgccct | gaaggaattg | tccattaggg | gtgatttcag | aactactgtg | 1620 |
| gaatacttga | tcaaactttt | ggaaactgaa | gatttcgagg | ataacactat | taccaccggt | 1680 |
| tggttggacg | atttgattac | tcataaaatg | accgctgaaa | agcctgatcc | aactcttgcc | 1740 |
| gtcatttgcg | gtgccgctac | aaaggctttc | ttagcatctg | aagaagcccg | ccacaagtat | 1800 |
| atcgaatcct | tacaaagggg | acaagttcta | tctaaagacc | tactgcaaac | tatgttccct | 1860 |
| gtagatttta | tccatgaggg | taaagatac | aagttcaccg | tagctaaatc | cggtaatgac | 1920 |
| cgttacacat | tatttatcaa | tggttctaaa | tgtgatatca | tactgcgtca | actatctgat | 1980 |
| ggtggtcttt | tgattgccat | aggcggtaaa | tcgcatacca | tctattggaa | agaagaagtt | 2040 |
| gctgctacaa | gattatccgt | tgactctatg | actactttgt | tggaagttga | aaacgatcca | 2100 |

```
acccagttgc gtactccatc ccctggtaaa ttggttaaat tcttggtgga aaatggtgaa    2160
cacattatca agggccaacc atatgcagaa attgaagtta tgaaaatgca aatgcctttg    2220
gtttctcaag aaaatggtat cgtccagtta ttaaagcaac ctggttctac cattgttgca    2280
ggtgatatca tggctattat gactcttgac gatccatcca aggtcaagca cgctctacca    2340
tttgaaggta tgctgccaga ttttggttct ccagttatcg aaggaaccaa acctgcctat    2400
aaattcaagt cattagtgtc tactttggaa aacattttga agggttatga caaccaagtt    2460
attatgaacg cttccttgca acaattgata gaggttttga gaaatccaaa actgccttac    2520
tcagaatgga aactacacat ctctgcttta cattcaagat tgcctgctaa gctagatgaa    2580
caaatggaag agttagttgc acgttctttg agacgtggtg ctgttttccc agctagacaa    2640
ttaagtaaat tgattgatat ggccgtgaag aatcctgaat acaacccga caaattgctg    2700 ggcgccgtcg tggaaccatt ggcggatatt gctcataagt actctaacgg gttagaagcc    2760
catgaacatt ctatatttgt ccatttcttg gaagaatatt acgaagttga aaagttattc    2820
aatggtccaa atgttcgtga ggaaaatatc attctgaaat tgcgtgatga aaaccctaaa    2880
gatctagata aagttgcgct aactgttttg tctcattcga aagtttcagc gaagaataac    2940
ctgatcctag ctatcttgaa acattatcaa ccattgtgca agttatcttc taagttttct    3000
gccattttct ctactcctct acaacatatt gttgaactag aatctaaggc taccgctaag    3060
gtcgctctac aagcaagaga aattttgatt caaggcgctt taccttcggt caaggaaaga    3120
actgaacaaa ttgaacatat cttaaaatcc tctgttgtga aggttgccta tggctcatcc    3180
aatccaaagc gctctgaacc agatttgaat atcttgaagg acttgatcga ttctaattac    3240
gttgtgttcg atgttttact tcaattccta acccatcaag acccagttgt gactgctgca    3300
gctgctcaag tctatattcg tcgtgcttat cgtgcttaca ccataggaga tattagagtt    3360
cacgaaggtg tcacagttcc aattgttgaa tggaaattcc aactaccttc agctgcgttc    3420
tccacctttc caactgttaa atctaaaatg gtatgaaca gggctgtttc tgtttcagat    3480
ttgtcatatg ttgcaaacag tcagtcatct ccgttaagag aaggtatttt gatggctgtg    3540
gatcatttag atgatgttga tgaaattttg tcacaaagtt tggaagttat tcctcgtcac    3600
caatcttctt ctaacggacc tgctcctgat cgttctggta gctccgcatc gttgagtaat    3660
gttgctaatg tttgtgttgc ttctacagaa ggtttcgaat ctgaagagga aattttggta    3720
aggttgagag aaattttgga tttgaataag caggaattaa tcaatgcttc tatccgtcgt    3780
atcacattta tgttcggttt taaagatggg tcttatccaa agtattatac ttttaacggt    3840
ccaaattata acgaaaatga aacaattcgt cacattgagc cggctttggc cttccaactg    3900
gaattaggaa gattgtccaa cttcaacatt aaaccaattt tcactgataa tagaaacatc    3960
catgtctacg aagctgttag taagacttct ccattggata agagattctt tacaagaggt    4020
attattagaa cgggtcatat ccgtgatgac atttctattc aagaatatct gacttctgaa    4080
gctaacagat tgatgagtga tatattggat aatttagaag tcaccgacac ttcaaattct    4140
gatttgaatc atatcttcat caacttcatt gcggtgtttg atatctctcc agaagatgtc    4200
gaagccgcct tcgtggggttt cttagaaaga tttggtaaga gattgttgag attgcgtgtt    4260
tcttctgccg aaattagaat catcatcaaa gatcctcaaa caggtgcccc agtaccattg    4320
cgtgccttga tcaataacgt ttctggttat gttatcaaaa cagaaatgta caccgaagtc    4380
aagaacgcaa aaggtgaatg ggtatttaag tcttgggta aacctggatc catgcattta    4440
agacctattg ctactcctta ccctgttaag gaatggttgc aaccaaaacg ttataaggca    4500
```

```
cacttgatgg gtaccacata tgtctatgac ttcccagaat tattccgcca agcatcgtca    4560
tcccaatgga aaaatttctc tgcagatgtt aagttaacag atgatttctt tatttccaac    4620
gagttgattg aagatgaaaa cggcgaatta actgaggtgg aaagagaacc tggtgccaac    4680
gctattggta tggttgcctt taagattact gtaaagactc tgaatatcc aagaggccgt     4740 caatttgttg ttgttgctaa cgatatcaca ttcaagatcg gttcctttgg tccacaagaa    4800
gacgaattct tcaataaggt tactgaatat gctagaaagc gtggtatccc aagaatttac    4860
ttggctgcaa actcaggtgc cagaattggt atggctgaag agattgttcc actatttcaa    4920
gttgcatgga atgatgctgc caatccggac aagggcttcc aatacttata cttaacaagt    4980
gaaggtatgg aaactttaaa gaaatttgac aaagaaaatt ctgttctcac tgaacgtact    5040
gttataaacg gtgaagaaag atttgtcatc aagacaatta ttggttctga agatgggtta    5100
ggtgtcgaat gtctacgtgg atctggttta attgctggtg caacgtcaag ggcttaccac    5160
gatatcttca ctatcacctt agtcacttgt agatccgtcg gtatcggtgc ttatttggtt    5220
cgtttgggtc aaagagctat tcaggtcgaa ggccagccaa ttatttaac tggtgctcct     5280 gcaatcaaca aatgctggg tagagaagtt tatacttcta acttacaatt gggtggtact     5340
caaatcatgt ataacaacgg tgtttcacat ttgactgctg ttgacgattt agctggtgta    5400
gagaagattt tgaatggat gtcttatgtt ccagccaagc gtaatatgcc agttcctatc     5460
ttggaaacta agacacatg ggatagacca gttgatttca ctccaactaa tgatgaaact     5520
tacgatgtaa gatggatgat tgaaggtcgt gagactgaaa gtggatttga atatggtttg    5580
tttgataaag ggtctttctt tgaaactttg tcaggatggg ccaaaggtgt tgtcgttggt    5640
agagcccgtc ttggtggtat tccactgggt gttattggtg ttgaaacaag aactgtcgag    5700
aacttgattc ctgctgatcc agctaatcca atagtgctg aaacattaat tcaagaacct     5760
ggtcaagttt ggcatccaaa ctccgccttc aagactgctc aagctatcaa tgactttaac    5820
aacggtgaac aattgccaat gatgattttg gccaactgga gaggtttctc tggtggtcaa    5880
cgtgatatgt tcaacgaagt cttgaagtat ggttcgttta ttgttgacgc attggtggat    5940
tacaaacaac caattattat ctatatccca cctaccggtg aactaagagg tggttcatgg    6000
gttgttgtcg atccaactat caacgctgac caaatggaaa tgtatgccga cgtcaacgct    6060
agagctggtg ttttggaacc acaaggtatg gttggtatca gttccgtag agaaaaattg     6120 ctggacacca tgaacagatt ggatgacaag tacagagaat tgagatctca attatccaac    6180
aagagtttgg ctccagaagt acatcagcaa atatccaagc aattagctga tcgtgagaga    6240
gaactattgc caatttacgg acaaatcagt cttcaatttg ctgatttgca cgataggtct    6300
tcacgtatgg tggccaaggg tgttatttct aaggaactgg aatggaccga ggcacgtcgt    6360
ttcttcttct ggagattgag aagaagattg aacgaagaat atttgattaa aaggttgagc    6420
catcaggtag gcgaagcatc aagattagaa aagatcgcaa gaattagatc gtggtaccct    6480
gcttcagtgg accatgaaga tgataggcaa gtcgcaacat ggattgaaga aaactacaaa    6540
actttggacg ataaactaaa gggttttgaaa ttagagtcat tcgctcaaga cttagctaaa    6600
aagatcagaa gcgaccatga caatgctatt gatggattat ctgaagttat caagatgtta    6660
tctaccgatg ataaagaaaa attgttgaag actttgaaat ag                       6702
```

<210> SEQ ID NO 10
<211> LENGTH: 9
<212> TYPE: PRT

```
<213> ORGANISM: Artificial Sequence
<220> FEATURE:
<223> OTHER INFORMATION: Domain 1 lipid phosphatase catalytic motif
<220> FEATURE:
<221> NAME/KEY: VARIANT
<222> LOCATION: 2, 3, 4, 5, 6, 7
<223> OTHER INFORMATION: Xaa = Any Amino Acid

<400> SEQUENCE: 10

Lys Xaa Xaa Xaa Xaa Xaa Xaa Arg Pro
 1               5

<210> SEQ ID NO 11
<211> LENGTH: 4
<212> TYPE: PRT
<213> ORGANISM: Artificial Sequence
<220> FEATURE:
<223> OTHER INFORMATION: Domain 2 lipid phosphatase catalytic motif

<400> SEQUENCE: 11

Pro Ser Gly His
 1

<210> SEQ ID NO 12
<211> LENGTH: 12
<212> TYPE: PRT
<213> ORGANISM: Artificial Sequence
<220> FEATURE:
<223> OTHER INFORMATION: Domain 3 lipid phosphatase catalytic motif
<220> FEATURE:
<221> NAME/KEY: VARIANT
<222> LOCATION: 3, 4, 5, 6, 7, 9, 10, 11
<223> OTHER INFORMATION: Xaa = Any Amino Acid

<400> SEQUENCE: 12

Ser Arg Xaa Xaa Xaa Xaa Xaa His Xaa Xaa Xaa Asp
 1               5                  10

<210> SEQ ID NO 13
<211> LENGTH: 7
<212> TYPE: PRT
<213> ORGANISM: Artificial Sequence
<220> FEATURE:
<223> OTHER INFORMATION: Heptapeptide retention motif
<220> FEATURE:
<221> NAME/KEY: VARIANT
<222> LOCATION: 3
<223> OTHER INFORMATION: Xaa = Any Amino Acid

<400> SEQUENCE: 13

Phe Tyr Xaa Asp Trp Trp Asn
 1               5

<210> SEQ ID NO 14
<211> LENGTH: 446
<212> TYPE: PRT
<213> ORGANISM: Streptomyces coelicolor

<400> SEQUENCE: 14

Met Thr Pro Asp Pro Leu Ala Pro Leu Asp Leu Ala Phe Trp Asn Ile
 1               5                  10                  15

Glu Ser Ala Glu His Pro Met His Leu Gly Ala Leu Gly Val Phe Glu
                20                  25                  30

Ala Asp Ser Pro Thr Ala Gly Ala Leu Ala Asp Leu Leu Ala Ala
            35                  40                  45

Arg Ala Pro Ala Val Pro Gly Leu Arg Met Arg Ile Arg Asp Thr Trp
 50                  55                  60
```

-continued

```
Gln Pro Pro Met Ala Leu Arg Arg Pro Phe Ala Phe Gly Gly Ala Thr
 65                  70                  75                  80

Arg Glu Pro Asp Pro Arg Phe Asp Pro Leu Asp His Val Arg Leu His
             85                  90                  95

Ala Pro Ala Thr Asp Phe His Ala Arg Ala Gly Arg Leu Met Glu Arg
            100                 105                 110

Pro Leu Glu Arg Gly Arg Pro Pro Trp Glu Ala His Val Leu Pro Gly
        115                 120                 125

Ala Asp Gly Gly Ser Phe Ala Val Leu Phe Lys Phe His His Ala Leu
130                 135                 140

Ala Asp Gly Leu Arg Ala Leu Thr Leu Ala Ala Gly Val Leu Asp Pro
145                 150                 155                 160

Met Asp Leu Pro Ala Pro Arg Pro Arg Pro Glu Gln Pro Pro Arg Gly
                165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Leu Ser
        195                 200                 205

Thr Leu Asp Val Arg Ser Ser Pro Ala Leu Thr Ala Ala Ser Ser Gly
    210                 215                 220

Thr Arg Arg Thr Ala Gly Val Ser Val Asp Leu Asp Val His His
225                 230                 235                 240

Val Arg Lys Thr Thr Gly Gly Thr Val Asn Asp Val Leu Ile Ala Val
                245                 250                 255

Val Ala Gly Ala Leu Arg Arg Trp Leu Asp Glu Arg Gly Asp Gly Ser
            260                 265                 270

Glu Gly Val Ala Pro Arg Ala Leu Ile Pro Val Ser Arg Arg Pro
        275                 280                 285

Arg Ser Ala His Pro Gln Gly Asn Arg Leu Ser Gly Tyr Leu Met Arg
290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
                325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
        355                 360                 365

Val Thr Ser Val Pro Leu Pro Ser Leu Gly Leu Arg Leu Gly Gly His
    370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
                405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
        435                 440                 445

<210> SEQ ID NO 15
<211> LENGTH: 457
<212> TYPE: PRT
<213> ORGANISM: Alcanivorax borkumensis
```

```
<400> SEQUENCE: 15

Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
                20                  25                  30

Glu Gly Ala Gly Pro Lys Tyr Val Ser Glu Leu Ala Gln Gln Met Arg
            35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
                100                 105                 110

Pro Met Trp Glu Ala His Leu Ile Glu Gly Ile Arg Gly Arg Gln Phe
            115                 120                 125

Ala Leu Tyr Tyr Lys Ile His His Ser Val Met Asp Gly Ile Ser Ala
130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
                180                 185                 190

Ser Ile Ser Lys Gln Ala Ala Thr Val Pro Gly Leu Ala Arg Glu Val
            195                 200                 205

Tyr Lys Val Thr Gln Lys Ala Lys Lys Asp Glu Asn Tyr Val Ser Ile
            210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
                260                 265                 270

His Ala Leu Arg Glu Tyr Leu Ile Ser Gln His Ala Leu Pro Asp Glu
                275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
            355                 360                 365

Ala Pro Lys Trp Arg Ala Phe Asn Val Val Ile Ser Asn Ile Pro Gly
            370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415
```

Ser Tyr Val Asp Gln Met Glu Phe Gly Leu Ile Ala Cys Arg Arg Thr
        420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
        450                 455

<210> SEQ ID NO 16
<211> LENGTH: 1341
<212> TYPE: DNA
<213> ORGANISM: Artificial Sequence
<220> FEATURE:
<223> OTHER INFORMATION: Codon-optimized Streptomyces coelicolor DGAT

<400> SEQUENCE: 16

| | | |
|---|---|---|
| atgacgcctg acccgttggc tcccttggac ttggctttct ggaatatcga aagtgccgag | 60 |
| cacccgatgc acttgggggc actggggggtc tttgaggcgg atagtccaac cgctggtgca | 120 |
| ctcgccgcgg atctcctggc tgcccgcgct cccgcagtgc ccgggctgcg catgcggatt | 180 |
| cgcgatacat ggcagccgcc tatggcgctc cgtcgccctt ttgcttttgg cggtgctaca | 240 |
| cgcgagcccg acccgcggtt tgatccactc gatcatgtgc ggctccatgc ccagcgacg | 300 |
| gatttccacg cacgcgcagg tcggttgatg gagcgccctc tggaacgagg ccgtcctcct | 360 |
| tgggaagccc atgtcctgcc aggggctgac ggtggatcgt ttgcggtctt gtttaagttc | 420 |
| catcatgccc tggccgacgg tctgcgggcg ctgacgctgg cggcgggcgt gctcgatccg | 480 |
| atggatctcc ccgctccacg gccccgccca gagcagcccc ccgtggtct cctgccggat | 540 |
| gtccgcgcgc tgccggatcg gctgcgaggg gctctgtctg acgcgggccg cgcgttggac | 600 |
| atcgcgcccg ccgcagccct cagcaccctg gatgtgcgga gcagtcccgc tctgactgcg | 660 |
| gcgtcctcgg gcacgcgacg taccgccggc gtgtccgtgg atctcgacga cgtgcaccat | 720 |
| gttcgcaaaa cgacaggcgg taccgttaac gatgttttga tcgccgttgt tgccggggcc | 780 |
| ctgcgacgct ggctggatga acgaggcgat gggtcggaag gcgtcgcccc gcgcgccctc | 840 |
| attcccgtca gccggcggcg acctcggagc gcacacccgc aaggcaaccg attgagtggc | 900 |
| tacctgatgc gcttgccggt cggcgacccg gaccctctcg cacggttggg aaccgtccgt | 960 |
| gccgcgatgg atcgaaataa ggatgcgggg cccggccgcg gagctggcgc agttgctctc | 1020 |
| ttggcagacc acgttcctgc cctgggccac cgcctgggtg gaccccctcgt ctcgggcgct | 1080 |
| gctcgactgt ggttcgatct gttggtcacg agcgtcccgt tgccctcttt ggggtttgcgc | 1140 |
| ctcggtgggc atccgctgac cgaagtgtac ccactggccc cctggcccg tggccactcc | 1200 |
| ttggcggtgg cggtgagcac ttatcgcggt cgggttcatt acggtctcct cgctgatgct | 1260 |
| aaagccgttc ctgatctgga tcgtctggca gtggccgtcg ccgaggaggt tgaaaccttg | 1320 |
| ctcactgcgt gccgcccta g | 1341 |

<210> SEQ ID NO 17
<211> LENGTH: 1374
<212> TYPE: DNA
<213> ORGANISM: Artificial Sequence
<220> FEATURE:
<223> OTHER INFORMATION: Codon-optimized Alcanivorax borkumensis DGAT

<400> SEQUENCE: 17

| | | |
|---|---|---|
| atgaaagctt tgagccccgt tgatcagctg tttctgtggt tggaaaaacg gcagcaaccc | 60 |
| atgcatgtgg gtgggttgca gctgttctcc tttcccgaag gcgcggggcc gaaatatgtc | 120 |

```
tcggaactgg cccaacagat gcgcgattat tgtcaccctg tcgccccgtt caaccaacgt    180
ctgacacggc gcctggggca atactactgg acacgtgata agcaatttga cattgaccat    240
cattttcggc acgaggccct gcccaaaccg ggtcggattc gcgagttgct cagcttggtg    300
agtgcggaac actccaactt gttggatcgt gaacgaccca tgtgggaagc gcacctgatc    360
gaaggaatcc gcgggcgcca atttgccttg tattacaaaa ttcatcactc cgtcatggac    420
ggtatctccg ctatgcggat tgcctctaag accttgtcca cggaccccag tgagcgggag    480
atggccccg cttgggcgtt taatactaag aagcgatcgc gcagcctgcc aagcaatccc    540
gtggatatgg cgagctcgat ggctcgactc actgcaagta tttcgaaaca gctgccacc    600
gtgcccggcc tggcacgaga ggtctacaag gtgacccaaa aagctaaaaa ggatgaaaat    660
tacgttagta ttttccaagc accagacacc atcctcaata tacgattac gggcagtcga    720
cgcttcgccg ctcagtcgtt ccctctcccc cgtctgaagg ttatcgctaa ggcttacaac    780
tgcactatta acacggttgt gctctcgatg tgcggccacg ccctgcgcga atacctcatc    840
agtcaacatg ccctgccgga tgaacccctg atcgcgatgg tccctatgag cctgcgccaa    900
gatgatagca ccggaggcaa ccagatcgga atgattttgg cgaatctggg cacgcatatc    960
tgcgatcctg ccaatcgcct gcgtgtcatc catgatagcg tggaggaggc gaaaagccgt   1020
tttagccaaa tgtctccgga ggagattctg aactttacag cactcactat ggcgccgacc   1080
ggtctgaact tgctcaccgg tttggctccc aaatggcgcg catttaacgt cgttatctct   1140
aacatcccag ggccaaagga accactgtac tggaatgggg cacagctcca gggtgtgtat   1200
ccggtctcca tcgccttgga tcggattgcc ctgaacatta cactgacgtc ttatgttgat   1260
cagatggagt tcggcttgat tgcgtgtcgc cggaccctcc cgtcgatgca acgactcctc   1320
gactatctcg aacagagtat ccgcgaactg gagattggcg cgggcatcaa atag         1374
```

<210> SEQ ID NO 18
<211> LENGTH: 460
<212> TYPE: PRT
<213> ORGANISM: Acinetobacter baylii sp.

<400> SEQUENCE: 18

```
Met Glu Phe Arg Pro Leu His Pro Ile Asp Phe Ile Phe Leu Ser Leu
 1               5                  10                  15

Glu Lys Arg Gln Gln Pro Met His Val Gly Gly Leu Phe Leu Phe Gln
            20                  25                  30

Ile Pro Asp Asn Ala Pro Asp Thr Phe Ile Gln Asp Leu Val Asn Asp
        35                  40                  45

Ile Arg Ile Ser Lys Ser Ile Pro Val Pro Pro Phe Asn Asn Lys Leu
    50                  55                  60

Asn Gly Leu Phe Trp Asp Glu Asp Glu Glu Phe Asp Leu Asp His His
65                  70                  75                  80

Phe Arg His Ile Ala Leu Pro His Pro Gly Arg Ile Arg Glu Leu Leu
                85                  90                  95

Ile Tyr Ile Ser Gln Glu His Ser Thr Leu Leu Asp Arg Ala Lys Pro
           100                 105                 110

Leu Trp Thr Cys Asn Ile Ile Glu Gly Ile Glu Gly Asn Arg Phe Ala
       115                 120                 125

Met Tyr Phe Lys Ile His His Ala Met Val Asp Gly Val Ala Gly Met
   130                 135                 140

Arg Leu Ile Glu Lys Ser Leu Ser His Asp Val Thr Glu Lys Ser Ile
```

```
                145                 150                 155                 160
        Val Pro Pro Trp Cys Val Glu Gly Lys Arg Ala Lys Arg Leu Arg Glu
                            165                 170                 175

Pro Lys Thr Gly Lys Ile Lys Lys Ile Met Ser Gly Ile Lys Ser Gln
                        180                 185                 190

Leu Gln Ala Thr Pro Thr Val Ile Gln Glu Leu Ser Gln Thr Val Phe
                    195                 200                 205

Lys Asp Ile Gly Arg Asn Pro Asp His Val Ser Ser Phe Gln Ala Pro
                210                 215                 220

Cys Ser Ile Leu Asn Gln Arg Val Ser Ser Arg Arg Phe Ala Ala
        225                 230                 235                 240

Gln Ser Phe Asp Leu Asp Arg Phe Arg Asn Ile Ala Lys Ser Leu Asn
                            245                 250                 255

Val Thr Ile Asn Asp Val Val Leu Ala Val Cys Ser Gly Ala Leu Arg
                        260                 265                 270

Ala Tyr Leu Met Ser His Asn Ser Leu Pro Ser Lys Pro Leu Ile Ala
                    275                 280                 285

Met Val Pro Ala Ser Ile Arg Asn Asp Asp Ser Asp Val Ser Asn Arg
                290                 295                 300

Ile Thr Met Ile Leu Ala Asn Leu Ala Thr His Lys Asp Asp Pro Leu
        305                 310                 315                 320

Gln Arg Leu Glu Ile Ile Arg Arg Ser Val Gln Asn Ser Lys Gln Arg
                            325                 330                 335

Phe Lys Arg Met Thr Ser Asp Gln Ile Leu Asn Tyr Ser Ala Val Val
                        340                 345                 350

Tyr Gly Pro Ala Gly Leu Asn Ile Ile Ser Gly Met Met Pro Lys Arg
                    355                 360                 365

Gln Ala Phe Asn Leu Val Ile Ser Asn Val Pro Gly Pro Arg Glu Pro
                370                 375                 380

Leu Tyr Trp Asn Gly Ala Lys Leu Asp Ala Leu Tyr Pro Ala Ser Ile
        385                 390                 395                 400

Val Leu Asp Gly Gln Ala Leu Asn Ile Thr Met Thr Ser Tyr Leu Asp
                            405                 410                 415

Lys Leu Glu Val Gly Leu Ile Ala Cys Arg Asn Ala Leu Pro Arg Met
                        420                 425                 430

Gln Asn Leu Leu Thr His Leu Glu Glu Glu Ile Gln Leu Phe Glu Gly
                    435                 440                 445

Val Ile Ala Lys Gln Glu Asp Ile Lys Thr Ala Asn
                450                 455                 460

<210> SEQ ID NO 19
<211> LENGTH: 1383
<212> TYPE: DNA
<213> ORGANISM: Artificial Sequence
<220> FEATURE:
<223> OTHER INFORMATION: Codon-optimized Acinetobacter baylii sp. DGATd

<400> SEQUENCE: 19
atggaattcc ggcccttgca ccccattgac ttcatctttc tgagtttgga gaaacggcaa      60
cagcccatgc atgtcggtgg cttgtttctc ttccaaatcc ccgataacgc cccggacacc     120
tttattcagg atctggtcaa tgatatccgg atctcgaaat cgatccccgt gccgccgttt     180
aataataaac tgaacggcct cttttgggac gaagacgagg aatttgatct ggatcaccat     240
tttcggcaca tcgctttgcc ccacccgggt cggattcgcg aactcctgat ctatattagc     300
```

```
caagaacaca gcacgttgtt ggaccgggcc aaaccgctct ggacgtgcaa tatcatcgaa      360
ggcatcgaag gcaaccgctt tgcgatgtac ttcaagattc atcacgcgat ggttgacggt      420
gtcgctggca tgcgcctgat cgaaaaatcg ctgagccatg atgtgaccga aagagtatc      480
gtccccccct ggtgcgtgga aggtaagcgc gccaagcgcc tccgcgaacc gaaaacgggc      540
aagattaaga aaatcatgag cggtatcaag tcgcagctgc aggctacccc gaccgtgatc      600
caggagctgt cgcaaaccgt gtttaaggat attggtcgga acccggatca tgtcagtagt      660
ttccaagctc cctgttcgat cttgaatcag cgcgttagca gcagccgccg gttcgctgct      720
caaagttttg atctcgatcg gtttcggaat attgccaagt cgctgaacgt caccatcaat      780
gatgtggttc tcgcggtttg ttcgggtgcc ctccgcgcgt atctgatgag ccataacagt      840
ctccccagta agccgctgat tgctatggtt cccgcgtcga ttcggaatga cgacagcgat      900
gtgagcaacc ggattaccat gatcctggct aacctcgcga cccacaaaga tgatccgttg      960
caacgcctgg agattatccg ccgcagtgtg cagaacagta acagcgcttt caaacggatg     1020
accagtgatc aaattctgaa ttacagcgct gtggtctatg gtcccgccgg cttgaatatt     1080
atcagtggta tgatgcccaa acgccaagcg tttaacttgg tgatcagtaa tgtgccgggt     1140
ccgcgcgaac ccttgtattg gaacggtgct aaactcgatg ccctctaccc cgccagtatc     1200
gtgctcgatg gccaggctct caatattacc atgaccagct atctcgataa actcgaggtg     1260
ggtttgattg cgtgccgcaa cgcgctgccc gcatgcaga acttgctgac ccacctggaa     1320
gaggaaatcc agctcttcga gggcgtgatt gcgaagcagg aagatattaa acggccaac      1380
tag                                                                   1383
```

<210> SEQ ID NO 20
<211> LENGTH: 325
<212> TYPE: PRT
<213> ORGANISM: Synechococcus sp. PCC7002

<400> SEQUENCE: 20

```
Met Pro Lys Thr Glu Arg Arg Thr Phe Leu Leu Asp Phe Glu Lys Pro
1               5                   10                  15

Leu Ser Glu Leu Glu Ser Arg Ile His Gln Ile Arg Asp Leu Ala Ala
            20                  25                  30

Glu Asn Asn Val Asp Val Ser Glu Gln Ile Gln Gln Leu Glu Ala Arg
        35                  40                  45

Ala Asp Gln Leu Arg Glu Glu Ile Phe Ser Thr Leu Thr Pro Ala Gln
    50                  55                  60

Arg Leu Gln Leu Ala Arg His Pro Arg Arg Pro Ser Thr Leu Asp Tyr
65                  70                  75                  80

Val Gln Met Met Ala Asp Glu Trp Phe Glu Leu His Gly Asp Arg Gly
                85                  90                  95

Gly Ser Asp Asp Pro Ala Leu Ile Gly Gly Val Ala Arg Phe Asp Gly
            100                 105                 110

Gln Pro Val Met Met Leu Gly His Gln Lys Gly Arg Asp Thr Lys Asp
        115                 120                 125

Asn Val Ala Arg Asn Phe Gly Met Pro Ala Pro Gly Gly Tyr Arg Lys
    130                 135                 140

Ala Met Arg Leu Met Asp His Ala Asn Arg Phe Gly Met Pro Ile Leu
145                 150                 155                 160

Thr Phe Ile Asp Thr Pro Gly Ala Trp Ala Gly Leu Glu Ala Glu Lys
                165                 170                 175
```

-continued

```
Leu Gly Gln Gly Glu Ala Ile Ala Phe Asn Leu Arg Glu Met Phe Ser
                180                 185                 190

Leu Asp Val Pro Ile Ile Cys Thr Val Ile Gly Glu Gly Ser Gly
            195                 200                 205

Gly Ala Leu Gly Ile Gly Val Gly Asp Arg Val Leu Met Leu Lys Asn
        210                 215                 220

Ser Val Tyr Thr Val Ala Thr Pro Glu Ala Cys Ala Ala Ile Leu Trp
225                 230                 235                 240

Lys Asp Ala Gly Lys Ser Glu Gln Ala Ala Ala Leu Lys Ile Thr
            245                 250                 255

Ala Glu Asp Leu Lys Ser Leu Glu Ile Ile Asp Glu Ile Val Pro Glu
            260                 265                 270

Pro Ala Ser Cys Ala His Ala Asp Pro Ile Gly Ala Ala Gln Leu Leu
            275                 280                 285

Lys Ala Ala Ile Gln Asp Asn Leu Gln Ala Leu Leu Lys Leu Thr Pro
        290                 295                 300

Glu Arg Arg Arg Glu Leu Arg Tyr Gln Arg Phe Arg Lys Ile Gly Val
305                 310                 315                 320

Phe Leu Glu Ser Ser
                325

<210> SEQ ID NO 21
<211> LENGTH: 165
<212> TYPE: PRT
<213> ORGANISM: Synechococcus sp. PCC 7002

<400> SEQUENCE: 21

Met Ala Ile Asn Leu Gln Glu Ile Gln Glu Leu Leu Ser Thr Ile Gly
  1               5                  10                  15

Gln Thr Asn Val Thr Glu Phe Glu Leu Lys Thr Asp Asp Phe Glu Leu
            20                  25                  30

Arg Val Ser Lys Gly Thr Val Val Ala Ala Pro Gln Thr Met Val Met
        35                  40                  45

Ser Glu Ala Ile Ala Gln Pro Ala Met Ser Thr Pro Val Val Ser Gln
50                  55                  60

Ala Thr Ala Thr Pro Glu Ala Ser Gln Ala Glu Thr Pro Ala Pro Ser
65                  70                  75                  80

Val Ser Ile Asp Asp Lys Trp Val Ala Ile Thr Ser Pro Met Val Gly
                85                  90                  95

Thr Phe Tyr Arg Ala Pro Ala Pro Gly Glu Asp Pro Phe Val Ala Val
            100                 105                 110

Gly Asp Arg Val Gly Asn Gly Gln Thr Val Cys Ile Ile Glu Ala Met
        115                 120                 125

Lys Leu Met Asn Glu Ile Glu Ala Glu Val Ser Gly Glu Val Val Lys
    130                 135                 140

Ile Ala Val Glu Asp Gly Glu Pro Ile Glu Phe Gly Gln Thr Leu Met
145                 150                 155                 160

Trp Val Asn Pro Thr
                165

<210> SEQ ID NO 22
<211> LENGTH: 448
<212> TYPE: PRT
<213> ORGANISM: Synechococcus sp. PCC 7002

<400> SEQUENCE: 22
```

```
Met Gln Phe Ser Lys Ile Leu Ile Ala Asn Arg Gly Glu Val Ala Leu
  1               5                  10                  15

Arg Ile Ile His Thr Cys Gln Glu Leu Gly Ile Ala Thr Val Ala Val
             20                  25                  30

His Ser Thr Val Asp Arg Gln Ala Leu His Val Gln Leu Ala Asp Glu
             35                  40                  45

Ser Ile Cys Ile Gly Pro Pro Gln Ser Ser Lys Ser Tyr Leu Asn Ile
 50                  55                  60

Pro Asn Ile Ile Ala Ala Leu Ser Ser Asn Ala Asp Ala Ile His
 65                  70                  75                  80

Pro Gly Tyr Gly Phe Leu Ala Glu Asn Ala Lys Phe Ala Glu Ile Cys
             85                  90                  95

Ala Asp His Gln Ile Thr Phe Ile Gly Pro Ser Pro Glu Ala Met Ile
             100                 105                 110

Ala Met Gly Asp Lys Ser Thr Ala Lys Lys Thr Met Gln Ala Ala Lys
             115                 120                 125

Val Pro Thr Val Pro Gly Ser Ala Gly Leu Val Ala Ser Glu Glu Gln
             130                 135                 140

Ala Leu Glu Ile Ala Gln Gln Ile Gly Tyr Pro Val Met Ile Lys Ala
145                 150                 155                 160

Thr Ala Gly Gly Gly Gly Arg Gly Met Arg Leu Val Pro Ser Ala Glu
             165                 170                 175

Glu Leu Pro Arg Leu Tyr Arg Ala Ala Gln Gly Glu Ala Glu Ala Ala
             180                 185                 190

Phe Gly Asn Gly Gly Val Tyr Ile Glu Lys Phe Ile Glu Arg Pro Arg
             195                 200                 205

His Ile Glu Phe Gln Ile Leu Ala Asp Gln Tyr Gly Asn Val Ile His
             210                 215                 220

Leu Gly Glu Arg Asp Cys Ser Ile Gln Arg Arg His Gln Lys Leu Leu
225                 230                 235                 240

Glu Glu Ala Pro Ser Ala Ile Leu Thr Pro Arg Leu Arg Asp Lys Met
             245                 250                 255

Gly Lys Ala Ala Val Lys Ala Ala Lys Ser Ile Asp Tyr Val Gly Ala
             260                 265                 270

Gly Thr Val Glu Phe Leu Val Asp Lys Asn Gly Asp Phe Tyr Phe Met
             275                 280                 285

Glu Met Asn Thr Arg Ile Gln Val Glu His Pro Val Thr Glu Met Val
             290                 295                 300

Thr Gly Leu Asp Leu Ile Ala Glu Gln Ile Lys Val Ala Gln Gly Asp
305                 310                 315                 320

Arg Leu Ser Leu Asn Gln Asn Gln Val Asn Leu Asn Gly His Ala Ile
             325                 330                 335

Glu Cys Arg Ile Asn Ala Glu Asp Pro Asp His Asp Phe Arg Pro Thr
             340                 345                 350

Pro Gly Lys Ile Ser Gly Tyr Leu Pro Gly Gly Pro Gly Val Arg
             355                 360                 365

Met Asp Ser His Val Tyr Thr Asp Tyr Glu Ile Ser Pro Tyr Tyr Asp
             370                 375                 380

Ser Leu Ile Gly Lys Leu Ile Val Trp Gly Pro Asp Arg Asp Thr Ala
385                 390                 395                 400

Ile Arg Arg Met Lys Arg Ala Leu Arg Glu Cys Ala Ile Thr Gly Val
             405                 410                 415

Ser Thr Thr Ile Ser Phe His Gln Lys Ile Leu Asn His Pro Ala Phe
```

```
                420                 425                 430
Leu Ala Ala Asp Val Asp Thr Asn Phe Ile Gln Gln His Met Leu Pro
            435                 440                 445

<210> SEQ ID NO 23
<211> LENGTH: 319
<212> TYPE: PRT
<213> ORGANISM: Synechococcus sp. PCC 7002

<400> SEQUENCE: 23

Met Ser Leu Phe Asp Trp Phe Ala Ala Asn Arg Gln Asn Ser Glu Thr
  1               5                  10                  15

Gln Leu Gln Pro Gln Gln Glu Arg Glu Ile Ala Asp Gly Leu Trp Thr
             20                  25                  30

Lys Cys Lys Ser Cys Asp Ala Leu Thr Tyr Thr Lys Asp Leu Arg Asn
         35                  40                  45

Asn Gln Met Val Cys Lys Glu Cys Gly Phe His Asn Arg Val Gly Ser
     50                  55                  60

Arg Glu Arg Val Arg Gln Leu Ile Asp Glu Gly Thr Trp Thr Glu Ile
 65                  70                  75                  80

Ser Gln Asn Val Ala Pro Thr Asp Pro Leu Lys Phe Arg Asp Lys Lys
                 85                  90                  95

Ala Tyr Ser Asp Arg Leu Lys Asp Tyr Gln Glu Lys Thr Asn Leu Thr
            100                 105                 110

Asp Ala Val Ile Thr Gly Thr Gly Leu Ile Asp Gly Leu Pro Leu Ala
        115                 120                 125

Leu Ala Val Met Asp Phe Gly Phe Met Gly Gly Ser Met Gly Ser Val
130                 135                 140

Val Gly Glu Lys Ile Cys Arg Leu Val Glu His Gly Thr Ala Glu Gly
145                 150                 155                 160

Leu Pro Val Val Val Cys Ala Ser Gly Gly Ala Arg Met Gln Glu
                165                 170                 175

Gly Met Leu Ser Leu Met Gln Met Ala Lys Ile Ser Gly Ala Leu Glu
            180                 185                 190

Arg His Arg Thr Lys Lys Leu Leu Tyr Ile Pro Val Leu Thr Asn Pro
        195                 200                 205

Thr Thr Gly Gly Val Thr Ala Ser Phe Ala Met Leu Gly Asp Leu Ile
    210                 215                 220

Leu Ala Glu Pro Lys Ala Thr Ile Gly Phe Ala Gly Arg Arg Val Ile
225                 230                 235                 240

Glu Gln Thr Leu Arg Glu Lys Leu Pro Asp Asp Phe Gln Thr Ser Glu
                245                 250                 255

Tyr Leu Leu Gln His Gly Phe Val Asp Ala Ile Val Pro Arg Thr Glu
            260                 265                 270

Leu Lys Lys Thr Leu Ala Gln Met Ile Ser Leu His Gln Pro Phe His
        275                 280                 285

Pro Ile Leu Pro Glu Leu Gln Leu Ala Pro His Val Glu Lys Glu Lys
    290                 295                 300

Val Tyr Glu Pro Ile Ala Ser Thr Ser Thr Asn Asp Phe Tyr Lys
305                 310                 315

<210> SEQ ID NO 24
<211> LENGTH: 978
<212> TYPE: DNA
<213> ORGANISM: Synechococcus sp. PCC 7002
```

<400> SEQUENCE: 24

```
atgccgaaaa cggagcgccg gacgtttctg cttgattttg aaaaacctct ttcggaatta      60
gaatcacgca tccatcaaat tcgtgatctt gctgcggaga ataatgttga tgtttcagaa     120
cagattcagc agctagaggc gcgggcagac cagctccggg aagaaatttt tagtaccctc     180
accccggccc aacggctgca attggcacgg catccccggc gtcccagcac ccttgattat     240
gttcaaatga tggcggacga atggtttgaa ctccatggcg atcgcggtgg atctgatgat     300
ccggctctca ttggcggggt ggcccgcttc gatggtcaac cggtgatgat gctagggcac     360
caaaaaggac gggatacgaa ggataatgtc gcccgcaatt ttggcatgcc agctcctggg     420
ggctaccgta aggcgatgcg gctgatggac catgccaacc gttttgggat gccgatttta     480
acgtttattg atactcctgg ggcttgggcg ggtttagaag cggaaaagtt gggcaagggg     540
gaggcgatcg cctttaacct ccgggaaatg tttagcctcg atgtgccgat tatttgcacg     600
gtcattggcg aaggcggttc cgtgggggcc ttagggattg gcgtgggcga tcgcgtcttg     660
atgttaaaaa attccgttta cacagtggcg accccagagg cttgtgccgc cattctctgg     720
aaagatgccg ggaaatcaga gcaggccgcc gccgccctca agattacagc agaggatctg     780
aaaagccttg agattatcga tgaaattgtc ccagagccag cctcctgcgc ccacgccgat     840
cccattgggg ccgcccaact cctgaaagca gcgatccaag ataacctcca agccttgctg     900
aagctgacgc cagaacgccg ccgtgaattg cgctaccagc ggttccggaa aattggtgtg     960
ttttttagaaa gttcctaa                                                  978
```

<210> SEQ ID NO 25
<211> LENGTH: 498
<212> TYPE: DNA
<213> ORGANISM: Synechococcus sp. PCC 7002

<400> SEQUENCE: 25

```
atggctatta atttacaaga gatccaagaa cttctatcca ccatcggcca aaccaatgtc      60
accgagtttg aactcaaaac cgatgatttt gaactccgtg tgagcaaagg tactgttgtg     120
gctgctcccc agacgatggt gatgtccgag gcgatcgccc aaccagcaat gtccactccc     180
gttgtttctc aagcaactgc aaccccagaa gcctcccaag cggaaacccc ggctcccagt     240
gtgagcattg atgataagtg ggtcgccatt acctcccccca tggtgggaac gttttaccgc     300
gcgccggccc ctggtgaaga tcccttcgtt gccgttggcg atcgcgttgg caatggtcaa     360
accgtttgca tcatcgaagc gatgaaatta tgaatgaga ttgaggcaga agtcagcggt     420
gaagttgtta aaattgccgt tgaagacggt gaacccattg aatttggtca gaccctaatg     480
tgggtcaacc caacctaa                                                   498
```

<210> SEQ ID NO 26
<211> LENGTH: 1347
<212> TYPE: DNA
<213> ORGANISM: Synechococcus sp. PCC 7002

<400> SEQUENCE: 26

```
atgcagtttt caaagattct catcgccaat cgcggagaag ttgccctacg cattatccac      60
acctgtcagg agctcggcat tgccacagtt gccgtccact ccaccgtaga tcgccaagcc     120
ctccacgttc agctcgccga tgagagcatt tgcattggcc cgccccagag cagcaaaagc     180
tatctcaaca ttcccaatat tatcgctgcg gccctcagca gtaacgccga cgcaatccac     240
ccaggctacg gtttcctcgc tgaaaatgcc aagtttgcag aaatttgtgc cgaccaccaa     300
```

```
atcaccttca ttggcccttc cccagaagca atgatcgcca tgggggacaa atccaccgcc      360
aaaaaaacga tgcaggcggc aaaagtccct accgtacccg gtagtgctgg gttggtggcc      420
tccgaagaac aagccctaga aatcgcccaa caaattggct accctgtgat gatcaaagcc      480
acggcgggtg gtggtggccg ggggatgcgc cttgtgccca gcgctgagga gttaccccgt      540
ttgtaccgag cggcccaggg ggaagcagaa gcagcctttg ggaatggcgg cgtttacatc      600
gaaaaattta ttgaacggcc ccgtcacatc gaatttcaga tcctcgcgga tcagtacggc      660
aatgtaattc acctcggcga acgggattgt tcgatccaac ggcggcacca aaaactcctc      720
gaagaagctc ccagcgcgat cctcaccccc agactgcggg acaaaatggg gaaagcggca      780
gtaaaagcgg cgaaatccat tgattatgtc ggggcgggga cggtggaatt cctcgtggat      840
aagaatgggg atttctactt tatggaaatg aataccgca ttcaggtgga cacccggtc       900 acagagatgg tgacgggact agatctgatc gccgagcaaa ttaaagttgc ccaaggcgat      960
cgcctcagtt tgaatcaaaa tcaagtgaac ttgaatggtc atgccatcga gtgccggatt     1020
aatgccgaag atcccgacca tgatttccga ccgaccccag gcaaaatcag tggctatctt     1080 cccccccggtg gccctggggt acggatggat tcccacgttt acaccgacta tgaaatttct     1140
ccttactacg attctttgat cggtaaatta atcgtttggg gaccagaccg agacaccgcc     1200
attcgccgca tgaagcgggc actccgagaa tgtgccatta ctggagtatc gaccaccatt     1260
agcttccacc aaaagatttt gaatcatccg gcttttttgg cggccgatgt cgatacaaac     1320
tttatccagc agcacatgtt gccctag                                         1347

<210> SEQ ID NO 27
<211> LENGTH: 960
<212> TYPE: DNA
<213> ORGANISM: Synechococcus sp. PCC 7002

<400> SEQUENCE: 27
atgtctcttt ttgattggtt tgccgcaaat cgccaaaatt ctgaaaccca gctccagccc       60
caacaggagc gcgagattgc cgatggcctc tggacgaaat gcaaatcctg cgatgctctc      120
acctacacta aagacctccg caacaatcaa atggtctgta aagagtgtgg cttccataac      180
cgggtcggca gtcgggaacg ggtacgccaa ttgattgacg aaggcacctg gacagaaatt      240
agtcagaatg tcgcgccgac cgacccctg aaattccgcg acaaaaaagc ctatagcgat      300
cgcctcaaag attaccaaga gaaaacgaac ctcaccgatg ctgtaatcac tggcacagga      360
ctgattgacg gtttaccccct tgctttggca gtgatggact ttggctttat gggcggcagc      420
atgggatccg ttgtcggcga aaaatttgt cgcctcgtag aacatggcac cgccgaaggt      480
ttacccgtgg tggttgtttg tgcttctggt ggagcaagaa tgcaagaggg catgctcagt      540
ctgatgcaga tggcgaaaat ctctggtgcc ctcgaacgcc atcgcaccaa aaaattactc      600
tacatccctg ttttgactaa tcccaccacc gggggcgtca ccgctagctt tgcgatgttg      660
ggcgatttga ttcttgccga acccaaagca accatcggtt ttgctggacg ccgcgtcatt      720
gaacaaacat tgcgcgaaaa acttcctgac gattttcaga catctgaata tttactccaa      780
catgggtttg tggatgcgat tgtgcccgc actgaattga aaaaaaccct cgcccaaatg      840
attagtctcc atcagcccctt tcacccgatt ctgccagagc tacaattggc tccccatgtg      900
gaaaaagaaa aagtttacga acccattgcc tctacttcaa ccaacgactt ttacaagtag      960

<210> SEQ ID NO 28
```

-continued

```
<211> LENGTH: 2311
<212> TYPE: PRT
<213> ORGANISM: Triticum aestivum

<400> SEQUENCE: 28

Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Arg Ala Ala
    130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Gly Gly Ser Gln Val Glu Ile Pro Leu Glu Val Cys Leu Asp
        275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
```

-continued

```
            385                 390                 395                 400
        Pro Val Thr Val Ala Pro Arg Glu Thr Val Lys Glu Leu Gly Gln Ala
                        405                 410                 415
        Ala Arg Arg Leu Ala Lys Ala Val Gly Tyr Val Gly Ala Ala Thr Val
                        420                 425                 430
        Glu Tyr Leu Tyr Ser Met Glu Thr Gly Glu Tyr Tyr Phe Leu Glu Leu
                        435                 440                 445
        Asn Pro Arg Leu Gln Val Glu His Pro Val Thr Glu Trp Ile Ala Glu
                        450                 455                 460
        Val Asn Leu Pro Ala Ala Gln Val Ala Val Gly Met Gly Ile Pro Leu
        465                 470                 475                 480
        Trp Gln Val Pro Glu Ile Arg Arg Phe Tyr Gly Met Asp Asn Gly Gly
                        485                 490                 495
        Gly Tyr Asp Ile Trp Arg Glu Thr Ala Ala Leu Ala Thr Pro Phe Asn
                        500                 505                 510
        Phe Asp Glu Val Asp Ser Gln Trp Pro Lys Gly His Cys Val Ala Val
                        515                 520                 525
        Arg Ile Thr Ser Glu Asp Pro Asp Gly Phe Lys Pro Thr Gly Gly
                        530                 535                 540
        Lys Val Lys Glu Ile Ser Phe Lys Ser Lys Pro Asn Val Trp Ala Tyr
        545                 550                 555                 560
        Phe Ser Val Lys Ser Gly Gly Ile His Glu Phe Ala Asp Ser Gln
                        565                 570                 575
        Phe Gly His Val Phe Ala Tyr Gly Val Ser Arg Ala Ala Ala Ile Thr
                        580                 585                 590
        Asn Met Ser Leu Ala Leu Lys Glu Ile Gln Ile Arg Gly Glu Ile His
                        595                 600                 605
        Ser Asn Val Asp Tyr Thr Val Asp Leu Leu Asn Ala Ser Asp Phe Lys
                        610                 615                 620
        Glu Asn Arg Ile His Thr Gly Trp Leu Asp Asn Arg Ile Ala Met Arg
        625                 630                 635                 640
        Val Gln Ala Glu Arg Pro Pro Trp Tyr Ile Ser Val Val Gly Gly Ala
                        645                 650                 655
        Leu Tyr Lys Thr Ile Thr Ser Asn Thr Asp Thr Val Ser Glu Tyr Val
                        660                 665                 670
        Ser Tyr Leu Val Lys Gly Gln Ile Pro Pro Lys His Ile Ser Leu Val
                        675                 680                 685
        His Ser Thr Val Ser Leu Asn Ile Glu Glu Ser Lys Tyr Thr Ile Glu
        690                 695                 700
        Thr Ile Arg Ser Gly Gln Gly Ser Tyr Arg Leu Arg Met Asn Gly Ser
        705                 710                 715                 720
        Val Ile Glu Ala Asn Val Gln Thr Leu Cys Asp Gly Gly Leu Leu Met
                        725                 730                 735
        Gln Leu Asp Gly Asn Ser His Val Ile Tyr Ala Glu Glu Ala Gly
                        740                 745                 750
        Gly Thr Arg Leu Leu Ile Asp Gly Lys Thr Tyr Leu Leu Gln Asn Asp
                        755                 760                 765
        His Asp Pro Ser Arg Leu Leu Ala Glu Thr Pro Cys Lys Leu Leu Arg
                        770                 775                 780
        Phe Leu Val Ala Asp Gly Ala His Val Glu Ala Asp Val Pro Tyr Ala
        785                 790                 795                 800
        Glu Val Glu Val Met Lys Met Cys Met Pro Leu Leu Ser Pro Ala Ala
                        805                 810                 815
```

```
Gly Val Ile Asn Val Leu Leu Ser Glu Gly Gln Pro Met Gln Ala Gly
                820                 825                 830

Asp Leu Ile Ala Arg Leu Asp Leu Asp Pro Ser Ala Val Lys Arg
            835                 840                 845

Ala Glu Pro Phe Asn Gly Ser Phe Pro Glu Met Ser Leu Pro Ile Ala
850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
            885                 890                 895

Asp Leu Val Ser Cys Leu Asp Ala Pro Glu Leu Pro Phe Leu Gln Trp
                900                 905                 910

Glu Glu Leu Met Ser Val Leu Ala Thr Arg Leu Pro Arg Leu Leu Lys
                915                 920                 925

Ser Glu Leu Glu Gly Lys Tyr Ser Glu Tyr Lys Leu Asn Val Gly His
            930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Leu Lys Ser Tyr Glu Gly Gly Arg
            980                 985                 990

Glu Ser His Ala His Phe Ile Val Lys Ser Leu Phe Glu Asp Tyr Leu
        995                 1000                1005

Ser Val Glu Glu Leu Phe Ser Asp Gly Ile Gln Ser Asp Val Ile Glu
    1010                1015                1020

Arg Leu Arg Gln Gln His Ser Lys Asp Leu Gln Lys Val Val Asp Ile
1025                1030                1035                1040

Val Leu Ser His Gln Gly Val Arg Asn Lys Thr Lys Leu Ile Leu Thr
            1045                1050                1055

Leu Met Glu Lys Leu Val Tyr Pro Asn Pro Ala Val Tyr Lys Asp Gln
                1060                1065                1070

Leu Thr Arg Phe Ser Ser Leu Asn His Lys Arg Tyr Tyr Lys Leu Ala
            1075                1080                1085

Leu Lys Ala Ser Glu Leu Leu Glu Gln Thr Lys Leu Ser Glu Leu Arg
            1090                1095                1100

Thr Ser Ile Ala Arg Ser Leu Ser Glu Leu Glu Met Phe Thr Glu Glu
1105                1110                1115                1120

Arg Thr Ala Ile Ser Glu Ile Met Gly Asp Leu Val Thr Ala Pro Leu
            1125                1130                1135

Pro Val Glu Asp Ala Leu Val Ser Leu Phe Asp Cys Ser Asp Gln Thr
            1140                1145                1150

Leu Gln Gln Arg Val Ile Glu Thr Tyr Ile Ser Arg Leu Tyr Gln Pro
        1155                1160                1165

His Leu Val Lys Asp Ser Ile Gln Leu Lys Tyr Gln Glu Ser Gly Val
        1170                1175                1180

Ile Ala Leu Trp Glu Phe Ala Glu Ala His Ser Glu Lys Arg Leu Gly
1185                1190                1195                1200

Ala Met Val Ile Val Lys Ser Leu Glu Ser Val Ser Ala Ala Ile Gly
            1205                1210                1215

Ala Ala Leu Lys Gly Thr Ser Arg Tyr Ala Ser Ser Glu Gly Asn Ile
            1220                1225                1230
```

```
Met His Ile Ala Leu Leu Gly Ala Asp Asn Gln Met His Gly Thr Glu
        1235                1240                1245

Asp Ser Gly Asp Asn Asp Gln Ala Gln Val Arg Ile Asp Lys Leu Ser
    1250                1255                1260

Ala Thr Leu Glu Gln Asn Thr Val Thr Ala Asp Leu Arg Ala Ala Gly
1265                1270                1275                1280

Val Lys Val Ile Ser Cys Ile Val Gln Arg Asp Gly Ala Leu Met Pro
            1285                1290                1295

Met Arg His Thr Phe Leu Leu Ser Asp Glu Lys Leu Cys Tyr Gly Glu
        1300                1305                1310

Glu Pro Val Leu Arg His Val Glu Pro Leu Ser Ala Leu Leu Glu
    1315                1320                1325

Leu Gly Lys Leu Lys Val Lys Gly Tyr Asn Glu Val Lys Tyr Thr Pro
1330                1335                1340

Ser Arg Asp Arg Gln Trp Asn Ile Tyr Thr Leu Arg Asn Thr Glu Asn
1345                1350                1355                1360

Pro Lys Met Leu His Arg Val Phe Phe Arg Thr Leu Val Arg Gln Pro
            1365                1370                1375

Gly Ala Ser Asn Lys Phe Thr Ser Gly Asn Ile Ser Asp Val Glu Val
        1380                1385                1390

Gly Gly Ala Glu Glu Ser Leu Ser Phe Thr Ser Ser Ile Leu Arg
    1395                1400                1405

Ser Leu Met Thr Ala Ile Glu Glu Leu Glu Leu His Ala Ile Arg Thr
    1410                1415                1420

Gly His Ser His Met Phe Leu Cys Ile Leu Lys Glu Arg Lys Leu Leu
1425                1430                1435                1440

Asp Leu Val Pro Val Ser Gly Asn Lys Val Val Asp Ile Gly Gln Asp
            1445                1450                1455

Glu Ala Thr Ala Cys Leu Leu Leu Lys Glu Met Ala Leu Gln Ile His
        1460                1465                1470

Glu Leu Val Gly Ala Arg Met His His Leu Ser Val Cys Gln Trp Glu
    1475                1480                1485

Val Lys Leu Lys Leu Asp Ser Asp Gly Pro Ala Ser Gly Thr Trp Arg
    1490                1495                1500

Val Val Thr Thr Asn Val Thr Ser His Thr Cys Thr Val Asp Ile Tyr
1505                1510                1515                1520

Arg Glu Val Glu Asp Thr Glu Ser Gln Lys Leu Val Tyr His Ser Ala
            1525                1530                1535

Pro Ser Ser Ser Gly Pro Leu His Gly Val Ala Leu Asn Thr Pro Tyr
        1540                1545                1550

Gln Pro Leu Ser Val Ile Asp Leu Lys Arg Cys Ser Ala Arg Asn Asn
    1555                1560                1565

Arg Thr Thr Tyr Cys Tyr Asp Phe Pro Leu Ala Phe Glu Thr Ala Val
    1570                1575                1580

Gln Lys Ser Trp Ser Asn Ile Ser Ser Asp Asn Arg Cys Tyr Val
1585                1590                1595                1600

Lys Ala Thr Glu Leu Val Phe Ala His Lys Asn Gly Ser Trp Gly Thr
            1605                1610                1615

Pro Val Ile Pro Met Glu Arg Pro Ala Gly Leu Asn Asp Ile Gly Met
        1620                1625                1630

Val Ala Trp Ile Leu Asp Met Ser Thr Pro Glu Tyr Pro Asn Gly Arg
    1635                1640                1645

Gln Ile Val Val Ile Ala Asn Asp Ile Thr Phe Arg Ala Gly Ser Phe
```

```
              1650                1655                1660

Gly Pro Arg Glu Asp Ala Phe Phe Glu Thr Val Thr Asn Leu Ala Cys
1665                1670                1675                1680

Glu Arg Arg Leu Pro Leu Ile Tyr Leu Ala Ala Asn Ser Gly Ala Arg
                1685                1690                1695

Ile Gly Ile Ala Asp Glu Val Lys Ser Cys Phe Arg Val Gly Trp Ser
                1700                1705                1710

Asp Asp Gly Ser Pro Glu Arg Gly Phe Gln Tyr Ile Tyr Leu Thr Glu
                1715                1720                1725

Glu Asp His Ala Arg Ile Ser Ala Ser Val Ile Ala His Lys Met Gln
                1730                1735                1740

Leu Asp Asn Gly Glu Ile Arg Trp Val Ile Asp Ser Val Val Gly Lys
1745                1750                1755                1760

Glu Asp Gly Leu Gly Val Glu Asn Ile His Gly Ser Ala Ala Ile Ala
                1765                1770                1775

Ser Ala Tyr Ser Arg Ala Tyr Glu Glu Thr Phe Thr Leu Thr Phe Val
                1780                1785                1790

Thr Gly Arg Thr Val Gly Ile Gly Ala Tyr Leu Ala Arg Leu Gly Ile
                1795                1800                1805

Arg Cys Ile Gln Arg Thr Asp Gln Pro Ile Ile Leu Thr Gly Phe Ser
                1810                1815                1820

Ala Leu Asn Lys Leu Leu Gly Arg Glu Val Tyr Ser Ser His Met Gln
1825                1830                1835                1840

Leu Gly Gly Pro Lys Ile Met Ala Thr Asn Gly Val Val His Leu Thr
                1845                1850                1855

Val Ser Asp Asp Leu Glu Gly Val Ser Asn Ile Leu Arg Trp Leu Ser
                1860                1865                1870

Tyr Val Pro Ala Asn Ile Gly Gly Pro Leu Pro Ile Thr Lys Ser Leu
                1875                1880                1885

Asp Pro Pro Asp Arg Pro Val Ala Tyr Ile Pro Glu Asn Thr Cys Asp
                1890                1895                1900

Pro Arg Ala Ala Ile Ser Gly Ile Asp Asp Ser Gln Gly Lys Trp Leu
1905                1910                1915                1920

Gly Gly Met Phe Asp Lys Asp Ser Phe Val Glu Thr Phe Glu Gly Trp
                1925                1930                1935

Ala Lys Ser Val Val Thr Gly Arg Ala Lys Leu Gly Gly Ile Pro Val
                1940                1945                1950

Gly Val Ile Ala Val Glu Thr Gln Thr Met Met Gln Leu Ile Pro Ala
                1955                1960                1965

Asp Pro Gly Gln Leu Asp Ser His Glu Arg Ser Val Pro Arg Ala Gly
                1970                1975                1980

Gln Val Trp Phe Pro Asp Ser Ala Thr Lys Thr Ala Gln Ala Met Leu
1985                1990                1995                2000

Asp Phe Asn Arg Glu Gly Leu Pro Leu Phe Ile Leu Ala Asn Trp Arg
                2005                2010                2015

Gly Phe Ser Gly Gly Gln Arg Asp Leu Phe Glu Gly Ile Leu Gln Ala
                2020                2025                2030

Gly Ser Thr Ile Val Glu Asn Leu Arg Ala Tyr Asn Gln Pro Ala Phe
                2035                2040                2045

Val Tyr Ile Pro Lys Ala Ala Glu Leu Arg Gly Gly Ala Trp Val Val
                2050                2055                2060

Ile Asp Ser Lys Ile Asn Pro Asp Arg Ile Glu Phe Tyr Ala Glu Arg
2065                2070                2075                2080
```

Thr Ala Lys Gly Asn Val Leu Glu Pro Gln Gly Leu Ile Glu Ile Lys
            2085                2090                2095

Phe Arg Ser Glu Glu Leu Gln Glu Cys Met Gly Arg Leu Asp Pro Glu
        2100                2105                2110

Leu Ile Asn Leu Lys Ala Lys Leu Gln Gly Val Lys His Glu Asn Gly
        2115                2120                2125

Ser Leu Pro Glu Ser Glu Ser Leu Gln Lys Ser Ile Glu Ala Arg Lys
        2130                2135                2140

Lys Gln Leu Leu Pro Leu Tyr Thr Gln Ile Ala Val Arg Phe Ala Glu
2145            2150                2155                2160

Leu His Asp Thr Ser Leu Arg Met Ala Ala Lys Gly Val Ile Lys Lys
                2165                2170                2175

Val Val Asp Trp Glu Asp Ser Arg Ser Phe Phe Tyr Lys Arg Leu Arg
            2180                2185                2190

Arg Arg Ile Ser Glu Asp Val Leu Ala Lys Glu Ile Arg Gly Val Ser
        2195                2200                2205

Gly Lys Gln Phe Ser His Gln Ser Ala Ile Glu Leu Ile Gln Lys Trp
        2210                2215                2220

Tyr Leu Ala Ser Lys Gly Ala Glu Thr Gly Ser Thr Glu Trp Asp Asp
2225            2230                2235                2240

Asp Asp Ala Phe Val Ala Trp Arg Glu Asn Pro Glu Asn Tyr Gln Glu
            2245                2250                2255

Tyr Ile Lys Glu Pro Arg Ala Gln Arg Val Ser Gln Leu Leu Ser Asp
            2260                2265                2270

Val Ala Asp Ser Ser Pro Asp Leu Glu Ala Leu Pro Gln Gly Leu Ser
            2275                2280                2285

Met Leu Leu Glu Lys Met Asp Pro Ala Lys Arg Glu Ile Val Glu Asp
            2290                2295                2300

Phe Glu Ile Asn Leu Val Lys
2305            2310

<210> SEQ ID NO 29
<211> LENGTH: 6936
<212> TYPE: DNA
<213> ORGANISM: Triticum aestivum

<400> SEQUENCE: 29
atgggatcca cacatttgcc cattgtcggc cttaatgcct cgacaacacc atcgctatcc        60
actattcgcc cggtaaattc agccggtgct gcattccaac catctgcccc ttctagaacc       120
tccaagaaga aaagtcgtcg tgttcagtca ttaagggatg gaggcgatgg aggcgtgtca       180
gaccctaacc agtctattcg ccaaggtctt gccggcatca ttgacctccc aaaggagggc       240
acatcagctc cggaagtgga tatttcacat gggtccgaag aacccagggg ctcctaccaa       300
atgaatggga tactgaatga agcacataat ggaggcatg cttcgctgtc taaggttgtc        360
gaattttgta tggcattggg cggcaaaaca ccaattcaca gtgtattagt tgcgaacaat       420
ggaagggcag cagctaagtt catgcggagt gtccgaacat gggctaatga acatttggg        480 tcagagaagg caattcagtt gatagctatg gctactccag aagacatgag gataaatgca       540
gagcacatta gaattgctga tcaatttgtt gaagtacccg gtgaacaaa caataacaac        600 tatgcaaatg tccaactcat agtggagata gcagtgagaa ccggtgtttc tgctgtttgg       660
cctggttggg gccatgcatc tgagaatcct gaacttccag atgcactaaa tgcaaacgga       720 attgttttc ttgggccacc atcatcatca atgaacgcac taggtgacaa ggttggttca        780

```
gctctcattg ctcaagcagc aggggttccg actcttcctt ggggtggatc acaggtggaa      840
attccattag aagtttgttt ggactcgata cctgcggaga tgtataggaa agcttgtgtt      900
agtactacgg aggaagcact tgcgagttgt cagatgattg ggtatccagc catgattaaa      960
gcatcatggg gtggtggtgg taaagggatc cgaaaggtta ataacgacga tgatgtcaga     1020
gcactgttta agcaagtgca aggtgaagtt cctggctccc caatatttat catgagactt     1080
gcatctcaga gtcgacatct tgaagttcag ttgctttgtg atcaatatgg caatgtagct     1140
gcgcttcaca gtcgtgactg cagtgtgcaa cggcgacacc aaaagattat tgaggaagga     1200
ccagttactg ttgctcctcg cgagacagtg aaagagctag agcaagcagc aaggaggctt     1260
gctaaggctg tgggttatgt tggtgctgct actgttgaat atctctacag catggagact     1320
ggtgaatact attttctgga acttaatcca cggttgcagg ttgagcatcc agtcaccgag     1380
tggatagctg aagtaaactt gcctgcagct caagttgcag ttggaatggg tatacccctt     1440
tggcaggttc cagagatcag acgtttctat ggaatggaca atggaggagg ctatgacatt     1500
tggagggaaa cagcagctct tgctactcca tttaacttcg atgaagtgga ttctcaatgg     1560
ccaaagggtc attgtgtagc agttaggata accagtgagg atccagatga cggattcaag     1620
cctaccggtg gaaaagtaaa ggagatcagt tttaaaagca agccaaatgt tgggcctat     1680 ttctctgtta gtccggtgg aggcattcat gaatttgctg attctcagtt tggacatgtt     1740
tttgcatatg gagtgtctag agcagcagca ataaccaaca tgtctcttgc gctaaaagag     1800
attcaaattc gtggagaaat tcattcaaat gttgattaca cagttgatct cttgaatgcc     1860
tcagacttca agaaaacag gattcatact ggctggctgg ataacagaat agcaatgcga     1920
gtccaagctg agagacctcc gtggtatatt tcagtggttg gaggagctct atataaaaca     1980
ataacgagca acacagacac tgtttctgaa tatgttagct atctcgtcaa gggtcagatt     2040
ccaccgaagc atatatccct tgtccattca actgtttctt tgaatataga ggaaagcaaa     2100
tatacaattg aaactataag gagcggacag ggtagctaca gattgcgaat gaatggatca     2160
gttattgaag caaatgtcca aacattatgt gatggtggac tttttaatgca gttggatgga     2220 aacagccatg taatttatgc tgaagaagag gccggtggta cacggcttct aattgatgga     2280
aagacatact tgttacagaa tgatcacgat ccttcaaggt tattagctga gacaccctgc     2340
aaacttcttc gtttcttggt tgccgatggt gctcatgttg aagctgatgt accatatgcg     2400
gaagttgagg ttatgaagat gtgcatgccc ctcttgtcac ctgctgctgg tgtcattaat     2460
gttttgttgt ctgagggcca gcctatgcag gctggtgatc ttatagcaag acttgatctt     2520
gatgaccctt ctgctgtgaa gagagctgag ccatttaacg gatctttccc agaaatgagc     2580
cttcctattg ctgcttctgg ccaagttcac aaaagatgtg ccacaagctt gaatgctgct     2640
cggatggtcc ttgcaggata tgatcacccg atcaacaaag ttgtacaaga tctggtatcc     2700
tgtctagatg ctcctgagct tccttttccta caatgggaag agcttatgtc tgttttagca     2760
actagacttc caaggcttct taagagcgag ttggagggta aatacagtga atataagtta     2820
aatgttggcc atgggaagag caaggatttc ccttccaaga tgctaagaga gataatcgag     2880
gaaaatcttg cacatggttc tgagaaggaa attgctacaa atgagaggct tgttgagcct     2940
cttatgagcc tactgaagtc atatgagggt ggcagagaaa gccatgcaca ctttattgtg     3000
aagtcccttt tcgaggacta tctctcggtt gaggaactat tcagtgatgg cattcagtct     3060
gatgtgattg aacgcctgcg ccaacaacat agtaaagatc tccagaaggt tgtagacatt     3120
```

```
gtgttgtctc accagggtgt gagaaacaaa actaagctga tactaacact catggagaaa    3180
ctggtctatc caaaccctgc tgtctacaag gatcagttga ctcgcttttc ctccctcaat    3240
cacaaaagat attataagtt ggcccttaaa gctagcgagc ttcttgaaca aaccaagctt    3300
agtgagctcc gcacaagcat tgcaaggagc ctttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattatacca gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat gcgccatacc    3900
ttcctcttgt cggatgaaaa gctttgttat ggggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatataca cacttagaaa tacagagaac    4080
cccaaaatgt tgcacagggt gttttttcga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
gcgattagga caggtcactc tcatatgttt ttgtgcatat tgaaagagcg aaagcttctt    4320
gatcttgttc ccgtttcagg gaacaaagtt gtggatattg ccaagatgaa agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggtta aagatacaga atcacagaaa ctagtatacc actctgctcc atcgtcatct    4620
ggtcctttgc atggcgttgc actgaatact ccatatcagc ctttgagtgt tattgatctg    4680
aaacgttgct ccgctagaaa caacagaact acatactgct atgattttcc gttggcattt    4740
gaaactgcag tgcagaagtc atggtctaac atttctagtg acaataaccg atgttatgtt    4800
aaagcaacgg agctggtgtt tgctcacaag aatgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tacttttaga    4980
gctggatcgt ttggtccaag ggaagatgca tttttttgaaa ctgttaccaa cctagcttgt    5040
gagaggaggc ttcctctcat ctacttggca gcaaactctg gtgctcggat cggcatagca    5100
gatgaagtaa atcttgcttc cgtgttgga tggtctgatg atggcagccc tgaacgtggg    5160
tttcaatata tttatctgac tgaagaagac catgctcgta ttagcgcttc tgttatagcg    5220
cacaagatgc agcttgataa tggtgaaatt aggtgggtta ttgattctgt tgtagggaag    5280
gaggatgggc taggtgtgga aacatacat ggaagtgctg ctattgccag tgcctattct    5340
agggcctatg aggagacatt tacgcttaca tttgtgactg gaaggactgt tggaatagga    5400
gcatatcttg ctcgacttgg catacggtgc attcagcgta ctgaccagcc cattatccta    5460
actgggtttt ctgccttgaa caagcttctt ggccgggaag tgtacagctc ccacatgcag    5520
```

```
ttgggtggcc ccaaaattat ggcgacaaac ggtgttgtcc atctgacagt ttcagatgac    5580
cttgaaggtg tatctaatat attgaggtgg ctcagctatg ttcctgccaa cattggtgga    5640
cctcttccta ttacaaaatc tttggaccca cctgacagac ccgttgctta catccctgag    5700
aatacatgcg atcctcgtgc tgccatcagt ggcattgatg atagccaagg gaaatggttg    5760
gggggcatgt tcgacaaaga cagttttgtg agacatttg aaggatgggc gaagtcagtt    5820
gttactggca gagcgaaact cggagggatt ccggtgggtg ttatagctgt ggagacacag    5880
actatgatgc agctcatccc tgctgatcca ggccagcttg attcccatga gcgatctgtt    5940
cctcgtgctg ggcaagtctg gtttccagat tcagctacta agacagcgca ggcaatgctg    6000
gacttcaacc gtgaaggatt acctctgttc atccttgcta actggagagg cttctctggt    6060
ggacaaagag atcttttga aggaatcctt caggctgggt caacaattgt tgagaacctt    6120
agggcataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct cgaacctcaa gggttgatcg agatcaagtt caggtcagag    6300
gaactccaag agtgcatggg taggcttgat ccagaattga taaatctgaa ggcaaagctc    6360
cagggagtaa agcatgaaaa tggaagtcta cctgagtcag aatcccttca aagagcata    6420 gaagcccgga gaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcgttctt ctacaagaga ttacggagga ggatatccga ggatgttctt    6600
gcgaaggaaa ttagaggtgt aagtggcaag cagttttctc accaatcggc aatcgagctg    6660
atccagaaat ggtacttggc ctctaaggga gctgaaacag gaagcactga atgggatgat    6720
gacgatgctt ttgttgcctg gagggaaaac cctgaaaact accaggagta tatcaaagaa    6780
cccagggctc aaagggtatc tcagttgctc tcagatgttg cagactccag tccagatcta    6840
gaagccttgc cacagggtct ttctatgcta ctagagaaga tggatcctgc aaagagggaa    6900
attgttgaag actttgaaat aaaccttgta aagtaa                             6936

<210> SEQ ID NO 30
<211> LENGTH: 5
<212> TYPE: PRT
<213> ORGANISM: Artificial Sequence
<220> FEATURE:
<223> OTHER INFORMATION: PAP1 enzyme catalytic motif
<220> FEATURE:
<221> NAME/KEY: VARIANT
<222> LOCATION: 2, 4
<223> OTHER INFORMATION: Xaa = Any Amino Acid

<400> SEQUENCE: 30

Asp Xaa Asp Xaa Thr
 1               5

<210> SEQ ID NO 31
<211> LENGTH: 2535
<212> TYPE: DNA
<213> ORGANISM: Synechococcus elongatus PCC 7942

<400> SEQUENCE: 31
atgagtgatt ccaccgccca actcagctac gaccccacca cgagctacct cgagcccagt     60
ggcttggtct gtgaggatga acggacttct gtgactcccg agaccttgaa acgggcttac    120
gaggcccatc tctactacag ccagggcaaa acctcagcga tcgccaccct gcgtgatcac    180
```

```
tacatggcac tggcctacat ggtccgcgat cgcctcctgc aacggtggct agcttcactg    240
tcgacctatc aacaacagca cgtcaaagtg gtctgttacc tgtccgctga gttttttgatg    300 ggtcggcacc tcgaaaactg cctgatcaac ctgcatcttc acgaccgcgt tcagcaagtt    360
ttggatgaac tgggtctcga ttttgagcaa ctgctagaga aagaggaaga acccgggcta    420
ggcaacggtg gcctcggtcg cctcgcagct tgtttcctcg actccatggc taccctcgac    480
attcctgccg tcggctatgg cattcgctat gagttcggta tcttccacca agaactccac    540
aacggctggc agatcgaaat ccccgataac tggctgcgct ttggcaaccc ttgggagcta    600
gagcggcgcg aacaggccgt ggaaattaag ttgggcggcc acacggaggc ctaccacgat    660
gcgcgaggcc gctactgcgt ctcttggatc cccgatcgcg tcattcgcgc catcccctac    720 gacaccccg taccgggcta cgacaccaat aacgtcagca tgttgcggct ctggaaggct    780
gagggcacca cggaactcaa ccttgaggct ttcaactcag gcaactacga cgatgcggtt    840
gccgacaaaa tgtcgtcgga aacgatctcg aaggtgctct atcccaacga caacaccccc    900
caagggcggg aactgcggct ggagcagcag tatttcttcg tctcggcttc gctccaagac    960
atcatccgtc gccacttgat gaaccacggt catcttgagc ggctgcatga ggcgatcgca    1020
gtccagctta acgacaccca tcccagcgtg gcggtgccgg agttgatgcg cctcctgatc    1080
gatgagcatc acctgacttg ggacaatgct tggacgatta cacagcgcac cttcgcctac    1140
accaaccaca cgctgctacc tgaagccttg aacgctggc ccgtgggcat gttccagcgc    1200
actttaccgc gcttgatgga gattatctac gaaatcaact ggcgcttctt ggccaatgtg    1260
cgggcctggt atcccggtga cgacacgaga gctcgccgcc tctccctgat tgaggaagga    1320
gctgagcccc aggtgcgcat ggctcacctc gcctgcgtgg gcagtcatgc catcaacggt    1380
gtggcagccc tgcatacgca actgctcaag caagaaaccc tgcgagattt ctacgagctt    1440
tggcccgaga aattcttcaa catgaccaac ggtgtgacgc cccgccgctg gctgctgcaa    1500
agtaatcctc gcctagccaa cctgatcagc gatcgcattg gcaatgactg gattcatgat    1560
ctcaggcaac tgcgacggct ggaagacagc gtgaacgatc gcgagttttt acagcgctgg    1620
gcagaggtca agcaccaaaa taaggtcgat ctgagccgct acatctacca gcagactcgc    1680
atagaagtcg atccgcactc tctctttgat gtgcaagtca acggattca cgaatacaaa    1740 cgccagctcc tcgctgtcat gcatatcgtg acgctctaca actggctgaa gcacaatccc    1800
cagctcaacc tggtgccgcg cacttttatc tttgcgggca agcggccc gggttactac    1860 cgtgccaagc aaatcgtcaa actgatcaat gcggtcggga gcatcatcaa ccatgatccc    1920
gatgtccaag ggcgactgaa ggtcgtcttc ctacctaact tcaacgtttc cttggggcag    1980
cgcatttatc cagctgccga tttgtcggag caaatctcaa ctgcagggaa agaagcgtcc    2040
ggcaccggca acatgaagtt caccatgaat ggcgcgctga caatcggaac ctacgatggt    2100
gccaacatcg agatccgcga ggaagtcggc cccgaaaact tcttcctgtt tggcctgcga    2160
gccgaagata tcgcccgacg ccaaagtcgg ggctatcgac ctgtggagtt ctggagcagc    2220
aatgcggaac tgcgggcagt cctcgatcgc tttagcagtg gtcacttcac accggatcag    2280
cccaacctct tccaagactt ggtcagcgat ctgctgcagc gggatgagta catgttgatg    2340
gcggactatc agtcctacat cgactgccag cgcgaagctg ctgctgccta ccgcgattcc    2400
gatcgctggt ggcggatgtc gctactcaac accgcgagat cgggcaagtt ctcctccgat    2460
cgcacgatcg ctgactacag cgaacagatc tgggaggtca aaccagtccc cgtcagccta    2520
```
agcactagct tttag                                                                  2535

<210> SEQ ID NO 32
<211> LENGTH: 844
<212> TYPE: PRT
<213> ORGANISM: Synechococcus elongatus PCC 7942

<400> SEQUENCE: 32

Met Ser Asp Ser Thr Ala Gln Leu Ser Tyr Asp Pro Thr Thr Ser Tyr
1               5                   10                  15

Leu Glu Pro Ser Gly Leu Val Cys Glu Asp Glu Arg Thr Ser Val Thr
            20                  25                  30

Pro Glu Thr Leu Lys Arg Ala Tyr Glu Ala His Leu Tyr Tyr Ser Gln
        35                  40                  45

Gly Lys Thr Ser Ala Ile Ala Thr Leu Arg Asp His Tyr Met Ala Leu
50                  55                  60

Ala Tyr Met Val Arg Asp Arg Leu Leu Gln Arg Trp Leu Ala Ser Leu
65                  70                  75                  80

Ser Thr Tyr Gln Gln Gln His Val Lys Val Val Cys Tyr Leu Ser Ala
                85                  90                  95

Glu Phe Leu Met Gly Arg His Leu Glu Asn Cys Leu Ile Asn Leu His
            100                 105                 110

Leu His Asp Arg Val Gln Gln Val Leu Asp Glu Leu Gly Leu Asp Phe
        115                 120                 125

Glu Gln Leu Leu Glu Lys Glu Glu Pro Gly Leu Gly Asn Gly Gly
130                 135                 140

Leu Gly Arg Leu Ala Ala Cys Phe Leu Asp Ser Met Ala Thr Leu Asp
145                 150                 155                 160

Ile Pro Ala Val Gly Tyr Gly Ile Arg Tyr Glu Phe Gly Ile Phe His
                165                 170                 175

Gln Glu Leu His Asn Gly Trp Gln Ile Glu Ile Pro Asp Asn Trp Leu
            180                 185                 190

Arg Phe Gly Asn Pro Trp Glu Leu Glu Arg Arg Glu Gln Ala Val Glu
        195                 200                 205

Ile Lys Leu Gly Gly His Thr Glu Ala Tyr His Asp Ala Arg Gly Arg
210                 215                 220

Tyr Cys Val Ser Trp Ile Pro Asp Arg Val Ile Arg Ala Ile Pro Tyr
225                 230                 235                 240

Asp Thr Pro Val Pro Gly Tyr Asp Thr Asn Asn Val Ser Met Leu Arg
                245                 250                 255

Leu Trp Lys Ala Glu Gly Thr Thr Glu Leu Asn Leu Glu Ala Phe Asn
            260                 265                 270

Ser Gly Asn Tyr Asp Asp Ala Val Ala Asp Lys Met Ser Ser Glu Thr
        275                 280                 285

Ile Ser Lys Val Leu Tyr Pro Asn Asp Asn Thr Pro Gln Gly Arg Glu
290                 295                 300

Leu Arg Leu Glu Gln Gln Tyr Phe Phe Val Ser Ala Ser Leu Gln Asp
305                 310                 315                 320

Ile Ile Arg Arg His Leu Met Asn His Gly His Leu Glu Arg Leu His
                325                 330                 335

Glu Ala Ile Ala Val Gln Leu Asn Asp Thr His Pro Ser Val Ala Val
            340                 345                 350

Pro Glu Leu Met Arg Leu Leu Ile Asp Glu His His Leu Thr Trp Asp
        355                 360                 365

-continued

```
Asn Ala Trp Thr Ile Thr Gln Arg Thr Phe Ala Tyr Thr Asn His Thr
370                 375                 380

Leu Leu Pro Glu Ala Leu Glu Arg Trp Pro Val Gly Met Phe Gln Arg
385                 390                 395                 400

Thr Leu Pro Arg Leu Met Glu Ile Ile Tyr Glu Ile Asn Trp Arg Phe
            405                 410                 415

Leu Ala Asn Val Arg Ala Trp Tyr Pro Gly Asp Asp Thr Arg Ala Arg
                420                 425                 430

Arg Leu Ser Leu Ile Glu Glu Gly Ala Glu Pro Gln Val Arg Met Ala
                435                 440                 445

His Leu Ala Cys Val Gly Ser His Ala Ile Asn Gly Val Ala Ala Leu
450                 455                 460

His Thr Gln Leu Leu Lys Gln Glu Thr Leu Arg Asp Phe Tyr Glu Leu
465                 470                 475                 480

Trp Pro Glu Lys Phe Phe Asn Met Thr Asn Gly Val Thr Pro Arg Arg
            485                 490                 495

Trp Leu Leu Gln Ser Asn Pro Arg Leu Ala Asn Leu Ile Ser Asp Arg
                500                 505                 510

Ile Gly Asn Asp Trp Ile His Asp Leu Arg Gln Leu Arg Arg Leu Glu
                515                 520                 525

Asp Ser Val Asn Asp Arg Glu Phe Leu Gln Arg Trp Ala Glu Val Lys
530                 535                 540

His Gln Asn Lys Val Asp Leu Ser Arg Tyr Ile Tyr Gln Gln Thr Arg
545                 550                 555                 560

Ile Glu Val Asp Pro His Ser Leu Phe Asp Val Gln Val Lys Arg Ile
            565                 570                 575

His Glu Tyr Lys Arg Gln Leu Leu Ala Val Met His Ile Val Thr Leu
            580                 585                 590

Tyr Asn Trp Leu Lys His Asn Pro Gln Leu Asn Leu Val Pro Arg Thr
            595                 600                 605

Phe Ile Phe Ala Gly Lys Ala Pro Gly Tyr Tyr Arg Ala Lys Gln
610                 615                 620

Ile Val Lys Leu Ile Asn Ala Val Gly Ser Ile Ile Asn His Asp Pro
625                 630                 635                 640

Asp Val Gln Gly Arg Leu Lys Val Val Phe Leu Pro Asn Phe Asn Val
                645                 650                 655

Ser Leu Gly Gln Arg Ile Tyr Pro Ala Ala Asp Leu Ser Glu Gln Ile
            660                 665                 670

Ser Thr Ala Gly Lys Glu Ala Ser Gly Thr Gly Asn Met Lys Phe Thr
            675                 680                 685

Met Asn Gly Ala Leu Thr Ile Gly Thr Tyr Asp Gly Ala Asn Ile Glu
690                 695                 700

Ile Arg Glu Glu Val Gly Pro Glu Asn Phe Phe Leu Phe Gly Leu Arg
705                 710                 715                 720

Ala Glu Asp Ile Ala Arg Arg Gln Ser Arg Gly Tyr Arg Pro Val Glu
                725                 730                 735

Phe Trp Ser Ser Asn Ala Glu Leu Arg Ala Val Leu Asp Arg Phe Ser
            740                 745                 750

Ser Gly His Phe Thr Pro Asp Gln Pro Asn Leu Phe Gln Asp Leu Val
                755                 760                 765

Ser Asp Leu Leu Gln Arg Asp Glu Tyr Met Leu Met Ala Asp Tyr Gln
770                 775                 780

Ser Tyr Ile Asp Cys Gln Arg Glu Ala Ala Ala Ala Tyr Arg Asp Ser
```

```
                        785                 790                 795                 800
                Asp Arg Trp Trp Arg Met Ser Leu Leu Asn Thr Ala Arg Ser Gly Lys
                                    805                 810                 815

Phe Ser Ser Asp Arg Thr Ile Ala Asp Tyr Ser Glu Gln Ile Trp Glu
                                820                 825                 830

Val Lys Pro Val Pro Val Ser Leu Ser Thr Ser Phe
                                835                 840

<210> SEQ ID NO 33
<211> LENGTH: 2085
<212> TYPE: DNA
<213> ORGANISM: Synechococcus elongatus PCC 7942

<400> SEQUENCE: 33
atgactgttt catcccgtcg ccctgaatcg accgtggctg ttgacccggg ccaaagctat      60
cccctcgggg caaccgtcta tcccaccggc gtcaacttct cgctctacac caagtacgcg     120
acgggcgttg aattactgct gtttgatgac cctgagggtg cccagcctca acggacagtg     180
cgcctcgatc cgcacctcaa tcgcacctct ttctactggc atgttttat tccgggcatt      240 cgctccggtc aggtttatgc ttaccgcgtc tttggcccct acgcacctga tcgcggcctc     300
tgttttaacc ccaacaaagt gctgctggat ccctacgctc gcggggttgt cggctggcag     360
cactacagtc gcgaagcggc tattaaaccc agtaataact gcgttcaagc cctgcgtagc     420
gtggttgttg accccagcga ctacgactgg gaaggcgatc gccatccacg cacaccctac     480
gctcgcacag taatctatga gctgcatgtt ggcggcttca ccaagcatcc caattccggc     540 gtcgccctg aaaaacgtgg cacctacgct ggtctaatcg aaaaaattcc ctacctgcaa      600
tccctcggcg tcacggccgt tgagttgctg ccggtgcacc agttcgatcg ccaagatgcc     660
cccttaggac gcgagaacta ctggggctac agcaccatgg cttttttgc gccccacgca     720 gcctacagct ctcgccatga tccacttggt ccagttgatg agttccgcga cctcgtcaag     780
gcgctccacc aagcagggat tgaggtgatt ctcgacgtgg tgttcaacca cactgctgaa     840
gggaatgaag acgtccaac gctgtctttc aaaggtctag cgaattcaac ctactatctg      900
ctggatgaac aggcgggcta tcgcaactac accggctgcg gcaacaccgt caaagctaac     960
aattcgatcg tgcgatcgct gattctcgat tgcctgcgtt attgggtctc ggaaatgcac    1020
gtcgatggct tccgctttga ccttgcgtcg gtgctgagtc gtgatgccaa tggcaacccc    1080
ctatcggatc cgcccttgct ttgggcgatt gattccgatc cggttttggc cggtacgaag    1140
ctcattgctg aagcttggga cgcagccggc ttatatcagg ttggtacctt tattggcgat    1200
cgctttggga cttggaacgg tcccttccgg gacgatattc ggcgttttg gcgtggagat    1260 cagggctgta cttacgccct cagtcaacgc tgctgggta gccccgatgt ctacagcaca     1320
gaccaatggt atgccggacg caccattaac ttcatcacct gccatgacgg ctttacgctg    1380
cgagatctag tcagctatag ccagaagcac aactttgcca atggagagaa caatcggac     1440 gggaccaatg acaactacag ctggaactac ggcattgaag gcgagaccga tgaccccacg    1500
attctgagct acgggaacg gcagcagcgc aatttgctcg ccacgttatt cctcgcccag    1560
ggcacaccga tgctgacgat gggcgatgag gtcaaacgca gtcagcaggg taacaataac    1620
gcctactgcc aagacaatga gatcagctgg tttgattggt cgctgtgcga tcgccatgcc    1680
gatttcttgg tgttcagtcg ccgcctgatt gaactttccc agtcgctggt gatgttccaa    1740
cagaacgaac tgctgcagaa cgaaccccat ccgcgtcgtc cctatgccat ctggcatggc    1800
```

-continued

```
gtcaaactca aacaacccga ttgggcgctg tggtcccaca gtctggccgt cagtctctgc    1860
catcctcgcc agcaggaatg gctttaccta gcctttaatg cttactggga agacctgcgc    1920
ttccagttgc cgaggcctcc tcgcggccgc gtttggtatc gcttgctcga tacttcactg    1980
ccgaatcttg aagcttgtca tctgccggat gaggcaaaac cctgcctacg gcgcgattac    2040
atcgtcccag cgcgatcgct cttactgttg atggctcgtg cttaa                    2085
```

<210> SEQ ID NO 34
<211> LENGTH: 694
<212> TYPE: PRT
<213> ORGANISM: Synechococcus elongatus PCC 7942

<400> SEQUENCE: 34

```
Met Thr Val Ser Ser Arg Arg Pro Glu Ser Thr Val Ala Val Asp Pro
  1               5                  10                  15

Gly Gln Ser Tyr Pro Leu Gly Ala Thr Val Tyr Pro Thr Gly Val Asn
                 20                  25                  30

Phe Ser Leu Tyr Thr Lys Tyr Ala Thr Gly Val Glu Leu Leu Leu Phe
             35                  40                  45

Asp Asp Pro Glu Gly Ala Gln Pro Gln Arg Thr Val Arg Leu Asp Pro
 50                  55                  60

His Leu Asn Arg Thr Ser Phe Tyr Trp His Val Phe Ile Pro Gly Ile
 65                  70                  75                  80

Arg Ser Gly Gln Val Tyr Ala Tyr Arg Val Phe Gly Pro Tyr Ala Pro
                 85                  90                  95

Asp Arg Gly Leu Cys Phe Asn Pro Asn Lys Val Leu Leu Asp Pro Tyr
            100                 105                 110

Ala Arg Gly Val Val Gly Trp Gln His Tyr Ser Arg Glu Ala Ala Ile
            115                 120                 125

Lys Pro Ser Asn Asn Cys Val Gln Ala Leu Arg Ser Val Val Val Asp
130                 135                 140

Pro Ser Asp Tyr Asp Trp Glu Gly Asp Arg His Pro Arg Thr Pro Tyr
145                 150                 155                 160

Ala Arg Thr Val Ile Tyr Glu Leu His Val Gly Gly Phe Thr Lys His
                165                 170                 175

Pro Asn Ser Gly Val Ala Pro Glu Lys Arg Gly Thr Tyr Ala Gly Leu
            180                 185                 190

Ile Glu Lys Ile Pro Tyr Leu Gln Ser Leu Gly Val Thr Ala Val Glu
        195                 200                 205

Leu Leu Pro Val His Gln Phe Asp Arg Gln Asp Ala Pro Leu Gly Arg
    210                 215                 220

Glu Asn Tyr Trp Gly Tyr Ser Thr Met Ala Phe Phe Ala Pro His Ala
225                 230                 235                 240

Ala Tyr Ser Ser Arg His Asp Pro Leu Gly Pro Val Asp Glu Phe Arg
                245                 250                 255

Asp Leu Val Lys Ala Leu His Gln Ala Gly Ile Glu Val Ile Leu Asp
            260                 265                 270

Val Val Phe Asn His Thr Ala Glu Gly Asn Glu Asp Gly Pro Thr Leu
        275                 280                 285

Ser Phe Lys Gly Leu Ala Asn Ser Thr Tyr Tyr Leu Leu Asp Glu Gln
    290                 295                 300

Ala Gly Tyr Arg Asn Tyr Thr Gly Cys Gly Asn Thr Val Lys Ala Asn
305                 310                 315                 320

Asn Ser Ile Val Arg Ser Leu Ile Leu Asp Cys Leu Arg Tyr Trp Val
```

```
                  325                 330                 335
Ser Glu Met His Val Asp Gly Phe Arg Phe Asp Leu Ala Ser Val Leu
            340                 345                 350
Ser Arg Asp Ala Asn Gly Asn Pro Leu Ser Asp Pro Leu Leu Trp
            355                 360                 365
Ala Ile Asp Ser Asp Pro Val Leu Ala Gly Thr Lys Leu Ile Ala Glu
    370                 375                 380
Ala Trp Asp Ala Ala Gly Leu Tyr Gln Val Gly Thr Phe Ile Gly Asp
385                 390                 395                 400
Arg Phe Gly Thr Trp Asn Gly Pro Phe Arg Asp Asp Ile Arg Arg Phe
                405                 410                 415
Trp Arg Gly Asp Gln Gly Cys Thr Tyr Ala Leu Ser Gln Arg Leu Leu
            420                 425                 430
Gly Ser Pro Asp Val Tyr Ser Thr Asp Gln Trp Tyr Ala Gly Arg Thr
            435                 440                 445
Ile Asn Phe Ile Thr Cys His Asp Gly Phe Thr Leu Arg Asp Leu Val
        450                 455                 460
Ser Tyr Ser Gln Lys His Asn Phe Ala Asn Gly Glu Asn Asn Arg Asp
465                 470                 475                 480
Gly Thr Asn Asp Asn Tyr Ser Trp Asn Tyr Gly Ile Glu Gly Glu Thr
                485                 490                 495
Asp Asp Pro Thr Ile Leu Ser Arg Glu Arg Gln Arg Asn Leu
            500                 505                 510
Leu Ala Thr Leu Phe Leu Ala Gln Gly Thr Pro Met Leu Thr Met Gly
        515                 520                 525
Asp Glu Val Lys Arg Ser Gln Gln Gly Asn Asn Asn Ala Tyr Cys Gln
    530                 535                 540
Asp Asn Glu Ile Ser Trp Phe Asp Trp Ser Leu Cys Asp Arg His Ala
545                 550                 555                 560
Asp Phe Leu Val Phe Ser Arg Arg Leu Ile Glu Leu Ser Gln Ser Leu
                565                 570                 575
Val Met Phe Gln Gln Asn Glu Leu Leu Gln Asn Glu Pro His Pro Arg
            580                 585                 590
Arg Pro Tyr Ala Ile Trp His Gly Val Lys Leu Lys Gln Pro Asp Trp
            595                 600                 605
Ala Leu Trp Ser His Ser Leu Ala Val Ser Leu Cys His Pro Arg Gln
        610                 615                 620
Gln Glu Trp Leu Tyr Leu Ala Phe Asn Ala Tyr Trp Glu Asp Leu Arg
625                 630                 635                 640
Phe Gln Leu Pro Arg Pro Arg Gly Arg Val Trp Tyr Arg Leu Leu
                645                 650                 655
Asp Thr Ser Leu Pro Asn Leu Glu Ala Cys His Leu Pro Asp Glu Ala
            660                 665                 670
Lys Pro Cys Leu Arg Arg Asp Tyr Ile Val Pro Ala Arg Ser Leu Leu
            675                 680                 685
Leu Leu Met Ala Arg Ala
        690

<210> SEQ ID NO 35
<211> LENGTH: 1500
<212> TYPE: DNA
<213> ORGANISM: Synechococcus elongatus PCC 7942

<400> SEQUENCE: 35
```

```
gtgtttacac gagccgccgg catttttgtta catcccactt cgttgccggg gccattcggc    60
agcggcgacc ttggtccggc ctcgcggcag tttcttgact ggttggcaac ggcgggacaa   120
caactgtggc aagtgttgcc ccttgggccg acaggctatg gctattcgcc ttacctctgc   180
tattccgcct tggctggcaa tcccgctctg atcagcctg aactcttggc agaagatggc    240
tggctccaag aatcggactg gcagactgt cctgcttttc gagcgatcg cgtcgatttt     300
gccagcgtct tgccctatcg cgatcaactg ctgcgccgtg cctacagcca attcctgcaa   360
agagcggctt ccagcgatcg ccaactcttt caagctttct gtgaacagga agcccattgg   420
ctggatgact acgccctgtt catggcgatt aagctggcta gccaaggtca gccttggaca   480
gaatggccgg aagcgctgcg tcagcggcaa cctcaagcct tggctaaagc ccgcgatcgc   540
tggggcggcg aaattggctt ccagcagttt ctgcagtggc aatttcgcga gcagtggttg   600
gccctgcggg aagaagccca agcccgccat atttcgctga ttggcgatat tccgatctac   660
gtcgctcatg acagtgcgga cgtttgggcc aatcctcagt tctttgccct cgatcctgaa   720
acgggcgcag ttgatcagca ggccggtgtg ccgcctgact atttctccga aaccggccaa   780
ctctggggca atcccgtcta caactgggct gcgctgcagg cggatggcta tcgctggtgg   840
ttgcaacggc tgcaacagct cctcagctta gtggactaca ttcgcatcga ccacttccgc   900
ggtttagagg cgttttggtc ggttcccgct ggtgaagaaa cggcgatcga cggagagtgg   960
gtcaaagccc caggcgctga tctgctgagc acgattcgcc aaaaactggg agcgctaccg  1020
attctggcag aggatctcgg tgtgattacg ccggaggtgg aagcgctgcg cgatcgcttt  1080
gagctgccgg gcatgaagat tctgcagttc gcctttgact ctggggccgg caatgcctat  1140
ctaccgcaca actactgggg tcgtcgctgg gtggcttaca ccggcaccca cgacaatgac  1200
acgaccgtcg gctggttcct gtcccgcaat gacagcgatc gccaaacggt gctggattat  1260
ctgggcgcag agtcgggctg ggaaattgag tggaagctga tccgcttggc ttggagctcg  1320
acggcagatt gggcgatcgc accgctccaa gatgtcttcg gctggatag cagcgcccgc   1380
atgaatcgac cggggcaagc caccggcaac tgggactggc gcttcagtgc cgactggctg  1440
acgggcgatc gtgcccaacg cctgcggcga ctctcgcagc tctatggacg ctgtagatga  1500
```

<210> SEQ ID NO 36
<211> LENGTH: 499
<212> TYPE: PRT
<213> ORGANISM: Synechococcus elongatus PCC 7942

<400> SEQUENCE: 36

Met Phe Thr Arg Ala Ala Gly Ile Leu Leu His Pro Thr Ser Leu Pro
 1               5                  10                  15

Gly Pro Phe Gly Ser Gly Asp Leu Gly Pro Ala Ser Arg Gln Phe Leu
             20                  25                  30

Asp Trp Leu Ala Thr Ala Gly Gln Gln Leu Trp Gln Val Leu Pro Leu
         35                  40                  45

Gly Pro Thr Gly Tyr Gly Tyr Ser Pro Tyr Leu Cys Tyr Ser Ala Leu
     50                  55                  60

Ala Gly Asn Pro Ala Leu Ile Ser Pro Glu Leu Leu Ala Glu Asp Gly
 65                  70                  75                  80

Trp Leu Gln Glu Ser Asp Trp Ala Asp Cys Pro Ala Phe Pro Ser Asp
                 85                  90                  95

Arg Val Asp Phe Ala Ser Val Leu Pro Tyr Arg Asp Gln Leu Leu Arg
            100                 105                 110

```
Arg Ala Tyr Ser Gln Phe Leu Gln Arg Ala Ala Ser Ser Asp Arg Gln
            115                 120                 125

Leu Phe Gln Ala Phe Cys Glu Gln Glu Ala His Trp Leu Asp Asp Tyr
130                 135                 140

Ala Leu Phe Met Ala Ile Lys Leu Ala Ser Gln Gly Gln Pro Trp Thr
145                 150                 155                 160

Glu Trp Pro Glu Ala Leu Arg Gln Arg Pro Gln Ala Leu Ala Lys
            165                 170                 175

Ala Arg Asp Arg Trp Gly Gly Glu Gly Phe Gln Gln Phe Leu Gln
            180                 185                 190

Trp Gln Phe Arg Glu Gln Trp Leu Ala Leu Arg Glu Glu Ala Gln Ala
            195                 200                 205

Arg His Ile Ser Leu Ile Gly Asp Ile Pro Ile Tyr Val Ala His Asp
            210                 215                 220

Ser Ala Asp Val Trp Ala Asn Pro Gln Phe Phe Ala Leu Asp Pro Glu
225                 230                 235                 240

Thr Gly Ala Val Asp Gln Gln Ala Gly Val Pro Pro Asp Tyr Phe Ser
                245                 250                 255

Glu Thr Gly Gln Leu Trp Gly Asn Pro Val Tyr Asn Trp Ala Ala Leu
            260                 265                 270

Gln Ala Asp Gly Tyr Arg Trp Trp Leu Gln Arg Leu Gln Gln Leu Leu
            275                 280                 285

Ser Leu Val Asp Tyr Ile Arg Ile Asp His Phe Arg Gly Leu Glu Ala
            290                 295                 300

Phe Trp Ser Val Pro Ala Gly Glu Glu Thr Ala Ile Asp Gly Glu Trp
305                 310                 315                 320

Val Lys Ala Pro Gly Ala Asp Leu Leu Ser Thr Ile Arg Gln Lys Leu
                325                 330                 335

Gly Ala Leu Pro Ile Leu Ala Glu Asp Leu Gly Val Ile Thr Pro Glu
            340                 345                 350

Val Glu Ala Leu Arg Asp Arg Phe Glu Leu Pro Gly Met Lys Ile Leu
            355                 360                 365

Gln Phe Ala Phe Asp Ser Gly Ala Gly Asn Ala Tyr Leu Pro His Asn
370                 375                 380

Tyr Trp Gly Arg Arg Trp Val Ala Tyr Thr Gly Thr His Asp Asn Asp
385                 390                 395                 400

Thr Thr Val Gly Trp Phe Leu Ser Arg Asn Asp Ser Asp Arg Gln Thr
                405                 410                 415

Val Leu Asp Tyr Leu Gly Ala Glu Ser Gly Trp Glu Ile Glu Trp Lys
            420                 425                 430

Leu Ile Arg Leu Ala Trp Ser Ser Thr Ala Asp Trp Ala Ile Ala Pro
            435                 440                 445

Leu Gln Asp Val Phe Gly Leu Asp Ser Ser Ala Arg Met Asn Arg Pro
450                 455                 460

Gly Gln Ala Thr Gly Asn Trp Asp Trp Arg Phe Ser Ala Asp Trp Leu
465                 470                 475                 480

Thr Gly Asp Arg Ala Gln Arg Leu Arg Arg Leu Ser Gln Leu Tyr Gly
                485                 490                 495

Arg Cys Arg

<210> SEQ ID NO 37
<211> LENGTH: 1632
<212> TYPE: DNA
<213> ORGANISM: Synechococcus elongatus PCC 7942
```

<400> SEQUENCE: 37

```
atgaatatcc acactgtcgc gacgcaagcc tttagcgacc aaaagcccgg tacctccggc        60
ctgcgcaagc aagttcctgt cttccaaaaa cggcactatc tcgaaaactt tgtccagtcg       120
atcttcgata gccttgaggg ttatcagggc agacgttag tgctgggggg tgatggccgc        180
tactacaatc gcacagccat ccaaaccatt ctgaaaatgg cggcggccaa tggttggggc       240
cgcgttttag ttggacaagg cggtattctc tccacgccag cagtctccaa cctaatccgc       300
cagaacggag ccttcggcgg catcatcctc tcggctagcc acaacccagg gggccctgag       360
ggcgatttcg gcatcaagta caacatcagc aacggtggcc ctgcacccga aaaagtcacc       420
gatgccatct atgcctgcag cctcaaaatt gaggcctacc gcattctcga agccggtgac       480
gttgacctcg atcgactcgg tagtcaacaa ctgggcgaga tgaccgttga ggtgatcgac       540
tcggtcgccg actacagccg cttgatgcaa tccctgtttg acttcgatcg cattcgcgat       600
cgcctgaggg gggggctacg gattgcgatc gactcgatgc atgccgtcac cggtccctac       660
gccaccacga tttttgagaa ggagctaggc gcggcggcag cactgttttt aatggcaag        720
ccgctggaag actttggcgg gggtcaccca gacccgaatt tggtctacgc ccacgacttg       780
gttgaactgt tgtttggcga tcgcgcccca gattttggcg cggcctccga tggcgatggc       840
gatcgcaaca tgatcttggg caatcacttt tttgtgaccc ctagcgacag cttggcgatt       900
ctcgcagcca atgccagcct agtgccggcc taccgcaatg gactgtctgg gattgcgcga       960
tccatgccca ccagtgcggc ggccgatcgc gtcgcccaag ccctcaacct gccctgctac      1020
gaaaccccaa cgggttggaa gttttttcggc aatctgctcg atgccgatcg cgtcacccta     1080
tgcggcgaag aaagctttgg cacaggctcc aaccatgtgc gcgagaagga tggcctgtgg      1140
gccgtgctgt tctggctgaa tattctggcg gtgcgcgagc aatccgtggc cgaaattgtc      1200
caagaacact ggcgcaccta cggccgcaac tactactctc gccacgacta cgaaggggtg      1260
gagagcgatc gagccagtac gctggtggac aaactgcgat cgcagctacc cagcctgacc      1320
ggacagaaac tggagcccta caccgttgcc tacgccgacg acttccgcta cgaagatccg      1380
gtcgatggca gcatcagcga acagcagggc attcgtattg cttttgaaga cggctcacgt      1440
atggtcttcc gcttgtctgg tactggtacg gcaggagcca ccctgcgcct ctacctcgag      1500
cgcttcgaag gggacaccac caaacagggt ctcgatcccc aagttgccct ggcagatttg      1560
attgcaatcg ccgatgaagt cgcccagatc acaaccttga cgggcttcga tcaaccgaca      1620
gtgatcacct ga                                                          1632
```

<210> SEQ ID NO 38
<211> LENGTH: 543
<212> TYPE: PRT
<213> ORGANISM: Synechococcus elongatus PCC 7942

<400> SEQUENCE: 38

```
Met Asn Ile His Thr Val Ala Thr Gln Ala Phe Ser Asp Gln Lys Pro
  1               5                  10                  15

Gly Thr Ser Gly Leu Arg Lys Gln Val Pro Val Phe Gln Lys Arg His
             20                  25                  30

Tyr Leu Glu Asn Phe Val Gln Ser Ile Phe Asp Ser Leu Glu Gly Tyr
         35                  40                  45

Gln Gly Gln Thr Leu Val Leu Gly Gly Asp Gly Arg Tyr Tyr Asn Arg
     50                  55                  60
```

Thr Ala Ile Gln Thr Ile Leu Lys Met Ala Ala Asn Gly Trp Gly
65                  70                  75                  80

Arg Val Leu Val Gly Gln Gly Gly Ile Leu Ser Thr Pro Ala Val Ser
                85                  90                  95

Asn Leu Ile Arg Gln Asn Gly Ala Phe Gly Gly Ile Ile Leu Ser Ala
            100                 105                 110

Ser His Asn Pro Gly Gly Pro Glu Gly Asp Phe Gly Ile Lys Tyr Asn
            115                 120                 125

Ile Ser Asn Gly Gly Pro Ala Pro Glu Lys Val Thr Asp Ala Ile Tyr
            130                 135                 140

Ala Cys Ser Leu Lys Ile Glu Ala Tyr Arg Ile Leu Glu Ala Gly Asp
145                 150                 155                 160

Val Asp Leu Asp Arg Leu Gly Ser Gln Gln Leu Gly Glu Met Thr Val
                165                 170                 175

Glu Val Ile Asp Ser Val Ala Asp Tyr Ser Arg Leu Met Gln Ser Leu
            180                 185                 190

Phe Asp Phe Asp Arg Ile Arg Asp Arg Leu Arg Gly Gly Leu Arg Ile
            195                 200                 205

Ala Ile Asp Ser Met His Ala Val Thr Gly Pro Tyr Ala Thr Thr Ile
210                 215                 220

Phe Glu Lys Glu Leu Gly Ala Ala Gly Thr Val Phe Asn Gly Lys
225                 230                 235                 240

Pro Leu Glu Asp Phe Gly Gly His Pro Asp Pro Asn Leu Val Tyr
                245                 250                 255

Ala His Asp Leu Val Glu Leu Leu Phe Gly Asp Arg Ala Pro Asp Phe
            260                 265                 270

Gly Ala Ala Ser Asp Gly Asp Gly Asp Arg Asn Met Ile Leu Gly Asn
            275                 280                 285

His Phe Phe Val Thr Pro Ser Asp Ser Leu Ala Ile Leu Ala Ala Asn
            290                 295                 300

Ala Ser Leu Val Pro Ala Tyr Arg Asn Gly Leu Ser Gly Ile Ala Arg
305                 310                 315                 320

Ser Met Pro Thr Ser Ala Ala Ala Asp Arg Val Ala Gln Ala Leu Asn
                325                 330                 335

Leu Pro Cys Tyr Glu Thr Pro Thr Gly Trp Lys Phe Phe Gly Asn Leu
            340                 345                 350

Leu Asp Ala Asp Arg Val Thr Leu Cys Gly Glu Glu Ser Phe Gly Thr
            355                 360                 365

Gly Ser Asn His Val Arg Glu Lys Asp Gly Leu Trp Ala Val Leu Phe
370                 375                 380

Trp Leu Asn Ile Leu Ala Val Arg Glu Gln Ser Val Ala Glu Ile Val
385                 390                 395                 400

Gln Glu His Trp Arg Thr Tyr Gly Arg Asn Tyr Tyr Ser Arg His Asp
                405                 410                 415

Tyr Glu Gly Val Glu Ser Asp Arg Ala Ser Thr Leu Val Asp Lys Leu
            420                 425                 430

Arg Ser Gln Leu Pro Ser Leu Thr Gly Gln Lys Leu Gly Ala Tyr Thr
            435                 440                 445

Val Ala Tyr Ala Asp Asp Phe Arg Tyr Glu Asp Pro Val Asp Gly Ser
            450                 455                 460

Ile Ser Glu Gln Gln Gly Ile Arg Ile Gly Phe Glu Asp Gly Ser Arg
465                 470                 475                 480

Met Val Phe Arg Leu Ser Gly Thr Gly Thr Ala Gly Ala Thr Leu Arg

```
                        485              490              495
Leu Tyr Leu Glu Arg Phe Glu Gly Asp Thr Thr Lys Gln Gly Leu Asp
            500              505              510

Pro Gln Val Ala Leu Ala Asp Leu Ile Ala Ile Ala Asp Glu Val Ala
            515              520              525

Gln Ile Thr Thr Leu Thr Gly Phe Asp Gln Pro Thr Val Ile Thr
            530              535              540
```

```
<210> SEQ ID NO 39
<211> LENGTH: 1038
<212> TYPE: DNA
<213> ORGANISM: Synechococcus elongatus PCC 7942

<400> SEQUENCE: 39
atgaccttgc tattggccgg ggatatcggc ggaaccaaaa cgaatttaat gttggcgatc    60
gcctctgatt gcgatcgttt agaaccgctc catcaggcca gttttgccag tgcggcctac   120
cctgatttag tgccgatggt gcaggagttt ttggctgccg caccctccgc cgaggtgcga   180
tcgccagttg tggcttgttt tggcattgcc ggccccgttg tccatggaac cgcgaagctg   240
acgaacctgc cttggcagct ctctgaagcg cggctggcga aggaattggg cattgcgcag   300
gtggcgttga tcaatgattt tgctgcgatc gcctacggcc tacccggctt gaccgccgaa   360
gatcaagtcg ttgtgcaagt cggtgaagcc gatccggcgg ctccgatcgc cattctgggg   420
gcaggaactg gcttgggcga aggcttcatc attcccacag cccaaggccg ccaagtgttt   480
ggcagcgaag gttctcacgc tgactttgcg ccgcaaaccg aactggagtc cgagttactg   540
cattttctac gcaatttta  cgcaatcgag catatctcgg tcgagcgagt ggtctccggc   600
caagggattg cagccatcta cgccttcctg cgcgatcgcc atcccgacca agaaaatcca   660
gcccttgggg cgattgcctc ggcttggcaa acgggcggcg accaagcccc tgatctggca   720
gcagccgtat cccaagcagc cttgagcgat cgcgatccgc tggccctaca agccatgcag   780
atatttgtca gtgcttacgg ggcggaagcc ggcaacctcg cgttgaaatt gctctcctac   840
ggcggggtct acgtcgccgg cgggattgcg ggcaaaatcc tgccgctctt gactgatggc   900
acttttctgc aagccttcca agccaaggga cgggtgaagg gctgctgac  gcggatgcct   960
atcacgatcg tcacgaacca cgaagtcggg ctgatcgggg ctggactgcg ggcggctgcg  1020
atcgctactc aaccatga                                                1038

<210> SEQ ID NO 40
<211> LENGTH: 345
<212> TYPE: PRT
<213> ORGANISM: Synechococcus elongatus PCC 7942

<400> SEQUENCE: 40

Met Thr Leu Leu Leu Ala Gly Asp Ile Gly Gly Thr Lys Thr Asn Leu
  1               5                  10                  15

Met Leu Ala Ile Ala Ser Asp Cys Asp Arg Leu Glu Pro Leu His Gln
             20                  25                  30

Ala Ser Phe Ala Ser Ala Ala Tyr Pro Asp Leu Val Pro Met Val Gln
         35                  40                  45

Glu Phe Leu Ala Ala Ala Pro Ser Ala Glu Val Arg Ser Pro Val Val
     50                  55                  60

Ala Cys Phe Gly Ile Ala Gly Pro Val Val His Gly Thr Ala Lys Leu
 65                  70                  75                  80

Thr Asn Leu Pro Trp Gln Leu Ser Glu Ala Arg Leu Ala Lys Glu Leu
```

```
            85                  90                  95
Gly Ile Ala Gln Val Ala Leu Ile Asn Asp Phe Ala Ala Ile Ala Tyr
        100                 105                 110
Gly Leu Pro Gly Leu Thr Ala Glu Asp Gln Val Val Gln Val Gly
        115                 120                 125
Glu Ala Asp Pro Ala Ala Pro Ile Ala Ile Leu Gly Ala Gly Thr Gly
        130                 135                 140
Leu Gly Glu Gly Phe Ile Ile Pro Thr Ala Gln Gly Arg Gln Val Phe
145                 150                 155                 160
Gly Ser Glu Gly Ser His Ala Asp Phe Ala Pro Gln Thr Glu Leu Glu
                165                 170                 175
Ser Glu Leu Leu His Phe Leu Arg Asn Phe Tyr Ala Ile Glu His Ile
                180                 185                 190
Ser Val Glu Arg Val Val Ser Gly Gln Gly Ile Ala Ala Ile Tyr Ala
                195                 200                 205
Phe Leu Arg Asp Arg His Pro Asp Gln Glu Asn Pro Ala Leu Gly Ala
        210                 215                 220
Ile Ala Ser Ala Trp Gln Thr Gly Gly Asp Gln Ala Pro Asp Leu Ala
225                 230                 235                 240
Ala Ala Val Ser Gln Ala Ala Leu Ser Asp Arg Asp Pro Leu Ala Leu
                245                 250                 255
Gln Ala Met Gln Ile Phe Val Ser Ala Tyr Gly Ala Glu Ala Gly Asn
                260                 265                 270
Leu Ala Leu Lys Leu Leu Ser Tyr Gly Gly Val Tyr Val Ala Gly Gly
                275                 280                 285
Ile Ala Gly Lys Ile Leu Pro Leu Leu Thr Asp Gly Thr Phe Leu Gln
        290                 295                 300
Ala Phe Gln Ala Lys Gly Arg Val Lys Gly Leu Leu Thr Arg Met Pro
305                 310                 315                 320
Ile Thr Ile Val Thr Asn His Glu Val Gly Leu Ile Gly Ala Gly Leu
                325                 330                 335
Arg Ala Ala Ala Ile Ala Thr Gln Pro
        340                 345

<210> SEQ ID NO 41
<211> LENGTH: 1587
<212> TYPE: DNA
<213> ORGANISM: Synechococcus elongatus PCC 7942

<400> SEQUENCE: 41
atgaccgccc agcagctctg caacgctac ctcgattggc tctactacga tccctcgctg      60
gagttttacc tcgacatcag ccgcatggga ttcgatgacg ctttcgttac tagcatgcag     120
cccaagttcc agcacgcctt tgcggcgatg cagagctcg aggccggagc gatcgccaac     180 ccgatgaac agcggatggt cggccactac tggctgcgcg atcctgagct ggcacccaca     240
ccggagctgc agacccaaat tcgcgacacg ctggccgcga tccaagactt cgccctcaaa     300
gtacacagtg gcgtgttgcg gccacccacc ggctcccgct tcaccgacat tctctcaatt     360
ggcattggcg gtcggccct agggccgcag tttgtctcag aagccctccg gcctcaagcg     420
gcactgctcc agattcactt cttttgacaac accgatccag ctggcttcga tcgcgtttta     480
gctgatctcg gcgatcgcct tgcttccacc ttagtaatcg ttatttccaa atctggcggc     540
actcccgaaa cccgcaacgg catgctggag gttcagtccg cctttgccca gcgagggatt    600
gcctttgcgc cccaagctgt cgccgtcaca ggggtgggga gccatctcga tcatgtagcg     660
```

```
atcacagaaa gatggctggc ccgtttcccc atggaagact gggtgggcgg ccgcacctct      720
gaactatctg cagtcggtct actctcggca gccctactgg gcatcgacat caccgccatg      780
ctggccgggg cgcggcaaat ggacgccctg acccgccatt ccgatttgcg acaaaatccg      840
gcagcgctct tggctttgag ctggtactgg gccggcaatg ggcaaggcaa aaagacatg       900 gtcatcctgc cctacaagga cagcctgctg ctgtttagcc gctatctgca gcagttgatc      960
atggagtcac tgggcaagga gcgcgatctg ctcggcaagg tagttcacca aggcatcgcc     1020
gtttacggca acaaaggctc gaccgatcaa catgcctacg tccagcaact gcgcgagggc     1080
attcctaact tctttgccac gtttatcgag gtgctcgaag accgacaggg gccgtcgcca     1140
gtcgtggagc ctggcatcac cagtggcgac tatctcagcg ggctgcttca aggcacccgc     1200
gcggcgcttt acgaaaatgg gcgtgagtcg atcacgatta cggtgccgcg cgttgatgca     1260
caacaggtgg gggccttgat cgcgctgtat gaacgggcgg tgggactcta tgccagcttg     1320
gttggcatca atgcctatca ccagccgggg gtggaagccg gcaaaaaggc tgctgccggt     1380
gttctcgaga tccagcgcca gattgtggag ttgctccaac agggacaacc actctcgatc     1440
gcagcgatcg cagacgattt aggtcagagt gagcagattg aaacgatcta caaaatcctg     1500
cgccatctcg aagccaatca acgcggcgtt cagttaaccg gcgatcgcca taatcccctc     1560
agtctgattg cgagttggca acgataa                                         1587
```

<210> SEQ ID NO 42
<211> LENGTH: 528
<212> TYPE: PRT
<213> ORGANISM: Synechococcus elongatus PCC 7942

<400> SEQUENCE: 42

```
Met Thr Ala Gln Gln Leu Trp Gln Arg Tyr Leu Asp Trp Leu Tyr Tyr
  1               5                  10                  15

Asp Pro Ser Leu Glu Phe Tyr Leu Asp Ile Ser Arg Met Gly Phe Asp
                 20                  25                  30

Asp Ala Phe Val Thr Ser Met Gln Pro Lys Phe Gln His Ala Phe Ala
             35                  40                  45

Ala Met Ala Glu Leu Glu Ala Gly Ala Ile Ala Asn Pro Asp Glu Gln
         50                  55                  60

Arg Met Val Gly His Tyr Trp Leu Arg Asp Pro Glu Leu Ala Pro Thr
 65                  70                  75                  80

Pro Glu Leu Gln Thr Gln Ile Arg Asp Thr Leu Ala Ala Ile Gln Asp
                 85                  90                  95

Phe Ala Leu Lys Val His Ser Gly Val Leu Arg Pro Thr Gly Ser
            100                 105                 110

Arg Phe Thr Asp Ile Leu Ser Ile Gly Ile Gly Gly Ser Ala Leu Gly
        115                 120                 125

Pro Gln Phe Val Ser Glu Ala Leu Arg Pro Gln Ala Ala Leu Leu Gln
    130                 135                 140

Ile His Phe Phe Asp Asn Thr Asp Pro Ala Gly Phe Asp Arg Val Leu
145                 150                 155                 160

Ala Asp Leu Gly Asp Arg Leu Ala Ser Thr Leu Val Ile Val Ile Ser
                165                 170                 175

Lys Ser Gly Gly Thr Pro Glu Thr Arg Asn Gly Met Leu Glu Val Gln
            180                 185                 190

Ser Ala Phe Ala Gln Arg Gly Ile Ala Phe Ala Pro Gln Ala Val Ala
        195                 200                 205
```

```
Val Thr Gly Val Gly Ser His Leu Asp His Val Ala Ile Thr Glu Arg
    210                 215                 220
Trp Leu Ala Arg Phe Pro Met Glu Asp Trp Val Gly Gly Arg Thr Ser
225                 230                 235                 240
Glu Leu Ser Ala Val Gly Leu Leu Ser Ala Ala Leu Leu Gly Ile Asp
            245                 250                 255
Ile Thr Ala Met Leu Ala Gly Ala Arg Gln Met Asp Ala Leu Thr Arg
        260                 265                 270
His Ser Asp Leu Arg Gln Asn Pro Ala Ala Leu Leu Ala Leu Ser Trp
    275                 280                 285
Tyr Trp Ala Gly Asn Gly Gln Gly Lys Lys Asp Met Val Ile Leu Pro
290                 295                 300
Tyr Lys Asp Ser Leu Leu Leu Phe Ser Arg Tyr Leu Gln Gln Leu Ile
305                 310                 315                 320
Met Glu Ser Leu Gly Lys Glu Arg Asp Leu Leu Gly Lys Val Val His
            325                 330                 335
Gln Gly Ile Ala Val Tyr Gly Asn Lys Gly Ser Thr Asp Gln His Ala
        340                 345                 350
Tyr Val Gln Gln Leu Arg Glu Gly Ile Pro Asn Phe Phe Ala Thr Phe
    355                 360                 365
Ile Glu Val Leu Glu Asp Arg Gln Gly Pro Ser Pro Val Val Glu Pro
370                 375                 380
Gly Ile Thr Ser Gly Asp Tyr Leu Ser Gly Leu Leu Gln Gly Thr Arg
385                 390                 395                 400
Ala Ala Leu Tyr Glu Asn Gly Arg Glu Ser Ile Thr Ile Thr Val Pro
            405                 410                 415
Arg Val Asp Ala Gln Gln Val Gly Ala Leu Ile Ala Leu Tyr Glu Arg
        420                 425                 430
Ala Val Gly Leu Tyr Ala Ser Leu Val Gly Ile Asn Ala Tyr His Gln
    435                 440                 445
Pro Gly Val Glu Ala Gly Lys Lys Ala Ala Ala Gly Val Leu Glu Ile
450                 455                 460
Gln Arg Gln Ile Val Glu Leu Leu Gln Gln Gly Gln Pro Leu Ser Ile
465                 470                 475                 480
Ala Ala Ile Ala Asp Asp Leu Gly Gln Ser Glu Gln Ile Glu Thr Ile
            485                 490                 495
Tyr Lys Ile Leu Arg His Leu Glu Ala Asn Gln Arg Gly Val Gln Leu
        500                 505                 510
Thr Gly Asp Arg His Asn Pro Leu Ser Leu Ile Ala Ser Trp Gln Arg
    515                 520                 525

<210> SEQ ID NO 43
<211> LENGTH: 1434
<212> TYPE: DNA
<213> ORGANISM: Synechocystis sp. PCC 6803

<400> SEQUENCE: 43
atgaagattt tatttgtggc ggcggaagta tccccctag caaaggtagg tggcatgggg      60
gatgtggtgg gttccctgcc taaagttctg catcagttgg ccatgatgt ccgtgtcttc     120 atgccctact acggtttcat cggcgacaag attgatgtgc caaggagcc ggtctggaaa     180 ggggaagcca tgttccagca gtttgctgtt taccagtcct atctaccgga caccaaaatt     240
cctctctact tgttcggcca tccagctttc gactcccgaa ggatctatgg cggagatgac     300
```

-continued

```
gaggcgtggc ggttcacttt tttttctaac ggggcagctg aatttgcctg gaaccattgg    360
aagccggaaa ttatccattg ccatgattgg cacactggca tgatccctgt ttggatgcat    420
cagtccccag acatcgccac cgttttcacc atccataatc ttgcttacca agggccctgg    480
cggggcttgc ttgaaactat gacttggtgt ccttggtaca tgcagggaga caatgtgatg    540
gcggcggcga ttcaatttgc caatcgggtg actaccgttt ctcccaccta tgcccaacag    600
atccaaaccc cggcctatgg ggaaaagctg aagggttat tgtcctacct gagtggtaat     660
ttagtcggta ttctcaacgg tattgatacg gagatttaca acccggcgga agaccgcttt    720
atcagcaatg ttttcgatgc ggacagtttg gacaagcggg tgaaaaataa aattgccatc    780
caggaggaaa cggggttaga aattaatcgt aatgccatgg tggtgggtat agtggctcgc    840
ttggtggaac aaaaggggat tgatttggtg attcagatcc ttgaccgctt catgtcctac    900
accgattccc agttaattat cctcggcact ggcgatcgcc attacgaaac ccaactttgg    960
cagatggctt cccgatttcc tgggcggatg gcggtgcaat tactccacaa cgatgccctt   1020
tcccgtcgag tctatgccgg ggcggatgtg tttttaatgc cttctcgctt tgagccctgt   1080
gggctgagtc aattgatggc catgcgttat ggctgtatcc ccattgtgcg gcggacaggg   1140
ggtttggtgg atacggtatc cttctacgat cctatcaatg aagccggcac cggctattgc   1200
tttgaccgtt atgaacccct ggattgcttt acggccatgg tgcgggcctg ggagggtttc   1260
cgtttcaagg cagattggca aaattacag caacgggcca tgcggcaga ctttagttgg     1320 taccgttccg ccggggaata tatcaaagtt tataagggcg tggtggggaa accggaggaa   1380
ttaagcccca tggaagagga aaaaatcgct gagttaactg cttcctatcg ctaa         1434
```

<210> SEQ ID NO 44
<211> LENGTH: 477
<212> TYPE: PRT
<213> ORGANISM: Synechocystis sp. PCC 6803

<400> SEQUENCE: 44

Met Lys Ile Leu Phe Val Ala Ala Glu Val Ser Pro Leu Ala Lys Val
1               5                   10                  15

Gly Gly Met Gly Asp Val Val Gly Ser Leu Pro Lys Val Leu His Gln
            20                  25                  30

Leu Gly His Asp Val Arg Val Phe Met Pro Tyr Tyr Gly Phe Ile Gly
        35                  40                  45

Asp Lys Ile Asp Val Pro Lys Glu Pro Val Trp Lys Gly Glu Ala Met
    50                  55                  60

Phe Gln Gln Phe Ala Val Tyr Gln Ser Tyr Leu Pro Asp Thr Lys Ile
65                  70                  75                  80

Pro Leu Tyr Leu Phe Gly His Pro Ala Phe Asp Ser Arg Arg Ile Tyr
                85                  90                  95

Gly Gly Asp Asp Glu Ala Trp Arg Phe Thr Phe Phe Ser Asn Gly Ala
            100                 105                 110

Ala Glu Phe Ala Trp Asn His Trp Lys Pro Glu Ile Ile His Cys His
        115                 120                 125

Asp Trp His Thr Gly Met Ile Pro Val Trp Met His Gln Ser Pro Asp
    130                 135                 140

Ile Ala Thr Val Phe Thr Ile His Asn Leu Ala Tyr Gln Gly Pro Trp
145                 150                 155                 160

Arg Gly Leu Leu Glu Thr Met Thr Trp Cys Pro Trp Tyr Met Gln Gly
                165                 170                 175

```
Asp Asn Val Met Ala Ala Ile Gln Phe Ala Asn Arg Val Thr Thr
            180                 185                 190

Val Ser Pro Thr Tyr Ala Gln Gln Ile Gln Thr Pro Ala Tyr Gly Glu
        195                 200                 205

Lys Leu Glu Gly Leu Leu Ser Tyr Leu Ser Gly Asn Leu Val Gly Ile
    210                 215                 220

Leu Asn Gly Ile Asp Thr Glu Ile Tyr Asn Pro Ala Glu Asp Arg Phe
225                 230                 235                 240

Ile Ser Asn Val Phe Asp Ala Asp Ser Leu Asp Lys Arg Val Lys Asn
                245                 250                 255

Lys Ile Ala Ile Gln Glu Glu Thr Gly Leu Glu Ile Asn Arg Asn Ala
            260                 265                 270

Met Val Val Gly Ile Val Ala Arg Leu Val Glu Gln Lys Gly Ile Asp
        275                 280                 285

Leu Val Ile Gln Ile Leu Asp Arg Phe Met Ser Tyr Thr Asp Ser Gln
    290                 295                 300

Leu Ile Ile Leu Gly Thr Gly Asp Arg His Tyr Glu Thr Gln Leu Trp
305                 310                 315                 320

Gln Met Ala Ser Arg Phe Pro Gly Arg Met Ala Val Gln Leu Leu His
                325                 330                 335

Asn Asp Ala Leu Ser Arg Arg Val Tyr Ala Gly Ala Asp Val Phe Leu
            340                 345                 350

Met Pro Ser Arg Phe Glu Pro Cys Gly Leu Ser Gln Leu Met Ala Met
        355                 360                 365

Arg Tyr Gly Cys Ile Pro Ile Val Arg Arg Thr Gly Gly Leu Val Asp
    370                 375                 380

Thr Val Ser Phe Tyr Asp Pro Ile Asn Glu Ala Gly Thr Gly Tyr Cys
385                 390                 395                 400

Phe Asp Arg Tyr Glu Pro Leu Asp Cys Phe Thr Ala Met Val Arg Ala
                405                 410                 415

Trp Glu Gly Phe Arg Phe Lys Ala Asp Trp Gln Lys Leu Gln Gln Arg
            420                 425                 430

Ala Met Arg Ala Asp Phe Ser Trp Tyr Arg Ser Ala Gly Glu Tyr Ile
        435                 440                 445

Lys Val Tyr Lys Gly Val Val Gly Lys Pro Glu Glu Leu Ser Pro Met
    450                 455                 460

Glu Glu Glu Lys Ile Ala Glu Leu Thr Ala Ser Tyr Arg
465                 470                 475

<210> SEQ ID NO 45
<211> LENGTH: 1419
<212> TYPE: DNA
<213> ORGANISM: Nostoc sp. PCC 7120

<400> SEQUENCE: 45
atgcggattc tatttgtggc agcagaagca gcacccattg caaaagtagg agggatgggt      60
gatgttgtcg gtgcattacc taaggtcttg agaaaaatgg ggcatgatgt acgtatcttc     120
ttgccctatt acggcttttt gccagacaaa atggagattc ccaaagatcc aatatggaag     180
ggatacgcca tgtttcagga ctttacagtt cacgaagcag ttctgcctgg tactgatgtt     240
cccttgtatt tatttggaca tccagccttt accccccggc ggattattc gggagatgat     300 gaagactggc gcttcacctt gttttccaat ggtgcggctg agtttgctg gaattactgg     360 aaacccgaca ttattcactg tcatgattgg cacacgggca tgattcctgt gtggatgaac     420
```

```
caatcaccag atatcaccac agtcttcact atccacaatc tggcttacca agggccttgg      480
cgttggtatt tagataaaat tacttggtgt ccttggtata tgcagggaca caacacaatg      540
gcggcggctg tccagtttgc ggacagggta aatacagttt ctcccacata cgccgagcaa      600
atcaagaccc cggcttacgg tgagaaaata gaaggtttgc tgtctttcat cagtggtaaa      660
ttatctggga ttgttaacgg tatagatacg gaagtttacg acccagctaa tgataaatat      720
attgctcaaa cgttcactgc cgatacttta gataaacgca aagccaacaa aattgcttta      780
caagaagaag taggattaga agttaacagc aatgcctttt taattggcat ggtgacaagg      840
ttagtcgagc agaagggctt agatttagtc atccaaatgc tcgatcgctt tatggcttat      900
actgatgctc agttcgtctt gttgggaaca ggcgatcgct actacgaaac ccaaatgtgg      960
caattagcat cccgctaccc cggtcgtatg gctacttacc tcctgtataa cgatgcccta     1020
tctcgccgca tctacgctgg tactgatgcc ttttgatgc ccagtcgctt tgaaccatgc     1080
ggtattagtc aaatgatggc tttacgctac ggttccattc ccatcgtccg ccgcactgga     1140
ggcttggttg acaccgtatc ccaccacgac cccatcaacg aagcaggtac aggctactgc     1200
ttcgaccgct acgaacccct cgacttattt acctgcatga ttcgcgcctg ggaaggcttc     1260
cgctacaaac cacaatggca agaactacaa aaacgcggta tgagtcaaga cttcagctgg     1320
tacaaatccg ctaaggaata cgacaaactc tatcgctcaa tgtacggttt gccagaccca     1380
gaagagacac agccggagtt aattctgaca aatcagtag                            1419
```

<210> SEQ ID NO 46
<211> LENGTH: 472
<212> TYPE: PRT
<213> ORGANISM: Nostoc sp. PCC 7120

<400> SEQUENCE: 46

Met Arg Ile Leu Phe Val Ala Glu Ala Ala Pro Ile Ala Lys Val
1               5                   10                  15

Gly Gly Met Gly Asp Val Val Gly Ala Leu Pro Lys Val Leu Arg Lys
            20                  25                  30

Met Gly His Asp Val Arg Ile Phe Leu Pro Tyr Tyr Gly Phe Leu Pro
        35                  40                  45

Asp Lys Met Glu Ile Pro Lys Asp Pro Ile Trp Lys Gly Tyr Ala Met
    50                  55                  60

Phe Gln Asp Phe Thr Val His Glu Ala Val Leu Pro Gly Thr Asp Val
65                  70                  75                  80

Pro Leu Tyr Leu Phe Gly His Pro Ala Phe Thr Pro Arg Arg Ile Tyr
                85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Asp Ile Ile His Cys His
        115                 120                 125

Asp Trp His Thr Gly Met Ile Pro Val Trp Met Asn Gln Ser Pro Asp
    130                 135                 140

Ile Thr Thr Val Phe Thr Ile His Asn Leu Ala Tyr Gln Gly Pro Trp
145                 150                 155                 160

Arg Trp Tyr Leu Asp Lys Ile Thr Trp Cys Pro Trp Tyr Met Gln Gly
                165                 170                 175

His Asn Thr Met Ala Ala Ala Val Gln Phe Ala Asp Arg Val Asn Thr
            180                 185                 190

Val Ser Pro Thr Tyr Ala Glu Gln Ile Lys Thr Pro Ala Tyr Gly Glu

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |
| Lys | Ile | Glu | Gly | Leu | Leu | Ser | Phe | Ile | Ser | Gly | Lys | Leu | Ser | Gly | Ile |     |     |
|     |     |     | 210 |     |     |     |     | 215 |     |     |     |     | 220 |     |     |     |     |
| Val | Asn | Gly | Ile | Asp | Thr | Glu | Val | Tyr | Asp | Pro | Ala | Asn | Asp | Lys | Tyr |     |     |
| 225 |     |     |     |     | 230 |     |     |     |     | 235 |     |     |     |     | 240 |     |     |
| Ile | Ala | Gln | Thr | Phe | Thr | Ala | Asp | Thr | Leu | Asp | Lys | Arg | Lys | Ala | Asn |     |     |
|     |     |     |     | 245 |     |     |     |     | 250 |     |     |     |     | 255 |     |     |     |
| Lys | Ile | Ala | Leu | Gln | Glu | Glu | Val | Gly | Leu | Glu | Val | Asn | Ser | Asn | Ala |     |     |
|     |     |     | 260 |     |     |     |     | 265 |     |     |     |     | 270 |     |     |     |     |
| Phe | Leu | Ile | Gly | Met | Val | Thr | Arg | Leu | Val | Glu | Gln | Lys | Gly | Leu | Asp |     |     |
|     |     | 275 |     |     |     |     | 280 |     |     |     |     | 285 |     |     |     |     |     |
| Leu | Val | Ile | Gln | Met | Leu | Asp | Arg | Phe | Met | Ala | Tyr | Thr | Asp | Ala | Gln |     |     |
|     | 290 |     |     |     |     | 295 |     |     |     |     | 300 |     |     |     |     |     |     |
| Phe | Val | Leu | Leu | Gly | Thr | Gly | Asp | Arg | Tyr | Tyr | Glu | Thr | Gln | Met | Trp |     |     |
| 305 |     |     |     |     | 310 |     |     |     |     | 315 |     |     |     |     | 320 |     |     |
| Gln | Leu | Ala | Ser | Arg | Tyr | Pro | Gly | Arg | Met | Ala | Thr | Tyr | Leu | Leu | Tyr |     |     |
|     |     |     |     | 325 |     |     |     |     | 330 |     |     |     |     | 335 |     |     |     |
| Asn | Asp | Ala | Leu | Ser | Arg | Arg | Ile | Tyr | Ala | Gly | Thr | Asp | Ala | Phe | Leu |     |     |
|     |     |     | 340 |     |     |     |     | 345 |     |     |     |     | 350 |     |     |     |     |
| Met | Pro | Ser | Arg | Phe | Glu | Pro | Cys | Gly | Ile | Ser | Gln | Met | Met | Ala | Leu |     |     |
|     |     | 355 |     |     |     |     | 360 |     |     |     |     | 365 |     |     |     |     |     |
| Arg | Tyr | Gly | Ser | Ile | Pro | Ile | Val | Arg | Arg | Thr | Gly | Gly | Leu | Val | Asp |     |     |
|     | 370 |     |     |     |     | 375 |     |     |     |     | 380 |     |     |     |     |     |     |
| Thr | Val | Ser | His | His | Asp | Pro | Ile | Asn | Glu | Ala | Gly | Thr | Gly | Tyr | Cys |     |     |
| 385 |     |     |     |     | 390 |     |     |     |     | 395 |     |     |     |     | 400 |     |     |
| Phe | Asp | Arg | Tyr | Glu | Pro | Leu | Asp | Leu | Phe | Thr | Cys | Met | Ile | Arg | Ala |     |     |
|     |     |     |     | 405 |     |     |     |     | 410 |     |     |     |     | 415 |     |     |     |
| Trp | Glu | Gly | Phe | Arg | Tyr | Lys | Pro | Gln | Trp | Gln | Glu | Leu | Gln | Lys | Arg |     |     |
|     |     |     | 420 |     |     |     |     | 425 |     |     |     |     | 430 |     |     |     |     |
| Gly | Met | Ser | Gln | Asp | Phe | Ser | Trp | Tyr | Lys | Ser | Ala | Lys | Glu | Tyr | Asp |     |     |
|     |     | 435 |     |     |     |     | 440 |     |     |     |     | 445 |     |     |     |     |     |
| Lys | Leu | Tyr | Arg | Ser | Met | Tyr | Gly | Leu | Pro | Asp | Pro | Glu | Glu | Thr | Gln |     |     |
|     | 450 |     |     |     |     | 455 |     |     |     |     | 460 |     |     |     |     |     |     |
| Pro | Glu | Leu | Ile | Leu | Thr | Asn | Gln |     |     |     |     |     |     |     |     |     |     |
| 465 |     |     |     |     | 470 |     |     |     |     |     |     |     |     |     |     |     |     |

<210> SEQ ID NO 47
<211> LENGTH: 1419
<212> TYPE: DNA
<213> ORGANISM: Anabaena variabilis

<400> SEQUENCE: 47

```
atgcggattc tatttgtggc agcagaagca gcacccatcg caaaagtagg agggatgggt      60
gatgttgtcg gtgcattacc taaggtcttg agaaaaatgg ggcatgatgt gcgtatcttc     120
ttgccctatt acggcttttt gccagacaaa atgaaattcc caaagatcc aatctggaag     180
ggatacgcca tgtttcagga ctttacagtt cacgaagcag ttctgcctgg tactgatgtt     240
cccttgtatt tatttggaca tccagccttc aaccccggc gaattattc gggagatgat     300
gaagactggc ggttcacctt gttttccaat ggtgcgcgg aattttgttg gaattactgg     360
aaaccagaaa ttattcactg tcacgattgg cacacaggca tgattcctgt gtggatgaac     420
caatcaccag atatcaccac agtcttcact atccacaacc tagcttacca agggccttgg     480
cgttggtatc tagataaaat tacttggtgt ccttggtata tgcagggaca caacacaatg     540
```

```
gcggcggctg tccagtttgc tgacagagta ataccgtttc tcctacata cgccgagcaa    600 atcaagaccc cggcttacgg tgagaaaata gaaggcttgc tgtctttcat cagtggtaaa    660
ttatctggga ttgttaacgg tatagatacg gaagtttatg acccagctaa tgataaattt    720
attgctcaaa cttttactgc tgatacttta gataaacgca aagccaacaa aattgcttta    780
caagaagaag tagggttaga agttaacagc aatgcctttt taattggcat ggtgacaagg    840
ttagtcgagc agaagggttt agatttagtc atccaaatgc tcgatcgctt tatggcttat    900
actgatgctc agttcgtctt gttaggaaca ggcgatcgct actacgaaac tcaaatgtgg    960
caattagcat cccgctaccc cggacgtatg gccacctatc tcctatacaa tgatgcccta   1020
tcccgccgca tctacgccgg ttctgatgcc tttttaatgc ccagccgctt tgaaccatgc   1080
ggtattagcc agatgatggc tttacgctac ggttccatcc ccatcgttcg ccgcactggg   1140
ggtttagttg acaccgtatc ccaccacgac cccgtaaacg aagccggtac aggctactgc   1200
tttgaccgct acgaacccct agacttattc acctgcatga ttcgcgcctg ggaaggcttc   1260
cgctacaaac cccaatggca agaactacaa aagcgtggta tgagtcaaga cttcagctgg   1320
tacaaatccg ctaaggaata cgacagactc tatcgctcaa tataccggttt gccagaagca   1380 gaagagacac agccagagtt aattctggca aatcagtag                           1419

<210> SEQ ID NO 48
<211> LENGTH: 472
<212> TYPE: PRT
<213> ORGANISM: Anabaena variabilis

<400> SEQUENCE: 48

Met Arg Ile Leu Phe Val Ala Glu Ala Ala Pro Ile Ala Lys Val
  1               5                  10                  15

Gly Gly Met Gly Asp Val Val Gly Ala Leu Pro Lys Val Leu Arg Lys
                 20                  25                  30

Met Gly His Asp Val Arg Ile Phe Leu Pro Tyr Tyr Gly Phe Leu Pro
             35                  40                  45

Asp Lys Met Glu Ile Pro Lys Asp Pro Ile Trp Lys Gly Tyr Ala Met
         50                  55                  60

Phe Gln Asp Phe Thr Val His Glu Ala Val Leu Pro Gly Thr Asp Val
 65                  70                  75                  80

Pro Leu Tyr Leu Phe Gly His Pro Ala Phe Asn Pro Arg Arg Ile Tyr
                 85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Glu Ile Ile His Cys His
        115                 120                 125

Asp Trp His Thr Gly Met Ile Pro Val Trp Met Asn Gln Ser Pro Asp
    130                 135                 140

Ile Thr Thr Val Phe Thr Ile His Asn Leu Ala Tyr Gln Gly Pro Trp
145                 150                 155                 160

Arg Trp Tyr Leu Asp Lys Ile Thr Trp Cys Pro Trp Tyr Met Gln Gly
                165                 170                 175

His Asn Thr Met Ala Ala Ala Val Gln Phe Ala Asp Arg Val Asn Thr
            180                 185                 190

Val Ser Pro Thr Tyr Ala Glu Gln Ile Lys Thr Pro Ala Tyr Gly Glu
        195                 200                 205

Lys Ile Glu Gly Leu Leu Ser Phe Ile Ser Gly Lys Leu Ser Gly Ile
    210                 215                 220
```

```
Val Asn Gly Ile Asp Thr Glu Val Tyr Asp Pro Ala Asn Asp Lys Phe
225                 230                 235                 240

Ile Ala Gln Thr Phe Thr Ala Asp Thr Leu Asp Lys Arg Lys Ala Asn
                245                 250                 255

Lys Ile Ala Leu Gln Glu Glu Val Gly Leu Glu Val Asn Ser Asn Ala
            260                 265                 270

Phe Leu Ile Gly Met Val Thr Arg Leu Val Glu Gln Lys Gly Leu Asp
        275                 280                 285

Leu Val Ile Gln Met Leu Asp Arg Phe Met Ala Tyr Thr Asp Ala Gln
    290                 295                 300

Phe Val Leu Leu Gly Thr Gly Asp Arg Tyr Tyr Glu Thr Gln Met Trp
305                 310                 315                 320

Gln Leu Ala Ser Arg Tyr Pro Gly Arg Met Ala Thr Tyr Leu Leu Tyr
                325                 330                 335

Asn Asp Ala Leu Ser Arg Arg Ile Tyr Ala Gly Ser Asp Ala Phe Leu
            340                 345                 350

Met Pro Ser Arg Phe Glu Pro Cys Gly Ile Ser Gln Met Met Ala Leu
        355                 360                 365

Arg Tyr Gly Ser Ile Pro Ile Val Arg Arg Thr Gly Gly Leu Val Asp
    370                 375                 380

Thr Val Ser His His Asp Pro Val Asn Glu Ala Gly Thr Gly Tyr Cys
385                 390                 395                 400

Phe Asp Arg Tyr Glu Pro Leu Asp Leu Phe Thr Cys Met Ile Arg Ala
                405                 410                 415

Trp Glu Gly Phe Arg Tyr Lys Pro Gln Trp Gln Glu Leu Gln Lys Arg
            420                 425                 430

Gly Met Ser Gln Asp Phe Ser Trp Tyr Lys Ser Ala Lys Glu Tyr Asp
        435                 440                 445

Arg Leu Tyr Arg Ser Ile Tyr Gly Leu Pro Glu Ala Glu Glu Thr Gln
    450                 455                 460

Pro Glu Leu Ile Leu Ala Asn Gln
465                 470
```

<210> SEQ ID NO 49
<211> LENGTH: 1383
<212> TYPE: DNA
<213> ORGANISM: Trichodesmium erythraeum IMS 101

<400> SEQUENCE: 49

```
atgcgaattt tatttgtgtc tgctgaagcg actcctttag caaaagttgg tggtatggca      60
gatgtagtgg gtgccttacc caaagtacta cggaaaatgg gtcacgatgt tcgtatcttc     120
atgccttatt atggcttttt aggcgacaag atggaagttc ctgaggaacc tatctgggaa     180
ggaacggcca tgtatcaaaa ctttaagatt tatgagacgg tactaccaaa aagtgacgtg     240
ccattgtacc tatttggtca cccggctttt tggccacgtc atatttacta tggagatgat     300
gaggactgga gattcactct atttgctaat ggggcggccg agttttgctg aatggctgg      360 aaaccagaga tagttcattg taatgactgg cacactggca tgattccagt ttggatgcac     420
gaaactccag acattaaaac cgtatttact attcataacc tagcttatca aggaccttgg     480
cgctggtact tggaaagaat tacttggtgt ccttggtaca tggaagggca ataccaatg      540 gcagcagcag ttcagtttgc agatcgggta actactgttt ctccaaccta tgctagtcag     600
atccaaacac ctgcctacgg agaaaatcta gatggtttaa tgtcttttat tacggggaaa     660
```

-continued

```
ctacacggta tcctcaatgg tattgatatg aacttttata atccagctaa tgacagatat    720
attcctcaaa cttatgatgt caataccctg gaaaaacggg ttgacaataa aattgctctt    780
caagaagaag taggttttga agttaacaaa aatagctttc tcatgggaat ggtctcccga    840
ctggtagaac aaaaaggact tgatttaatg ctgcaagtct tagatcggtt tatggcttat    900
actgatactc agtttatttt gttgggtaca ggcgatcgct tctatgaaac ccaaatgtgg    960
caaatagcaa gtcgttatcc tggtcggatg agtgtccaac ttttacataa tgatgccctt   1020
tcccgacgaa tatatgcagg tactgatgct ttcttaatgc ccagtcgatt tgagccttgt   1080
ggtattagtc agttattggc aatgcgttat ggtagtatac ctattgtccg tcgcacaggt   1140
gggttagttg atactgtctc tttctatgat cctattaata atgtaggtac tggctattct   1200
tttgatcgct atgaaccact agacctgctt actgcaatgg tccgagccta tgaaggtttc   1260
cggttcaaag atcaatggca ggagttacag aagcgtggca tgagagagaa ctttagctgg   1320
gataagtcag ctcaaggtta tatcaaaatg tacaaatcaa tgctcggatt acctgaagaa   1380
taa                                                                 1383
```

<210> SEQ ID NO 50
<211> LENGTH: 460
<212> TYPE: PRT
<213> ORGANISM: Trichodesmium erythraeum IMS 101

<400> SEQUENCE: 50

Met Arg Ile Leu Phe Val Ser Ala Glu Ala Thr Pro Leu Ala Lys Val
1               5                   10                  15
Gly Gly Met Ala Asp Val Val Gly Ala Leu Pro Lys Val Leu Arg Lys
            20                  25                  30
Met Gly His Asp Val Arg Ile Phe Met Pro Tyr Tyr Gly Phe Leu Gly
        35                  40                  45
Asp Lys Met Glu Val Pro Glu Glu Pro Ile Trp Glu Gly Thr Ala Met
    50                  55                  60
Tyr Gln Asn Phe Lys Ile Tyr Glu Thr Val Leu Pro Lys Ser Asp Val
65                  70                  75                  80
Pro Leu Tyr Leu Phe Gly His Pro Ala Phe Trp Pro Arg His Ile Tyr
                85                  90                  95
Tyr Gly Asp Asp Glu Asp Trp Arg Phe Thr Leu Phe Ala Asn Gly Ala
            100                 105                 110
Ala Glu Phe Cys Trp Asn Gly Trp Lys Pro Glu Ile Val His Cys Asn
        115                 120                 125
Asp Trp His Thr Gly Met Ile Pro Val Trp Met His Glu Thr Pro Asp
    130                 135                 140
Ile Lys Thr Val Phe Thr Ile His Asn Leu Ala Tyr Gln Gly Pro Trp
145                 150                 155                 160
Arg Trp Tyr Leu Glu Arg Ile Thr Trp Cys Pro Trp Tyr Met Glu Gly
                165                 170                 175
His Asn Thr Met Ala Ala Ala Val Gln Phe Ala Asp Arg Val Thr Thr
            180                 185                 190
Val Ser Pro Thr Tyr Ala Ser Gln Ile Gln Thr Pro Ala Tyr Gly Glu
        195                 200                 205
Asn Leu Asp Gly Leu Met Ser Phe Ile Thr Gly Lys Leu His Gly Ile
    210                 215                 220
Leu Asn Gly Ile Asp Met Asn Phe Tyr Asn Pro Ala Asn Asp Arg Tyr
225                 230                 235                 240

```
Ile Pro Gln Thr Tyr Asp Val Asn Thr Leu Glu Lys Arg Val Asp Asn
            245                 250                 255

Lys Ile Ala Leu Gln Glu Val Gly Phe Glu Val Asn Lys Asn Ser
        260                 265                 270

Phe Leu Met Gly Met Val Ser Arg Leu Val Glu Gln Lys Gly Leu Asp
        275                 280                 285

Leu Met Leu Gln Val Leu Asp Arg Phe Met Ala Tyr Thr Asp Thr Gln
        290                 295                 300

Phe Ile Leu Leu Gly Thr Gly Asp Arg Phe Tyr Glu Thr Gln Met Trp
305                 310                 315                 320

Gln Ile Ala Ser Arg Tyr Pro Gly Arg Met Ser Val Gln Leu Leu His
                325                 330                 335

Asn Asp Ala Leu Ser Arg Arg Ile Tyr Ala Gly Thr Asp Ala Phe Leu
                340                 345                 350

Met Pro Ser Arg Phe Glu Pro Cys Gly Ile Ser Gln Leu Leu Ala Met
                355                 360                 365

Arg Tyr Gly Ser Ile Pro Ile Val Arg Thr Gly Gly Leu Val Asp
        370                 375                 380

Thr Val Ser Phe Tyr Asp Pro Ile Asn Asn Val Gly Thr Gly Tyr Ser
385                 390                 395                 400

Phe Asp Arg Tyr Glu Pro Leu Asp Leu Leu Thr Ala Met Val Arg Ala
                405                 410                 415

Tyr Glu Gly Phe Arg Phe Lys Asp Gln Trp Gln Leu Gln Lys Arg
        420                 425                 430

Gly Met Arg Glu Asn Phe Ser Trp Asp Lys Ser Ala Gln Gly Tyr Ile
            435                 440                 445

Lys Met Tyr Lys Ser Met Leu Gly Leu Pro Glu Glu
450                 455                 460

<210> SEQ ID NO 51
<211> LENGTH: 1398
<212> TYPE: DNA
<213> ORGANISM: Synechococcus elongatus PCC 7942

<400> SEQUENCE: 51
atgcggattc tgttcgtggc tgccgaatgt gctcccttcg ccaaagtggg aggcatggga      60
gatgtggttg ttccctgcc caaagtgctg aaagctctgg ccatgatgt ccgaatcttc       120 atgccgtact acggctttct gaacagtaag ctcgatattc ccgctgaacc gatctggtgg     180
ggctacgcga tgtttaatca cttcgcggtt tacgaaacgc agctgcccgg ttcagatgtg     240
ccgctctact taatggggca tccagctttt gatccgcatc gcatctactc aggagaagac     300
gaagactggc gcttcacgtt ttttgccaat ggggctgctg aattttcttg gaactactgg     360
aaaccacaag tcattcactg ccacgattgg cacactggga tgattccggt ttggatgcac     420
cagtccccgg atatctcgac tgtcttcacc attcataact ggcctaccag agggccgtgg     480
cgctggaagc tcgagaaaat cacctggtgc ccttggtaca tgcagggcga cagcaccatg     540
gcggcggcct tgctctatgc cgatcgcgtc aacacggtat cgcccaccta tgcccagcag     600
attcaaacac cgacctacgg tgaaaagctg gagggtcttc tctcatttat cagtggcaag     660
ctaagcggca tccttaacgg gattgatgtt gatagctaca accctgcaac ggatacgcgg     720
attgtggcca actacgatcg cgacactctt gataaacgac tgaacaataa gctggcgctc     780
caaaaggaga tggggcttga ggtcaatccc gatcgcttcc tgattggctt tgtggctcgt     840
ctagtcgagc agaagggcat tgacttgctg ctgcaaattc ttgatcgctt tctgtcttac     900
```

```
agcgatgccc aatttgttgt cttaggaacg ggcgagcgct actacgaaac ccagctctgg   960
gagttggcga cccgctatcc gggccggatg tccacttatc tgatgtacga cgaggggctg  1020
tcgcgacgca tttatgccgg tagcgacgcc ttcttggtgc cctctcgttt tgaaccttgc  1080
ggtatcacgc aaatgctggc actgcgctac ggcagtgtgc cgattgtgcg ccgtacgggg  1140
gggttggtcg atacggtctt ccaccacgat ccgcgtcatg ccgagggcaa tggctattgc  1200
ttcgatcgct acgagccgct ggacctctat acctgtctgg tgcgggcttg ggagagttac  1260
cagtaccagc cccaatggca aaagctacag caacggggta tggccgttga tctgagctgg  1320
aaacaatcgg cgatcgccta cgaacagctc tacgctgaag cgattgggct accgatcgat  1380
gtcttacagg aggcctag                                                1398
```

<210> SEQ ID NO 52
<211> LENGTH: 465
<212> TYPE: PRT
<213> ORGANISM: Synechococcus elongatus PCC 7942

<400> SEQUENCE: 52

```
Met Arg Ile Leu Phe Val Ala Ala Glu Cys Ala Pro Phe Ala Lys Val
 1               5                  10                  15

Gly Gly Met Gly Asp Val Val Gly Ser Leu Pro Lys Val Leu Lys Ala
            20                  25                  30

Leu Gly His Asp Val Arg Ile Phe Met Pro Tyr Tyr Gly Phe Leu Asn
        35                  40                  45

Ser Lys Leu Asp Ile Pro Ala Glu Pro Ile Trp Trp Gly Tyr Ala Met
 50                  55                  60

Phe Asn His Phe Ala Val Tyr Glu Thr Gln Leu Pro Gly Ser Asp Val
 65                  70                  75                  80

Pro Leu Tyr Leu Met Gly His Pro Ala Phe Asp Pro His Arg Ile Tyr
                85                  90                  95

Ser Gly Glu Asp Glu Asp Trp Arg Phe Thr Phe Ala Asn Gly Ala
            100                 105                 110

Ala Glu Phe Ser Trp Asn Tyr Trp Lys Pro Gln Val Ile His Cys His
        115                 120                 125

Asp Trp His Thr Gly Met Ile Pro Val Trp Met His Gln Ser Pro Asp
130                 135                 140

Ile Ser Thr Val Phe Thr Ile His Asn Leu Ala Tyr Gln Gly Pro Trp
145                 150                 155                 160

Arg Trp Lys Leu Glu Lys Ile Thr Trp Cys Pro Trp Tyr Met Gln Gly
                165                 170                 175

Asp Ser Thr Met Ala Ala Ala Leu Leu Tyr Ala Asp Arg Val Asn Thr
            180                 185                 190

Val Ser Pro Thr Tyr Ala Gln Gln Ile Gln Thr Pro Thr Tyr Gly Glu
        195                 200                 205

Lys Leu Glu Gly Leu Leu Ser Phe Ile Ser Gly Lys Leu Ser Gly Ile
    210                 215                 220

Leu Asn Gly Ile Asp Val Asp Ser Tyr Asn Pro Ala Thr Asp Thr Arg
225                 230                 235                 240

Ile Val Ala Asn Tyr Asp Arg Asp Thr Leu Asp Lys Arg Leu Asn Asn
                245                 250                 255

Lys Leu Ala Leu Gln Lys Glu Met Gly Leu Glu Val Asn Pro Asp Arg
            260                 265                 270

Phe Leu Ile Gly Phe Val Ala Arg Leu Val Glu Gln Lys Gly Ile Asp
```

```
                275                 280                 285
Leu Leu Leu Gln Ile Leu Asp Arg Phe Leu Ser Tyr Ser Asp Ala Gln
    290                 295                 300
Phe Val Val Leu Gly Thr Gly Glu Arg Tyr Tyr Glu Thr Gln Leu Trp
305                 310                 315                 320
Glu Leu Ala Thr Arg Tyr Pro Gly Arg Met Ser Thr Tyr Leu Met Tyr
                325                 330                 335
Asp Glu Gly Leu Ser Arg Arg Ile Tyr Ala Gly Ser Asp Ala Phe Leu
            340                 345                 350
Val Pro Ser Arg Phe Glu Pro Cys Gly Ile Thr Gln Met Leu Ala Leu
                355                 360                 365
Arg Tyr Gly Ser Val Pro Ile Val Arg Arg Thr Gly Gly Leu Val Asp
            370                 375                 380
Thr Val Phe His His Asp Pro Arg His Ala Glu Gly Asn Gly Tyr Cys
385                 390                 395                 400
Phe Asp Arg Tyr Glu Pro Leu Asp Leu Tyr Thr Cys Leu Val Arg Ala
                405                 410                 415
Trp Glu Ser Tyr Gln Tyr Gln Pro Gln Trp Gln Lys Leu Gln Gln Arg
                420                 425                 430
Gly Met Ala Val Asp Leu Ser Trp Lys Gln Ser Ala Ile Ala Tyr Glu
            435                 440                 445
Gln Leu Tyr Ala Glu Ala Ile Gly Leu Pro Ile Asp Val Leu Gln Glu
        450                 455                 460
Ala
465

<210> SEQ ID NO 53
<211> LENGTH: 1542
<212> TYPE: DNA
<213> ORGANISM: Synechococcus sp. WH8102

<400> SEQUENCE: 53
atgcgcatcc tcttcgctgc cgcggaatgc gccccgatga tcaaggtcgg tggcatgggg      60
gatgtggtgg atcgctgcc tccggctctg gccaagcttg ccacgacgt gcggctgatc      120
atgccgggct actccaagct ctggaccaag ctgacgatct cggacgaacc catctggcgc      180
gcccagacga tggtacgga attcgcggtt tacgagacga agcatccagg caatgggatg      240
accatctacc tggtgggaca tccggtgttc gatcccgagc ggatctatgg cggtgaagat      300
gaggactggc gcttcacctt ctttgccagt gccgccgctg aattcgcctg gaatgtctgg      360
aagccgaatg ttcttcactg ccacgactgg cacaccggca tgattccggt ctggatgcac      420
caggacccgg agatcagcac ggtcttcacc atccacaacc tcaagtacca gggcccctgg      480
cgttggaagc tggatcgcat cacctggtgc ccctggtaca tgcagggaga tcacaccatg      540
gcggcggcac ttctgtacgc cgaccgggtc aacgccgtct cccccaccta cgccgaggaa      600
atccgtacgg cggagtacgg cgaaaagctg gatggtttgc tcaatttcgt ctccggcaag      660
ctgcgcggca tcctcaatgg cattgacctc gaggcctgga cccccagac cgatggggct      720
ctgccggcca cctcagcgc cgacgacctc tccggtaaag cggtctgcaa gcgggtgttg      780
caggagcgca tgggtcttga ggtgcgtgac gacgcctttg tcctcggcat ggtcagccga      840
ctcgtcgatc agaagggcgt cgatctgctt ctgcaggtgg cggaccgttt gctcgcctac      900
accgacacgc agatcgtggt gctcggcacc ggtgaccgtg gctggaatc cggcctgtgg      960
cagctggccct cccgccatgc cggccgttgc gccgtcttcc tcacctacga cgacgacctc     1020
```

```
tcccgactga tctatgccgg cagtgacgcc ttcctgatgc ccagtcgctt cgagccctgc    1080
ggcatcagcc agctgtacgc catgcgttac ggctccgttc ctgtggtgcg caaggtgggc    1140
ggcctggtgg acaccgttcc tccccacagt ccagctgatg ccagcgggac cggcttctgc    1200
ttcgatcgtt ttgagccggt cgacttctac accgcattgg tgcgtgcctg ggaggcctac    1260
cgccatcgcg acagctggca ggagttgcag aagcgcggca tgcagcagga ctacagctgg    1320
gaccgttcgg ccatcgatta cgacgtcatg taccgcgatg tctgcggtct gaaggaaccc    1380 accccctgatg ccgcgatggt ggaacagttc tcccagggac aggctgcgga tccctcccgc    1440
ccagaggatg atgcgatcaa tgctgctccc gaggcggtca ccgcgccgtc cggccccagc    1500 cgcaacccc ttaatcgtct cttcggccgc agggccgact ga                       1542
```

<210> SEQ ID NO 54
<211> LENGTH: 513
<212> TYPE: PRT
<213> ORGANISM: Synechococcus sp. WH8102

<400> SEQUENCE: 54

```
Met Arg Ile Leu Phe Ala Ala Ala Glu Cys Ala Pro Met Ile Lys Val
 1               5                  10                  15

Gly Gly Met Gly Asp Val Val Gly Ser Leu Pro Pro Ala Leu Ala Lys
             20                  25                  30

Leu Gly His Asp Val Arg Leu Ile Met Pro Gly Tyr Ser Lys Leu Trp
         35                  40                  45

Thr Lys Leu Thr Ile Ser Asp Glu Pro Ile Trp Arg Ala Gln Thr Met
     50                  55                  60

Gly Thr Glu Phe Ala Val Tyr Glu Thr Lys His Pro Gly Asn Gly Met
 65                  70                  75                  80

Thr Ile Tyr Leu Val Gly His Pro Val Phe Asp Pro Glu Arg Ile Tyr
                 85                  90                  95

Gly Gly Glu Asp Glu Asp Trp Arg Phe Thr Phe Phe Ala Ser Ala Ala
            100                 105                 110

Ala Glu Phe Ala Trp Asn Val Trp Lys Pro Asn Val Leu His Cys His
        115                 120                 125

Asp Trp His Thr Gly Met Ile Pro Val Trp Met His Gln Asp Pro Glu
    130                 135                 140

Ile Ser Thr Val Phe Thr Ile His Asn Leu Lys Tyr Gln Gly Pro Trp
145                 150                 155                 160

Arg Trp Lys Leu Asp Arg Ile Trp Cys Pro Trp Tyr Met Gln Gly
                165                 170                 175

Asp His Thr Met Ala Ala Ala Leu Leu Tyr Ala Asp Arg Val Asn Ala
            180                 185                 190

Val Ser Pro Thr Tyr Ala Glu Glu Ile Arg Thr Ala Glu Tyr Gly Glu
        195                 200                 205

Lys Leu Asp Gly Leu Leu Asn Phe Val Ser Gly Lys Leu Arg Gly Ile
    210                 215                 220

Leu Asn Gly Ile Asp Leu Glu Ala Trp Asn Pro Gln Thr Asp Gly Ala
225                 230                 235                 240

Leu Pro Ala Thr Phe Ser Ala Asp Leu Ser Gly Lys Ala Val Cys
                245                 250                 255

Lys Arg Val Leu Gln Glu Arg Met Gly Leu Glu Val Arg Asp Asp Ala
            260                 265                 270

Phe Val Leu Gly Met Val Ser Arg Leu Val Asp Gln Lys Gly Val Asp
```

```
              275                 280                 285
Leu Leu Leu Gln Val Ala Asp Arg Leu Leu Ala Tyr Thr Asp Thr Gln
    290                 295                 300

Ile Val Val Leu Gly Thr Gly Asp Arg Gly Leu Glu Ser Gly Leu Trp
305                 310                 315                 320

Gln Leu Ala Ser Arg His Ala Gly Arg Cys Ala Val Phe Leu Thr Tyr
                325                 330                 335

Asp Asp Asp Leu Ser Arg Leu Ile Tyr Ala Gly Ser Asp Ala Phe Leu
            340                 345                 350

Met Pro Ser Arg Phe Glu Pro Cys Gly Ile Ser Gln Leu Tyr Ala Met
                355                 360                 365

Arg Tyr Gly Ser Val Pro Val Val Arg Lys Val Gly Leu Val Asp
    370                 375                 380

Thr Val Pro Pro His Ser Pro Ala Asp Ala Ser Gly Thr Gly Phe Cys
385                 390                 395                 400

Phe Asp Arg Phe Glu Pro Val Asp Phe Tyr Thr Ala Leu Val Arg Ala
                405                 410                 415

Trp Glu Ala Tyr Arg His Arg Asp Ser Trp Gln Glu Leu Gln Lys Arg
            420                 425                 430

Gly Met Gln Gln Asp Tyr Ser Trp Asp Arg Ser Ala Ile Asp Tyr Asp
                435                 440                 445

Val Met Tyr Arg Asp Val Cys Gly Leu Lys Glu Pro Thr Pro Asp Ala
    450                 455                 460

Ala Met Val Glu Gln Phe Ser Gln Gly Gln Ala Ala Asp Pro Ser Arg
465                 470                 475                 480

Pro Glu Asp Asp Ala Ile Asn Ala Ala Pro Glu Ala Val Thr Ala Pro
                485                 490                 495

Ser Gly Pro Ser Arg Asn Pro Leu Asn Arg Leu Phe Gly Arg Arg Ala
            500                 505                 510

Asp

<210> SEQ ID NO 55
<211> LENGTH: 1524
<212> TYPE: DNA
<213> ORGANISM: Synechococcus sp RCC 307

<400> SEQUENCE: 55
atgcgcatcc tctttgctgc ggccgaatgc gcaccgatgg tgaaagtcgg cggcatggga      60
gatgtggtgg atctctgcc tccagccctc gctgagttgg tcacgacgt gcgcgtgatc     120 atgcccggct acggcaagct ctggtcccag cttgatgtgc ccagcgagcc gatctggcgt     180
gcccaaacca tgggcaccga ttttgctgtc tatgagaccc gtcacccaa gaccgggctc     240 acgatctatt tggtgggcca tccggttttt gatggtgagc gcatctatgg aggtgaagac     300
gaggactggc gcttcaccct cttcgctagc gccacctccg aatttgcctg gaacgcttgg     360
aagccccagg tgctgcattg ccatgactgg cacaccggca tgattccggt gtggatgcac     420
caagaccccg agatcagcac ggtcttcacc atccacaacc tcaaatatca aggtccctgg     480
cgctggaagc tcgagcgcat gacctggtgc cctggtaca tgcagggcga ccacaccatg     540
gcggcagcct tgctgtatgc cgaccgcgtc aatgcggttt cacccaccta cgcccaagag     600
atccgcacgc cggaatacgg cgaacaactg gaggggttgc tgaactacat cagcggcaag     660
ctgcgaggca tcctcaatgg catcgatgtg gaggcttgga atcccgccac tgattcgcgg     720
attccggcca cctacagcac tgctgaccct cagtggcaaag ccgtctgcaa gcgggctctg     780
```

-continued

```
caagagcgca tggggcttca ggtgaacccc gacacctttg tgatcggttt ggtgagccgt      840
ttggtggacc aaaaaggcgt cgacctgctg ctgcaggttg ccgaacgctt ccttgcctac      900
accgatacgc agatcgttgt gttgggcacc ggggatcgcc atttggaatc gggcctgtgg      960
caaatggcga gtcagcacag cggccgcttc gcttccttcc tcacctacga cgatgatctc     1020
tcccggctga tctacgccgg cagtgatgcc ttcttgatgc cctcgcgctt tgagccctgc     1080
ggcatcagcc agttgctctc gatgcgctac ggcaccatcc cggtggtgcg ccgcgtcggt     1140
ggactggtcg acaccgtgcc tccctatgtt cccgccaccc aagagggcaa tggcttctgc     1200
ttcgaccgct atgaagcgat cgacctttac accgccttgg tgcgcgcctg ggaggcctac     1260
cgccatcaag acagctggca gcaattgatg aagcgggtga tgcaggttga tttcagctgg     1320
gctcgttccg ccttggaata cgaccgcatg tatcgcgatg tttgcggaat gaaggagccc     1380
acgccggaag ccgatgcggt ggcggccttc tccattcccc agccgcctga acagcaggcc     1440
gcacgtgctg ccgctgaagc cgctgacccc aaccccaac ggcgctttaa tccccttgga     1500
ttgctgcgcc gaaacggcgg ttga                                             1524
```

<210> SEQ ID NO 56
<211> LENGTH: 507
<212> TYPE: PRT
<213> ORGANISM: Synechococcus sp RCC 307

<400> SEQUENCE: 56

```
Met Arg Ile Leu Phe Ala Ala Ala Glu Cys Ala Pro Met Val Lys Val
1               5                   10                  15

Gly Gly Met Gly Asp Val Val Gly Ser Leu Pro Pro Ala Leu Ala Glu
            20                  25                  30

Leu Gly His Asp Val Arg Val Ile Met Pro Gly Tyr Gly Lys Leu Trp
        35                  40                  45

Ser Gln Leu Asp Val Pro Ser Glu Pro Ile Trp Arg Ala Gln Thr Met
    50                  55                  60

Gly Thr Asp Phe Ala Val Tyr Glu Thr Arg His Pro Lys Thr Gly Leu
65                  70                  75                  80

Thr Ile Tyr Leu Val Gly His Pro Val Phe Asp Gly Glu Arg Ile Tyr
                85                  90                  95

Gly Gly Glu Asp Glu Asp Trp Arg Phe Thr Phe Phe Ala Ser Ala Thr
            100                 105                 110

Ser Glu Phe Ala Trp Asn Ala Trp Lys Pro Gln Val Leu His Cys His
        115                 120                 125

Asp Trp His Thr Gly Met Ile Pro Val Trp Met His Gln Asp Pro Glu
    130                 135                 140

Ile Ser Thr Val Phe Thr Ile His Asn Leu Lys Tyr Gln Gly Pro Trp
145                 150                 155                 160

Arg Trp Lys Leu Glu Arg Met Thr Trp Cys Pro Trp Tyr Met Gln Gly
                165                 170                 175

Asp His Thr Met Ala Ala Ala Leu Leu Tyr Ala Asp Arg Val Asn Ala
            180                 185                 190

Val Ser Pro Thr Tyr Ala Gln Glu Ile Arg Thr Pro Glu Tyr Gly Glu
        195                 200                 205

Gln Leu Glu Gly Leu Leu Asn Tyr Ile Ser Gly Lys Leu Arg Gly Ile
    210                 215                 220

Leu Asn Gly Ile Asp Val Glu Ala Trp Asn Pro Ala Thr Asp Ser Arg
225                 230                 235                 240
```

```
Ile Pro Ala Thr Tyr Ser Thr Ala Asp Leu Ser Gly Lys Ala Val Cys
                245                 250                 255
Lys Arg Ala Leu Gln Glu Arg Met Gly Leu Gln Val Asn Pro Asp Thr
            260                 265                 270
Phe Val Ile Gly Leu Val Ser Arg Leu Val Asp Gln Lys Gly Val Asp
        275                 280                 285
Leu Leu Leu Gln Val Ala Glu Arg Phe Leu Ala Tyr Thr Asp Thr Gln
    290                 295                 300
Ile Val Val Leu Gly Thr Gly Asp Arg His Leu Glu Ser Gly Leu Trp
305                 310                 315                 320
Gln Met Ala Ser Gln His Ser Gly Arg Phe Ala Ser Phe Leu Thr Tyr
                325                 330                 335
Asp Asp Asp Leu Ser Arg Leu Ile Tyr Ala Gly Ser Asp Ala Phe Leu
            340                 345                 350
Met Pro Ser Arg Phe Glu Pro Cys Gly Ile Ser Gln Leu Leu Ser Met
        355                 360                 365
Arg Tyr Gly Thr Ile Pro Val Val Arg Val Gly Gly Leu Val Asp
    370                 375                 380
Thr Val Pro Pro Tyr Val Pro Ala Thr Gln Glu Gly Asn Gly Phe Cys
385                 390                 395                 400
Phe Asp Arg Tyr Glu Ala Ile Asp Leu Tyr Thr Ala Leu Val Arg Ala
                405                 410                 415
Trp Glu Ala Tyr Arg His Gln Asp Ser Trp Gln Leu Met Lys Arg
            420                 425                 430
Val Met Gln Val Asp Phe Ser Trp Ala Arg Ser Ala Leu Glu Tyr Asp
        435                 440                 445
Arg Met Tyr Arg Asp Val Cys Gly Met Lys Glu Pro Thr Pro Glu Ala
    450                 455                 460
Asp Ala Val Ala Ala Phe Ser Ile Pro Gln Pro Glu Gln Ala
465                 470                 475                 480
Ala Arg Ala Ala Ala Glu Ala Ala Asp Pro Asn Pro Gln Arg Arg Phe
                485                 490                 495
Asn Pro Leu Gly Leu Leu Arg Arg Asn Gly Gly
            500                 505

<210> SEQ ID NO 57
<211> LENGTH: 1437
<212> TYPE: DNA
<213> ORGANISM: Synechococcus sp. PCC 7002

<400> SEQUENCE: 57
atgcgtattt tgtttgtttc tgccgaggct gctcccatcg ctaaagctgg aggcatggga      60
gatgtggtgg atcactgcc taaagttta cggcagttag acatgacgc gagaattttc       120 ttaccctatt acggctttct caacgacaaa ctcgacatcc ctgcagaacc cgtttggtgg     180
ggcagtgcga tgttcaatac ttttgccgtt tatgaaactg tgttgcccaa caccgatgtc    240
cccctttatc tgtttggcca tcccgccttt gatggacggc atatttatgg tgggcaggat    300
gaattttggc gctttacctt ttttgccaat ggggccgctg aatttatgtg gaaccactgg    360
aaaccccaga tcgcccactg tcacgactgg cacacgggca tgattccggt atggatgcac    420
caatcgccgg atatcagtac ggtgtttacg atccacaact tagcctacca agggcttggg    480
cggggtttcc tggagcgcaa tacttggtgt ccctggtata tggatggtga taacgtgatg    540
gcttcggcgc tgatgtttgc cgatcaggtg aacaccgtat ctcccaccta tgcccaacaa    600
```

```
atccaaacca aagtctatgg tgaaaaatta gagggtttgt tgtcttggat cagtggcaaa    660
agtcgcggca tcgtgaatgg tattgacgta aactttata atccttctaa cgatcaagcc    720
ctggtgaagc aatttttctac gactaatctt gaggatcggg ccgccaacaa agtgattatc    780
caagaagaaa cggggctaga ggtcaactcc aaggctttt tgatggcgat ggtcacccgc    840
ttagtggaac aaaagggcat tgatctgctg ctaaatatcc tggagcagtt tatggcatac    900
actgacgccc agctcattat cctcggcact ggcgatcgcc actacgaaac ccaactctgg    960
cagactgcct accgctttaa ggggcggatg tccgtgcaac tgctctataa tgatgccctc   1020
tcccgccgga tttacgctgg atccgatgtc ttttgatgc cgtcacgctt tgagccctgt   1080
ggcattagtc aaatgatggc gatgcgctac ggttctgtac cgattgtgcg gcgcaccggg   1140
ggtttggtgg atacggtctc tttccatgat ccgattcacc aaaccgggac aggctttagt   1200
tttgaccgct acgaaccgct ggatatgtac acctgcatgg tgcgggcttg ggaaagtttc   1260
cgctacaaaa aagactgggc tgaactacaa agacgaggca tgagccatga ctttagttgg   1320
tacaaatctg ccggggaata tctcaagatg taccgccaaa gcattaaaga agctccggaa   1380
ttaacgaccg atgaagccga aaaaatcacc tatttagtga aaaaacacgc catttaa      1437
```

<210> SEQ ID NO 58
<211> LENGTH: 478
<212> TYPE: PRT
<213> ORGANISM: Synechococcus sp. PCC 7002

<400> SEQUENCE: 58

```
Met Arg Ile Leu Phe Val Ser Ala Glu Ala Ala Pro Ile Ala Lys Ala
  1               5                  10                  15

Gly Gly Met Gly Asp Val Val Gly Ser Leu Pro Lys Val Leu Arg Gln
             20                  25                  30

Leu Gly His Asp Ala Arg Ile Phe Leu Pro Tyr Tyr Gly Phe Leu Asn
         35                  40                  45

Asp Lys Leu Asp Ile Pro Ala Glu Pro Val Trp Trp Gly Ser Ala Met
     50                  55                  60

Phe Asn Thr Phe Ala Val Tyr Glu Thr Val Leu Pro Asn Thr Asp Val
 65                  70                  75                  80

Pro Leu Tyr Leu Phe Gly His Pro Ala Phe Asp Gly Arg His Ile Tyr
                 85                  90                  95

Gly Gly Gln Asp Glu Phe Trp Arg Phe Thr Phe Phe Ala Asn Gly Ala
            100                 105                 110

Ala Glu Phe Met Trp Asn His Trp Lys Pro Gln Ile Ala His Cys His
        115                 120                 125

Asp Trp His Thr Gly Met Ile Pro Val Trp Met His Gln Ser Pro Asp
    130                 135                 140

Ile Ser Thr Val Phe Thr Ile His Asn Leu Ala Tyr Gln Gly Pro Trp
145                 150                 155                 160

Arg Gly Phe Leu Glu Arg Asn Thr Trp Cys Pro Trp Tyr Met Asp Gly
                165                 170                 175

Asp Asn Val Met Ala Ser Ala Leu Met Phe Ala Asp Gln Val Asn Thr
            180                 185                 190

Val Ser Pro Thr Tyr Ala Gln Gln Ile Gln Thr Lys Val Tyr Gly Glu
        195                 200                 205

Lys Leu Glu Gly Leu Leu Ser Trp Ile Ser Gly Lys Ser Arg Gly Ile
    210                 215                 220
```

Val Asn Gly Ile Asp Val Glu Leu Tyr Asn Pro Ser Asn Asp Gln Ala
225                 230                 235                 240

Leu Val Lys Gln Phe Ser Thr Thr Asn Leu Glu Asp Arg Ala Ala Asn
            245                 250                 255

Lys Val Ile Ile Gln Glu Thr Gly Leu Glu Val Asn Ser Lys Ala
            260                 265                 270

Phe Leu Met Ala Met Val Thr Arg Leu Val Glu Gln Lys Gly Ile Asp
            275                 280                 285

Leu Leu Leu Asn Ile Leu Glu Gln Phe Met Ala Tyr Thr Asp Ala Gln
            290                 295                 300

Leu Ile Ile Leu Gly Thr Gly Asp Arg His Tyr Glu Thr Gln Leu Trp
305                 310                 315                 320

Gln Thr Ala Tyr Arg Phe Lys Gly Arg Met Ser Val Gln Leu Leu Tyr
                325                 330                 335

Asn Asp Ala Leu Ser Arg Arg Ile Tyr Ala Gly Ser Asp Val Phe Leu
            340                 345                 350

Met Pro Ser Arg Phe Glu Pro Cys Gly Ile Ser Gln Met Met Ala Met
            355                 360                 365

Arg Tyr Gly Ser Val Pro Ile Val Arg Arg Thr Gly Gly Leu Val Asp
370                 375                 380

Thr Val Ser Phe His Asp Pro Ile His Gln Thr Gly Thr Gly Phe Ser
385                 390                 395                 400

Phe Asp Arg Tyr Glu Pro Leu Asp Met Tyr Thr Cys Met Val Arg Ala
                405                 410                 415

Trp Glu Ser Phe Arg Tyr Lys Lys Asp Trp Ala Glu Leu Gln Arg Arg
                420                 425                 430

Gly Met Ser His Asp Phe Ser Trp Tyr Lys Ser Ala Gly Glu Tyr Leu
            435                 440                 445

Lys Met Tyr Arg Gln Ser Ile Lys Glu Ala Pro Glu Leu Thr Thr Asp
450                 455                 460

Glu Ala Glu Lys Ile Thr Tyr Leu Val Lys Lys His Ala Ile
465                 470                 475

<210> SEQ ID NO 59
<211> LENGTH: 1320
<212> TYPE: DNA
<213> ORGANISM: Synechocystis sp. PCC 6803

<400> SEQUENCE: 59
gtgtgttgtt ggcaatcgag aggtctgctt gtgaaacgtg tcttagcgat tatcctgggc    60
ggtggggccg ggacccgcct ctatccttta accaaactca gagccaaacc cgcagttccc   120
ttggccggaa agtatcgcct catcgatatt cccgtcagta attgcatcaa ctcagaaatc   180
gttaaaattt acgtccttac ccagtttaat tccgcctccc ttaaccgtca catcagccgg   240
gcctataatt tttccggctt ccaagaagga tttgtggaag tcctcgccgc caacaaaacc   300
aaagataatc ctgattggtt tcagggcact gctgatgcgg tacggcaata cctctggttg   360
tttagggaat gggacgtaga tgaatatctt attctgtccg gcgaccatct ctaccgcatg   420
gattacgccc aatttgttaa aagacaccgg gaaaccaatg ccgacataac cctttccgtt   480
gtgcccgtgg atgacagaaa ggcacccgag ctgggcttaa tgaaaatcga cgcccagggc   540
agaattactg acttttctga aaagccccag ggggaagccc tccgggccat gcaggtggac   600
accagcgttt gggcctaagt gcgagaagaa gctaagctta atccttacat tgcctccatg   660
ggcatttacg ttttcaagaa ggaagtattg cacaacctcc tggaaaaata tgaaggggca   720

```
acggactttg gcaaagaaat cattcctgat tcagccagtg atcacaatct gcaagcctat    780
ctctttgatg actattggga agacattggt accattgaag ccttctatga ggctaattta    840
gccctgacca aacaacctag tcccgacttt agttttata cgaaaaagc ccccatctat      900 accagggtc gttatcttcc ccccaccaaa atgttgaatt ccaccgtgac ggaatccatg     960
atcggggaag gttgcatgat taagcaatgt cgcatccacc actcagtttt aggcattcgc   1020
agtcgcattg aatctgattg caccattgag atactttgg tgatgggcaa tgatttctac    1080
gaatcttcat cagaacgaga caccctcaaa gcccggggg aaattgccgc tggcataggt    1140
tccggcacca ctatccgccg agccatcatc gacaaaaatg cccgcatcgg caaaaacgtc   1200
atgattgtca acaaggaaaa tgtccaggag gctaaccggg aagagttagg ttttacatc    1260 cgcaatggca tcgtagtagt gattaaaaat gtcacgatcg ccgacggcac ggtaatctag   1320
```

<210> SEQ ID NO 60
<211> LENGTH: 439
<212> TYPE: PRT
<213> ORGANISM: Synechocystis sp. PCC 6803

<400> SEQUENCE: 60

```
Met Cys Cys Trp Gln Ser Arg Gly Leu Leu Val Lys Arg Val Leu Ala
1               5                   10                  15

Ile Ile Leu Gly Gly Gly Ala Gly Thr Arg Leu Tyr Pro Leu Thr Lys
            20                  25                  30

Leu Arg Ala Lys Pro Ala Val Pro Leu Ala Gly Lys Tyr Arg Leu Ile
        35                  40                  45

Asp Ile Pro Val Ser Asn Cys Ile Asn Ser Glu Ile Val Lys Ile Tyr
    50                  55                  60

Val Leu Thr Gln Phe Asn Ser Ala Ser Leu Asn Arg His Ile Ser Arg
65                  70                  75                  80

Ala Tyr Asn Phe Ser Gly Phe Gln Glu Gly Phe Val Glu Val Leu Ala
                85                  90                  95

Ala Gln Gln Thr Lys Asp Asn Pro Asp Trp Phe Gln Gly Thr Ala Asp
            100                 105                 110

Ala Val Arg Gln Tyr Leu Trp Leu Phe Arg Glu Trp Asp Val Asp Glu
        115                 120                 125

Tyr Leu Ile Leu Ser Gly Asp His Leu Tyr Arg Met Asp Tyr Ala Gln
    130                 135                 140

Phe Val Lys Arg His Arg Glu Thr Asn Ala Asp Ile Thr Leu Ser Val
145                 150                 155                 160

Val Pro Val Asp Asp Arg Lys Ala Pro Glu Leu Gly Leu Met Lys Ile
                165                 170                 175

Asp Ala Gln Gly Arg Ile Thr Asp Phe Ser Glu Lys Pro Gln Gly Glu
            180                 185                 190

Ala Leu Arg Ala Met Gln Val Asp Thr Ser Val Leu Gly Leu Ser Ala
        195                 200                 205

Glu Lys Ala Lys Leu Asn Pro Tyr Ile Ala Ser Met Gly Ile Tyr Val
    210                 215                 220

Phe Lys Lys Glu Val Leu His Asn Leu Leu Glu Lys Tyr Glu Gly Ala
225                 230                 235                 240

Thr Asp Phe Gly Lys Glu Ile Ile Pro Asp Ser Ala Ser Asp His Asn
                245                 250                 255

Leu Gln Ala Tyr Leu Phe Asp Asp Tyr Trp Glu Asp Ile Gly Thr Ile
            260                 265                 270
```

```
Glu Ala Phe Tyr Glu Ala Asn Leu Ala Leu Thr Lys Gln Pro Ser Pro
        275                 280                 285

Asp Phe Ser Phe Tyr Asn Glu Lys Ala Pro Ile Tyr Thr Arg Gly Arg
    290                 295                 300

Tyr Leu Pro Pro Thr Lys Met Leu Asn Ser Thr Val Thr Glu Ser Met
305                 310                 315                 320

Ile Gly Glu Gly Cys Met Ile Lys Gln Cys Arg Ile His His Ser Val
                325                 330                 335

Leu Gly Ile Arg Ser Arg Ile Glu Ser Asp Cys Thr Ile Glu Asp Thr
            340                 345                 350

Leu Val Met Gly Asn Asp Phe Tyr Glu Ser Ser Glu Arg Asp Thr
        355                 360                 365

Leu Lys Ala Arg Gly Glu Ile Ala Ala Gly Ile Gly Ser Gly Thr Thr
    370                 375                 380

Ile Arg Arg Ala Ile Ile Asp Lys Asn Ala Arg Ile Gly Lys Asn Val
385                 390                 395                 400

Met Ile Val Asn Lys Glu Asn Val Gln Glu Ala Asn Arg Glu Glu Leu
                405                 410                 415

Gly Phe Tyr Ile Arg Asn Gly Ile Val Val Ile Lys Asn Val Thr
            420                 425                 430

Ile Ala Asp Gly Thr Val Ile
            435
```

<210> SEQ ID NO 61
<211> LENGTH: 1290
<212> TYPE: DNA
<213> ORGANISM: Nostoc sp. PCC 7120

<400> SEQUENCE: 61

```
gtgaaaaaag tcttagcaat tattcttggt ggtggtgcgg gtactcgcct ttacccacta      60
accaaactcc gcgctaaacc ggcagtacca gtggcaggga ataccgcct aatagatatc     120
cctgtcagta actgcattaa ttcggaaatt tttaaaatct acgtattaac acaatttaac    180
tcagcttctc tcaatcgcca cattgcccgt acctacaact ttagtggttt tagcgagggt    240
tttgtggaag tgctggccgc ccagcagaca ccagagaacc ctaactggtt ccaaggtaca    300
gccgatgctg tacgtcagta tctctggatg ttacaagagt gggacgtaga tgaattttg    360
atcctgtcgg gggatcacct gtaccggatg gactatcgcc tatttatcca gcgccatcga    420
gaaaccaatg cggatatcac actttccgta attcccattg atgatcgccg cgcctcggat    480
tttggtttaa tgaaaatcga taactctgga cgagtcattg atttcagtga aaacccaag    540
ggcgaagcct taaccaaaat gcgtgttgat accacggttt taggcttgac accagaacag    600
gcggcatcac agccttacat tgcctcgatg gggattacg tatttaaaaa agacgttttg    660
atcaagctgt tgaaggaagc tttagaacgt actgatttcg gcaaagaaat tattcctgat    720
gccgccaaag atcacaacgt tcaagcttac ctattcgatg actactggga agatattggg    780
acaatcgaag cttttttataa cgccaattta gcgttaactc agcagcccat gccgcccttt    840
agcttctacg atgaagaagc acctatttat cccgcgctc gttacttacc acccacaaaa    900
ctattagatt gccacgttac agaatcaatc attggcgaag ctgtattct gaaaaactgt    960
cgcattcaac actcagtatt gggagtgcga tcgcgtattg aaactggctg catgatcgaa   1020
gaatctttac tcatgggtgc cgacttctac caagcttcag tggaacgcca gtgcagcatc   1080
gataaaggag acatccctgt aggcatcggt ccagatacaa tcattcgccg tgccatcatc   1140
```

```
gataaaaatg cccgcatcgg tcacgatgtc aaaattatca ataaagacaa cgtgcaagaa      1200
gccgaccgcg aaagtcaagg attttacatc cgcagtggca ttgtcgtcgt cctcaaaaat      1260
gccgttatta cagatggcac aatcatttag                                       1290
```

<210> SEQ ID NO 62
<211> LENGTH: 429
<212> TYPE: PRT
<213> ORGANISM: Nostoc sp. PCC 7120

<400> SEQUENCE: 62

```
Met Lys Lys Val Leu Ala Ile Ile Leu Gly Gly Gly Ala Gly Thr Arg
 1               5                  10                  15

Leu Tyr Pro Leu Thr Lys Leu Arg Ala Lys Pro Ala Val Pro Val Ala
            20                  25                  30

Gly Lys Tyr Arg Leu Ile Asp Ile Pro Val Ser Asn Cys Ile Asn Ser
        35                  40                  45

Glu Ile Phe Lys Ile Tyr Val Leu Thr Gln Phe Asn Ser Ala Ser Leu
    50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
        115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ala Leu Glu Arg Thr Asp Phe Gly Lys Glu Ile Ile Pro Asp
225                 230                 235                 240

Ala Ala Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285

Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Met Ile Glu Glu Ser Leu Leu Met Gly Ala Asp Phe Tyr Gln Ala
```

```
                340             345             350
Ser Val Glu Arg Gln Cys Ser Ile Asp Lys Gly Asp Ile Pro Val Gly
            355                 360                 365

Ile Gly Pro Asp Thr Ile Ile Arg Arg Ala Ile Ile Asp Lys Asn Ala
        370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
                420                 425

<210> SEQ ID NO 63
<211> LENGTH: 1290
<212> TYPE: DNA
<213> ORGANISM: Anabaena variabilis

<400> SEQUENCE: 63
gtgaaaaaag tcttagcaat tattcttggt ggtggtgcgg gtactcgcct ttacccacta      60
accaaactcc gcgctaaacc ggcagtacca gtggcaggga ataccgcct aatagatatc     120 cctgtcagta actgcattaa ttcggaaatt tttaaaatct acgtattaac acaatttaac    180
tcagcttctc tcaatcgcca cattgcccgt acctacaact ttagtggttt tagcgagggt    240
tttgtggaag tgctggccgc cagcagaca ccagagaacc ctaactggtt ccaaggtaca     300
gccgatgctg tacgtcagta tctctggatg ttacaagagt gggacgtaga tgaattttg     360 atcctgtcag gagatcacct gtaccggatg gattatcgcc tatttatcca gcgccatcga    420
gaaaccaatg cggatatcac actttccgta attcccattg acgatcgccg cgcctcggat    480
tttggtttaa tgaagatcga taactctgga cgagtcatcg attttagcga aaacccaaa    540 ggcgaagcct taaccaaaat gcgtgttgat accaccgttt taggcttgac accagaacag    600
gcagcatcac agccttacat cgcctcgatg gggatttacg tatttaaaaa agatgttttg    660
atcaaactgt tgaaggaatc tttagaacgt actgatttcg gcaaagaaat tattcctgat    720
gcctccaaag atcacaacgt tcaagcttac ttattcgatg actactggga agatattggg    780
acaatcgaag cttttatata tgctaattta gcattgactc agcagcccat gccgcccttt    840
agcttctacg acgaagaagc accaatttat acccgcgcac gttacttacc acccacaaaa    900
ctattagatt gccacgttac agaatcaatc attggcgaag gctgtattct gaaaaactgt    960
cgcattcaac actcagtatt gggagtgcga tcgcgtattg aaaccggctg cgtcatcgaa   1020
gaatctttac tcatgggtgc cgacttctac caagcttcag tggaacgcca gtgcagcatt   1080
gacaaaggag acatccccgt aggcatcggc ccagatacca ttattcgccg tgccatcatc   1140
gataaaaatg cccgcatcgg tcacgatgtc aaaattatca ataaagacaa cgtgcaggaa   1200
gccgaccgcg aaagtcaagg attttacatc gcagtggca ttgtcgtcgt tctcaaaaat    1260
gccgtcatta ccgatggcac aataattag                                     1290

<210> SEQ ID NO 64
<211> LENGTH: 429
<212> TYPE: PRT
<213> ORGANISM: Anabaena variabilis

<400> SEQUENCE: 64

Met Lys Lys Val Leu Ala Ile Ile Leu Gly Gly Gly Ala Gly Thr Arg
1               5                   10                  15
```

```
Leu Tyr Pro Leu Thr Lys Leu Arg Ala Lys Pro Ala Val Pro Val Ala
            20                  25                  30

Gly Lys Tyr Arg Leu Ile Asp Ile Pro Val Ser Asn Cys Ile Asn Ser
            35                  40                  45

Glu Ile Phe Lys Ile Tyr Val Leu Thr Gln Phe Asn Ser Ala Ser Leu
50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
            115                 120                 125

Arg Met Asp Tyr Arg Leu Phe Ile Gln Arg His Arg Glu Thr Asn Ala
130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
            195                 200                 205

Ser Met Gly Ile Tyr Val Phe Lys Lys Asp Val Leu Ile Lys Leu Leu
210                 215                 220

Lys Glu Ser Leu Glu Arg Thr Asp Phe Gly Lys Glu Ile Ile Pro Asp
225                 230                 235                 240

Ala Ser Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
            275                 280                 285

Ile Tyr Thr Arg Ala Arg Tyr Leu Pro Pro Thr Lys Leu Leu Asp Cys
290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Val Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
            355                 360                 365

Ile Gly Pro Asp Thr Ile Ile Arg Arg Ala Ile Ile Asp Lys Asn Ala
            370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
            420                 425
```

<210> SEQ ID NO 65
<211> LENGTH: 1287
<212> TYPE: DNA
<213> ORGANISM: Trichodesmium erythraeum IMS 101

<400> SEQUENCE: 65

| | | |
|---|---|---|
| gtgaaaaacg tactaagtat aattctaggc ggtggcgcag gtacccgttt atatccctta | 60 |
| acaaaactac gggccaagcc tgcagtgccc ctagcaggaa atatcgtttt aatagatatt | 120 |
| cctataagta attgcataaa ctcagaaatc cagaaaattt atgttttgac ccaatttaac | 180 |
| tcagcttctc taaaccgcca tatcactcgt acctataact tctcaggttt cagtgatggt | 240 |
| tttgtcgaag ttctagcagc tcaacaaact aaagataatc cagagtggtt tcaaggaaca | 300 |
| gcagatgctg tccgtaaata tatatggtta ttcaaagagt gggatattga ttattatcta | 360 |
| attctctctg gagaccatct ctaccgtatg gactaccgag actttgtcca acgccatatc | 420 |
| gacaccaagg cagatatcac cctttctgtc ttgcctattg atgaagcacg ggcctccgag | 480 |
| tttggcgtca tgaaaattga taactcaggt cgaattgttg aatttagtga aaaaccgaaa | 540 |
| ggtaatgccc ttaaagctat ggcagttgat acttctattt taggagtcag tccagaaata | 600 |
| gctacaaaac aaccttatat tgcttctatg ggaatttatg tatttaataa agatgcaatg | 660 |
| atcaaactta tagaagattc agaggataca gatttggta ggaaatttt acccaagtcg | 720 |
| gctcaatctt ataatcttca agcctaccca ttccaaggtt actgggaaga catcggaacc | 780 |
| atcaaatcat tttatgaagc taatttggct ttgactcaac agcctcagcc acccttagc | 840 |
| ttttatgatg aacaagcccc tatctatacc cgctctcgtt atttacctcc gagcaaactt | 900 |
| ttggactgtg agattacaga gtcaattgtg ggagaaggtt gtattcttaa aaaatgtcgg | 960 |
| attgaccatt gtgtcttagg agtgcgatcg cgtatagaag ctaattgtat aattcaagat | 1020 |
| tctctgctaa tgggttcaga tttctatgaa tctcctacag aacgtcgata tggcctaaaa | 1080 |
| aaaggttctg tacctttggg tattggtgct gaaacgaaaa ttcgtggagc aattattgac | 1140 |
| aaaaatgccc gcattggttg taatgtccaa ataatcaata aggacaatgt agaagaagcc | 1200 |
| caacgtgagg aggaagggtt tatcattcgc agtggtattg ttgttgtttt gaaaaatgct | 1260 |
| actattcccg atggtacagt gatttag | 1287 |

<210> SEQ ID NO 66
<211> LENGTH: 428
<212> TYPE: PRT
<213> ORGANISM: Trichodesmium erythraeum IMS 101

<400> SEQUENCE: 66

Met Lys Asn Val Leu Ser Ile Ile Leu Gly Gly Gly Ala Gly Thr Arg
1               5                   10                  15

Leu Tyr Pro Leu Thr Lys Leu Arg Ala Lys Pro Ala Val Pro Leu Ala
            20                  25                  30

Gly Lys Tyr Arg Leu Ile Asp Ile Pro Ile Ser Asn Cys Ile Asn Ser
        35                  40                  45

Glu Ile Gln Lys Ile Tyr Val Leu Thr Gln Phe Asn Ser Ala Ser Leu
    50                  55                  60

Asn Arg His Ile Thr Arg Thr Tyr Asn Phe Ser Gly Phe Ser Asp Gly
65                  70                  75                  80

Phe Val Glu Val Leu Ala Ala Gln Gln Thr Lys Asp Asn Pro Glu Trp
                85                  90                  95

Phe Gln Gly Thr Ala Asp Ala Val Arg Lys Tyr Ile Trp Leu Phe Lys

```
                100             105             110
Glu Trp Asp Ile Asp Tyr Tyr Leu Ile Leu Ser Gly Asp His Leu Tyr
            115             120             125

Arg Met Asp Tyr Arg Asp Phe Val Gln Arg His Ile Asp Thr Lys Ala
            130             135             140

Asp Ile Thr Leu Ser Val Leu Pro Ile Asp Glu Ala Arg Ala Ser Glu
145             150             155             160

Phe Gly Val Met Lys Ile Asp Asn Ser Gly Arg Ile Val Glu Phe Ser
            165             170             175

Glu Lys Pro Lys Gly Asn Ala Leu Lys Ala Met Ala Val Asp Thr Ser
            180             185             190

Ile Leu Gly Val Ser Pro Glu Ile Ala Thr Lys Gln Pro Tyr Ile Ala
            195             200             205

Ser Met Gly Ile Tyr Val Phe Asn Lys Asp Ala Met Ile Lys Leu Ile
            210             215             220

Glu Asp Ser Glu Asp Thr Asp Phe Gly Lys Glu Ile Leu Pro Lys Ser
225             230             235             240

Ala Gln Ser Tyr Asn Leu Gln Ala Tyr Pro Phe Gln Gly Tyr Trp Glu
            245             250             255

Asp Ile Gly Thr Ile Lys Ser Phe Tyr Glu Ala Asn Leu Ala Leu Thr
            260             265             270

Gln Gln Pro Gln Pro Pro Phe Ser Phe Tyr Asp Glu Gln Ala Pro Ile
            275             280             285

Tyr Thr Arg Ser Arg Tyr Leu Pro Pro Ser Lys Leu Leu Asp Cys Glu
            290             295             300

Ile Thr Glu Ser Ile Val Gly Glu Gly Cys Ile Leu Lys Lys Cys Arg
305             310             315             320

Ile Asp His Cys Val Leu Gly Val Arg Ser Arg Ile Glu Ala Asn Cys
            325             330             335

Ile Ile Gln Asp Ser Leu Leu Met Gly Ser Asp Phe Tyr Glu Ser Pro
            340             345             350

Thr Glu Arg Arg Tyr Gly Leu Lys Lys Gly Ser Val Pro Leu Gly Ile
            355             360             365

Gly Ala Glu Thr Lys Ile Arg Gly Ala Ile Ile Asp Lys Asn Ala Arg
            370             375             380

Ile Gly Cys Asn Val Gln Ile Ile Asn Lys Asp Asn Val Glu Glu Ala
385             390             395             400

Gln Arg Glu Glu Glu Gly Phe Ile Ile Arg Ser Gly Ile Val Val Val
            405             410             415

Leu Lys Asn Ala Thr Ile Pro Asp Gly Thr Val Ile
            420             425

<210> SEQ ID NO 67
<211> LENGTH: 1293
<212> TYPE: DNA
<213> ORGANISM: Synechococcus elongatus PCC 7942

<400> SEQUENCE: 67
gtgaaaaacg tgctggcgat cattctcggt ggaggcgcag gcagtcgtct ctatccacta      60
accaaacagc gcgccaaacc agcggtcccc ctggcgggca ataccgcttt gatcgatatt     120
cccgtcagca attgcatcaa cgctgacatc aacaaaatct atgtgctgac gcagtttaac     180
tctgcctcgc tcaaccgcca cctcagtcag acctacaacc tctccagcgg ctttggcaat     240
ggctttgttg aggtgctagc agctcagatt acgccggaga ccccaactg gttccaaggc     300
```

```
accgccgatg cggttcgcca gtatctctgg ctaatcaaag agtgggatgt ggatgagtac    360
ctgatcctgt cggggggatca tctctaccgc atggactata gccagttcat tcagcggcac    420
cgagacacca atgccgacat cacactctcg gtcttgccga tcgatgaaaa gcgcgcctct    480
gattttggcc tgatgaagct agatggcagc ggccgggtgg tcgagttcag cgaaaagccc    540
aaaggggatg aactcagggc gatgcaagtc gataccacga tcctcgggct tgaccctgtc    600
gctgctgctg cccagcccttt cattgcctcg atgggcatct acgtcttcaa gcgggatgtt    660
ctgatcgatt tgctcagcca tcatcccgag caaaccgact tggcaaagga agtgattccc    720
gctgcagcca cccgctacaa cacccaagcc tttctgttca cgactactg ggaagacatc    780 ggcacgatcg cctcattcta cgaggccaat ctggcgctga ctcagcaacc tagcccaccc    840
ttcagcttct acgacgagca ggcgccgatt tacacccgcg ctcgctacct gccgccaacc    900
aagctgctcg attgccaggt gacccagtcg atcattggcg agggctgcat tctcaagcaa    960
tgcaccgttc agaattccgt cttagggatt cgctcccgca ttgaggccga ctgcgtgatc    1020
caggacgcct tgttgatggg cgctgacttc tacgaaacct cggagctacg gcaccagaat    1080
cgggccaatg gcaaagtgcc gatgggaatc ggcagtggca gcaccatccg tcgcgccatc    1140
gtcgacaaaa atgcccacat tggccagaac gttcagatcg tcaacaaaga ccatgtggaa    1200
gaggccgatc gcgaagatct gggctttatg atccgcagcg gcattgtcgt tgtggtcaaa    1260
ggggcggtta ttcccgacaa cacggtgatc taa                                  1293

<210> SEQ ID NO 68
<211> LENGTH: 430
<212> TYPE: PRT
<213> ORGANISM: Synechococcus elongatus PCC 7942

<400> SEQUENCE: 68

Met Lys Asn Val Leu Ala Ile Ile Leu Gly Gly Gly Ala Gly Ser Arg
 1               5                  10                  15

Leu Tyr Pro Leu Thr Lys Gln Arg Ala Lys Pro Ala Val Pro Leu Ala
            20                  25                  30

Gly Lys Tyr Arg Leu Ile Asp Ile Pro Val Ser Asn Cys Ile Asn Ala
        35                  40                  45

Asp Ile Asn Lys Ile Tyr Val Leu Thr Gln Phe Asn Ser Ala Ser Leu
    50                  55                  60

Asn Arg His Leu Ser Gln Thr Tyr Asn Leu Ser Ser Gly Phe Gly Asn
65                  70                  75                  80

Gly Phe Val Glu Val Leu Ala Ala Gln Ile Thr Pro Glu Asn Pro Asn
                85                  90                  95

Trp Phe Gln Gly Thr Ala Asp Ala Val Arg Gln Tyr Leu Trp Leu Ile
            100                 105                 110

Lys Glu Trp Asp Val Asp Glu Tyr Leu Ile Leu Ser Gly Asp His Leu
        115                 120                 125

Tyr Arg Met Asp Tyr Ser Gln Phe Ile Gln Arg His Arg Asp Thr Asn
    130                 135                 140

Ala Asp Ile Thr Leu Ser Val Leu Pro Ile Asp Glu Lys Arg Ala Ser
145                 150                 155                 160

Asp Phe Gly Leu Met Lys Leu Asp Gly Ser Gly Arg Val Val Glu Phe
                165                 170                 175

Ser Glu Lys Pro Lys Gly Asp Glu Leu Arg Ala Met Gln Val Asp Thr
            180                 185                 190
```

```
Thr Ile Leu Gly Leu Asp Pro Val Ala Ala Ala Gln Pro Phe Ile
            195                 200                 205
Ala Ser Met Gly Ile Tyr Val Phe Lys Arg Asp Val Leu Ile Asp Leu
210                 215                 220
Leu Ser His His Pro Glu Gln Thr Asp Phe Gly Lys Glu Val Ile Pro
225                 230                 235                 240
Ala Ala Ala Thr Arg Tyr Asn Thr Gln Ala Phe Leu Phe Asn Asp Tyr
                245                 250                 255
Trp Glu Asp Ile Gly Thr Ile Ala Ser Phe Tyr Glu Ala Asn Leu Ala
                260                 265                 270
Leu Thr Gln Gln Pro Ser Pro Pro Phe Ser Phe Tyr Asp Glu Gln Ala
            275                 280                 285
Pro Ile Tyr Thr Arg Ala Arg Tyr Leu Pro Pro Thr Lys Leu Leu Asp
        290                 295                 300
Cys Gln Val Thr Gln Ser Ile Ile Gly Glu Gly Cys Ile Leu Lys Gln
305                 310                 315                 320
Cys Thr Val Gln Asn Ser Val Leu Gly Ile Arg Ser Arg Ile Glu Ala
                325                 330                 335
Asp Cys Val Ile Gln Asp Ala Leu Leu Met Gly Ala Asp Phe Tyr Glu
                340                 345                 350
Thr Ser Glu Leu Arg His Gln Asn Arg Ala Asn Gly Lys Val Pro Met
            355                 360                 365
Gly Ile Gly Ser Gly Ser Thr Ile Arg Arg Ala Ile Val Asp Lys Asn
        370                 375                 380
Ala His Ile Gly Gln Asn Val Gln Ile Val Asn Lys Asp His Val Glu
385                 390                 395                 400
Glu Ala Asp Arg Glu Asp Leu Gly Phe Met Ile Arg Ser Gly Ile Val
                405                 410                 415
Val Val Val Lys Gly Ala Val Ile Pro Asp Asn Thr Val Ile
                420                 425                 430
```

<210> SEQ ID NO 69
<211> LENGTH: 1296
<212> TYPE: DNA
<213> ORGANISM: Synechococcus sp. WH8102

<400> SEQUENCE: 69

| | | | | | |
|---|---|---|---|---|---|
| atgaagcggg | ttttggccat | cattctcggc | ggcggtgccg | ggactcgtct | ctacccgctc | 60 |
| accaagatgc | gcgccaagcc | ggccgtcccc | ttggccggta | agtatcgact | gattgatatc | 120 |
| cccatcagca | actgcatcaa | ctcgaacatc | aacaagatgt | acgtgatgac | gcagttcaac | 180 |
| agtgcgtctc | tcaatcgtca | cctcagccag | acgttcaacc | tgagcgcatc | cttcggtcag | 240 |
| ggattcgtcg | aggtgcttgc | tgcccagcag | acgcctgaca | gtccatcctg | gtttgaaggc | 300 |
| actgccgacg | ctgtgcggaa | gtaccagtgg | ctgttccagg | aatgggatgt | cgatgaatac | 360 |
| ctgatcctgt | ccggtgacca | gctgtaccgg | atgattaca | gcctgttcgt | tgaacatcac | 420 |
| cgcagcactg | gtgctgacct | caccgttgca | gcccttcctg | tggacccgaa | acaggccgag | 480 |
| gcgttcggct | tgatgcgcac | ggatggtgac | ggagacatca | aggagttccg | cgaaaagccc | 540 |
| aagggtgatt | ctttgcttga | gatggcggtt | gacaccagcc | gatttggact | cagtgcgaat | 600 |
| tcggccaagg | agcgtcccta | cctggcgtcg | atggggattt | atgtcttcag | cagagacact | 660 |
| ctgttcgacc | tgctcgattc | caatcctggt | tataaggact | tcggcaagga | agtcattcct | 720 |
| gaggccctca | agcgtggcga | caagctgaag | agctatgtct | ttgacgatta | ttgggaagat | 780 |

```
atcggaacga tcggagcgtt ctacgaggcc aacctggcgc tcacccagca acccacaccc    840
cccttcagct tctacgacga gaagttcccg atctacactc gtccccgcta tttaccccg     900 agcaaactgg ttgatgctca gatcaccaat tcgatcgttg gcgaaggctc aattttgaag    960
tcatgcagca ttcatcactg cgttttgggt gttcgcagtc gcattgaaac cgatgtggtg   1020
ctgcaagaca ccttggtgat gggcgctgac ttctttgaat ccagtgatga gcgtgccgtg   1080
cttcgcgagc gtggtggtat tccggtcggg gtgggccaag gtacgactgt gaagcgcgcc   1140
atcctcgata aaaacgctcg catcggatcc aacgtcacca tcgtcaacaa ggatcacgtc   1200
gaggaagctg atcgttccga tcagggcttc tatattcgta atggcattgt tgttgttgtc   1260
aagaacgcca ccatccagga cggaactgtg atctga                             1296
```

<210> SEQ ID NO 70
<211> LENGTH: 431
<212> TYPE: PRT
<213> ORGANISM: Synechococcus sp. WH8102

<400> SEQUENCE: 70

```
Met Lys Arg Val Leu Ala Ile Ile Leu Gly Gly Ala Gly Thr Arg
 1               5                  10                  15

Leu Tyr Pro Leu Thr Lys Met Arg Ala Lys Pro Ala Val Pro Leu Ala
                20                  25                  30

Gly Lys Tyr Arg Leu Ile Asp Ile Pro Ile Ser Asn Cys Ile Asn Ser
            35                  40                  45

Asn Ile Asn Lys Met Tyr Val Met Thr Gln Phe Asn Ser Ala Ser Leu
        50                  55                  60

Asn Arg His Leu Ser Gln Thr Phe Asn Leu Ser Ala Ser Phe Gly Gln
65                  70                  75                  80

Gly Phe Val Glu Val Leu Ala Ala Gln Gln Thr Pro Asp Ser Pro Ser
                85                  90                  95

Trp Phe Glu Gly Thr Ala Asp Ala Val Arg Lys Tyr Gln Trp Leu Phe
            100                 105                 110

Gln Glu Trp Asp Val Asp Glu Tyr Leu Ile Leu Ser Gly Asp Gln Leu
        115                 120                 125

Tyr Arg Met Asp Tyr Ser Leu Phe Val Glu His His Arg Ser Thr Gly
    130                 135                 140

Ala Asp Leu Thr Val Ala Ala Leu Pro Val Asp Pro Lys Gln Ala Glu
145                 150                 155                 160

Ala Phe Gly Leu Met Arg Thr Asp Gly Asp Gly Asp Ile Lys Glu Phe
                165                 170                 175

Arg Glu Lys Pro Lys Gly Asp Ser Leu Leu Glu Met Ala Val Asp Thr
            180                 185                 190

Ser Arg Phe Gly Leu Ser Ala Asn Ser Ala Lys Glu Arg Pro Tyr Leu
        195                 200                 205

Ala Ser Met Gly Ile Tyr Val Phe Ser Arg Asp Thr Leu Phe Asp Leu
    210                 215                 220

Leu Asp Ser Asn Pro Gly Tyr Lys Asp Phe Gly Lys Glu Val Ile Pro
225                 230                 235                 240

Glu Ala Leu Lys Arg Gly Asp Lys Leu Lys Ser Tyr Val Phe Asp Asp
                245                 250                 255

Tyr Trp Glu Asp Ile Gly Thr Ile Gly Ala Phe Tyr Glu Ala Asn Leu
            260                 265                 270

Ala Leu Thr Gln Gln Pro Thr Pro Pro Phe Ser Phe Tyr Asp Glu Lys
        275                 280                 285
```

```
Phe Pro Ile Tyr Thr Arg Pro Arg Tyr Leu Pro Pro Ser Lys Leu Val
    290                 295                 300

Asp Ala Gln Ile Thr Asn Ser Ile Val Gly Glu Gly Ser Ile Leu Lys
305                 310                 315                 320

Ser Cys Ser Ile His His Cys Val Leu Gly Val Arg Ser Arg Ile Glu
                325                 330                 335

Thr Asp Val Val Leu Gln Asp Thr Leu Val Met Gly Ala Asp Phe Phe
            340                 345                 350

Glu Ser Ser Asp Glu Arg Ala Val Leu Arg Glu Arg Gly Gly Ile Pro
        355                 360                 365

Val Gly Val Gly Gln Gly Thr Thr Val Lys Arg Ala Ile Leu Asp Lys
    370                 375                 380

Asn Ala Arg Ile Gly Ser Asn Val Thr Ile Val Asn Lys Asp His Val
385                 390                 395                 400

Glu Glu Ala Asp Arg Ser Asp Gln Gly Phe Tyr Ile Arg Asn Gly Ile
                405                 410                 415

Val Val Val Val Lys Asn Ala Thr Ile Gln Asp Gly Thr Val Ile
            420                 425                 430
```

<210> SEQ ID NO 71
<211> LENGTH: 1296
<212> TYPE: DNA
<213> ORGANISM: Synechococcus sp. RCC 307

<400> SEQUENCE: 71

```
atgaaacggg ttctcgcaat cattctcggt ggcggtgcgg gtacgcggct ctatccgctg    60
accaaaatgc gggccaaacc agccgtgccg ctggcgggta agtaccgcct catcgacatc   120
cccgttagca actgcatcaa cagcgggatc aacaagatct atgtgctgac gcagttcaac   180
agcgcatcac tgaatcgcca catcgctcaa accttcaacc tctcctcggg gtttgatcaa   240
gggtttgttg aagttctggc ggcccagcag accccagata gccccagttg gtttgaagga   300
acagccgatg ctgttcgtaa atacgaatgg ctgctgcagg agtgggacat cgacgaagtg   360
ctgatccttt cgggtgacca gctctaccgg atggactatg cccatttttgt ggctcagcac   420
cgcgccagcg gcgctgacct caccgtggcc gccctcccgg ttgatcgcga gcaagcccag   480
agctttggct tgatgcacac cggtgcagaa gcctccatca ccaagttccg cgaaaagccc   540
aaaggcgagg cactcgatga gatgtcctgc gataccgcca gcatgggctt gagcgctgag   600
gaagcccatc gccggccgtt cctggcttcc atgggcatct acgtgttcaa gcgggacgtg   660
ctcttccgct tactggctga aaaccccggt gccactgact tcggtaagga gatcatcccc   720
aaggcactcg acgatggctt caaactccgc tcctatctct tcgacgatta ctgggaagac   780
atcggaacca tccgtgcttt ctatgaagcg aatctggcgc tgacgaccca gccgcgtccg   840
cccttctctt tctacgacaa gcgtttcccg atctacacac gtcatcgcta cctgccgccc   900
tccaagcttc aagatgcgca ggtcaccgac tccattgttg gtgagggggtc cattttgaag   960
gcttgcagta ttcaccactg cgtcttgggt gtgcgcagcc gcattgaaga cgaggttgcc  1020
ttgcaagaca ccctggtgat gggcaacgac ttctatgagt ccggcgaaga gcgggccatc  1080
ctgcgggaac gtggtggcat ccccatgggt gtgggccgag aaccacggt gaaaaggcc  1140
atcctcgata gaacgtccg catcggcagc aacgtcagca tcatcaacaa agacaacgtt  1200
gaggaagccg accgcgctga gcagggcttc tacatccgtg cgggattgt ggtgatcacc  1260
aaaaacgctt cgattcccga cgggatggtg atctga                            1296
```

<210> SEQ ID NO 72
<211> LENGTH: 431
<212> TYPE: PRT
<213> ORGANISM: Synechococcus sp. RCC 307

<400> SEQUENCE: 72

| | | | | | | | | | | | | | | |
|---|---|---|---|---|---|---|---|---|---|---|---|---|---|---|
| Met | Lys | Arg | Val | Leu | Ala | Ile | Ile | Leu | Gly | Gly | Ala | Gly | Thr | Arg |
| 1 | | | | 5 | | | | | 10 | | | | | 15 |
| Leu | Tyr | Pro | Leu | Thr | Lys | Met | Arg | Ala | Lys | Pro | Ala | Val | Pro | Leu | Ala |
| | | | 20 | | | | | 25 | | | | | 30 | | |
| Gly | Lys | Tyr | Arg | Leu | Ile | Asp | Ile | Pro | Val | Ser | Asn | Cys | Ile | Asn | Ser |
| | | | 35 | | | | | 40 | | | | | 45 | | |
| Gly | Ile | Asn | Lys | Ile | Tyr | Val | Leu | Thr | Gln | Phe | Asn | Ser | Ala | Ser | Leu |
| 50 | | | | | 55 | | | | | 60 | | | | | |
| Asn | Arg | His | Ile | Ala | Gln | Thr | Phe | Asn | Leu | Ser | Ser | Gly | Phe | Asp | Gln |
| 65 | | | | | 70 | | | | | 75 | | | | | 80 |
| Gly | Phe | Val | Glu | Val | Leu | Ala | Ala | Gln | Gln | Thr | Pro | Asp | Ser | Pro | Ser |
| | | | | 85 | | | | | 90 | | | | | 95 | |
| Trp | Phe | Glu | Gly | Thr | Ala | Asp | Ala | Val | Arg | Lys | Tyr | Glu | Trp | Leu | Leu |
| | | | 100 | | | | | 105 | | | | | 110 | | |
| Gln | Glu | Trp | Asp | Ile | Asp | Glu | Val | Leu | Ile | Leu | Ser | Gly | Asp | Gln | Leu |
| | | | 115 | | | | | 120 | | | | | 125 | | |
| Tyr | Arg | Met | Asp | Tyr | Ala | His | Phe | Val | Ala | Gln | His | Arg | Ala | Ser | Gly |
| | | 130 | | | | | 135 | | | | | 140 | | | |
| Ala | Asp | Leu | Thr | Val | Ala | Ala | Leu | Pro | Val | Asp | Arg | Glu | Gln | Ala | Gln |
| 145 | | | | | 150 | | | | | 155 | | | | | 160 |
| Ser | Phe | Gly | Leu | Met | His | Thr | Gly | Ala | Glu | Ala | Ser | Ile | Thr | Lys | Phe |
| | | | | 165 | | | | | 170 | | | | | 175 | |
| Arg | Glu | Lys | Pro | Lys | Gly | Glu | Ala | Leu | Asp | Glu | Met | Ser | Cys | Asp | Thr |
| | | | 180 | | | | | 185 | | | | | 190 | | |
| Ala | Ser | Met | Gly | Leu | Ser | Ala | Glu | Glu | Ala | His | Arg | Arg | Pro | Phe | Leu |
| | | | 195 | | | | | 200 | | | | | 205 | | |
| Ala | Ser | Met | Gly | Ile | Tyr | Val | Phe | Lys | Arg | Asp | Val | Leu | Phe | Arg | Leu |
| | | 210 | | | | | 215 | | | | | 220 | | | |
| Leu | Ala | Glu | Asn | Pro | Gly | Ala | Thr | Asp | Phe | Gly | Lys | Glu | Ile | Ile | Pro |
| 225 | | | | | 230 | | | | | 235 | | | | | 240 |
| Lys | Ala | Leu | Asp | Asp | Gly | Phe | Lys | Leu | Arg | Ser | Tyr | Leu | Phe | Asp | Asp |
| | | | | 245 | | | | | 250 | | | | | 255 | |
| Tyr | Trp | Glu | Asp | Ile | Gly | Thr | Ile | Arg | Ala | Phe | Tyr | Glu | Ala | Asn | Leu |
| | | | 260 | | | | | 265 | | | | | 270 | | |
| Ala | Leu | Thr | Thr | Gln | Pro | Arg | Pro | Phe | Ser | Phe | Tyr | Asp | Lys | Arg | |
| | | | 275 | | | | | 280 | | | | | 285 | | |
| Phe | Pro | Ile | Tyr | Thr | Arg | His | Arg | Tyr | Leu | Pro | Pro | Ser | Lys | Leu | Gln |
| | | 290 | | | | | 295 | | | | | 300 | | | |
| Asp | Ala | Gln | Val | Thr | Asp | Ser | Ile | Val | Gly | Glu | Gly | Ser | Ile | Leu | Lys |
| 305 | | | | | 310 | | | | | 315 | | | | | 320 |
| Ala | Cys | Ser | Ile | His | His | Cys | Val | Leu | Gly | Val | Arg | Ser | Arg | Ile | Glu |
| | | | | 325 | | | | | 330 | | | | | 335 | |
| Asp | Glu | Val | Ala | Leu | Gln | Asp | Thr | Leu | Val | Met | Gly | Asn | Asp | Phe | Tyr |
| | | | 340 | | | | | 345 | | | | | 350 | | |
| Glu | Ser | Gly | Glu | Glu | Arg | Ala | Ile | Leu | Arg | Glu | Arg | Gly | Gly | Ile | Pro |
| | | | 355 | | | | | 360 | | | | | 365 | | |
| Met | Gly | Val | Gly | Arg | Gly | Thr | Thr | Val | Lys | Lys | Ala | Ile | Leu | Asp | Lys |

```
                370              375             380
Asn Val Arg Ile Gly Ser Asn Val Ser Ile Ile Asn Lys Asp Asn Val
385                 390              395                  400

Glu Glu Ala Asp Arg Ala Glu Gln Gly Phe Tyr Ile Arg Gly Gly Ile
                405             410                  415

Val Val Ile Thr Lys Asn Ala Ser Ile Pro Asp Gly Met Val Ile
            420              425              430

<210> SEQ ID NO 73
<211> LENGTH: 1290
<212> TYPE: DNA
<213> ORGANISM: Synechococcus sp. PCC 7002

<400> SEQUENCE: 73
gtgaaacgag tcctaggaat catacttggc ggcggcgcag gtactcgcct atatccgcta      60
acaaaactca gagctaagcc cgcagtacct ctagcaggca aatatcgtct cattgatatt    120
cctgttagca attgcattaa ttctgaaatt cataaaatct acattttaac ccaatttaat    180
tcagcatctt taaatcgtca cattagtcga acctacaact ttaccggctt caccgaaggc    240
tttaccgaag tactcgcagc ccaacaaact aaagaaaatc ccgattggtt ccaaggcacc    300
gccgacgctg tccgacagta cagttggctt ctagaagact gggatgtcga tgaatacatc    360
attctctccg gtgatcacct ctaccgtatg gattaccgtg aatttatcca gcgccaccgt    420
gacactgggg cagacatcac cctgtctgtg gttcccgtgg gcgaaaaagt agccccccgcc    480 tttgggttga tgaaaattga tgccaatggt cgtgtcgtgg actttagtga aaagcccact    540
ggtgaagccc ttaaggcgat gcaggtggat acccagtcct gggtctcga tccagagcag    600 gcgaaagaaa agccctacat tgcgtcgatg gggatctacg tctttaagaa acaagtactc    660
ctcgatctac tcaaagaagg caaagataaa accgatttcg ggaaagaaat tattcctgat    720
gcggccaagg actacaacgt tcaggcctat ctctttgatg attattgggc tgacattggg    780
accatcgaag cgttctatga agcaaacctt ggcttgacga agcagccgat cccacccttt    840
agtttctatg acgaaaaggc tcccatctac acccgggcgc gctacttacc gccgacgaag    900
gtgctcaacg ctgacgtgac agaatcgatg atcagcgaag gttgcatcat taaaaactgc    960
cgcattcacc actcagttct tggcattcgc accgtgtcg aagcggactg cactatcgaa   1020
gatacgatga tcatgggcgc agattattat cagcccctatg agaagcgcca ggattgtctc   1080
cgtcgtggca agcctcccat tgggattggt gaagggacaa cgattcgccg ggcgatcatc   1140
gataaaaatg cacgcatcgg taaaaacgtg atgatcgtca ataaggaaaa tgtggaggag   1200
tcaaaccgtg aggagcttgg ctactacatt cgcagcggca ttacagtggt gctaaagaac   1260
gccgttattc ccgacggtac ggtcatttaa                                   1290

<210> SEQ ID NO 74
<211> LENGTH: 429
<212> TYPE: PRT
<213> ORGANISM: Synechococcus sp. PCC 7002

<400> SEQUENCE: 74

Met Lys Arg Val Leu Gly Ile Ile Leu Gly Gly Gly Ala Gly Thr Arg
1               5                  10                  15

Leu Tyr Pro Leu Thr Lys Leu Arg Ala Lys Pro Ala Val Pro Leu Ala
            20                  25                  30

Gly Lys Tyr Arg Leu Ile Asp Ile Pro Val Ser Asn Cys Ile Asn Ser
        35                  40                  45
```

Glu Ile His Lys Ile Tyr Ile Leu Thr Gln Phe Asn Ser Ala Ser Leu
         50                  55                  60

Asn Arg His Ile Ser Arg Thr Tyr Asn Phe Thr Gly Phe Thr Glu Gly
 65                  70                  75                  80

Phe Thr Glu Val Leu Ala Ala Gln Gln Thr Lys Glu Asn Pro Asp Trp
                 85                  90                  95

Phe Gln Gly Thr Ala Asp Ala Val Arg Gln Tyr Ser Trp Leu Leu Glu
             100                 105                 110

Asp Trp Asp Val Asp Glu Tyr Ile Ile Leu Ser Gly Asp His Leu Tyr
         115                 120                 125

Arg Met Asp Tyr Arg Glu Phe Ile Gln Arg His Arg Asp Thr Gly Ala
130                 135                 140

Asp Ile Thr Leu Ser Val Val Pro Val Gly Glu Lys Val Ala Pro Ala
145                 150                 155                 160

Phe Gly Leu Met Lys Ile Asp Ala Asn Gly Arg Val Val Asp Phe Ser
                165                 170                 175

Glu Lys Pro Thr Gly Glu Ala Leu Lys Ala Met Gln Val Asp Thr Gln
            180                 185                 190

Ser Leu Gly Leu Asp Pro Glu Gln Ala Lys Lys Pro Tyr Ile Ala
        195                 200                 205

Ser Met Gly Ile Tyr Val Phe Lys Lys Gln Val Leu Leu Asp Leu Leu
    210                 215                 220

Lys Glu Gly Lys Asp Lys Thr Asp Phe Gly Lys Glu Ile Ile Pro Asp
225                 230                 235                 240

Ala Ala Lys Asp Tyr Asn Val Gln Ala Tyr Leu Phe Asp Asp Tyr Trp
                245                 250                 255

Ala Asp Ile Gly Thr Ile Glu Ala Phe Tyr Glu Ala Asn Leu Gly Leu
            260                 265                 270

Thr Lys Gln Pro Ile Pro Pro Phe Ser Phe Tyr Asp Glu Lys Ala Pro
        275                 280                 285

Ile Tyr Thr Arg Ala Arg Tyr Leu Pro Pro Thr Lys Val Leu Asn Ala
    290                 295                 300

Asp Val Thr Glu Ser Met Ile Ser Glu Gly Cys Ile Ile Lys Asn Cys
305                 310                 315                 320

Arg Ile His His Ser Val Leu Gly Ile Arg Thr Arg Val Glu Ala Asp
                325                 330                 335

Cys Thr Ile Glu Asp Thr Met Ile Met Gly Ala Asp Tyr Tyr Gln Pro
            340                 345                 350

Tyr Glu Lys Arg Gln Asp Cys Leu Arg Arg Gly Lys Pro Pro Ile Gly
        355                 360                 365

Ile Gly Glu Gly Thr Thr Ile Arg Arg Ala Ile Ile Asp Lys Asn Ala
    370                 375                 380

Arg Ile Gly Lys Asn Val Met Ile Val Asn Lys Glu Asn Val Glu Glu
385                 390                 395                 400

Ser Asn Arg Glu Glu Leu Gly Tyr Tyr Ile Arg Ser Gly Ile Thr Val
                405                 410                 415

Val Leu Lys Asn Ala Val Ile Pro Asp Gly Thr Val Ile
            420                 425

<210> SEQ ID NO 75
<211> LENGTH: 1704
<212> TYPE: DNA
<213> ORGANISM: Synechocystis sp. PCC 6803

<400> SEQUENCE: 75

```
gtgtctaagc ccctgatcgc cgccctccat tttttacaat ttttgtatat gacaagcaga    60
attaatcccc tcgccggcca gcatcccccc gccgacagcc ttttggatgt ggccaaactt   120
ttagacgact attaccgtca gcaaccggac ccggaaaatc ccgcccagtt agtgagcttt   180
ggtacctctg gccatcgggg ttctgccctc aacggtactt ttaatgaagc ccatattttg   240
gcggtgaccc aggcagtggt ggactatcgc caagcccagg cattacgggc cccctttat    300
atggggatgg atagccatgc tctgtcggaa ccagcccaga aaacggcgtt ggaagtgttg   360
gccgctaacc aagtagaaac tttttttaacc accgccacgg atttaacccg tttcaccccc   420
actccggcgg tatcctacgc cattttgacc cacaaccagg gacgtaaaga aggtttagcg   480
gacggcatta ttattacccc ttcccacaat cccccactg atggaggctt taaatataat    540
ccccctccg gtggcccggc ggaaccggaa gcgacccaat ggattcagaa ccgggccaat    600
gagttgctga aaatggcaa taaaacagtt aaacggctgg attacgagca ggcattaaaa   660
gccaccacca cccatgccca tgattttgtc actcccatg tggccggtct gcggacatc     720
attgacttgg atgtaattcg ttcagcgggc ttgcgcttgg gagttgaccc cctgggggga   780
gccaatgtgg gctattggga acccattgcc gctaaataca atttgaacat cagcttggtt   840
aatcccgggg tagatcccac gtttaaattt atgaccctgg attgggacgg caaaatccgc   900
atggattgtt cttccccta cgccatggcc agtttggtga aatcaaaga ccattacgac    960
attgcctttg caacgacac cgacggcgat cgccatggca ttgtcacccc cagcgtgggt  1020
ttgatgaatc ccaatcattt tctttccgtg gccatttggt atttgtttag tcagcggcaa  1080
cagtggtcag ggctgtcggc gatcggcaaa accctagtca gcagcagcat gattgaccgg  1140
gtgggggcca tgattaatcg ccaagtttac gaagtgcccg tgggctttaa atggtttgtc  1200
agcggtttgc tagatggttc ctttggcttt ggggtgaag aaagtgccgg gcttcgttt    1260
ttgaaaaaaa atggcaccgt ttggaccacc gacaaagatg gcaccattat ggatttattg  1320
gcggcggaaa tcaccgctaa aaccggcaaa gatcccggcc tccattacca ggatttgacc  1380
gctaagttag gtaatcccat ttaccaacgc attgatgccc cgccactcc ggcccaaaaa   1440
gaccgcttga aaaaactgtc ccccgatgac gttacagcta cctccttagc tggggatgcc  1500
attactgcta aattaaccaa agcccctggc aaccaagcgg cgatcggtgg gttgaaggtg  1560
accactgcgg aaggttggtt tgcggcccgg ccctccggca cggaaaatgt ttacaaaatc  1620
tatgccgaaa gtttcaaaga cgaagcccat ctccaggcta ttttcacgga ggcggaagcc  1680
attgttacct cggctttggg ctaa                                         1704
```

<210> SEQ ID NO 76
<211> LENGTH: 567
<212> TYPE: PRT
<213> ORGANISM: Synechocystis sp. PCC 6803

<400> SEQUENCE: 76

```
Met Ser Lys Pro Leu Ile Ala Ala Leu His Phe Leu Gln Phe Leu Tyr
  1               5                  10                  15

Met Thr Ser Arg Ile Asn Pro Leu Ala Gly Gln His Pro Ala Asp
             20                  25                  30

Ser Leu Leu Asp Val Ala Lys Leu Leu Asp Asp Tyr Tyr Arg Gln Gln
         35                  40                  45

Pro Asp Pro Glu Asn Pro Ala Gln Leu Val Ser Phe Gly Thr Ser Gly
     50                  55                  60
```

```
His Arg Gly Ser Ala Leu Asn Gly Thr Phe Asn Glu Ala His Ile Leu
 65                  70                  75                  80

Ala Val Thr Gln Ala Val Val Asp Tyr Arg Gln Ala Gln Gly Ile Thr
                 85                  90                  95

Gly Pro Leu Tyr Met Gly Met Asp Ser His Ala Leu Ser Glu Pro Ala
            100                 105                 110

Gln Lys Thr Ala Leu Glu Val Leu Ala Ala Asn Gln Val Glu Thr Phe
        115                 120                 125

Leu Thr Thr Ala Thr Asp Leu Thr Arg Phe Thr Pro Thr Pro Ala Val
    130                 135                 140

Ser Tyr Ala Ile Leu Thr His Asn Gln Gly Arg Lys Glu Gly Leu Ala
145                 150                 155                 160

Asp Gly Ile Ile Ile Thr Pro Ser His Asn Pro Pro Thr Asp Gly Gly
                165                 170                 175

Phe Lys Tyr Asn Pro Pro Ser Gly Gly Pro Ala Glu Pro Glu Ala Thr
            180                 185                 190

Gln Trp Ile Gln Asn Arg Ala Asn Glu Leu Leu Lys Asn Gly Asn Lys
        195                 200                 205

Thr Val Lys Arg Leu Asp Tyr Glu Gln Ala Leu Lys Ala Thr Thr Thr
    210                 215                 220

His Ala His Asp Phe Val Thr Pro Tyr Val Ala Gly Leu Ala Asp Ile
225                 230                 235                 240

Ile Asp Leu Asp Val Ile Arg Ser Ala Gly Leu Arg Leu Gly Val Asp
                245                 250                 255

Pro Leu Gly Gly Ala Asn Val Gly Tyr Trp Glu Pro Ile Ala Ala Lys
            260                 265                 270

Tyr Asn Leu Asn Ile Ser Leu Val Asn Pro Gly Val Asp Pro Thr Phe
        275                 280                 285

Lys Phe Met Thr Leu Asp Trp Asp Gly Lys Ile Arg Met Asp Cys Ser
    290                 295                 300

Ser Pro Tyr Ala Met Ala Ser Leu Val Lys Ile Lys Asp His Tyr Asp
305                 310                 315                 320

Ile Ala Phe Gly Asn Asp Thr Asp Gly Asp Arg His Gly Ile Val Thr
                325                 330                 335

Pro Ser Val Gly Leu Met Asn Pro Asn His Phe Leu Ser Val Ala Ile
            340                 345                 350

Trp Tyr Leu Phe Ser Gln Arg Gln Gln Trp Ser Gly Leu Ser Ala Ile
        355                 360                 365

Gly Lys Thr Leu Val Ser Ser Ser Met Ile Asp Arg Val Gly Ala Met
    370                 375                 380

Ile Asn Arg Gln Val Tyr Glu Val Pro Val Gly Phe Lys Trp Phe Val
385                 390                 395                 400

Ser Gly Leu Leu Asp Gly Ser Phe Gly Phe Gly Gly Glu Glu Ser Ala
                405                 410                 415

Gly Ala Ser Phe Leu Lys Lys Asn Gly Thr Val Trp Thr Thr Asp Lys
            420                 425                 430

Asp Gly Thr Ile Met Asp Leu Leu Ala Ala Glu Ile Thr Ala Lys Thr
        435                 440                 445

Gly Lys Asp Pro Gly Leu His Tyr Gln Asp Leu Thr Ala Lys Leu Gly
    450                 455                 460

Asn Pro Ile Tyr Gln Arg Ile Asp Ala Pro Ala Thr Pro Ala Gln Lys
465                 470                 475                 480
```

```
Asp Arg Leu Lys Lys Leu Ser Pro Asp Asp Val Thr Ala Thr Ser Leu
                485                 490                 495

Ala Gly Asp Ala Ile Thr Ala Lys Leu Thr Lys Ala Pro Gly Asn Gln
        500                 505                 510

Ala Ala Ile Gly Gly Leu Lys Val Thr Thr Ala Glu Gly Trp Phe Ala
        515                 520                 525

Ala Arg Pro Ser Gly Thr Glu Asn Val Tyr Lys Ile Tyr Ala Glu Ser
        530                 535                 540

Phe Lys Asp Glu Ala His Leu Gln Ala Ile Phe Thr Glu Ala Glu Ala
545                 550                 555                 560

Ile Val Thr Ser Ala Leu Gly
                565
```

<210> SEQ ID NO 77
<211> LENGTH: 1632
<212> TYPE: DNA
<213> ORGANISM: Synechococcus elongatus PCC 7942

<400> SEQUENCE: 77

```
atgaatatcc acactgtcgc gacgcaagcc tttagcgacc aaaagcccgg tacctccggc     60
ctgcgcaagc aagttcctgt cttccaaaaa cggcactatc tcgaaaactt tgtccagtcg    120
atcttcgata gccttgaggg ttatcagggc cagacgttag tgctgggggg tgatggccgc    180
tactacaatc gcacagccat ccaaaccatt ctgaaaatgg cggcggccaa tggttggggc    240
cgcgttttag ttggacaagg cggtattctc tccacgccag cagtctccaa cctaatccgc    300
cagaacggag ccttcggcgg catcatcctc tcggctagcc acaacccagg ggccctgag    360
ggcgatttcg gcatcaagta caacatcagc aacggtggcc ctgcacccga aaaagtcacc    420
gatgccatct atgcctgcag cctcaaaatt gaggcctacc gcattctcga agccggtgac    480
gttgacctcg atcgactcgg tagtcaacaa ctgggcgaga tgaccgttga ggtgatcgac    540
tcggtcgccg actacagccg cttgatgcaa tccctgtttg acttcgatcg cattcgcgat    600
cgcctgaggg gggggctacg gattgcgatc gactcgatgc atgccgtcac cggtccctac    660
gccaccacga ttttgagaa ggagctaggc gcggcggcag gcactgtttt taatggcaag    720
ccgctggaag actttggcgg gggtcaccca gacccgaatt tggtctacgc ccacgacttg    780
gttgaactgt tgtttggcga tcgcgcccca gattttggcg cggcctccga tggcgatggc    840
gatcgcaaca tgatcttggg caatcacttt tttgtgaccc ctagcgacag cttggcgatt    900
ctcgcagcca atgccagcct agtgccggcc taccgcaatg gactgtctgg gattgcgcga    960
tccatgccca ccgtgcggc ggccgatcgc gtcgcccaag ccctcaacct gccctgctac   1020
gaaaccccaa cggggttgaa gttttcggc aatctgctcg atgccgatcg cgtcaccctc   1080
tgcggcgaag aaagctttgg cacaggctcc aaccatgtgc gcgagaagga tggcctgtgg   1140
gccgtgctgt tctggctgaa tattctggcg gtgcgcgagc aatccgtggc cgaaattgtc   1200
caagaacact ggcgcaccta cggccgcaac tactactctc gccacgacta cgaaggggtg   1260
gagagcgatc gagccagtac gctggtggac aaactgcgat cgcagctacc agcctgacc   1320
ggacagaaac tgggagccta caccgttgcc tacgccgacg acttccgcta cgaagatccg   1380
gtcgatggca gcatcagcga acagcagggc attcgtattg ctttgaaga cggctcacgt   1440
atggtcttcc gcttgtctgg tactggtacg gcaggagcca ccctgcgcct ctacctcgag   1500
cgcttcgaag gggacaccac caaacagggt ctcgatcccc aagttgccct ggcagatttg   1560
```

```
attgcaatcg ccgatgaagt cgcccagatc acaaccttga cgggcttcga tcaaccgaca      1620
gtgatcacct ga                                                         1632
```

<210> SEQ ID NO 78
<211> LENGTH: 543
<212> TYPE: PRT
<213> ORGANISM: Synechococcus elongatus PCC 7942

<400> SEQUENCE: 78

```
Met Asn Ile His Thr Val Ala Thr Gln Ala Phe Ser Asp Gln Lys Pro
 1               5                  10                  15

Gly Thr Ser Gly Leu Arg Lys Gln Val Pro Val Phe Gln Lys Arg His
            20                  25                  30

Tyr Leu Glu Asn Phe Val Gln Ser Ile Phe Asp Ser Leu Glu Gly Tyr
        35                  40                  45

Gln Gly Gln Thr Leu Val Leu Gly Gly Asp Gly Arg Tyr Tyr Asn Arg
    50                  55                  60

Thr Ala Ile Gln Thr Ile Leu Lys Met Ala Ala Asn Gly Trp Gly
65                  70                  75                  80

Arg Val Leu Val Gly Gln Gly Gly Ile Leu Ser Thr Pro Ala Val Ser
                85                  90                  95

Asn Leu Ile Arg Gln Asn Gly Ala Phe Gly Gly Ile Ile Leu Ser Ala
            100                 105                 110

Ser His Asn Pro Gly Gly Pro Glu Gly Asp Phe Gly Ile Lys Tyr Asn
        115                 120                 125

Ile Ser Asn Gly Gly Pro Ala Pro Glu Lys Val Thr Asp Ala Ile Tyr
    130                 135                 140

Ala Cys Ser Leu Lys Ile Glu Ala Tyr Arg Ile Leu Glu Ala Gly Asp
145                 150                 155                 160

Val Asp Leu Asp Arg Leu Gly Ser Gln Gln Leu Gly Glu Met Thr Val
                165                 170                 175

Glu Val Ile Asp Ser Val Ala Asp Tyr Ser Arg Leu Met Gln Ser Leu
            180                 185                 190

Phe Asp Phe Asp Arg Ile Arg Asp Arg Leu Arg Gly Gly Leu Arg Ile
        195                 200                 205

Ala Ile Asp Ser Met His Ala Val Thr Gly Pro Tyr Ala Thr Thr Ile
    210                 215                 220

Phe Glu Lys Glu Leu Gly Ala Ala Ala Gly Thr Val Phe Asn Gly Lys
225                 230                 235                 240

Pro Leu Glu Asp Phe Gly Gly Gly His Pro Asp Pro Asn Leu Val Tyr
                245                 250                 255

Ala His Asp Leu Val Glu Leu Leu Phe Gly Asp Arg Ala Pro Asp Phe
            260                 265                 270

Gly Ala Ala Ser Asp Gly Asp Gly Asp Arg Asn Met Ile Leu Gly Asn
        275                 280                 285

His Phe Phe Val Thr Pro Ser Asp Ser Leu Ala Ile Leu Ala Ala Asn
    290                 295                 300

Ala Ser Leu Val Pro Ala Tyr Arg Asn Gly Leu Ser Gly Ile Ala Arg
305                 310                 315                 320

Ser Met Pro Thr Ser Ala Ala Ala Asp Arg Val Ala Gln Ala Leu Asn
                325                 330                 335

Leu Pro Cys Tyr Glu Thr Pro Thr Gly Trp Lys Phe Phe Gly Asn Leu
            340                 345                 350
```

Leu Asp Ala Asp Arg Val Thr Leu Cys Gly Glu Glu Ser Phe Gly Thr
                355                 360                 365

Gly Ser Asn His Val Arg Glu Lys Asp Gly Leu Trp Ala Val Leu Phe
        370                 375                 380

Trp Leu Asn Ile Leu Ala Val Arg Glu Gln Ser Val Ala Glu Ile Val
385                 390                 395                 400

Gln Glu His Trp Arg Thr Tyr Gly Arg Asn Tyr Tyr Ser Arg His Asp
                405                 410                 415

Tyr Glu Gly Val Glu Ser Asp Arg Ala Ser Thr Leu Val Asp Lys Leu
            420                 425                 430

Arg Ser Gln Leu Pro Ser Leu Thr Gly Gln Lys Leu Gly Ala Tyr Thr
        435                 440                 445

Val Ala Tyr Ala Asp Asp Phe Arg Tyr Glu Asp Pro Val Asp Gly Ser
    450                 455                 460

Ile Ser Glu Gln Gln Gly Ile Arg Ile Gly Phe Glu Asp Gly Ser Arg
465                 470                 475                 480

Met Val Phe Arg Leu Ser Gly Thr Gly Thr Ala Gly Ala Thr Leu Arg
                485                 490                 495

Leu Tyr Leu Glu Arg Phe Glu Gly Asp Thr Thr Lys Gln Gly Leu Asp
            500                 505                 510

Pro Gln Val Ala Leu Ala Asp Leu Ile Ala Ile Ala Asp Glu Val Ala
        515                 520                 525

Gln Ile Thr Thr Leu Thr Gly Phe Asp Gln Pro Val Ile Thr
    530                 535                 540

<210> SEQ ID NO 79
<211> LENGTH: 1659
<212> TYPE: DNA
<213> ORGANISM: Synechococcus sp. WH8102

<400> SEQUENCE: 79

```
atgaccacct cggcccccgc ggaaccgacc ctgcgcctgg tgcgcctgga cgcacctttc      60
acggatcaga aacccggcac atccggtttg cgcaaaagca gccagcagtt cgagcaagcg     120
aactatctgg agagctttgt ggaagccgta ttccgcacct gcccggtgt tcaaggggc      180
acgctggtgt tgggaggtga cggccgttac ggcaaccgcc gtgccatcga cgtgatcctg     240
cgcatgggcg cggcccacgg cctcagcaag gtgatcgtca ccaccggcgg catcctctcc     300
accccggcgg cctcgaacct gattcgccag cgtcaggcca tcggcggcat catcctctcg     360
gcaagccaca accctggcgg ccccaatgga gacttcggcg tcaaggtgaa tggcgccaac     420
ggtggcccga ccccggcctc gttcaccgat gcggtgttcg agtgcaccaa gaccttggag     480
caatacacga tcgttgatgc cgcggccatc gccatcgata cccccggcag ctacagcatc     540
ggcgccatgc aggtggaggt gatcgacggc gtcgacgact tcgtggctct gatgcaacag     600
ctgttcgact tgatcggat ccgggagctg atccgcagcg acttcccgct ggcgtttgat     660
gcgatgcatg cggtcactgg ccctacgcc actcgcctgt ggaagagat cctcggcgct     720
cctgccggca gcgtccgcaa cggcgttcct ctggaggact cggcggcgg ccaccccgac     780
cccaacctca cctacgccca cgagctgccg gaacttctgc tcgacgggga ggagttccgc     840
ttcggggccg cctgcgacgg cgatggtgac cgcaacatga tcctgggca gcactgcttc     900
gtaaacccca cgacagcct ggcggtgctc acagccaacg ccacggtggc accggcctat     960
gccgatggtt tggctggcgt ggcccgctcg atgcccacca gctctgccgt ggatgtggtg    1020
gccaaggaac tgggcatcga ctgctacgag accccaccg gctggaagtt cttcggcaat    1080
```

```
ctgctggatg ccggcaaaat cacgctctgc ggtgaagaga gcttcggcac cggcagcaac    1140
cacgtgcgtg aaaaggatgg cctctgggct gttctgttct ggctgcagat cctggccgag    1200
cgccgctgca gcgtcgccga gatcatggct gagcattgga agcgcttcgg ccgccactac    1260
tactctcgcc acgactacga agccgtcgcc agcgacgcag cccatgggct gttccaccgc    1320
ctcgagggca tgctccctgg tctggtgggg cagagcttcg ctggccgcag cgtcagcgca    1380
gccgacaact tcagctacac cgatcccgtt gatggctctg tgaccaaggg ccagggcctg    1440
cgcatcctgc tggaggatgg cagccgcgtg atggtgcgcc tctcgggcac cggcaccaag    1500
ggcgccacga tccgcgtcta tctggagagt tatgtaccga gcagcggtga tctcaaccag    1560
gatccccagg tcgctctggc cgacatgatc agcgccatca atgaactggc ggagatcaag    1620
cagcgcaccg gcatggatcg gcccaccgtg atcacctga                           1659
```

<210> SEQ ID NO 80
<211> LENGTH: 552
<212> TYPE: PRT
<213> ORGANISM: Synechococcus sp. WH8102

<400> SEQUENCE: 80

Met Thr Thr Ser Ala Pro Ala Glu Pro Thr Leu Arg Leu Val Arg Leu
1               5                   10                  15

Asp Ala Pro Phe Thr Asp Gln Lys Pro Gly Thr Ser Gly Leu Arg Lys
            20                  25                  30

Ser Ser Gln Gln Phe Glu Gln Ala Asn Tyr Leu Glu Ser Phe Val Glu
        35                  40                  45

Ala Val Phe Arg Thr Leu Pro Gly Val Gln Gly Gly Thr Leu Val Leu
    50                  55                  60

Gly Gly Asp Gly Arg Tyr Gly Asn Arg Arg Ala Ile Asp Val Ile Leu
65                  70                  75                  80

Arg Met Gly Ala Ala His Gly Leu Ser Lys Val Ile Val Thr Thr Gly
                85                  90                  95

Gly Ile Leu Ser Thr Pro Ala Ala Ser Asn Leu Ile Arg Gln Arg Gln
            100                 105                 110

Ala Ile Gly Gly Ile Ile Leu Ser Ala Ser His Asn Pro Gly Gly Pro
        115                 120                 125

Asn Gly Asp Phe Gly Val Lys Val Asn Gly Ala Asn Gly Gly Pro Thr
    130                 135                 140

Pro Ala Ser Phe Thr Asp Ala Val Phe Glu Cys Thr Lys Thr Leu Glu
145                 150                 155                 160

Gln Tyr Thr Ile Val Asp Ala Ala Ile Ala Ile Asp Thr Pro Gly
                165                 170                 175

Ser Tyr Ser Ile Gly Ala Met Gln Val Glu Val Ile Asp Gly Val Asp
            180                 185                 190

Asp Phe Val Ala Leu Met Gln Gln Leu Phe Asp Phe Asp Arg Ile Arg
        195                 200                 205

Glu Leu Ile Arg Ser Asp Phe Pro Leu Ala Phe Asp Ala Met His Ala
    210                 215                 220

Val Thr Gly Pro Tyr Ala Thr Arg Leu Leu Glu Glu Ile Leu Gly Ala
225                 230                 235                 240

Pro Ala Gly Ser Val Arg Asn Gly Val Pro Leu Glu Asp Phe Gly Gly
                245                 250                 255

Gly His Pro Asp Pro Asn Leu Thr Tyr Ala His Glu Leu Ala Glu Leu
            260                 265                 270

-continued

```
Leu Leu Asp Gly Glu Glu Phe Arg Phe Gly Ala Ala Cys Asp Gly Asp
            275                 280                 285

Gly Asp Arg Asn Met Ile Leu Gly Gln His Cys Phe Val Asn Pro Ser
        290                 295                 300

Asp Ser Leu Ala Val Leu Thr Ala Asn Ala Thr Val Ala Pro Ala Tyr
305                 310                 315                 320

Ala Asp Gly Leu Ala Gly Val Ala Arg Ser Met Pro Thr Ser Ser Ala
                325                 330                 335

Val Asp Val Val Ala Lys Glu Leu Gly Ile Asp Cys Tyr Glu Thr Pro
            340                 345                 350

Thr Gly Trp Lys Phe Phe Gly Asn Leu Leu Asp Ala Gly Lys Ile Thr
        355                 360                 365

Leu Cys Gly Glu Glu Ser Phe Gly Thr Gly Ser Asn His Val Arg Glu
370                 375                 380

Lys Asp Gly Leu Trp Ala Val Leu Phe Trp Leu Gln Ile Leu Ala Glu
                390                 395                 400
385

Arg Arg Cys Ser Val Ala Glu Ile Met Ala Glu His Trp Lys Arg Phe
            405                 410                 415

Gly Arg His Tyr Tyr Ser Arg His Asp Tyr Glu Ala Val Ala Ser Asp
        420                 425                 430

Ala Ala His Gly Leu Phe His Arg Leu Glu Gly Met Leu Pro Gly Leu
    435                 440                 445

Val Gly Gln Ser Phe Ala Gly Arg Ser Val Ser Ala Ala Asp Asn Phe
            450                 455                 460

Ser Tyr Thr Asp Pro Val Asp Gly Ser Val Thr Lys Gly Gln Gly Leu
465                 470                 475                 480

Arg Ile Leu Leu Glu Asp Gly Ser Arg Val Met Val Arg Leu Ser Gly
                485                 490                 495

Thr Gly Thr Lys Gly Ala Thr Ile Arg Val Tyr Leu Glu Ser Tyr Val
            500                 505                 510

Pro Ser Ser Gly Asp Leu Asn Gln Asp Pro Gln Val Ala Leu Ala Asp
        515                 520                 525

Met Ile Ser Ala Ile Asn Glu Leu Ala Glu Ile Lys Gln Arg Thr Gly
530                 535                 540

Met Asp Arg Pro Thr Val Ile Thr
545                 550

<210> SEQ ID NO 81
<211> LENGTH: 1662
<212> TYPE: DNA
<213> ORGANISM: Synechococcus sp. RCC 307

<400> SEQUENCE: 81
gtgacgcttt cctcacccag cactgagttc tccgtgcagc agatcaagct gccagaagcg      60
tttcaagacc agaagcctgg cacctcggga ctgcgcaaga gcacccaaca atttgaacag     120
cctcattacc tcgaaagttt tatcgaggcg atcttccgca ccctccctgg tgtgcaaggc     180
gggaccttgg tggtgggcgg tgatggccgc tacggcaacc gccgcgccat cgatgtcatc     240
acccggatgg cggcagccca tggactgggg cggattgtgc tgaccaccgg cggcatcctc     300 tccaccctg ccgcttccaa cttgatccgc caacgccagg ccattggcgg catcatcctc     360
tcggccagcc acaaccctgg agggcccaaa ggcgactttg cgtcaaggt caatggcgcc     420 aacggcggcc ctgcccctga atctcttacc gatgccatct acgcctgcag ccagcagctc     480
gatggctacc gcatcgcaag tggaaccgca ctgcccctcg acgccccagc cgagcatcaa     540
```

-continued

```
atcggtgcgt tgaacgtgga ggtgatcgac ggcgtcgacg actacctgca actgatgcag    600
cacttgttcg acttcgatct gatcagcgat ttgctcaagg gctcatggcc aatggccttt    660
gacgccatgc atgccgtcac tggtccctac gccagcaaac tctttgagca gctcctagga    720
gccccaagcg ggaccgtgcg caacgggcgc tgcctcgaag actttggtgg cggccatccc    780
gatcccaacc tcacctacgc caaagagctg gcgacgctgc tgctggatgg tgatgactat    840
cgctttggcg cggcctgtga tggcgatggc gaccgcaaca tgattttggg gcagcgctgc    900
tttgtgaacc ccagcgacag cctcgctgtc ttaacggcga acgccacctt ggtgaagggc    960
tatgcctccg gcctggccgg cgttgctcgc tcgatgccca ccagtgccgc agtggatgtg   1020
gtggccaagc agctggggat caattgcttt gagaccccca ccggttggaa attttttcggc   1080 aacctgctcg atgccggacg catcacccct tgcggggaag agagctttgg aacaggcagt   1140
gatcacatcc gcgaaaaaga tggcctctgg gctgtgttgt tttggctctc gatcctggcc   1200
aagcgccaat gctctgttgc ggaggtgatg cagcagcact ggagcaccta cgggcgtcat   1260
tactactcgc gccatgacta cgaaggtgtc gaaaccgatc gggcccatgg gctctacaac   1320
ggcctgcgcg atcggcttgg cgagctgact ggaaccagct ttgccgatag ccgcatcgcc   1380
aatgctgact acttcgccta cagcgacccc gtcgatggct cactgaccca gaagcaaggc   1440
ctacgtctgc tcctggagga cggcagccgc atcatcctgc ggctctcggg aaccggcacc   1500
aaaggagcca cgctgcggct ctatctcgag cgctatgtcg ccactggcgg caacctcgat   1560
caaaatcccc agcaagcctt agccggcatg attgcggccg ccgatgccct cgccggcatc   1620
cggtcaacca ccggcatgga tgtccccacg gtgatcacct ga                      1662
```

<210> SEQ ID NO 82
<211> LENGTH: 553
<212> TYPE: PRT
<213> ORGANISM: Synechococcus sp. RCC 307

<400> SEQUENCE: 82

```
Met Thr Leu Ser Ser Pro Ser Thr Glu Phe Ser Val Gln Gln Ile Lys
  1               5                  10                  15

Leu Pro Glu Ala Phe Gln Asp Gln Lys Pro Gly Thr Ser Gly Leu Arg
             20                  25                  30

Lys Ser Thr Gln Gln Phe Glu Gln Pro His Tyr Leu Glu Ser Phe Ile
         35                  40                  45

Glu Ala Ile Phe Arg Thr Leu Pro Gly Val Gln Gly Gly Thr Leu Val
     50                  55                  60

Val Gly Gly Asp Gly Arg Tyr Gly Asn Arg Arg Ala Ile Asp Val Ile
 65                  70                  75                  80

Thr Arg Met Ala Ala Ala His Gly Leu Gly Arg Ile Val Leu Thr Thr
                 85                  90                  95

Gly Gly Ile Leu Ser Thr Pro Ala Ala Ser Asn Leu Ile Arg Gln Arg
            100                 105                 110

Gln Ala Ile Gly Gly Ile Ile Leu Ser Ala Ser His Asn Pro Gly Gly
        115                 120                 125

Pro Lys Gly Asp Phe Gly Val Lys Val Asn Gly Ala Asn Gly Gly Pro
    130                 135                 140

Ala Pro Glu Ser Leu Thr Asp Ala Ile Tyr Ala Cys Ser Gln Gln Leu
145                 150                 155                 160

Asp Gly Tyr Arg Ile Ala Ser Gly Thr Ala Leu Pro Leu Asp Ala Pro
                165                 170                 175
```

```
Ala Glu His Gln Ile Gly Ala Leu Asn Val Glu Val Ile Asp Gly Val
            180                 185                 190

Asp Asp Tyr Leu Gln Leu Met Gln His Leu Phe Asp Phe Asp Leu Ile
        195                 200                 205

Ser Asp Leu Leu Lys Gly Ser Trp Pro Met Ala Phe Asp Ala Met His
210                 215                 220

Ala Val Thr Gly Pro Tyr Ala Ser Lys Leu Phe Glu Gln Leu Leu Gly
225                 230                 235                 240

Ala Pro Ser Gly Thr Val Arg Asn Gly Arg Cys Leu Glu Asp Phe Gly
                245                 250                 255

Gly Gly His Pro Asp Pro Asn Leu Thr Tyr Ala Lys Glu Leu Ala Thr
            260                 265                 270

Leu Leu Leu Asp Gly Asp Asp Tyr Arg Phe Gly Ala Ala Cys Asp Gly
        275                 280                 285

Asp Gly Asp Arg Asn Met Ile Leu Gly Gln Arg Cys Phe Val Asn Pro
290                 295                 300

Ser Asp Ser Leu Ala Val Leu Thr Ala Asn Ala Thr Leu Val Lys Gly
305                 310                 315                 320

Tyr Ala Ser Gly Leu Ala Gly Val Ala Arg Ser Met Pro Thr Ser Ala
                325                 330                 335

Ala Val Asp Val Val Ala Lys Gln Leu Gly Ile Asn Cys Phe Glu Thr
            340                 345                 350

Pro Thr Gly Trp Lys Phe Phe Gly Asn Leu Leu Asp Ala Gly Arg Ile
        355                 360                 365

Thr Leu Cys Gly Glu Glu Ser Phe Gly Thr Gly Ser Asp His Ile Arg
370                 375                 380

Glu Lys Asp Gly Leu Trp Ala Val Leu Phe Trp Leu Ser Ile Leu Ala
385                 390                 395                 400

Lys Arg Gln Cys Ser Val Ala Glu Val Met Gln Gln His Trp Ser Thr
                405                 410                 415

Tyr Gly Arg His Tyr Tyr Ser Arg His Asp Tyr Glu Gly Val Glu Thr
            420                 425                 430

Asp Arg Ala His Gly Leu Tyr Asn Gly Leu Arg Asp Arg Leu Gly Glu
        435                 440                 445

Leu Thr Gly Thr Ser Phe Ala Asp Ser Arg Ile Ala Asn Ala Asp Asp
450                 455                 460

Phe Ala Tyr Ser Asp Pro Val Asp Gly Ser Leu Thr Gln Lys Gln Gly
465                 470                 475                 480

Leu Arg Leu Leu Leu Glu Asp Gly Ser Arg Ile Ile Leu Arg Leu Ser
                485                 490                 495

Gly Thr Gly Thr Lys Gly Ala Thr Leu Arg Leu Tyr Leu Glu Arg Tyr
            500                 505                 510

Val Ala Thr Gly Gly Asn Leu Asp Gln Asn Pro Gln Gln Ala Leu Ala
        515                 520                 525

Gly Met Ile Ala Ala Asp Ala Leu Ala Gly Ile Arg Ser Thr Thr
530                 535                 540

Gly Met Asp Val Pro Thr Val Ile Thr
545                 550

<210> SEQ ID NO 83
<211> LENGTH: 1467
<212> TYPE: DNA
<213> ORGANISM: Synechococcus sp PCC 7002
```

<400> SEQUENCE: 83

```
gtgttggcgt ttgggaatca acagccgatt cggttcggca cagacggttg gcgtggcatt      60
attgcggcgg atttaccctt tgaacgggtg caacgggtgg cgatcgccac agcccatgtt     120
ttaaaagaaa atttcgcaaa ccaagccatt gataacacga taatcgtcgg ctacgaccgg     180
cggtttctcg cagatgaatt tgcccttgct gccgccgaag cgatccaggg ggaaggattt     240
cacgtacttc tagccaatag ttttgcgcca accccagccc tgagctatgc cgcccaccac     300
cacaaggctc tgggggcgat cgccttaacg gccagccata atccagcggg ttatttagga     360
ttaaaagtga aggggctttt cggcggctcg gtttccgaag aaattacggc tcagattgaa     420
gcgcgactgg aagccgggat tgatcctcaa cattcaacga cgggccgttt agattatttt     480
gatccctggc aggactattg cgccggatta cagcaactgg ttgatttaga aaaaattcgc     540
caggcgatcg ccgctggtcg tctccaggtc tttgccgatg taatgtatgg cgcagcggcg     600
ggcggtttga cccaactgct caatgcggcg atccaagaaa tccattgtga accagatcct     660
ttgttcggcg gccgcccacc agagccttta gaaaaacatt tgtctcaact gcaacgcacc     720
attcgcgccg cccataatca agatttagag gcaattcagg tgggatttgt ctttgatggt     780
gatggcgatc gcattgctgc tgtggctggg atggtgagt ttctcagttc ccaaaagcta     840
atcccgattt tgctggccca tttgtcccaa atcgccaat atcaagggga agtggtaaaa     900
actgtcagcg gctctgattt aatccccgt ttgagcgaat actacggttt gccagtcttt     960
gaaacacca tcggctacaa atacattgcc gaacgaatgc aacagaccca ggtgcttctt    1020
ggtggcgaag aatccggcgg cattggctac ggccaccaca tcccgaacg ggatgcgctg    1080
ctggcggcat tgtatctcct agaggcgatc gccatttttg atcaagacct cggcgagatt    1140
taccagagtc ttcaaagcaa agctaatttt tatggcgcct acgaccgcat tgatttacat    1200
ttgcgggatt tctccagccg cgatcgccta ttaaaaatcc tcgcgacaaa tccccccaag    1260
gcgatctcca accatgacgt aattcacagc gaccccaaag atggctataa attccgcctt    1320
gctgatcaaa gttggttgct gattcgcttc agtggtaccg agcctgtact gcggttatat    1380
agtgaagcgg tcaatcctaa agccgtacaa gaaatcctcg cctgggcgca aacctgggct    1440
gaggctgccg accaagccga aggttag                                        1467
```

<210> SEQ ID NO 84
<211> LENGTH: 488
<212> TYPE: PRT
<213> ORGANISM: Synechococcus sp PCC 7002

<400> SEQUENCE: 84

```
Met Leu Ala Phe Gly Asn Gln Gln Pro Ile Arg Phe Gly Thr Asp Gly
  1               5                  10                  15

Trp Arg Gly Ile Ile Ala Ala Asp Phe Thr Phe Glu Arg Val Gln Arg
             20                  25                  30

Val Ala Ile Ala Thr Ala His Val Leu Lys Glu Asn Phe Ala Asn Gln
         35                  40                  45

Ala Ile Asp Asn Thr Ile Ile Val Gly Tyr Asp Arg Arg Phe Leu Ala
     50                  55                  60

Asp Glu Phe Ala Leu Ala Ala Ala Glu Ala Ile Gln Gly Glu Gly Phe
 65                  70                  75                  80

His Val Leu Leu Ala Asn Ser Phe Ala Pro Thr Pro Ala Leu Ser Tyr
                 85                  90                  95
```

```
Ala Ala His His His Lys Ala Leu Gly Ala Ile Ala Leu Thr Ala Ser
        100                 105                 110
His Asn Pro Ala Gly Tyr Leu Gly Leu Lys Val Lys Gly Ala Phe Gly
        115                 120                 125
Gly Ser Val Ser Glu Glu Ile Thr Ala Gln Ile Glu Ala Arg Leu Glu
130                 135                 140
Ala Gly Ile Asp Pro Gln His Ser Thr Thr Gly Arg Leu Asp Tyr Phe
145                 150                 155                 160
Asp Pro Trp Gln Asp Tyr Cys Ala Gly Leu Gln Gln Leu Val Asp Leu
                    165                 170                 175
Glu Lys Ile Arg Gln Ala Ile Ala Ala Gly Arg Leu Gln Val Phe Ala
                180                 185                 190
Asp Val Met Tyr Gly Ala Ala Gly Gly Leu Thr Gln Leu Leu Asn
                195                 200                 205
Ala Ala Ile Gln Glu Ile His Cys Glu Pro Asp Pro Leu Phe Gly Gly
        210                 215                 220
Arg Pro Pro Glu Pro Leu Glu Lys His Leu Ser Gln Leu Gln Arg Thr
225                 230                 235                 240
Ile Arg Ala Ala His Asn Gln Asp Leu Glu Ala Ile Gln Val Gly Phe
                245                 250                 255
Val Phe Asp Gly Asp Gly Asp Arg Ile Ala Ala Val Ala Gly Asp Gly
                260                 265                 270
Glu Phe Leu Ser Ser Lys Leu Ile Pro Ile Leu Leu Ala His Leu
        275                 280                 285
Ser Gln Asn Arg Gln Tyr Gln Gly Glu Val Val Lys Thr Val Ser Gly
        290                 295                 300
Ser Asp Leu Ile Pro Arg Leu Ser Glu Tyr Tyr Gly Leu Pro Val Phe
305                 310                 315                 320
Glu Thr Pro Ile Gly Tyr Lys Tyr Ile Ala Glu Arg Met Gln Gln Thr
                325                 330                 335
Gln Val Leu Leu Gly Gly Glu Glu Ser Gly Gly Ile Gly Tyr Gly His
                340                 345                 350
His Ile Pro Glu Arg Asp Ala Leu Leu Ala Ala Leu Tyr Leu Leu Glu
        355                 360                 365
Ala Ile Ala Ile Phe Asp Gln Asp Leu Gly Glu Ile Tyr Gln Ser Leu
        370                 375                 380
Gln Ser Lys Ala Asn Phe Tyr Gly Ala Tyr Asp Arg Ile Asp Leu His
385                 390                 395                 400
Leu Arg Asp Phe Ser Ser Arg Asp Arg Leu Leu Lys Ile Leu Ala Thr
                405                 410                 415
Asn Pro Pro Lys Ala Ile Ser Asn His Asp Val Ile His Ser Asp Pro
                420                 425                 430
Lys Asp Gly Tyr Lys Phe Arg Leu Ala Asp Gln Ser Trp Leu Leu Ile
        435                 440                 445
Arg Phe Ser Gly Thr Glu Pro Val Leu Arg Leu Tyr Ser Glu Ala Val
        450                 455                 460
Asn Pro Lys Ala Val Gln Glu Ile Leu Ala Trp Ala Gln Thr Trp Ala
465                 470                 475                 480
Glu Ala Ala Asp Gln Ala Glu Gly
                485
```

MODIFIED PHOTOSYNTHETIC MICROORGANISMS WITH REDUCED GLYCOGEN AND THEIR USE IN PRODUCING CARBON-BASED PRODUCTS

CROSS-REFERENCE TO RELATED APPLICATION

This application claims the benefit under 35 U.S.C. §119(e) of U.S. Provisional Patent Application No. 61/140,545 filed Dec. 23, 2008, where this provisional application is incorporated herein by reference in its entirety.

SEQUENCE LISTING

The Sequence Listing associated with this application is provided in text format in lieu of a paper copy, and is hereby incorporated by reference into the specification. The name of the text file containing the Sequence Listing is 890071_402_SEQUENCE_LISTING.txt. The text file is 274 KB, was created on Dec. 22, 2009, and is being submitted electronically via EFS-Web.

BACKGROUND

1. Technical Field

The present invention relates generally to genetically modified photosynthetic microorganisms, including Cyanobacteria, having a disabled glycogen biosynthesis or storage pathway, and related methods of using the genetically modified Cyanobacteria as a feedstock, e.g., for producing biofuels and other specialty chemicals.

2. Description of the Related Art

Triglycerides are neutral polar molecules consisting of glycerol esterified with three fatty acid molecules. Triglycerides are utilized as carbon and energy storage molecules by most eukaryotic organisms, including plants and algae, and by certain prokaryotic organisms, including certain species of actinomycetes and members of the genus *Acinetobacter*.

Triglycerides may also be utilized as a feedstock in the production of biofuels and/or various specialty chemicals. For example, triglycerides may be subject to a transesterification reaction, in which an alcohol reacts with triglyceride oils, such as those contained in vegetable oils, animal fats, recycled greases, to produce biodiesels such as fatty acid alkyl esters. Such reactions also produce glycerin as a by-product, which can be purified for use in the pharmaceutical and cosmetic industries Certain organisms can be utilized as a source of triglycerides in the production of biofuels. For example, algae naturally produce triglycerides as energy storage molecules, and certain biofuel-related technologies are presently focused on the use of algae as a feedstock for biofuels. Algae are photosynthetic organisms, and the use of triglyceride-producing organisms such as algae provides the ability to produce biodiesel from sunlight, water, $CO_2$, macronutrients, and micronutrients. Algae, however, cannot be readily genetically manipulated, and produce much less oil (i.e., triglycerides) under culture conditions than in the wild.

Like algae, Cyanobacteria obtain energy from photosynthesis, utilizing chlorophyll A and water to reduce $CO_2$. Certain Cyanobacteria can produce metabolites, such as carbohydrates, proteins, and fatty acids, from just sunlight, water, $CO_2$, and inorganic salts. Unlike algae, Cyanobacteria can be genetically manipulated. For example, *Synechococcus elongatus* PCC 7942 (also referred to as "*S. elongatus* PCC 7942") is a genetically manipulable, oligotrophic Cyanobacterium that thrives in low nutrient level conditions, and in the wild accumulates fatty acids in the form of lipid membranes to about 4% or 8% by dry weight. Cyanobacteria such as *Synechococcus*, however, produce no triglyceride energy storage molecules, since Cyanobacteria typically lack the essential enzymes involved in triglyceride synthesis. Instead, *Synechococcus* in the wild typically accumulates glycogen as its primary carbon storage form.

Clearly, therefore, there is a need in the art for modified photosynthetic microorganisms, including Cyanobacteria, capable of producing triglycerides and fatty acids, e.g., to be used as feed stock in the production of biofuels and/or various specialty chemicals.

BRIEF SUMMARY

In various embodiments, the present invention provides a modified photosynthetic microorganism having a disabled glycogen biosynthesis or storage pathway, and those that are capable of synthesizing triglycerides, as well as related methods of using the genetically modified photosynthetic microorganism, e.g., as a feedstock for producing biofuels and other specialty chemicals. In particular embodiments, the modified photosynthetic microorganisms are Cyanobacteria.

In one embodiment, the present invention includes a modified photosynthetic microorganism having a reduced level of expression of one or more genes of a glycogen biosynthesis or storage pathway as compared to the level of expression of the one or more genes in a wild type photosynthetic microorganism, e.g., a wild type photosynthetic microorganism of the same species. In particular embodiments, the modified photosynthetic microorganism comprises a mutation in one or more genes of a glycogen biosynthesis or storage pathway. In particular embodiments, the mutation is a complete or partial gene deletion.

In a related embodiment, the present invention includes a modified photosynthetic microorganism comprising one or more introduced polynucleotides encoding proteins of a glycogen breakdown pathway or a functional fragment or variant thereof. In certain embodiments, the introduced polynucleotide is exogenous to the photosynthetic microorganism's native genome, e.g., it may be a polynucleotide derived from a different species. In other embodiments, the introduced polynucleotide is a polynucleotide native to the photosynthetic microorganism's genome, i.e., corresponding to a gene or protein normally present in the photosynthetic microorganism, but it is overexpressed, e.g., from an introduced expression vector. In certain embodiments, the vector is an inducible vector. In particular embodiments, an introduced polynucleotide is present in the photosynthetic microorganism either transiently or stably. Thus, in various embodiments, the introduced polynucleotide is introduced into the photosynthetic microorganism or an ancestor thereof. In particular embodiments, the introduced polynucleotide encodes glycogen phosphorylase (GlgP), glycogen debranching enzyme (GlgX), amylomaltase (MalQ), phosphoglucomutase (Pgm), glucokinase (Glk), and/or phosphoglucose isomerase (Pgi), or a functional fragment or variant thereof.

In further related embodiments, the present invention includes a modified photosynthetic microorganism having a reduced level of expression of one or more genes of a glycogen biosynthesis or storage pathway as compared to the level of expression of the one or more genes in a wild type photosynthetic microorganism, and which also comprises one or more introduced polynucleotides encoding proteins of a glycogen breakdown pathway or a functional fragment or variant thereof.

In particular embodiments, modified photosynthetic microorganisms of the present invention, e.g., Cyanobacteria, synthesize or accumulate a reduced amount of glycogen under stress conditions as compared to a wild type photosynthetic microorganism. In related embodiments, this photosynthetic microorganism synthesizes or accumulates an increased amount of lipid as compared to a wild type photosynthetic microorganism. In certain embodiments, the stress conditions are reduced nitrogen conditions. In various other embodiments, modified photosynthetic microorganisms of the present invention synthesize or accumulate a reduced amount of glycogen and/or an increased amount of lipid as compared to a wild photosynthetic microorganism under non-stress conditions.

In certain embodiments, the one or more genes having reduced expression in a modified photosynthetic microorganism of the present invention are selected from glucose-1-phosphate adenyltransferase (glgC), phosphoglucomutase (pgm), and/or glycogen synthase (glgA). In particular embodiments, the modified photosynthetic microorganism comprises a mutation of one or more genes of a glycogen biosynthesis or storage pathway. In one specific embodiment, the photosynthetic microorganism comprises mutations of the glgC gene or the pgm gene. In one specific embodiment, the photosynthetic microorganism comprises mutations of the glgC gene and the pgm gene. In various embodiments, the mutations are complete or partial gene deletions.

In particular embodiments, the modified photosynthetic microorganism is a *Synechococcus elongatus*. In one embodiment, the *Synechococcus elongatus* is strain PCC 7942. In certain embodiments, the modified photosynthetic microorganism is a salt tolerant variant of *S. elongatus* PCC 7942. In other embodiments, the modified photosynthetic microorganism is *Synechococcus* sp. PCC 7002 or *Synechocystis* sp. PCC 6803.

In a further related embodiment, the present invention provides a method of producing a photosynthetic microorganism, e.g., a Cyanobacterium, that accumulates a reduced amount of glycogen as compared to a wild type photosynthetic microorganism, comprising modifying a photosynthetic microorganism to reduce the level of expression of one or more genes of a glycogen biosynthesis or storage pathway in the photosynthetic microorganism and/or introducing into the photosynthetic microorganism one or more polynucleotides encoding a protein of a glycogen breakdown pathway or a functional fragment or variant thereof. In certain embodiments, the one or more genes having reduced expression are glucose-1-phosphate adenyltransferase (glgC), phosphoglucomutase (pgm), and/or glycogen synthase (glgA). In certain embodiments, the one or more genes are mutated. In particular embodiments, the mutating comprises deleting a portion of or the entire gene. In one particular embodiment, the glgC gene and the pgm gene are mutated. In certain embodiments, the modified photosynthetic microorganism accumulates a reduced amount of glycogen under stress conditions. In one embodiment, the stress conditions are reduced nitrogen conditions. In other embodiments, the modified photosynthetic microorganism accumulates a reduced amount of glycogen under non-stress conditions.

In another related embodiment, the present invention provides a method of producing a carbon-based product other than glycogen, comprising producing said carbon-based product in a modified photosynthetic microorganism, e.g., a Cyanobacterium, having a reduced level of expression of one or more genes of a glycogen biosynthesis or storage pathway and/or comprising one or more polynucleotides encoding a protein of a glycogen breakdown pathway or a functional fragment or variant thereof. In certain embodiments, the photosynthetic microorganism accumulates a reduced amount of glycogen under stress conditions, e.g., reduced nitrogen conditions, as compared to a wild type photosynthetic microorganism. In certain embodiments, the photosynthetic microorganism accumulates an increased amount of said carbon based product as compared to a wild type photosynthetic microorganism. In particular embodiments, the one or more genes are glucose-1-phosphate adenyltransferase (glgC), phosphoglucomutase (pgm), and/or glycogen synthase (glgA). In one particular embodiment, the photosynthetic microorganism comprises mutations in the one or more genes having reduced expression. In particular embodiments, the genes include the glgC gene and/or the pgm gene. In some embodiments, the mutations are complete or partial gene deletions.

In particular embodiments of the methods of the present invention, the photosynthetic microorganism is a Cyanobacterium. In certain embodiments, the Cyanobacterium is a *Synechococcus elongatus*. In one embodiment, the *Synechococcus elongatus* is strain PCC 7942. In certain embodiments, the modified photosynthetic microorganism is a salt tolerant variant of *S. elongatus* PCC 7942. In other embodiments, the modified photosynthetic microorganism is *Synechococcus* sp. PCC 7002 or *Synechocystis* sp. PCC 6803.

In various embodiments of the compositions and methods of the present invention, the carbon-based product comprises a lipid. In one embodiment, the lipid is a fatty acid. In one embodiment, the carbon-based product is a triglyceride.

In certain embodiments, any of the modified photosynthetic microorganisms described above further comprise one or more introduced polynucleotides encoding one or more enzymes associated with fatty acid, triglyceride, or lipid biosynthesis. In particular embodiments, the one or more polynucleotides are exogenous to the photosynthetic microorganism's native genome. In particular embodiments, the one or more enzymes include acetyl-CoA carboxylase (ACCase). In particular embodiments, the one or more enzymes comprise diacylglycerol acyltransferase (DGAT) or phosphatidate phosphatase.

In particular embodiments of the invention, the carbon-based product is a feedstock for biofuel or other specialty chemical. In one embodiment, the carbon-based product is a biofuel or other specialty chemical.

BRIEF DESCRIPTION OF THE SEVERAL VIEWS OF THE DRAWINGS

FIG. 4A shows the amount of various acyl chains in TAGs from cells expressing ADGATd, and FIG. 4B shows the amount of various acyl chains in TAGs from cells expressing ScoGAT.

FIG. 5A shows the TAGs expressed by a *Synechocystis* sp. strain PCC 6803 that carried ADP1-DGAT (+) or a vector control (−), following induction. FIG. 5B shows the TAGs expressed by a salt tolerant *S. elongatus* PCC 7942 that carried ADP1-DGAT, when grown in salt water, either uninduced (−) or induced (+) with IPTG. Control TAG (C16TAG) and fatty acid (palmitate) standards are also shown.

DETAILED DESCRIPTION

Figure 1:
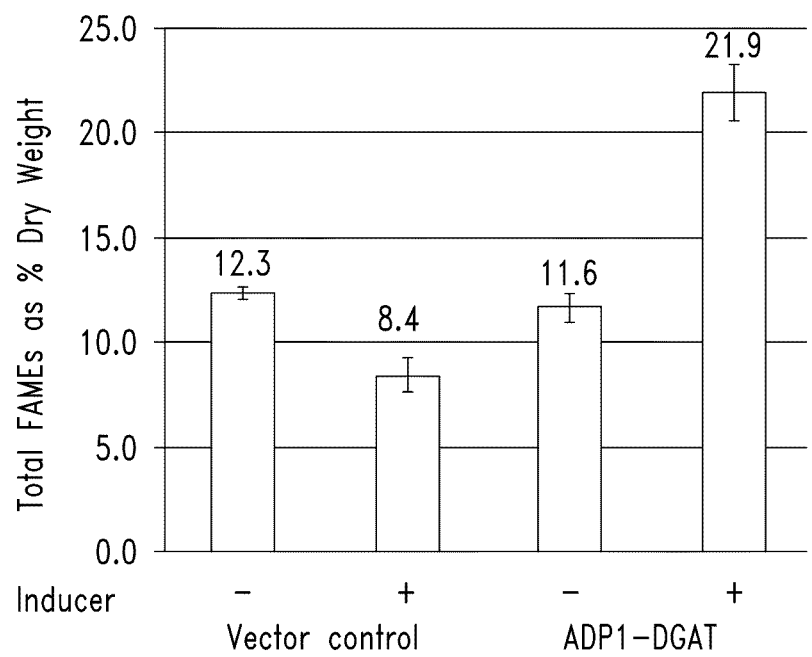
FIG. 1 shows the lipid content as measured by gas chromatography (GC) of *S. elongatus* PCC 7942 strain transformed with a diacylglycerol acyltransferase (ADP1-DGAT) gene from *Acinetobacter baylii* as compared to an empty vector control. Expression of the DGAT gene was under the control of an IPTG inducible promoter.

The present invention relates, in part, to the discovery that reducing the expression level of certain genes involved in glycogen synthesis, such as by mutation or deletion, leads to reduced glycogen synthesis and/or storage or accumulation in modified photosynthetic microorganisms, such as Cyanobacteria. For instance, Cyanobacteria, such as *Synechococcus*, which contain deletions of the glucose-1-phosphate adenylyltransferase gene (glgC), the phosphoglucomutase gene (pgm), and/or the glycogen synthase gene (glgA), individually or in various combinations, may produce and accumulate significantly reduced levels of glycogen as compared to wild type Cyanobacteria. The reduction of glycogen synthesis or accumulation may be especially pronounced under stress conditions, including the reduction of nitrogen. In addition, the present invention further relates to the discovery that the overexpression in photosynthetic microorganisms, including Cyanobacteria, of genes or proteins involved in glycogen breakdown also leads to reduced glycogen synthesis and/or storage.

Accordingly, the present invention further relates to the discovery that by blocking, disrupting, or down-regulating the natural glycogen synthesis and storage pathway, e.g., by gene mutation or deletion, or by increasing, enhancing, or up-regulating the natural glycogen breakdown pathway in modified photosynthetic microorganisms, such as Cyanobacteria, the resulting strains of photosynthetic microorganisms increase carbon flow into other biosynthetic pathways. Examples of other biosynthetic pathways include existing pathways, such as existing lipid biosynthetic pathways, or pathways that are introduced through genetic engineering, such as fatty acid or triglyceride biosynthesis pathways.

The present invention, therefore, relates generally to modified photosynthetic microorganisms, including modified Cyanobacteria, and methods of use thereof, which have been modified to produce or store reduced levels of glycogen as compared to wild-type photosynthetic microorganisms. In particular embodiments, the modified photosynthetic microorganism is genetically modified. In certain embodiments, the modified photosynthetic microorganism has a reduced level of expression of one or more genes of a glycogen biosynthesis or storage pathway and/or overexpresses one or more genes or proteins of a glycogen breakdown pathway, such that said photosynthetic microorganisms synthesizes or accumulates a reduced amount of glycogen, e.g., under stress conditions, e.g., reduced nitrogen, as compared to a wild type photosynthetic microorganism. In one embodiment, the modified photosynthetic microorganism comprises one or more mutations or deletions in one or more genes of a glycogen biosynthesis or storage pathway, which may be, e.g., complete or partial gene deletions. In other embodiments, the modified photosynthetic microorganism comprises one or more polynucleotides comprising an antisense RNA sequence that targets, e.g., hybridizes to, one or more genes or mRNAs of a glycogen biosynthesis or storage pathway, such as an antisense oligonucleotide or a short interfering RNA (siRNA), or a vector that expresses one or more such polynucleotides.

In particular embodiments, the modified photosynthetic microorganism produces an increased amount of a carbon-based product other than glycogen. Examples of such carbon-based products include lipids, fatty acids, e.g., free fatty acids, and/or triglycerides. Moreover, by further modifying a given photosynthetic microorganism of the present invention having a disrupted/reduced glycogen biosynthesis or storage pathway and/or an enhanced glycogen breakdown pathway, so as to increase the production of other carbon molecules, such as lipids or fatty acids, which are necessary for the production of triglycerides, and by also modifying that photosynthetic microorganism to produce triglycerides, certain of the modified photosynthetic microorganism of the present invention can be used to produce higher amounts of triglycerides than would otherwise be possible absent the discovery that disruption of glycogen pathways in photosynthetic microorganism could be utilized to increase the production of other carbon molecules.

In view of these discoveries, embodiments of the present invention may be useful in combination with the related discovery that photosynthetic microorganisms, including Cyanobacteria, such as *Synechococcus*, which do not naturally produce triglycerides, can be genetically modified to synthesize triglycerides, as described herein and in International Patent Application PCT/U.S.2009/061936, filed Oct. 23, 2009, titled Modified Photosynthetic Microorganisms for Producing Triglycerides. For instance, the addition of one or more polynucleotide sequences that encode one or more enzymes associated with triglyceride synthesis renders Cyanobacteria capable of converting their naturally-occurring fatty acids into triglyceride energy storage molecules. Examples of enzymes associated with triglyceride synthesis include enzymes having a phosphatidate phosphatase activity and enzymes having a diacylglycerol acyltransferase activity (DGAT). Specifically, phosphatidate phosphatase enzymes catalyze the production of diacylglycerol molecules, an immediate pre-cursor to triglycerides, and DGAT enzymes catalyze the final step of triglyceride synthesis by converting the diacylglycerol precursors to triglycerides.

Aspects of the present invention can also be combined with the discovery that photosynthetic microorganisms such as Cyanobacteria can be genetically modified in other ways to increase the production of fatty acids, as described herein and in International Patent Application PCT/U.S.2009/061936. Since fatty acids provide the starting material for triglycerides, increasing the production of fatty acids in genetically modified photosynthetic microorganisms may be utilized to increase the production of triglycerides, as described herein and in International Patent Application PCT/U.S.2009/061936. In addition to diverting carbon usage away from glycogen synthesis and towards lipid production, photosynthetic microorganisms of the present invention can also be modified to increase the production of fatty acids by introducing one or more exogenous polynucleotide sequences that encode one or more enzymes associated with fatty acid synthesis. In certain aspects, the exogenous polynucleotide sequence encodes an enzyme that comprises an acyl-CoA carboxylase (ACCase) activity, typically allowing increased ACCase expression, and, thus, increased intracellular ACCase activity. Increased intracellular ACCase activity contributes to the increased production of fatty acids because this enzyme catalyzes the "commitment step" of fatty acid synthesis. Specifically, ACCase catalyzes the production of a fatty acid synthesis precursor molecule, malonyl-CoA. In certain embodiments, the polynucleotide sequence encoding the ACCase is not native the photosynthetic microorganisms's genome.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. The term "reference sequence" refers generally to a nucleic acid coding sequence, or amino acid sequence, to which another sequence is being compared.

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an activity of a reference polynucleotide or polypeptide. Representative biologically active fragments generally participate in an interaction, e.g., an intra-molecular or an inter-molecular interaction. An inter-molecular interaction can be a specific binding interaction or an enzymatic interaction. Examples of enzymatic interactions or activities include diacylglycerol acyltransferase activity, phosphatidate phosphatase activity, and/or acetyl-CoA carboxylase activity, as described herein.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

By "increased" or "increasing" is meant the ability of one or more modified photosynthetic microorganisms, e.g., Cyanobacteria, to produce or store a greater amount of a given fatty acid, lipid molecule, or triglyceride as compared to a control photosynthetic microorganism, such as an unmodified Cyanobacteria or a differently modified Cyanobacteria. Production of fatty acids can be measured according to techniques known in the art, such as Nile Red staining, thin layer chromatography and gas chromatography. Production of triglycerides can be measured, for example, using commercially available enzymatic tests, including colorimetric enzymatic tests using glycerol-3-phosphate-oxidase. In particular embodiments, production or storage of a given fatty acid, lipid molecule, or triglyceride is increased by at least 10%, at least 20%, at least 30%, at least 40%, at least 50%, at least 60%, at least 70%, at least 80%, at least 90%, at least 100%, at least 150%, at least 200%, at least 300%, at least 400%, at least 500%, or at least 1000%. In certain embodiments, production or storage of a given fatty acid, lipid molecule, or triglyceride is increased by 50% to 200%.

In certain instances, by "decreased" or "reduced" is meant the ability of one or more modified photosynthetic microorganisms, e.g., Cyanobacteria, to produce or accumulate a lesser amount (e.g., a statistically significant amount) of a given carbon-based product, such as glycogen, as compared to a control photosynthetic microorganism, such as an unmodified Cyanobacteria or a differently modified Cyanobacteria. Production of glycogen and related molecules can be measured according to techniques known in the art, as exemplified herein (see Example 6; and Suzuki et al., *Biochimica et Biophysica Acta* 1770:763-773, 2007). In certain instances, by "decreased" or "reduced" is meant a lesser level of expression (e.g., a statistically significant amount), by a modified photosynthetic microorganism, e.g., Cyanobacteria, of one or more genes associated with a glycogen biosynthesis or storage pathway, as compared to the level of expression in a control phosynthetic microorganism, such as an unmodified Cyanobacteria or a differently modified Cyanobacteria. In particular embodiments, production or accumulation of a carbon-based product, or expression of one or more genes associated with glycogen biosynthesis or storage is reduced by at least 10%, at least 20%, at least 30%, at least 40%, at least 50%, at least 60%, at least 70%, at least 80%, at least 90%, or 100%. In particular embodiments, production or accumulation of a carbon-based product, or expression of one or more genes associated with glycogen biosynthesis or storage is reduced by 50-100%.

"Stress conditions" refers to any condition that imposes stress upon the Cyanobacteria, including both environmental and physical stresses. Examples of stresses include but not limited to: reduced or increased temperature as compared to standard; nutrient deprivation; reduced or increased light exposure, e.g., intensity or duration, as compared to standard; exposure to reduced or increased nitrogen, iron, sulfur, phosphorus, and/or copper as compared to standard; altered pH, e.g., more or less acidic or basic, as compared to standard; altered salt conditions as compared to standard; exposure to an agent that causes DNA synthesis inhibitor or protein synthesis inhibition; and increased or decreased culture density as compared to standard. Standard growth and culture conditions for various Cyanobacteria are known in the art.

"Reduced nitrogen conditions," or conditions of "nitrogen limitation," refer generally to culture conditions in which a certain fraction or percentage of a standard nitrogen concentration is present in the culture media. Such fractions typically include, but are not limited to, about $1/50$, $1/40$, $1/30$, $1/10$, $1/5$, $1/4$, or about $1/2$ the standard nitrogen conditions. Such percentages typically include, but are not limited to, less than about 1%, 2%, 3%, 4%, 5%, 6%, 7%, 8%, 9%, 10%, 15%, 20%, 30%, 40%, or 50% the standard nitrogen conditions. "Standard" nitrogen conditions can be estimated, for example, by the amount of nitrogen present in BG11 media, as exemplified herein and known in the art. For instance, BG11 media usually contains nitrogen in the form of $NaNO_3$ at a concentration of about 1.5 grams/liter (see, e.g., Rippka et al., *J. Gen Microbiol.* 111:1-61, 1979).

By "obtained from" is meant that a sample such as, for example, a polynucleotide or polypeptide is isolated from, or derived from, a particular source, such as a desired organism or a specific tissue within a desired organism. "Obtained from" can also refer to the situation in which a polynucleotide or polypeptide sequence is isolated from, or derived from, a particular organism or tissue within an organism. For example, a polynucleotide sequence encoding a diacylglycerol acyltransferase, phosphatidate phosphatase, and/or acetyl-CoA carboxylase enzyme may be isolated from a variety of prokaryotic or eukaryotic organisms, or from particular tissues or cells within certain eukaryotic organism.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the gene from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence that encodes a diacylglycerol acyltransferase, a phosphatidate phosphatase, and/or an acetyl-CoA carboxylase enzyme. The terms "polynucleotide variant" and "variant" also include naturally-occurring allelic variants and orthologs that encode these enzymes.

With regard to polynucleotides, the term "exogenous" refers to a polynucleotide sequence that does not naturally occur in a wild type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally occurring polynucleotide sequences that may be found in a given wild type cell or organism. For example, certain Cyanobacterial species do not typically contain a DGAT gene, and, therefore, do not comprise an "endogenous" polynucleotide sequence that encodes a DGAT polypeptide. Also, a particular polynucleotide sequence that is isolated from a first organism and transferred to second organism by molecular biological techniques is typically considered an "exogenous" polynucleotide with respect to the second organism.

The recitations "mutation" or "deletion," in relation to the genes of a "glycogen biosynthesis or storage pathway," refer generally to those changes or alterations in a photosynthetic microorganism, e.g., a Cyanobacterium, that render the product of that gene non-functional or having reduced function with respect to the synthesis and/or storage of glycogen. Examples of such changes or alterations include nucleotide substitutions, deletions, or additions to the coding or regulatory sequences of a targeted gene (e.g., glgA, glgC, and pgm), in whole or in part, which disrupt, eliminate, down-regulate, or significantly reduce the expression of the polypeptide encoded by that gene, whether at the level of transcription or translation. Techniques for producing such alterations or changes, such as by recombination with a vector having a selectable marker, are exemplified herein and known in the molecular biological art. In particular embodiments, one or more alleles of a gene, e.g., two or all alleles, may be mutated or deleted within a photosynthetic microorganism. In particular embodiments, modified photosynthetic microorganisms, e.g., Cyanobacteria, of the present invention are merodiploids or partial diploids.

The "deletion" of a targeted gene may also be accomplished by targeting the mRNA of that gene, such as by using various antisense technologies (e.g., antisense oligonucleotides and siRNA) known in the art. Accordingly, targeted genes may be considered "non-functional" when the polypeptide or enzyme encoded by that gene is not expressed by the modified photosynthetic microorganism, or is expressed in negligible amounts, such that the modified photosynthetic microorganism produces or accumulates less glycogen than an unmodified or differently modified photosynthetic microorganism.

In certain aspects, a targeted gene may be rendered "non-functional" by changes or mutations at the nucleotide level that alter the amino acid sequence of the encoded polypeptide, such that a modified polypeptide is expressed, but which has reduced function or activity with respect to glycogen biosynthesis or storage, whether by modifying that polypeptide's active site, its cellular localization, its stability, or other functional features apparent to a person skilled in the art. Such modifications to the coding sequence of a polypeptide involved in glycogen biosynthesis or storage may be accomplished according to known techniques in the art, such as site directed mutagenesis at the genomic level and/or natural selection (i.e., directed evolution) of a given photosynthetic microorganism.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length enzymes having diacylglycerol acyltransferase activity, phosphatidate phosphatase activity, and/or acetyl-CoA carboxylase activity, polypeptides associated with a glycogen breakdown pathway, truncated fragments of these full-length enzymes and polypeptides, variants of truncated fragments, as well as their related biologically active fragments. Typically, biologically active fragments of a polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken). Biologically active fragments of a polypeptide/enzyme having a diacylglycerol acyltransferase activity, a phosphatidate phosphatase activity, and/or acetyl-CoA carboxylase activity, or polypeptides associated with a glycogen breakdown pathway, include peptides comprising amino acid sequences sufficiently similar to, or derived from, the amino acid sequences of a (putative) full-length reference polypeptide sequence. Typically, biologically active fragments comprise a domain or motif with at least one activity of a diacylglycerol acyltransferase polypeptide, phosphatidate phosphatase polypeptide, acetyl-CoA carboxylase polypeptide, or polypeptide associated with a glycogen breakdown pathway, and may include one or more (and in some cases all) of the various active domains. A biologically active fragment of a diacylglycerol acyltransferase, phosphatidate phosphatase, acetyl-CoA carboxylase polypeptide, or a polypeptide associated with a glycogen breakdown pathway can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "triglyceride" (triacylglycerol or neutral fat) refers to a fatty acid triester of glycerol. Triglycerides are typically non-polar and water-insoluble. Phosphoglycerides (or glycerophospholipids) are major lipid components of biological membranes, and include, for example, any derivative of sn-glycero-3-phosphoric acid that contains at least one O-acyl, or O-alkyl or O-alk-1'-enyl residue attached to the glycerol moiety and a polar head made of a nitrogenous base, a glycerol, or an inositol unit. Phosphoglycerides can also be characterized as amphipathic lipids formed by esters of acylglycerols with phosphate and another hydroxylated compound.

"Transformation" refers to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a photosynthetic microorganism cell, such as a Cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild type" form of the gene.

Modified Photosynthetic Microorganisms

Certain embodiments of the present invention relate to modified photosynthetic microorganisms, including Cyanobacteria, and methods of use thereof, wherein the modified photosynthetic microorganisms have a reduced level of expression of one or more genes of a glycogen biosynthesis or storage pathway, as compared to the level of expression of the one or more genes in a control photosynthetic microorganism. In certain embodiments, the modified photosynthetic microorganism comprises one or more mutations or deletions in one or more genes of a glycogen biosynthesis or storage pathway. In particular embodiments, said one or more genes include a glucose-1-phosphate adenyltransferase (glgC), a phosphoglucomutase (pgm), and/or a glycogen synthase (glgA) gene. The present invention contemplates the use of any method to reduce expression of the one or more genes in the modified photosynthetic microorganism, including the use of any type of mutation or deletion in the one or more genes associated with glycogen biosynthesis or storage, as long as the modified Cyanobacterium accumulates a reduced amount of glycogen as compared to a wild type Cyanobacterium (e.g., under reduced nitrogen conditions).

Certain embodiments of the present invention relate to modified photosynthetic microorganisms, including Cyanobacteria, and methods of use thereof, wherein the modified photosynthetic microorganisms have an increased level of expression of one or more polynucleotides encoding one or more enzymes or proteins associated with glycogen breakdown, removal, and/or elimination, or a functional fragment thereof, as compare to a control or unmodified photosynthetic microorganism. In particular embodiments, the modified photosynthetic microorganisms comprise one or more polynucleotides encoding one or more enzymes or proteins associated with glycogen breakdown, removal, and/or elimination, or a functional fragment thereof. In particular embodiments, said one or more polynucleotides encode a glycogen phosphorylase (GlgP), a glycogen debranching enzyme (GlgX), an amylomaltase (MalQ), a phosphoglucomutase (Pgm), a glucokinase (Glk), and/or a phosphoglucose isomerase (Pgi), or a functional fragment or variant thereof. Pgm, Glk, and Pgi are bidirectional enzymes that can promote glycogen synthesis or breakdown depending on conditions. The present invention contemplates the use of any type of polynucleotide encoding a protein or enzyme associated with glycogen breakdown, removal, and/or elimination, as long as the modified photosynthetic microorganism accumulates a reduced amount of glycogen as compared to the wild type photosynthetic microorganism (e.g., under stress conditions).

In particular embodiments, the present invention includes a modified photosynthetic microorganism, such as a Cyanobacterium, having a reduced level of expression of one or more genes of a glycogen biosynthesis or storage pathway and an increased level of expression of one or more polynucleotides encoding one or more enzymes or proteins associated with glycogen breakdown, removal, and/or elimination, or a functional fragment or variant thereof. In particular embodiments, the modified photosynthetic microorganism comprises one or more mutations or deletions of one or more genes of a glycogen biosynthesis or storage pathway, as well as one or more introduced polynucleotides encoding one or more enzymes or proteins associated with glycogen breakdown, removal, and/or elimination, or a functional fragment or variant thereof.

Certain embodiments of the present invention also relate to modified photosynthetic microorganisms, e.g., Cyanobacteria, and methods of use thereof, wherein the modified photosynthetic microorganisms has either or both: (1) reduced levels of expression of one or more one or more genes of a glycogen biosynthesis or storage; and/or (2) increased levels of expression of one or more polynucleotides encoding one or more enzymes or proteins associated with glycogen breakdown, removal, and/or elimination, or a functional fragment or variant thereof, wherein the modified photosynthetic microorganisms comprise: (3) one or more polynucleotides encoding one or more enzymes associated with triglyceride biosynthesis, such as wherein the enzymes comprise a diacylglycerol acyltransferase (DGAT) activity and/or a phosphatidate phosphatase activity. In particular embodiments, the modified photosynthetic microorganisms comprise a mutation or deletion of one or more genes of a glycogen biosynthesis or storage pathway and/or comprises one or more introduced polynucleotides encoding one or more enzymes or proteins associated with glycogen breakdown, removal, and/or elimination, or a functional fragment or variant thereof. The present invention contemplates the use of naturally-occurring and non-naturally-occurring variants of these DGAT and phosphatidate phosphatase enzymes, as well as variants of their encoding polynucleotides. In certain aspects, the DGAT encoding polynucleotide sequence is derived from *Acinetobacter baylii* (ADP1-DGAT) and the phosphatidate phosphatase encoding polynucleotide sequence is from *Saccharomyces cerevisiae* (yPah1). These enzyme encoding sequences, however, may be derived from any organism having a suitable DGAT or phosphatidate phosphatase enzyme, and may also include any man-made variants thereof, such as any optimized coding sequences (i.e., codon-optimized polynucleotides) or optimized polypeptide sequences. Thus, in certain embodiments, modified Cyanobacterium that comprise one or more mutations or deletions in one or more genes of a glycogen biosynthesis or storage pathway may also comprise one or more polynucleotides encoding one or more enzymes associated with triglyceride biosynthesis.

In certain embodiments, the modified photosynthetic microorganisms of the present invention may comprise two or more polynucleotides that encode DGAT or a variant or fragment thereof. In particular embodiments, the two or more polynucleotides are identical or express the same DGAT. In certain embodiments, these two or more polynucletoides may be different or may encode two different DGAT polypeptides. For example, in one embodiment, one of the polynucleotides may encode ADGATd, while another polynucleotide may encode ScoDGAT. In particular embodiments, the following DGATs are coexpressed in modified photosynthetic microorganisms, e.g., Cyanobacteria, using one of the following double DGAT strains: ADGATd(NS1)::ADGATd(NS2); ADGATn(NS1)::ADGATn(NS2); ADGATn(NS1)::SDGAT (NS2); SDGAT(NS1)::ADGATn(NS2); SDGAT(NS1)::SDGAT(NS2). For the NS1 vector, pAM2291, EcoRI follows ATG and is part of the open reading frame (ORF). For the NS2 vector, pAM1579, EcoRI follows ATG and is part of the ORF. A DGAT having EcoRI nucleotides following ATG may be cloned in either pAM2291 or pAM1579; such a DGAT is referred to as ADGATd. Other embodiments utilize the vector, pAM2314FTrc3, which is an NS1 vector with Nde/BgIII sites, or the vector, pAM1579FTrc3, which is the NS2 vector with Nde/BgIII sites. A DGAT without EcoRI nucleotides may be cloned into either of these last two vectors. Such a DGAT is referred to as ADGATn. As shown in the accompanying Examples, modified photosynthetic microorganisms expressing different DGATs express TAGs having different fatty acid compositions. Accordingly, certain embodiments of the present invention contemplate expressing two or more different DGATs, in order to produce TAGs having varied fatty acid compositions.

Related embodiments contemplate expressing two or more different phosphatidate phosphatase and/or two or more different acetyl-CoA carboxylases.

Embodiments of the present invention also relate to modified photosynthetic microorganisms, e.g., Cyanobacteria, and methods of use thereof, wherein the modified photosynthetic microorganisms has either or both: (1) reduced levels of expression of one or more one or more genes of a glycogen biosynthesis or storage; and/or (2) increased levels of expression of one or more polynucleotides encoding one or more enzymes or proteins associated with glycogen breakdown, removal, and/or elimination, or a functional fragment or variant thereof, wherein the modified photosynthetic microorganisms comprise: (3) one or more polynucleotides encoding enzymes associated with fatty acid biosynthesis, such as wherein said polynucleotides are exogenous to the photosynthetic microorganisms's native genome. In particular embodiments, the modified photosynthetic microorganisms comprise a mutation or deletion of one or more genes of a glycogen biosynthesis or storage pathway and/or comprise one or more introduced polynucleotides encoding one or more enzymes or proteins associated with glycogen breakdown, removal, and/or elimination, or a functional fragment or variant thereof. In certain aspects, the enzymes associated with fatty acid synthesis comprise an acetyl-CoA carboxylase (ACCase) activity, including naturally-occurring and non-naturally-occurring functional variants of such enzymes and their encoding polynucleotides. In certain embodiments, the polynucleotide sequences encoding the ACCase enzyme is derived from Synechococcus sp. PCC 7002 (7002-ACCase). As above, however, these ACCase enzyme encoding sequences may be derived from any organism having a suitable ACCase enzyme, and may also include any man-made variants thereof, such as any optimized coding sequences (i.e., codon-optimized polynucleotides) or optimized polypeptide sequences.

Since, as noted above, fatty acids provide the starting material for triglyceride production, genetically modified photosynthetic microorganisms, e.g., Cyanobacteria, having increased fatty acid production may by utilized to improve the overall production of triglycerides. Accordingly, certain embodiments relate to further modified photosynthetic microorganisms, and methods of use thereof, wherein the modified photosynthetic microorganisms comprise one or more polynucleotides encoding enzymes associated with fatty acid synthesis and triglyceride synthesis. As such, in certain embodiments, the modified photosynthetic microorganisms of the present invention comprise one or more polynucleotides encoding enzymes that comprise a DGAT activity, a phosphatidate phosphatase activity, and/or an ACCase activity. Moreover, in certain embodiments, modified photosynthetic microorganisms having an increased level of expression of one or more genes of a glycogen biosynthesis or storage pathway (e.g., due to the presence of one or more mutations or deletions in one or more genes of a glycogen biosynthesis or storage pathway) and/or an increase level of expression of one or more polynucleotides encoding one or more enzymes or proteins associated with lycogen breakdown, removal, and/or elimination (e.g., due to the presence of one or more introduced polynucleotides encoding one or more enzymes or proteins associated with glycogen breakdown, removal, and/or elimination, or a functional fragment or varian thereof), may further comprise one or more polynucleotides encoding enzymes associated with fatty acid biosynthesis and/or triglyceride biosynthesis, including various combinations thereof, which will be apparent to a person skilled in the art.

In one particular embodiment, a modified photosynthetic microorganism, e.g., a Cyanobacterium, may comprise one or more mutations in one or more genes of a glycogen biosynthesis or storage pathway, as described herein, and may comprise one or more exogenous polynucleotides encoding enzymes that comprise a DGAT activity, a phosphatidate phosphatase activity, and/or an ACCase activity.

In another particular embodiment, a modified photosynthetic microorganism, e.g., a Cyanobacterium, may comprise one or more introduced polynucleotides encoding one or more polypeptides associated with glycogen breakdown, as described herein, and may comprise one or more exogenous polynucleotides encoding enzymes that comprise a DGAT activity, a phosphatidate phosphatase activity, and/or an ACCase activity.

Photosynthetic Microorganisms

Modified photosynthetic microorganisms of the present invention may be produced using any type of photosynthetic microorganism. These include, but are not limited to photosynthetic bacteria, green algae, and cyanobacteria. The photosynthetic microorganism can be, for example, a naturally photosynthetic microorganism, such as a Cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; eukaryotes, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix*.

A modified Cyanobacteria of the present invention may be from any genera or species of Cyanobacteria that is genetically manipulable, i.e., permissible to the introduction and expression of exogenous genetic material. Examples of Cyanobacteria that can be engineered according to the methods of the present invention include, but are not limited to, the genus *Synechocystis, Synechococcus, Thermosynechococcus, Nostoc, Prochlorococcu, Microcystis, Anabaena, Spirulina,* and *Gloeobacter.*

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the present invention.

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Heterocysts may also form under the appropriate environmental conditions (e.g., anoxic) whenever nitrogen is necessary. Heterocyst-forming species are specialized for nitrogen fixation and are able to fix nitrogen gas, which cannot be used by plants, into ammonia ($NH_3$), nitrites ($NO_2^-$), or nitrates ($NO_3^-$), which can be absorbed by plants and converted to protein and nucleic acids.

Many Cyanobacteria also form motile filaments, called hormogonia, which travel away from the main biomass to bud and form new colonies elsewhere. The cells in a hormogonium are often thinner than in the vegetative state, and the cells on either end of the motile chain may be tapered. In order to break away from the parent colony, a hormogonium often must tear apart a weaker cell in a filament, called a necridium.

Each individual Cyanobacterial cell typically has a thick, gelatinous cell wall. Cyanobacteria differ from other gram-negative bacteria in that the quorum sensing molecules autoinducer-2 and acyl-homoserine lactones are absent. They lack flagella, but hormogonia and some unicellular species may move about by gliding along surfaces. In water columns some Cyanobacteria float by forming gas vesicles, like in archaea.

Cyanobacteria have an elaborate and highly organized system of internal membranes that function in photosynthesis. Photosynthesis in Cyanobacteria generally uses water as an electron donor and produces oxygen as a by-product, though some Cyanobacteria may also use hydrogen sulfide, similar to other photosynthetic bacteria. Carbon dioxide is reduced to form carbohydrates via the Calvin cycle. In most forms the photosynthetic machinery is embedded into folds of the cell membrane, called thylakoids. Due to their ability to fix nitrogen in aerobic conditions, Cyanobacteria are often found as symbionts with a number of other groups of organisms such as fungi (e.g., lichens), corals, pteridophytes (e.g., *Azolla*), and angiosperms (e.g., *Gunnera*), among others.

Cyanobacteria are the only group of organisms that are able to reduce nitrogen and carbon in aerobic conditions. The water-oxidizing photosynthesis is accomplished by coupling the activity of photosystem (PS) II and I (Z-scheme). In anaerobic conditions, Cyanobacteria are also able to use only PS I (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property; the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes, attached to the thylakoid membrane, act as light harvesting antennae for the photosystems of Cyanobacteria. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

In particular embodiments, the Cyanobacteria may be, e.g., a marine form of Cyanobacteria or a fresh water form of Cyanobacteria. Examples of marine forms of Cynobacteria include, but are not limited to *Synechococcus* WH8102, *Synechococcus* RCC307, *Synechococcus* NKBG 15041c, and *Trichodesmium*. Examples of fresh water forms of Cyanobacteria include, but are not limited to, *S. elongatus* PCC 7942, *Synechocystis* PCC 6803, *Plectonema boryanum*, and *Anabaena* sp. Exogenous genetic material encoding the desired enzymes may be introduced either transiently, such as in certain self-replicating vectors, or stably, such as by integration (e.g., recombination) into the Cyanobacterium's native genome.

In other embodiments, a genetically modified Cyanobacteria of the present invention may be capable of growing in brackish or salt water. When using a fresh water form of Cyanobacteria, the overall net cost for production of triglycerides will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It consists of liquid waste released from domestic and commercial properties, industry, and/or agriculture and can encompass a wide range of possible contaminants at varying concentrations.

There is a broad distribution of Cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In particular embodiments, the present invention contemplates the use of a Cyanobacteria *S. elongatus* PCC 7942, altered in a way that allows for growth in either waste water or salt/brackish water. A *S. elongatus* PCC 7942 mutant resistant to sodium chloride stress has been described (Bagchi, S, N. et al., Photosynth Res. 2007, 92:87-101), and a genetically modified *S. elongatus* PCC 7942 tolerant of growth in salt water has been described (Waditee, R. et al., PNAS 2002, 99:4109-4114). Salt water tolerant Cyanobacteria may also be prepared as described in the accompanying Examples. According to the present invention a salt water tolerant strain is capable of growing in water or media having a salinity in the range of 0.5% to 4.0% salinity, although it is not necessarily capable of growing in all salinities encompassed by this range. In one embodiment, a salt tolerant strain is capable of growth in water or media having a salinity in the range of 1.0% to 2.0% salinity. In another embodiment, a salt water tolerant strain is capable of growth in water or media having a salinity in the range of 2.0% to 3.0% salinity.

Examples of Cyanobacteria that may be utilized and/or genetically modified according to the methods described herein include, but are not limited to, *Chroococcales* Cyanobacteria from the genera *Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloeocapsa, Gloeothece, Merismopedia, Microcystis, Radiocystis, Rhabdoderma, Snowella, Synychococcus, Synechocystis, Thermosenechococcus*, and *Woronichinia; Nostocales* Cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis*, and *Toypothrix; Oscillatoriales* Cyanobacteria from the genera *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Spirulina, Symploca, Trichodesmium, Tychonema; Pleurocapsales* cyanobacterium from the genera *Chroococcidiopsis, Dermocarpa, Dermocarpella, Myxosarcina, Pleurocapsa, Stanieria, Xenococcus; Prochlorophytes* Cyanobacterium from the genera *Prochloron, Prochlorococcus, Prochlorothrix*; and *Stigonematales* cyanobacterium from the genera *Capsosira, Chlorogeoepsis, Fischerella, Hapalosiphon, Mastigocladopsis, Nostochopsis, Stigonema, Symphyonema, Symphonemopsis, Umezakia*, and *Westiellopsis*. In certain embodiments, the Cyanobacterium is from the genus *Synechococcus*, including, but not limited to *Synechococcus bigranulatus, Synechococcus elongatus, Synechococcus leopoliensis, Synechococcus lividus, Synechococcus nidulans*, and *Synechococcus rubescens*.

In certain embodiments, the Cyanobacterium is *Anabaena* sp. strain PCC 7120, *Synechocystis* sp. strain PCC 6803, *Nostoc muscorum, Nostoc ellipsosporum*, or *Nostoc* sp. strain PCC 7120. In certain preferred embodiments, the Cyanobacterium is *S. elongatus* sp. strain PCC 7942.

Additional examples of Cyanobacteria that may be utilized in the methods provided herein include, but are not limited to, *Synechococcus* sp. strains WH7803, WH8102, WH8103 (typically genetically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), and Heterocyst-forming strains *Anabaena* sp. strains ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In certain preferred embodiments, the Cyanobacterium may be *S. elongatus* sp. strain PCC 7942 or *Synechococcus* sp. PCC 7002 (originally known as *Agmenellum quadruplicatum*).

In particular embodiments, the genetically modified, photosynthetic microorganism, e.g., Cyanobacteria, of the present invention may be used to produce triglycerides and/or other carbon-based products from just sunlight, water, air, and minimal nutrients, using routine culture techniques of any reasonably desired scale. In particular embodiments, the present invention contemplates using spontaneous mutants of photosynthetic microorganisms that demonstrate a growth advantage under a defined growth condition. Among other benefits, the ability to produce large amounts of triglycerides from minimal energy and nutrient input makes the modified photosynthetic microorganism, e.g., Cyanobacteria, of the present invention a readily manageable and efficient source of feedstock in the subsequent production of both biofuels, such as biodiesel, as well as specialty chemicals, such as glycerin.

Methods of Producing Modified Photosynthetic Microorganisms

Embodiments of the present invention also include methods of producing a modified photosynthetic microorganism, e.g., a Cyanobacterium, that accumulates a reduced amount of glycogen under stress conditions, e.g., reduced nitrogen, as compared to a wild type photosynthetic microorganism, comprising modifying the photosynthetic microorganism so that it has a reduced level of expression of one or more genes of a glycogen biosynthesis or storage pathway. In certain embodiments, said one or more genes include glucose-1-phosphate adenyltransferase (glgC), phosphoglucomutase (pgm), and/or glycogen synthase (glgA). In particular embodiments, expression or activity is reduced by mutating or deleting a portion or all of said one or more genes. In particular embodiments, expression or activity is reduced by knocking out or knocking down one or more alleles of said one or more genes. In particular embodiments, expression or activity of the one or more genes is reduced by contacting the photosynthetic microorganism with an antisense oligonucleotide or interfering RNA, e.g., an siRNA, that targets said one or more genes. In particular embodiments, a vector that expresses a polynucleotide that hybridizes to said one or more genes, e.g., an antisense oligonucleotide or an siRNA is introduced into said photosynthetic microorganism.

Photosynthetic microorganisms, e.g., Cyanobacteria may be genetically modified according to techniques known in the art, e.g., to delete a portion or all of a gene or to introduce a polynucleotide that expresses a functional polypeptide. As noted above, in certain aspects, genetic manipulation in photosynthetic microorganisms, e.g., Cyanobacteria, can be performed by the introduction of non-replicating vectors which contain native photosynthetic microorganism sequences, exogenous genes of interest, and selectable markers or drug resistance genes. Upon introduction into the photosynthetic microorganism, the vectors may be integrated into the photosynthetic microorganism's genome through homologous recombination. In this way, an exogenous gene of interest and the drug resistance gene are stably integrated into the photosynthetic microorganism's genome. Such recombinants cells can then be isolated from non-recombinant cells by drug selection. Cell transformation methods and selectable markers for Cyanobacteria are also well known in the art (see, e.g., Wirth, *Mol Gen Genet.* 216:175-7, 1989; and Koksharova, *Appl Microbiol Biotechnol* 58:123-37, 2002; and THE CYANOBACTERIA: MOLECULAR BIOLOGY, GENETICS, AND EVOLUTION (eds. Antonio Herrera and Enrique Flores) Caister Academic Press, 2008, each of which is incorporated by reference for their description on gene transfer into Cyanobacteria, and other information on Cyanobacteria).

Generation of deletions or mutations of any of the one or more genes associated with the biosynthesis or storage of glycogen can be accomplished according to a variety of methods known in the art, including those described and exemplified herein. For instance, the instant application describes the use of a non-replicating, selectable vector system that is targeted to the upstream and downstream flanking regions of a given gene (e.g., glgC, pgm), and which recombines with the Cyanobacterial genome at those flanking regions to replace the endogenous coding sequence with the vector sequence. Given the presence of a selectable marker in the vector sequence, such as a drug selectable marker, Cyanobacterial cells containing the gene deletion can be readily isolated, identified and characterized. Such selectable vector-based recombination methods need not be limited to targeting upstream and downstream flanking regions, but may also be targeted to internal sequences within a given gene, as long as that gene is rendered "non-functional," as described herein.

The generation of deletions or mutations can also be accomplished using antisense-based technology. For instance, Cyanobacteria have been shown to contain natural regulatory events that rely on antisense regulation, such as a 177-nt ncRNA that is transcribed in antisense to the central portion of an iron-regulated transcript and blocks its accumulation through extensive base pairing (see, e.g., Dühring, et al., *Proc. Natl. Acad. Sci. USA* 103:7054-7058, 2006), as well as a alr1690 mRNA that overlaps with, and is complementary to, the complete furA gene, which acts as an antisense RNA (α-furA RNA) interfering with furA transcript translation (see, e.g., Hernandez et al., *Journal of Molecular Biology* 355:325-334, 2006). Thus, the incorporation of antisense molecules targeted to genes involved in glycogen biosynthesis or storage would be similarly expected to negatively regulate the expression of these genes, rendering them "non-functional," as described herein.

As used herein, antisense molecules encompass both single and double-stranded polynucleotides comprising a strand having a sequence that is complementary to a target coding strand of a gene or mRNA. Thus, antisense molecules include both single-stranded antisense oligonucleotides and double-stranded siRNA molecules.

The present invention also relates to methods of preparing a modified photosynthetic microorganism, such as by genetic modification, to increase production of naturally-occurring fatty acids, and/or to produce triglycerides. Accordingly, in certain aspects, modified photosynthetic microorganisms, e.g., Cyanobacteria, may be prepared by: (i) modifying a photosynthetic microorganism so that it expresses a reduced amount of one or more genes associated with a glycogen biosynthesis or storage pathway and/or an increased amount of one or more polynucleotides encoding a polypeptide associated with a glycogen breakdown pathway; and (ii) introducing one or more desired polynucleotides encoding one or more enzymes associated with fatty acid and/or triglyceride biosynthesis into the photosynthetic microorganism. The method may further comprise a step of: (iii) selecting for photosynthetic microorganisms in which the one or more desired polynucletodes were successfully introduced, where the polynucleotides were, e.g., present in a vector the expressed a selectable marker, such as an antibiotic resistance gene. As one example, selection and isolation may include the use of antibiotic resistant markers known in the art (e.g., kanamycin, spectinomycin, and streptomycin).

In certain embodiments, the one or more enzymes associated with triglyceride synthesis comprise a diacylglycerol acyltransferase (DGAT) enzymatic activity and/or a phosphatidate phosphatase enzymatic activity. In certain embodiments the one or more enzymes associated fatty acid biosynthesis comprise an acyl-CoA carboxylase (ACCase) enzymatic activity.

Photosynthetic microorganism may be cultured according to techniques known in the art. For example, Cyanobacteria may be cultured or cultivated according to techniques known in the art, such as those described in Acreman et al. (*Journal of Industrial Microbiology and Biotechnology* 13:193-194, 1994), in addition to photobioreactor based techniques, such as those described in Nedbal et al. (*Biotechnol Bioeng.* 100: 902-10, 2008). One example of typical laboratory culture conditions for Cyanobacterium is growth in BG-11 medium (ATCC Medium 616) at 30° C. in a vented culture flask with constant agitation and constant illumination at 30-100 µmole photons $m^{-2}$ $sec^{-1}$.

A wide variety of mediums are available for culturing Cyanobacteria, including, for example, Aiba and Ogawa (AO) Medium, Allen and Arnon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [BG-11 medium]), ATCC Medium 819 (Blue-green Nitrogen-fixing Medium; ATCC Medium 616 [BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), *Beggiatoa* Medium (ATCC Medium 138), *Beggiatoa* Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (*Halophilic cyanobacteria*), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erdschreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Spirulina*: ATCC Medium 1679, *Spirulina* (SP) Medium, van Rijn and Cohen (RC) Medium, Walsby's Medium, Yopp Medium, and Z8 Medium, among others.

In certain embodiments, modified photosynthetic microorganisms, e.g., Cyanobacteria, are grown under conditions favorable for producing triglycerides and/or fatty acids. In particular embodiments, light intensity is between 100 and 2000 uE/m2/s, or between 200 and 1000 uE/m2/s. In particular embodiments, the pH range of culture media is between 7.0 and 10.0. In certain embodiments, $CO_2$ is injected into the culture apparatus to a level in the range of 1% to 10%. In particular embodiments, the range of $CO_2$ is between 2.5% and 5%. In certain embodiments, nutrient supplementation is performed during the linear phase of growth. Each of these conditions is desirable for triglyceride production.

Nucleic Acids and Polypeptides

In certain embodiments, modified photosynthetic microorganisms, e.g., Cyanobacteria, of the present invention comprise one or more exogenous or introduced nucleic acids that encode a polypeptide having an activity associated with a glycogen breakdown or triglyceride or fatty acid biosynthesis, including but not limited to any of those described herein. In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

In various embodiments, modified photosynthetic microorganisms, e.g., Cyanobacteria, of the present invention have reduced expression of one or more genes associated with glycogen synthesis and/or storage. In particular embodiments, these modified photosynthetic microorganisms have a mutated or deleted gene associated with glycogen synthesis and/or storage. In particular embodiments, these modified photosynthetic microorganisms comprise a vector that includes a portion of a mutated or deleted gene, e.g., a targeting vector used to generate a knockout or knockdown of one or more alleles of the mutated or deleted gene. In certain embodiments, these modified photosynthetic microorganisms comprise an antisense RNA or siRNA that binds to an mRNA expressed by a gene associated with glycogen synthesis and/or storage.

Glycogen Synthesis and Storage

In particular embodiments, a modified photosynthetic microorganism has reduced expression of one or more genes associated with a glycogen synthesis or storage pathway and/or increased expression of one or more polynucleotides that encode a protein associated with a glycogen breakdown pathway, or a functional variant of fragment thereof.

Glycogen is a polysaccharide of glucose, which functions as a means of carbon and energy storage in most cells, including animal and bacterial cells. More specifically, glycogen is a very large branched glucose homopolymer containing about 90% $\alpha$-1,4-glucosidic linkages and 10% $\alpha$-1,6 linkages. For bacteria in particular, the biosynthesis and storage of glycogen in the form of $\alpha$-1,4-polyglucans represents an important strategy to cope with transient starvation conditions in the environment.

Glycogen biosynthesis involves the action of several enzymes. For instance, bacterial glycogen biosynthesis occurs generally through the following general steps: (1) formation of glucose-1-phosphate, catalyzed by phosphoglucomutase (Pgm), followed by (2) ADP-glucose synthesis from ATP and glucose 1-phosphate, catalyzed by glucose-1-phosphate adenylyltransferase (GlgC), followed by (3) transfer of the glucosyl moiety from ADP-glucose to a pre-existing $\alpha$-1,4 glucan primer, catalyzed by glycogen synthase (GlgA). This latter step of glycogen synthesis typically occurs by utilizing ADP-glucose as the glucosyl donor for elongation of the $\alpha$-1,4-glucosidic chain.

In bacteria, the main regulatory step in glycogen synthesis takes place at the level of ADP-glucose synthesis, or step (2) above, the reaction catalyzed by glucose-1-phosphate adenylyltransferase (GlgC), also known as ADP-glucose pyrophosphorylase (see, e.g., Ballicora et al., *Microbiology and Molecular Biology Reviews* 6:213-225, 2003). In contrast, the main regulatory step in mammalian glycogen synthesis occurs at the level of glycogen synthase. As shown herein, by altering the regulatory and/or other active components in the glycogen synthesis pathway of photosynthetic microorganisms such as Cyanobacteria, and thereby reducing the biosynthesis and storage of glycogen, the carbon that would have otherwise been stored as glycogen can be utilized by said photosynthetic microorganism to synthesize other carbon-based storage molecules, such as lipids, fatty acids, and triglycerides.

Therefore, certain modified photosynthetic microorganisms, e.g., Cyanobacteria, of the present invention may comprise a mutation, deletion, or any other alteration that disrupts one or more of these steps (i.e., renders the one or more steps "non-functional" with respect to glycogen biosynthesis and/or storage), or alters any one or more of the enzymes directly involved in these steps, or the genes encoding them. As noted above, such modified photosynthetic microorganisms, e.g., Cyanobacteria, are typically capable of producing and/or accumulating an increased amount of lipids, such as fatty acids, as compared to a wild type photosynthetic microorganism.

a. Phosphoglucomutase Gene (pgm)

In one embodiment, a modified photosynthetic microorganism, e.g., a Cyanobacteria, expresses a reduced amount of the phosphoglucomutase gene. In particular embodiments, it may comprise a mutation or deletion in the phosphoglucomutase gene, including any of its regulatory elements (e.g., promoters, enhancers, transcription factors, positive or negative regulatory proteins, etc.). Phosphoglucomutase (Pgm), encoded by the gene pgm, catalyzes the reversible transformation of glucose 1-phosphate into glucose 6-phosphate, typically via the enzyme-bound intermediate, glucose 1,6-biphosphate (see, e.g., Lu et al., *Journal of Bacteriology* 176:5847-5851, 1994). Although this reaction is reversible, the formation of glucose-6-phosphate is markedly favored.

However, typically when a large amount of glucose-6-phosphate is present, Pgm catalyzes the phosphorylation of the 1-carbon and the dephosphorylation of the c-carbon, resulting in glucose-1-phosphate. The resulting glucose-1-phosphate is then converted to UDP-glucose by a number of intermediate steps, including the catalytic activity of GlgC, which can then be added to a glycogen storage molecule by the activity of glycogen synthase, described below. Thus, under certain conditions, the Pgm enzyme plays an intermediary role in the biosynthesis and storage of glycogen.

The pgm gene is expressed in a wide variety of organisms, including most, if not all, Cyanobacteria. The pgm gene is also fairly conserved among Cyanobacteria, as can be appreciated upon comparison of SEQ ID NOs:37 (*S. elongatus* PCC 7942), 75 (*Synechocystis* sp. PCC 6803), and 79 (*Synechococcus* sp. WH8102), which provide the polynucleotide sequences of various pgm genes from Cyanobacteria.

Deletion of the pgm gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

b. Glucose-1-Phosphate Adenylyltransferase (glgC)

In one embodiment, a modified photosynthetic microorganism, e.g., a Cyanobacteria, expresses a reduced amount of a glucose-1-phosphate adenylyltransferase (glgC) gene. In certain embodiments, it may comprise a mutation or deletion in the glgC gene, including any of its regulatory elements. The enzyme encoded by the glgC gene (e.g., EC 2.7.7.27) participates generally in starch, glycogen and sucrose metabolism by catalyzing the following chemical reaction:

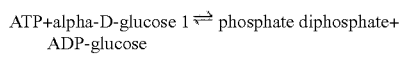

Thus, the two substrates of this enzyme are ATP and alpha-D-glucose 1-phosphate, whereas its two products are diphosphate and ADP-glucose. The glgC-encoded enzyme catalyzes the first committed and rate-limiting step in starch biosynthesis in plants and glycogen biosynthesis in bacteria. It is the enzymatic site for regulation of storage polysaccharide accumulation in plants and bacteria, being allosterically activated or inhibited by metabolites of energy flux.

The enzyme encoded by the glgC gene belongs to a family of transferases, specifically those transferases that transfer phosphorus-containing nucleotide groups (i.e., nucleotidyl-transferases). The systematic name of this enzyme class is typically referred to as ATP:alpha-D-glucose-1-phosphate adenylyltransferase. Other names in common use include ADP glucose pyrophosphorylase, glucose 1-phosphate adenylyltransferase, adenosine diphosphate glucose pyrophosphorylase, adenosine diphosphoglucose pyrophosphorylase, ADP-glucose pyrophosphorylase, ADP-glucose synthase, ADP-glucose synthetase, ADPG pyrophosphorylase, and ADP:alpha-D-glucose-1-phosphate adenylyltransferase.

The glgC gene is expressed in a wide variety of plants and bacteria, including most, if not all, Cyanobacteria. The glgC gene is also fairly conserved among Cyanobacteria, as can be appreciated upon comparison of SEQ ID NOs:67 (*S. elongatus* PCC 7942), 59 (*Synechocystis* sp. PCC 6803), 73 (*Synechococcus* sp. PCC 7002), 69 (*Synechococcus* sp. WH8102), 71 (*Synechococcus* sp. RCC 307), 65 (*Trichodesmium etythraeum* IMS 101), 63 (*Anabaena varibilis*), and 61 (*Nostoc* sp. PCC 7120), which describe the polynucleotide sequences of various glgC genes from Cyanobacteria.

Deletion of the glgC gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

c. Glycogen Synthase (glgA)

In one embodiment, a modified photosynthetic microorganism, e.g., a Cyanobacteria, expresses a reduced amount of a glycogen synthase gene. In particular embodiments, it may comprise a deletion or mutation in the glycogen synthase gene, including any of is regulatory elements. Glycogen synthase (GlgA), also known as UDP-glucose-glycogen glucosyltransferase, is a glycosyltransferase enzyme that catalyses the reaction of UDP-glucose and $(1,4\text{-}\alpha\text{-D-glucosyl})_n$ to yield UDP and $(1,4\text{-}\alpha\text{-D-glucosyl})_{n+1}$. Glycogen synthase is an $\alpha$-retaining glucosyltransferase that uses ADP-glucose to incorporate additional glucose monomers onto the growing glycogen polymer. Essentially, GlgA catalyzes the final step of converting excess glucose residues one by one into a polymeric chain for storage as glycogen.

Classically, glycogen synthases, or $\alpha$-1,4-glucan synthases, have been divided into two families, animal/fungal glycogen synthases and bacterial/plant starch synthases, according to differences in sequence, sugar donor specificity and regulatory mechanisms. However, detailed sequence analysis, predicted secondary structure comparisons, and threading analysis show that these two families are structurally related and that some domains of animal/fungal synthases were acquired to meet the particular regulatory requirements of those cell types.

Crystal structures have been established for certain bacterial glycogen synthases (see, e.g., Buschiazzo et al., *The EMBO Journal* 23, 3196-3205, 2004). These structures show that reported glycogen synthase folds into two Rossmann-fold domains organized as in glycogen phosphorlyase and other glycosyltransferases of the glycosyltransferases superfamily, with a deep fissure between both domains that includes the catalytic center. The core of the N-terminal domain of this glycogen synthase consists of a nine-stranded, predominantly parallel, central $\beta$-sheet flanked on both sides by seven $\alpha$-helices. The C-terminal domain (residues 271-456) shows a similar fold with a six-stranded parallel $\beta$-sheet and nine $\alpha$-helices. The last $\alpha$-helix of this domain undergoes a kink at position 457-460, with the final 17 residues of the protein (461-477) crossing over to the N-terminal domain and continuing as $\alpha$-helix, a typical feature of glycosyltransferase enzymes.

These structures also show that the overall fold and the active site architecture of glycogen synthase are remarkably similar to those of glycogen phosphorylase, the latter playing a central role in the mobilization of carbohydrate reserves, indicating a common catalytic mechanism and comparable substrate-binding properties. In contrast to glycogen phosphorylase, however, glycogen synthase has a much wider catalytic cleft, which is predicted to undergo an important interdomain 'closure' movement during the catalytic cycle.

Crystal structures have been established for certain GlgA enzymes (see, e.g., Jin et al., *EMBO J* 24:694-704, 2005, incorporated by reference). These studies show that the N-terminal catalytic domain of GlgA resembles a dinucleotide-binding Rossmann fold and the C-terminal domain adopts a left-handed parallel beta helix that is involved in cooperative allosteric regulation and a unique oligomerization. Also, communication between the regulator-binding sites and the active site involves several distinct regions of the enzyme, including the N-terminus, the glucose-1-phosphate-binding site, and the ATP-binding site.

The glgA gene is expressed in a wide variety of cells, including animal, plant, fungal, and bacterial cells, including most, if not all, Cyanobacteria. The glgA gene is also fairly conserved among Cyanobacteria, as can be appreciated upon comparison of SEQ ID NOs:51 (*S. elongatus* PCC 7942), 43 (*Synechocosystis* sp. PCC 6803), 57 (*Synechococcus* sp. PCC 7002), 53 (*Snyechococcus* sp. WH8102), 55 (*Synechococcus* sp. RCC 307), 49 (*Trichodesmium erythraeum* IMS101), 47 (*Anabaena variabilis*), and 45 (*Nostoc* sp. PCC 7120), which describe the polynucleotide sequences of various glgA genes from Cyanobacteria.

d. Glycogen Breakdown Genes

In certain embodiments, a modified photosynthetic microorganism of the present invention expresses an increased amount of one or more genes associated with a glycogen breakdown pathway. In particular embodiments, said one or more polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. Pgm, Glk, and Pgi are bidirectional enzymes that can promote glycogen synthesis or breakdown depending on conditions.

Triglyceride and Fatty Acid Biosynthesis

In various embodiments, modified photosynthetic microorganisms, e.g., Cyanobacteria, of the present invention comprise one or more exogenous or introduced nucleic acids that encode a polypeptide having an activity associated with triglyceride or fatty acid biosynthesis, including but not limited to any of those described herein. In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

a. Triglyceride Biosynthesis

Triglycerides, or triacylglycerols (TAGs), consist primarily of glycerol esterified with three fatty acids, and yield more energy upon oxidation than either carbohydrates or proteins. Triglycerides provide an important mechanism of energy storage for most eukaryotic organisms. In mammals, TAGs are synthesized and stored in several cell types, including adipocytes and hepatocytes (Bell et al. *Annu. Rev. Biochem.* 49:459-487, 1980) (herein incorporated by reference). In plants, TAG production is mainly important for the generation of seed oils.

In contrast to eukaryotes, the observation of triglyceride production in prokaryotes has been limited to certain actinomycetes, such as members of the genera *Mycobacterium, Nocardia, Rhodococcus* and *Streptomyces*, in addition to certain members of the genus *Acinetobacter*. In certain Actinomycetes species, triglycerides may accumulate to nearly 80% of the dry cell weight, but accumulate to only about 15% of the dry cell weight in *Acinetobacter*. In general, triglycerides are stored in spherical lipid bodies, with quantities and diameters depending on the respective species, growth stage, and cultivation conditions. For example, cells of *Rhodococcus opacus* and *Streptomyces lividans* contain only few TAGs when cultivated in complex media with a high content of carbon and nitrogen; however, the lipid content and the number of TAG bodies increase drastically when the cells are cultivated in mineral salt medium with a low nitrogen-to-carbon ratio, yielding a maximum in the late stationary growth phase. At this stage, cells can be almost completely filled with lipid bodies exhibiting diameters ranging from 50 to 400 nm. One example is *R. opacus* PD630, in which lipids can reach more than 70% of the total cellular dry weight.

In bacteria, TAG formation typically starts with the docking of a diacylglycerol acyltransferase enzyme to the plasma membrane, followed by formation of small lipid droplets (SLDs). These SLDs are only some nanometers in diameter and remain associated with the membrane-docked enzyme. In this phase of lipid accumulation, SLDs typically form an emulsive, oleogenous layer at the plasma membrane. During prolonged lipid synthesis, SLDs leave the membrane-associated acyltransferase and conglomerate to membrane-bound lipid prebodies. These lipid prebodies reach distinct sizes, e.g., about 200 nm in *A. calcoaceticus* and about 300 nm in *R. opacus*, before they lose contact with the membrane and are released into the cytoplasm. Free and membrane-bound lipid prebodies correspond to the lipid domains occurring in the cytoplasm and at the cell wall, as observed in *M. smegmatis* during fluorescence microscopy and also confirmed in *R. opacus* PD630 and *A. calcoaceticus* ADP1 (see, e.g., Christensen et al., *Mol. Microbiol.* 31:1561-1572, 1999; and Walternann et al., *Mol. Microbiol.* 55:750-763, 2005). Inside the lipid prebodies, SLDs coalesce with each other to form the homogenous lipid core found in mature lipid bodies, which often appear opaque in electron microscopy.

The compositions and structures of bacterial TAGs vary considerably depending on the microorganism and on the carbon source. In addition, unusual acyl moieties, such as phenyldecanoic acid and 4,8,12 trimethyl tridecanoic acid, may also contribute to the structural diversity of bacterial TAGs (see, e.g., Alvarez et al., *Appl Microbiol Biotechnol.* 60:367-76, 2002).

As with eukaryotes, the main function of TAGs in prokaryotes is to serve as a storage compound for energy and carbon. TAGs, however, may provide other functions in prokaryotes. For example, lipid bodies may act as a deposit for toxic or useless fatty acids formed during growth on recalcitrant carbon sources, which must be excluded from the plasma membrane and phospholipid (PL) biosynthesis. Furthermore, many TAG-accumulating bacteria are ubiquitous in soil, and in this habitat, water deficiency causing dehydration is a frequent environmental stress. Storage of evaporation-resistant lipids might be a strategy to maintain a basic water supply, since oxidation of the hydrocarbon chains of the lipids under conditions of dehydration would generate considerable amounts of water. Cyanobacteria such as *Synechococcus*, however, do not produce triglycerides, because these organisms lack the enzymes necessary for triglyceride biosynthesis.

Triglycerides are synthesized from fatty acids and glycerol. As one mechanism of triglyceride (TAG) synthesis, sequential acylation of glycerol-3-phosphate via the "Kennedy Pathway" leads to the formation of phosphatidate. Phosphatidate is then dephosphorylated by the enzyme phosphatidate phosphatase to yield 1,2 diacylglycerol (DAG). Using DAG as a substrate, at least three different classes of enzymes are capable of mediating TAG formation. As one example, an enzyme having diacylglycerol transferase (DGAT) activity catalyzes the acylation of DAG using acyl-CoA as a substrate. Essentially, DGAT enzymes combine acyl-CoA with 1,2 diacylglycerol molecule to form a TAG. As an alternative, Acyl-CoA-independent TAG synthesis may be mediated by a phospholipid:DAG acyltransferase found in yeast and plants, which uses phospholipids as acyl donors for DAG esterification. Third, TAG synthesis in animals and plants may be mediated by a DAG-DAG-transacylase, which uses DAG as both an acyl donor and acceptor, yielding TAG and monoacylglycerol.

Modified photosynthetic microorganisms, e.g., Cyanobacteria, of the present invention may comprise one or more exogenous polynucleotides encoding polypeptides comprising one or more of the polypeptides and enzymes described above. In particular embodiments, the one or more exogenous polynucleotides encode a diacylglycerol transferase and/or a phosphatidate phosphatase, or a variant or function fragment thereof.

Since wild type Cyanobacteria do not typically encode the enzymes necessary for triglyceride synthesis, such as the enzymes having phosphatidate phosphatase activity and diacylglycerol transferase activity, embodiments of the present invention include genetically modified Cyanobacteria that comprise polynucleotides encoding one or more enzymes having a phosphatidate phosphatase activity and/or one or more enzymes having a diacylglycerol transferase activity.

Moreover, since triglycerides are typically formed from fatty acids, the level of fatty acid biosynthesis in a cell may limit the production of triglycerides. Increasing the level of fatty acid biosynthesis may, therefore, allow increased production of triglycerides. As discussed below, Acetyl-CoA carboxylase catalyzes the commitment step to fatty acid biosynthesis. Thus, certain embodiments of the present invention include Cyanobacterium, and methods of use thereof, comprising polynucleotides that encode one or more enzymes having Acetyl-CoA carboxylase activity to increase fatty acid biosynthesis and lipid production, in addition to one or more enzymes having phosphatidate phosphatase and/or diacylglycerol transferase activity to catalyze triglyceride production.

As used herein, a "phosphatidate phosphatase" gene of the present invention includes any polynucleotide sequence encoding amino acids, such as protein, polypeptide or peptide, obtainable from any cell source, which demonstrates the ability to catalyze the dephosphorylation of phosphatidate (PtdOH) under enzyme reactive conditions, yielding diacylglycerol (DAG) and inorganic phosphate, and further includes any naturally-occurring or non-naturally occurring variants of a phosphatidate phosphatase sequence having such ability.

Phosphatidate phosphatases (PAP, 3-sn-phosphatidate phosphohydrolase) catalyze the dephosphorylation of phosphatidate (PtdOH), yielding diacylglycerol (DAG) and inorganic phosphate. This enzyme belongs to the family of hydrolases, specifically those acting on phosphoric monoester bonds. The systematic name of this enzyme class is 3-sn-phosphatidate phosphohydrolase. Other names in common use include phosphatic acid phosphatase, acid phosphatidyl phosphatase, and phosphatic acid phosphohydrolase. This enzyme participates in at least 4 metabolic pathways: glycerolipid metabolism, glycerophospholipid metabolism, ether lipid metabolism, and sphingolipid metabolism.

PAP enzymes have roles in both the synthesis of phospholipids and triacylglycerol through its product diacylglycerol, as well as the generation or degradation of lipid-signaling molecules in eukaryotic cells. PAP enzymes are typically classified as either $Mg^{2+}$-dependent (referred to as PAP1 enzymes) or $Mg^{2+}$-independent (PAP2 or lipid phosphate phosphatase (LPP) enzymes) with respect to their cofactor requirement for catalytic activity. In both yeast and mammalian systems, PAP2 enzymes are known to be involved in lipid signaling. By contrast, PAP1 enzymes, such as those found in Saccharomyces cerevisiae, play a role in de novo lipid synthesis (Han, et al. J Biol Chem. 281:9210-9218, 2006), thereby revealing that the two types of PAP are responsible for different physiological functions.

In both yeast and higher eukaryotic cells, the PAP reaction is the committed step in the synthesis of the storage lipid triacylglycerol (TAG), which is formed from PtdOH through the intermediate DAG. The reaction product DAG is also used in the synthesis of the membrane phospholipids phosphatidylcholine (PtdCho) and phosphatidylethanolamine. The substrate PtdOH is used for the synthesis of all membrane phospholipids (and the derivative inositol-containing sphingolipids) through the intermediate CDP-DAG. Thus, regulation of PAP activity might govern whether cells make storage lipids and phospholipids through DAG or phospholipids through CDP-DAG. In addition, PAP is involved in the transcriptional regulation of phospholipid synthesis.

PAP1 enzymes have been purified and characterized from the membrane and cytosolic fractions of yeast, including a gene (Pah1, formerly known as Smp2) been identified to encode a PAP1 enzyme in S. cerevisiae. The Pah1-encoded PAP1 enzyme is found in the cytosolic and membrane fractions of the cell, and its association with the membrane is peripheral in nature. As expected from the multiple forms of PAP1 that have been purified from yeast, pah1Δ mutants still contain PAP1 activity, indicating the presence of an additional gene or genes encoding enzymes having PAP1 activity.

Analysis of mutants lacking the Pah1-encoded PAP1 has provided evidence that this enzyme generates the DAG used for lipid synthesis. Cells containing the pah1Δ mutation accumulate PtdOH and have reduced amounts of DAG and its acylated derivative TAG. Phospholipid synthesis predominates over the synthesis of TAG in exponentially growing yeast, whereas TAG synthesis predominates over the synthesis of phospholipids in the stationary phase of growth. The effects of the pah1Δ mutation on TAG content are most evident in the stationary phase. For example, stationary phase cells devoid of the Pah1 gene show a reduction of >90% in TAG content. Likewise, the pah1Δ mutation shows the most marked effects on phospholipid composition (e.g. the consequent reduction in PtdCho content) in the exponential phase of growth. The importance of the Pah1-encoded PAP1 enzyme to cell physiology is further emphasized because of its role in the transcriptional regulation of phospholipid synthesis.

The requirement of $Mg^{2+}$ ions as a cofactor for PAP enzymes is correlated with the catalytic motifs that govern the phosphatase reactions of these enzymes. For example, the Pah1-encoded PAP1 enzyme has a DxDxT (SEQ ID NO:30) catalytic motif within a haloacid dehalogenase (HAD)-like domain ("x" is any amino acid). This motif is found in a superfamily of $Mg^{2+}$-dependent phosphatase enzymes, and its first aspartate residue is responsible for binding the phosphate moiety in the phosphatase reaction. By contrast, the DPP1- and LPP1-encoded PAP2 enzymes contain a three-domain lipid phosphatase motif that is localized to the hydrophilic surface of the membrane. This catalytic motif, which comprises the consensus sequences KxxxxxxRP (domain 1) (SEQ ID NO:10), PSGH (domain 2) (SEQ ID NO:11), and SRxxxxxHxxxD (domain 3) (SEQ ID NO:12), is shared by a superfamily of lipid phosphatases that do not require $Mg^{2+}$ ions for activity. The conserved arginine residue in domain 1 and the conserved histidine residues in domains 2 and 3 may be essential for the catalytic activity of PAP2 enzymes. Accordingly, a phosphatide phosphatase polypeptide may comprise one or more of the above-described catalytic motifs.

A polynucleotide encoding a polypeptide having a phosphatidate phosphatase enzymatic activity may be obtained from any organism having a suitable, endogenous phosphatidate phosphatase gene. Examples of organisms that may be used to obtain a phosphatidate phosphatase encoding polynucleotide sequence include, but are not limited to, Homo sapiens, Mus musculus, Rattus norvegicus, Bos taurus, Drosophila melanogaster, Arabidopsis thaliana, Magnaporthe grisea, Saccharomyces cerevisiae, Schizosaccharomyces pombe, Cryptococcus neoformans, and Bacillus pumilus, among others. As used herein, a "diacylglycerol acyltransferase" (DGAT) gene of the present invention includes any polynucleotide sequence encoding amino acids, such as protein, polypeptide or peptide, obtainable from any cell source, which demonstrates the ability to catalyze the production of triacylglycerol from 1,2-diacylglycerol and fatty acyl substrates under enzyme reactive conditions, in addition to any naturally-occurring (e.g., allelic variants, orthologs) or non-naturally occurring variants of a diacylglycerol acyltransferase sequence having such ability. DGAT genes of the present invention also polynucleotide sequences that encode bi-functional proteins, such as those bi-functional proteins that exhibit a DGAT activity as well as a CoA:fatty alcohol acyltransferase activity, i.e., a wax ester synthesis (WS) activity, as often found in many TAG producing bacteria.

Diacylglycerol acyltransferases (DGATs) are members of the O-acyltransferase superfamily, which esterify either sterols or diacyglycerols in an oleoyl-CoA-dependent manner. DGAT in particular esterifies diacylglycerols, which reaction represents the final enzymatic step in the production of triacylglycerols in plants, fungi and mammals. Specifically, DGAT is responsible for transferring an acyl group from acyl-coenzyme-A to the sn-3 position of 1,2-diacylglycerol (DAG) to form triacylglycerol (TAG). DGAT is an integral membrane protein that has been generally described in Harwood (*Biochem. Biophysics. Acta*, 1301:7-56, 1996), Daum et al. (*Yeast* 16:1471-1510, 1998), and Coleman et al. (*Annu. Rev. Nutr.* 20:77-103, 2000) (each of which are herein incorporated by reference).

In plants and fungi, DGAT is associated with the membrane and lipid body fractions. In catalyzing TAGs, DGAT contributes mainly to the storage of carbon used as energy reserves. In animals, however, the role of DGAT is more complex. DGAT not only plays a role in lipoprotein assembly and the regulation of plasma triacylglycerol concentration (Bell, R. M., et al.), but participates as well in the regulation of diacylglycerol levels (Brindley, *Biochemistry of Lipids, Lipoproteins and Membranes*, eds. Vance, D. E. & Vance, J. E. (Elsevier, Amsterdam), 171-203; and Nishizuka, *Science* 258:607-614 (1992) (each of which are herein incorporated by reference)).

In eukaryotes, at least three independent DGAT gene families (DGAT1, DGAT2, and PDAT) have been described that encode proteins with the capacity to form TAG. Yeast contain all three of DGAT1, DGAT2, and PDAT, but the expression levels of these gene families varies during different phases of the life cycle (Dahlqvst, A., et al. *Proc. Natl. Acad. Sci. USA* 97:6487-6492 (2000) (herein incorporated by reference).

In prokaryotes, WS/DGAT from *Acinetobacter* calcoaceticus ADP1 represents the first identified member of a widespread class of bacterial wax ester and TAG biosynthesis enzymes. This enzyme comprises a putative membrane-spanning region but shows no sequence homology to the DGAT1 and DGAT2 families from eukaryotes. Under in vitro conditions, WS/DGAT shows a broad capability of utilizing a large variety of fatty alcohols, and even thiols as acceptors of the acyl moieties of various acyl-CoA thioesters. WS/DGAT acyltransferase enzymes exhibit extraordinarily broad substrate specificity. Genes for homologous acyltransferases have been found in almost all bacteria capable of accumulating neutral lipids, including, for example, *Acinetobacter baylii, A. baumanii*, and *M. avium*, and *M. tuberculosis* CDC1551, in which about 15 functional homologues are present (see, e.g., Daniel et al., *J. Bacteriol.* 186:5017-5030, 2004; and Kalscheuer et al., *J. Biol. Chem.* 287:8075-8082, 2003).

DGAT proteins may utilize a variety of acyl substrates in a host cell, including fatty acyl-CoA and fatty acyl-ACP molecules. In addition, the acyl substrates acted upon by DGAT enzymes may have varying carbon chain lengths and degrees of saturation, although DGAT may demonstrate preferential activity towards certain molecules.

Like other members of the eukaryotic O-acyltransferase superfamily, eukaryotic DGAT polypeptides typically contain a FYxDWWN (SEQ ID NO:13) heptapeptide retention motif, as well as a histidine (or tyrosine)-serine-phenylalanine (H/YSF) tripeptide motif, as described in Zhongmin et al. (*Journal of Lipid Research*, 42:1282-1291, 2001) (herein incorporated by reference). The highly conserved FYxDWWN (SEQ ID NO:13) is believed to be involved in fatty Acyl-CoA binding.

DGAT enzymes utilized according to the present invention may be isolated from any organism, including eukaryotic and prokaryotic organisms. Eukaryotic organisms having a DGAT gene are well-known in the art, and include various animals (e.g., mammals, fruit flies, nematodes), plants, parasites, and fungi (e.g., yeast such as *S. cerevisiae* and *Schizosaccharomyces pombe*). Examples of prokaryotic organisms include certain actinomycetes, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of actinomycetes that have one or more genes encoding a DGAT activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having a DGAT activity include members of the genera *Acinetobacter*, such as *A. calcoaceticus, A. baumanii*, and *A. baylii*. In certain embodiments, a DGAT gene or enzyme is isolated from *Acinetobacter baylii* sp. ADP1, a gram-negative triglyceride forming prokaryote, which contains a well-characterized DGAT (AtfA).

b. Fatty Acid Biosynthesis

Fatty acids are a group of negatively charged, linear hydrocarbon chains of various length and various degrees of oxidation states. The negative charge is located at a carboxyl end group and is typically deprotonated at physiological pH values (pK~2-3). The length of the fatty acid 'tail' determines its water solubility (or rather insolubility) and amphipathic characteristics. Fatty acids are components of phospholipids and sphingolipids, which form part of biological membranes, as well as triglycerides, which are primarily used as energy storage molecules inside cells.

Fatty acids are formed from acetyl-CoA and malonyl-CoA precursors. Malonyl-CoA is a carboxylated form of acetyl-CoA, and contains a 3-carbon dicarboxylic acid, malonate, bound to Coenzyme A. Acetyl-CoA carboxylase catalyzes the 2-step reaction by which acetyl-CoA is carboxylated to form malonyl-CoA. In particular, malonate is formed from acetyl-CoA by the addition of $CO_2$ using the biotin cofactor of the enzyme acetyl-CoA carboxylase.

Fatty acid synthase (FAS) carries out the chain elongation steps of fatty acid biosynthesis. FAS is a large multienzyme complex. In mammals, FAS contains two subunits, each containing multiple enzyme activities. In bacteria and plants, individual proteins, which associate into a large complex, catalyze the individual steps of the synthesis scheme. For example, in bacteria and plants, the acyl carrier protein is a smaller, independent protein.

Fatty acid synthesis starts with acetyl-CoA, and the chain grows from the "tail end" so that carbon 1 and the alpha-carbon of the complete fatty acid are added last. The first reaction is the transfer of an acetyl group to a pantothenate group of acyl carrier protein (ACP), a region of the large mammalian fatty acid synthase (FAS) protein. In this reaction, acetyl CoA is added to a cysteine —SH group of the condensing enzyme (CE) domain: acetyl CoA+CE-cys-SH→acetyl-cys-CE+CoASH. Mechanistically, this is a two step process, in which the group is first transferred to the ACP (acyl carrier peptide), and then to the cysteine —SH group of the condensing enzyme domain.

In the second reaction, malonyl CoA is added to the ACP sulfhydryl group: malonyl CoA+ACP-SH→malonyl ACP+CoASH. This —SH group is part of a phosphopantethenic acid prosthetic group of the ACP.

In the third reaction, the acetyl group is transferred to the malonyl group with the release of carbon dioxide: malonyl ACP+acetyl-cys-CE→beta-ketobutyryl-ACP+$CO_2$.

In the fourth reaction, the keto group is reduced to a hydroxyl group by the beta-ketoacyl reductase activity: beta-ketobutyryl-ACP+NADPH+$H^+$→beta-hydroxybutyryl-ACP+$NAD^+$.

In the fifth reaction, the beta-hydroxybutyryl-ACP is dehydrated to form a trans-monounsaturated fatty acyl group by the beta-hydroxyacyl dehydratase activity: beta-hydroxybutyryl-ACP→2-butenoyl-ACP+$H_2O$.

In the sixth reaction, the double bond is reduced by NADPH, yielding a saturated fatty acyl group two carbons longer than the initial one (an acetyl group was converted to a butyryl group in this case): 2-butenoyl-ACP+NADPH+$H^+$→butyryl-ACP+$NADP^+$. The butyryl group is then transferred from the ACP sulfhydryl group to the CE sulfhydryl: butyryl-ACP+CE-cys-SH→ACP-SH+butyryl-cys-CE. This step is catalyzed by the same transferase activity utilized previously for the original acetyl group. The butyryl group is now ready to condense with a new malonyl group (third reaction above) to repeat the process. When the fatty acyl group becomes 16 carbons long, a thioesterase activity hydrolyses it, forming free palmitate: palmitoyl-ACP+$H_2O$→palmitate+ACP-SH. Fatty acid molecules can undergo further modification, such as elongation and/or desaturation.

Modified photosynthetic microorganisms, e.g., Cyanobacteria, may comprise one or more exogenous polynucleotides encoding any of the above polypeptides or enzymes involved in fatty acid synthesis. In particular embodiments, the enzyme is an acetyl-CoA carboxylase or a variant or functional fragment thereof.

As used herein, an "acetyl CoA carboxylase" gene of the present invention includes any polynucleotide sequence encoding amino acids, such as protein, polypeptide or peptide, obtainable from any cell source, which demonstrates the ability to catalyze the carboxylation of acetyl-CoA to produce malonyl-CoA under enzyme reactive conditions, and further includes any naturally-occurring or non-naturally occurring variants of an acetyl-CoA carboxylase sequence having such ability.

Acetyl-CoA carboxylase (ACCase) is a biotin-dependent enzyme that catalyses the irreversible carboxylation of acetyl-CoA to produce malonyl-CoA through its two catalytic activities, biotin carboxylase (BC) and carboxyltransferase (CT). The biotin carboxylase (BC) domain catalyzes the first step of the reaction: the carboxylation of the biotin prosthetic group that is covalently linked to the biotin carboxyl carrier protein (BCCP) domain. In the second step of the reaction, the carboxyltransferase (CT) domain catalyzes the transfer of the carboxyl group from (carboxy) biotin to acetyl-CoA. Formation of malonyl-CoA by acetyl-CoA carboxylase (ACCase) represents the commitment step for fatty acid synthesis, because malonyl-CoA has no metabolic role other than serving as a precursor to fatty acids. Because of this reason, acetyl-CoA carboxylase represents a pivotal enzyme in the synthesis of fatty acids.

In most prokaryotes, ACCase is a multi-subunit enzyme, whereas in most eukaryotes it is a large, multi-domain enzyme. In yeast, the crystal structure of the CT domain of yeast ACCase has been determined at 2.7 Å resolution (Zhang et al., *Science*, 299:2064-2067 (2003). This structure contains two domains, which share the same backbone fold. This fold belongs to the crotonase/ClpP family of proteins, with a b-b-a superhelix. The CT domain contains many insertions on its surface, which are important for the dimerization of ACCase. The active site of the enzyme is located at the dimer interface.

Although Cyanobacteria, such as *Synechococcus*, express a native ACCase enzyme, these bacteria typically do not produce or accumulate significant amounts of fatty acids. For example, *Synechococcus* in the wild accumulates fatty acids in the form of lipid membranes to a total of about 4% by dry weight.

Given the role of ACCase in the commitment step of fatty acid biosynthesis, embodiments of the present invention include methods of increasing the production of fatty acid biosynthesis, and, thus, lipid production, in Cyanobacteria by introducing one or more polynucleotides that encode an ACC enzyme that is exogenous to the Cyanobacterium's native genome. Embodiments of the present invention also include a modified Cyanobacterium, and compositions comprising said Cyanobacterium, comprising one or more polynucleotides that encode an ACCase enzyme that is exogenous to the Cyanobacterium's native genome.

A polynucleotide encoding an ACCase enzyme may be isolated or obtained from any organism, such as any prokaryotic or eukaryotic organism that contains an endogenous ACCase gene. Examples of eukaryotic organisms having an ACCase gene are well-known in the art, and include various animals (e.g., mammals, fruit flies, nematodes), plants, parasites, and fungi (e.g., yeast such as *S. cerevisiae* and *Schizosaccharomyces pombe*). In certain embodiments, the ACCase encoding polynucleotide sequences are obtained from *Synechococcus* sp. PCC7002.

Examples of prokaryotic organisms that may be utilized to obtain a polynucleotide encoding an enzyme having ACCase activity include, but are not limited to, *Escherichia coli, Legionella pneumophila, Listeria monocytogenes, Streptococcus pneumoniae, Bacillus subtilis, Ruminococcus obeum* ATCC 29174, marine gamma proteobacterium HTCC2080, *Roseovarius* sp. HTCC2601, *Oceanicola granulosus* HTCC2516, *Bacteroides caccae* ATCC 43185, *Vibrio alginolyticus* 12G01, *Pseudoalteromonas tunicata* D2, *Marinobacter* sp. ELB17, marine gamma proteobacterium HTCC2143, *Roseobacter* sp. SK209-2-6, *Oceanicola batsensis* HTCC2597, *Rhizobium leguminosarum* bv. *trifolii* WSM1325, *Nitrobacter* sp. Nb-311A, *Chloroflexus aggregans* DSM 9485, *Chlorobaculum parvum, Chloroherpeton thalassium, Acinetobacter baumannii, Geobacillus*, and *Stenotrophomonas maltophilia*, among others.

Polynucleotides and Vectors

In certain embodiments, the present invention includes modified photosynthetic microorganisms comprising one or more exogenous polynucleotides encoding a polypeptide associated with glycogen breakdown or with triglyceride or fatty acid biosynthesis, or a variant or a functional fragment thereof. Accordingly, the present invention utilizes isolated polynucleotides that encode the various glycogen breakdown pathway proteins and triglyceride and lipid biosynthesis enzymes utilized herein, such as diacylglycerol acyltransferase, phosphatidate phosphatase, and acetyl-CoA carboxylase, in addition to nucleotide sequences that encode any functional naturally-occurring variants or fragments (i.e., allelic variants, orthologs, splice variants) or non-naturally occurring variants or fragments of these native enzymes (i.e., optimized by engineering), as well as compositions comprising such polynucleotides, including, e.g., cloning and expression vectors.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a diacylglycerol acyltransferase, a phosphatidate phosphatase, an acetyl-CoA carboxylase, or a portion thereof) or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide. The effect on the enzymatic activity of the encoded polypeptide may generally be assessed as described herein.

In certain embodiments of the present invention, a modified photosynthetic mciroogansim comprise one or more polynucleotides encoding one or more polypeptides associated with a glycogen breakdown, or a fragment or variant thereof. In particular embodiments, the one or more polypeptides are glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. A representative glgP polynucleotide sequence is provided in SEQ ID NO:31, and a representative GlgP polypeptide sequence is provided in SEQ ID NO:32. A representative glgX polynucleotide sequence is provided in SEQ ID NO:33, and a representative GlgX polypeptide sequence is provided in SEQ ID NO:34. A representative malQ polynucleotide sequence is provided in SEQ ID NO:35, and a representative MalQ polypeptide sequence is provide in SEQ ID NO:36. A representative phosphoglucomutase (pgm) polynucleotide sequence is provided in SEQ ID NO:37, and a representative phosphoglucomutase (Pgm) polypeptide sequence is provided in SEQ ID NO:38, with others provided infra (SEQ ID NOs:75-84). A representative glk polynucleotide sequence is provided in SEQ ID NO:39, and a representative Glk polypeptide sequence is provided in SEQ ID NO:40. A representative pgi polynucleotide sequence is provided in SEQ ID NO:41, and a representative Pgi polypeptide sequence is provided in SEQ ID NO:42. In particular embodiments of the present invention, a polynucleotide comprises one of these polynucleotide sequences, or a fragment or variant thereof, or encodes one of these polypeptide sequences, or a fragment or variant thereof.

In certain embodiments of the present invention, a polynucleotide encodes a DGAT comprising of consisting of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd (*Acinetobacter baylii* sp.). In certain embodiments of the present invention, a DGAT polynucleotide comprises or consists of a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd. DGATn and DGATd correspond to *Acinetobacter baylii* DGAT and a modified form thereof, which includes two additional amino acid residues immediately following the initiator methionine.

In certain embodiments of the present invention, a polynucleotide encodes a phosphatidate phosphatase comprising or consisting of a polypeptide sequence set forth in SEQ ID NO:2, or a fragment or variant thereof. In particular embodiments, a phosphatidate phosphatase polynucleotide comprises or consists of a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPAH1), and SEQ ID NO:5 is a codon-optimized for expression in Cyanobacteria sequence that encodes yPAH1.

In certain embodiments of the present invention, a polynucleotide encodes an acetyl-CoA carboxylase (ACCase) comprising or consisting of a polypeptide sequence set forth in any of SEQ ID NOs:3, 20, 21, 22, 23, or 28, or a fragment or variant thereof. In particular embodiments, a ACCase polynucleotide comprises or consists of a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *Triticum aestivum* ACCase; and SEQ ID NO:29 encodes this *Triticum aestivum* ACCase.

In certain embodiments, the present invention provides isolated polynucleotides comprising various lengths of contiguous stretches of sequence identical to or complementary to a diacylglycerol acyltransferase, a phosphatidate phosphatase, or an acetyl-CoA carboxylase, wherein the isolated polynucleotides encode a biologically active, truncated enzyme.

Exemplary nucleotide sequences that encode the enzymes of the application encompass full-length diacylglycerol acyltransferases, phosphatidate phosphatases, and/or acetyl-CoA carboxylases, as well as portions of the full-length or substantially full-length nucleotide sequences of these genes or their transcripts or DNA copies of these transcripts. Portions of a nucleotide sequence may encode polypeptide portions or segments that retain the biological activity of the reference polypeptide. A portion of a nucleotide sequence that encodes a biologically active fragment of an enzyme provided herein may encode at least about 20, 21, 22, 23, 24, 25, 30, 40, 50, 60, 70, 80, 90, 100, 120, 150, 200, 300, 400, 500, 600, or more contiguous amino acid residues, almost up to the total number of amino acids present in a full-length enzyme. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the nucleotide sequences of the diacylglycerol acyltransferases, phosphatidate phosphatases, and acetyl-CoA carboxylases utilized according to methods and compositions provided herein. Nucleic acid variants can be naturally-occurring, such as allelic variants (same locus), homologs (different locus), and orthologs (different organism) or can be non naturally-occurring. Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having a diacylglycerol acyltransferase activity, a phosphatidate phosphatase activity, and/or a acetyl-CoA carboxylase activity. Embodiments of the present invention, therefore, encompass Cyanobacteria comprising such naturally occurring polynucleotide variants.

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in Cyanobacteria, such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide, such as a polypeptide having either a diacylglycerol acyltransferase activity, a phosphatidate phosphatase activity, or a acetyl-CoA carboxylase activity. Generally, variants of a particular reference nucleotide sequence will have at least about 30%, 40% 50%, 55%, 60%, 65%, 70%, generally at least about 75%, 80%, 85%, 90%, 95% or 98% or more sequence identity to that particular nucleotide sequence as determined by sequence alignment programs described elsewhere herein using default parameters.

Known glycogen breakdown polypeptide, diacylglycerol acyltransferase, phosphatidate phosphatase, and/or acetyl-CoA carboxylase nucleotide sequences can be used to isolate corresponding sequences and alleles from other organisms, particularly other microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other reference coding sequences present in a population of cloned genomic DNA fragments or cDNA fragments (i.e., genomic or cDNA libraries) from a chosen organism.

Accordingly, the present invention also contemplates polynucleotides that hybridize to reference glycogen breakdown polypeptides, diacylglycerol acyltransferase, phosphatidate phosphatase, or acetyl-CoA carboxylase nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a glycogen breakdown polypeptide, diacylglycerol acyltransferase enzyme, a phosphatidate phosphatase enzyme, or a acetyl-CoA carboxylase enzyme is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6 (\log_{10} M)+0.41 (\% G+C)-0.63 (\% \text{formamide})-(600/\text{length})$ wherein: M is the concentration of $Na^+$, preferably in the range of 0.01 molar to 0.4 molar; % G+C is the sum of guano sine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5× Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a triglyceride or lipid biosynthesis enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized."

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. The polynucleotides of the present invention will typically be introduced and expressed in Cyanobacterial systems. As such, the present invention contemplates the use of vector and plasmid systems having regulatory sequences (e.g., promoters and enhancers) that are suitable for use in various Cyanobacteria (see, e.g., Koksharova et al. *Applied Microbiol Biotechnol* 58:123-37, 2002). For example, the promiscuous RSF1010 plasmid provides autonomous replication in several Cyanobacteria of the genera *Synechocystis* and *Synechococcus* (see, e.g., Mermet-Bouvier et al., *Curr Microbiol* 26:323-327, 1993). As another example, the pFC1 expression vector is based on the promiscuous plasmid RSF1010. pFC1 harbors the lambda c1857 repressor-encoding gene and pR promoter, followed by the lambda cro ribosome-binding site and ATG translation initiation codon (see, e.g., Mermet-Bouvier et al., *Curr Microbiol* 28:145-148, 1994). The latter is located within the unique NdeI restriction site (CATATG) of pFC1 and can be exposed after cleavage with this enzyme for in-frame fusion with the protein-coding sequence to be expressed.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. Generally, it is well-known that strong *E. coli* promoters work well in Cyanobacteria. Also, when cloning in cyanobacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. Other vectors containing IPTG inducible promoters, such as pAM1579 and pAM2991trc, may be utilized according to the present invention.

Certain embodiments may employ a temperature inducible system. As one example, an operon with the bacterial phage left-ward promoter ($P_L$) and a temperature sensitive repressor gene CI857 may be employed to produce a temperature inducible system for producing fatty acids and/or triglycerides in Cyanobacteria (see, e.g., U.S. Pat. No. 6,306,639, herein incorporated by reference). It is believed that at a non-permissible temperature (low temperature, 30 degrees Celsius), the repressor binds to the operator sequence, and thus prevents RNA polymerase from initiating transcription at the $P_L$ promoter. Therefore, the expression of encoded gene or genes is repressed. When the cell culture is transferred to a permissible temperature (37-42 degrees Celsius), the repressor can not bind to the operator. Under these conditions, RNA polymerase can initiate the transcription of the encoded gene or genes.

In Cyanobacterial systems, a number of expression vectors may be selected depending upon the use intended for the expressed polypeptide. When large quantities are needed, vectors which direct high level expression of encoded proteins may be used. For example, overexpression of ACCase enzymes may be utilized to increase fatty acid biosynthesis. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST).

Certain embodiments may employ Cyanobacterial promoters or regulatory operons. In certain embodiments, a promoter may comprise an rbcLS operon of *Synechococcus*, as described, for example, in Ronen-Tarazi et al. (*Plant Physiology* 18:1461-1469, 1995), or a cpc operon of *Synechocystis* sp. strain PCC 6714, as described, for example, in Imashimizu et al. (*J. Bacteriol.* 185:6477-80, 2003). In certain embodiments, the tRNApro gene from *Synechococcus* may also be utilized as a promoter, as described in Chungjatupornchai et al. (*Curr Microbiol.* 38:210-216, 1999). Certain embodiments may employ the nirA promoter from *Synechococcus* sp. strain PCC 7942, which is repressed by ammonium and induced by nitrite (see, e.g., Maeda et al., *J. Bacteriol.* 180:4080-4088, 1998; and Qi et al., *Applied and Environmental Microbiology* 71:5678-5684, 2005). The efficiency of expression may be enhanced by the inclusion of enhancers which are appropriate for the particular cyanobacterial cell system which is used, such as those described in the literature.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983). The presence of a desired polynucleotide, such as a diacylglycerol acyltransferase, phosphatidate phosphatase, and/or an acetyl-CoA carboxylase encoding polypeptide, may also be confirmed by PCR.

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Cyanobacterial host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct localization of the encoded polypeptide to a desired site within the cell. Other recombinant constructions may be used to join sequences encoding a polypeptide of interest to nucleotide sequence encoding a polypeptide domain which will direct secretion of the encoded protein.

In particular embodiments of the present invention, a modified photosynthetic microorganism of the present invention has reduced expression of one or more genes selected from glucose-1-phosphate adenyltransferase (glgC), phosphoglucomutase (pgm), and/or glycogen synthase (glgA). In particular embodiments, the modified photosynthetic microorganism comprises a mutation of one or more of these genes. Specific glgC, pgm, and glgA sequences may be mutated or modified, or targeted to reduce expression.

Examples of such glgC polynucleotide sequences are provided in SEQ ID NOs:59 (*Synechocystis* sp. PCC 6803), 61 (*Nostoc* sp. PCC 7120), 63 (*Anabaena variabilis*), 65 (*Trichodesmium erythraeum* IMS101), 67 (*Synechococcus elongatus* PCC 7942), 69 (*Synechococcus* sp. WH8102), 71 (*Synechococcus* sp. RCC 307), and 73 (*Synechococcus* sp. PCC 7002), which respectively encode GlgC polypeptides having sequences set forth in SEQ ID NOs: 60, 62, 64, 66, 68, 70, 72, and 74.

Examples of such pgm polynucleotide sequences are provided in SEQ ID NOs: 75 (*Synechocystis* sp. PCC 6803), 77

(*Synechococcus elongatus* PCC 7942), 79 (*Synechococcus* sp. WH8102), 81 (*Synechococcus* RCC307), and 83 (*Synechococcus* 7002), which respectively encode Pgm polypeptides having sequences set forth in SEQ ID NOs:76, 78, 80, 82, and 84.

Examples of such glgA polynucleotide sequences are provided in SEQ ID NOs:43 (*Synechocystis* sp. PCC 6803), 45 (*Nostoc* sp. PCC 7120), 47 (*Anabaena variabilis*), 49 (*Trichodesmium erythraeum* IMS101), 51 (*Synechococcus elongatus* PCC 7942), 53 (*Synechococcus* sp. WH8102), 55 (*Synechococcus* sp. RCC 307), and 57 (*Synechococcus* sp. PCC 7002), which respectively encode GlgA polypeptides having sequences set forth in SEQ ID NOs:44, 46, 48, 50, 52, 54, 56, and 58.

Polypeptides

Embodiments of the present invention contemplate the use of modified Cyanobacteria comprising introduced polypeptides, including those associated with a glycogen breakdown pathway or having a diacylglycerol acyltransferase activity, a phosphatidate phosphatase activity, and/or an acetyl-CoA carboxylase activity, including truncated, variant and/or modified polypeptides thereof, for increasing lipid production and/or producing triglycerides in said Cyanobacteria.

In particular embodiments, said one or more polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof, including, e.g., those provided in SEQ ID NOs:32, 34, 36, 38, 40 or 41. Examples of additional Pgm polypeptide sequences useful according to the present invention are provided in SEQ ID NOs:76, 78, 80, 82, and 84.

In certain embodiments of the present invention, a DGAT polypeptide comprises or consists of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd. In certain embodiments of the present invention, a DGAT polypeptide is encoded by a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd.

In certain embodiments of the present invention, a phosphatidate phosphatase polypeptide comprises or consists of a polypeptide sequence set forth in SEQ ID NO:2, or a fragment or variant thereof. In particular embodiments, a phosphatidate phosphatase is encoded by a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPah1), and SEQ ID NO:5 is a codon-optimized for expression in Cyanobacteria sequence that encodes yPah1.

In certain embodiments of the present invention, an acetyl-CoA carboxylase (ACCase) polypeptide comprises or consists of a polypeptide sequence set forth in any of SEQ ID NOs:3, 20, 21, 22, 23, or 28, or a fragment or variant thereof. In particular embodiments, an ACCase polypeptide is encoded by a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *T. aestivum* ACCase; and SEQ ID NO:29 encodes this *Triticum aestivum* ACCase.

Variant proteins encompassed by the present application are biologically active, that is, they continue to possess the enzymatic activity of a reference polypeptide. Such variants may result from, for example, genetic polymorphism or from human manipulation. Biologically active variants of a reference diacylglycerol acyltransferase, phosphatidate phosphatase, and/or acetyl-CoA carboxylase polypeptide, or other polypeptide involved in fatty acid or triglyceride biosynthesis, will have at least 40%, 50%, 60%, 70%, generally at least 75%, 80%, 85%, usually about 90% to 95% or more, and typically about 97% or 98% or more sequence similarity or identity to the amino acid sequence for a reference protein as determined by sequence alignment programs described elsewhere herein using default parameters. A biologically active variant of a reference polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the reference sequences in SEQ ID NOs: 1, 2, 3, 6, 8, 10, 12, and 14 by at least one but by less than 15, 10 or 5 amino acid residues. In other embodiments, it differs from the reference sequences by at least one residue but less than 20%, 15%, 10% or 5% of the residues.

A glycogen breakdown polypeptide, diacylglycerol acyltransferase, phosphatidate phosphatase, or acetyl-CoA carboxylase polypeptide may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of diacylglycerol acyltransferase, phosphatidate phosphatase, and/or acetyl-CoA carboxylase polypeptides. Recursive ensemble mutagenesis (REM), a technique which enhances the frequency of functional mutants in the libraries, can be used in combination with the screening assays to identify polypeptide variants (Arkin and Yourvan (1992) *Proc. Natl. Acad. Sci. USA* 89: 7811-7815; Delgrave et al., (1993) *Protein Engineering*, 6: 327-331). Conservative substitutions, such as exchanging one amino acid with another having similar properties, may be desirable as discussed in more detail below.

Polypeptide variants may contain conservative amino acid substitutions at various locations along their sequence, as compared to a reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science*, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant polypeptide can readily be determined by assaying its enzymatic activity, as described herein (see, e.g., Example 3). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a glycogen breakdown polypeptide, diacylglycerol acyltransferase, phosphatidate phosphatase, or acetyl-CoA carboxylase polypeptide is typically replaced with another amino acid residue from the same side chain family. Alternatively, mutations can be introduced randomly along all or part of a coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference polypeptide, results in abolition of an activity of the parent molecule such that less than 20% of the wild-type activity is present. For example, such essential amino acid residues may include those that are conserved in glycogen breakdown polypeptides, diacylglycerol acyltransferase, phosphatidate phosphatase, or acetyl-CoA carboxylase polypeptides across different species, including those sequences that are conserved in the enzymatic sites of polypeptides from various sources.

Accordingly, the present invention also contemplates variants of the naturally-occurring glycogen breakdown polypeptides, diacylglycerol acyltransferase, phosphatidate phosphatase, or acetyl-CoA carboxylase polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference polypeptide sequence. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of a parent or reference polypeptide sequence are contemplated.

In some embodiments, variant polypeptides differ from a reference glycogen breakdown polypeptides, diacylglycerol acyltransferase, phosphatidate phosphatase, or acetyl-CoA carboxylase polypeptide sequence by at least one but by less than 50, 40, 30, 20, 15, 10, 8, 6, 5, 4, 3 or 2 amino acid residue(s). In other embodiments, variant polypeptides differ from a reference by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of a glycogen breakdown polypeptides, diacylglycerol acyltransferase, phosphatidate phosphatase, or acetyl-CoA carboxylase reference polypeptide, and retains the enzymatic activity of that reference polypeptide.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res*, 25: 3389-3402). When utilizing BLAST and Gapped BLAST programs, the default parameters of the respective programs (e.g., XBLAST and NBLAST) can be used.

Variants of a glycogen breakdown polypeptide, diacylglycerol acyltransferase, phosphatidate phosphatase, or acetyl-coA carboxylase reference polypeptide can be identified by screening combinatorial libraries of mutants of a reference polypeptide. Libraries or fragments e.g., N terminal, C terminal, or internal fragments, of protein coding sequence can be used to generate a variegated population of fragments for screening and subsequent selection of variants of a reference polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of polypeptides.

The present invention also contemplates the use of chimeric or fusion proteins for increasing lipid production and/or producing triglycerides. As used herein, a "chimeric protein" or "fusion protein" includes a glycogen breakdown polypeptide, diacylglycerol acyltransferase, phosphatidate phosphatase, or acetyl-CoA carboxylase reference polypeptide or polypeptide fragment linked to either another reference polypeptide (e.g., to create multiple fragments), to a non-reference polypeptide, or to both. A "non-reference polypeptide" refers to a "heterologous polypeptide" having an amino acid sequence corresponding to a protein which is different from the diacylglycerol acyltransferase, phosphatidate phosphatase, or acetyl-CoA carboxylase protein sequence, and which is derived from the same or a different organism. The reference polypeptide of the fusion protein can correspond to all or a portion of a biologically active amino acid sequence. In certain embodiments, a fusion protein includes at least one (or two) biologically active portion of a diacylglycerol acyltransferase, phosphatidate phosphatase, or acetyl-CoA carboxylase protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the enzymatic activity of the polypeptide. For example, in one embodiment, a fusion partner may comprise a sequence that assists in expressing the protein (an expression enhancer) at higher yields than the native recombinant protein. Other fusion partners may be selected so as to increase the solubility or stability of the protein or to enable the protein to be targeted to desired intracellular compartments.

The fusion protein can include a moiety which has a high affinity for a ligand. For example, the fusion protein can be a GST-fusion protein in which the diacylglycerol acyltransferase, phosphatidate phosphatase, or acetyl-CoA carboxylase sequences are fused to the C-terminus of the GST sequences. Such fusion proteins can facilitate the purification and/or identification of the resulting polypeptide. Alternatively, the fusion protein can be a glycogen breakdown polypeptide, diacylglycerol acyltransferase, phosphatidate phosphatase, or acetyl-CoA carboxylase protein containing a heterologous signal sequence at its N-terminus. In certain host cells, expression and/or secretion of such proteins can be increased through use of a heterologous signal sequence.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Methods of Producing Carbon Based Products

Also contemplated are methods of producing a carbon-based product other than glycogen, comprising producing said carbon-based product in a modified photosynthetic microorganism, e.g., a Cyanobacterium, of the present invention, including any of those described above. In particular embodiments, the modified photosynthetic microorganism expresses a reduced level of one or more genes associated with a glycogen biosynthesis or storage pathway and/or expresses an increased level of a polypeptide associated with glycogen breakdown, or a functional variant or fragment thereof. In certain embodiments, the photosynthetic microorganism accumulates a reduced amount of glycogen under reduced nitrogen conditions as compared to a wild type photosynthetic microorganism. In particular embodiments, the modified photosynthetic microorganism has reduced expression of or comprises a mutation in one or more genes of a glycogen biosynthesis or storage pathway. As above, in certain embodiments, said one or more genes may include glucose-1-phosphate adenyltransferase (glgC), phosphoglucomutase (pgm), and/or glycogen synthase (glgA).

In other embodiments, the modified photosynthetic microorganism has an increased level of expression of one or more polynucleotides encoding one or more polypeptides associated with glycogen breakdown, or a functional variant or fragment thereof.

Accordingly, the present invention includes a method of producing a carbon-based product, comprising growing or culturing a modified photosynthetic microorganism of the present invention under conditions wherein the modified photosynthetic microorganism produces a reduced amount of glycogen. In particular embodiments, the modified photosynthetic microorganism is grown under stress conditions. In particular embodiments, the method further comprises producing the modified photosynthetic microorganism, e.g., using methods described herein.

In certain embodiments, said carbon-based product is a lipid, such as a fatty acid and/or a triglyceride. In certain embodiments, said carbon-based product may be useful as a feedstock for the production of biofuels or other specialty chemicals. In certain embodiments, said carbon-based product is a biofuel or other specialty chemical.

In certain embodiments of the methods provided herein, the photosynthetic microorganisms comprising a mutation in one or more genes of a glycogen biosynthesis or storage pathway may also comprise one or more polynucleotides encoding one or more enzymes associated with lipid biosynthesis, wherein said polynucleotides are exogenous to the photosynthetic microorganisms's native genome. In certain embodiments, said one or more enzymes comprise acetyl-CoA carboxylase (ACCase), diacylglycerol acyltransferase (DGAT), and/or phosphatidate phosphatase.

Embodiments of the present invention also include methods of producing triglyceride in a photosynthetic microorganism, e.g., a Cyanobacterium, comprising introducing one or more polynucleotides encoding one or more enzymes associated with triglyceride biosynthesis into a photosynthetic microorganism, and/or introducing one or more deletions or mutations of genes involved in glycogen biosynthesis or storage, incubating the photosynthetic microorganism for a time sufficient to allow triglyceride production, thereby producing triglyceride in the photosynthetic microorganisms. Also contemplated are methods of producing a triglyceride in a photosynthetic microorganism, comprising culturing a photosynthetic microorganism comprising one or more polynucleotides encoding one or more enzymes associated with triglyceride biosynthesis. In certain embodiments, the one or more enzymes comprise a diacylglycerol acyltransferase (DGAT) enzymatic activity and a phosphatidate phosphatase enzymatic activity. In certain embodiments the one or more enzymes comprise an acetyl-CoA carboxylase (ACCase) enzymatic activity, a diacylglycerol DGAT enzymatic activity, and a phosphatidate phosphatase enzymatic activity. In particular embodiments, one or more of the polynucleotides are exogenous to the photosynthetic microorganism's native genome.

The present invention also relates to methods of producing an increased amount of fatty acid, e.g., a free fatty acid, in a Cyanobacterium, comprising introducing one or more polynucleotides encoding one or more enzymes associated with fatty acid biosynthesis into a Cyanobacterium, wherein said polynucleotides are exogenous to the Cyanobacterium's native genome, and/or introducing one or more deletions or mutations of one or more genes involved in glycogen biosynthesis or storage, and culturing the Cyanobacterium for a time sufficient to allow increased fatty acid production, thereby producing an increased amount of fatty acid in the Cyanobacterium. Also contemplated are methods of producing an increased amount of fatty acid in a Cyanobacterium, comprising culturing a Cyanobacterium comprising one or more polynucleotides encoding one or more enzymes associated with fatty acid biosynthesis, wherein said polynucleotides are exogenous to the Cyanobacterium's native genome. In certain embodiments, the one or more enzymes comprise an ACCase enzymatic activity. In producing triglycerides, the modified Cyanobacteria of the present invention may be cultured according to routine techniques known in the art and exemplified herein, such as photobioreactor based culture techniques.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of

EXAMPLES

Example 1

Preparation of DGAT and PAP-Expressing Cyanobacteria

*Acinetobacter baylii* sp. ADP1, a gram-negative TAG forming prokaryote, contains a well-characterized DGAT gene (AtfA, also referred to herein as ADP1-DGAT). The ADP1-DGAT nucleotide sequence was synthesized and codon optimized for *S. elongatus* PCC 7942 expression using DNA2.0, received in a plasmid, subcloned using established molecular biology techniques into the IPTG-inducible vector pAM2991trc (this vector contains sequences encoding the lacI transcriptional repressor, and the pTrc promoter which is repressed by LacI), and recombined into neutral site 1 (NS1) of *S. elongatus* PCC 7942. Colonies were selected from BG11-spec/strep plates, restreaked for isolation, and tested by PCR for positive colonies. Inducible transcription of the gene was verified by real-time PCR

*Saccharomyces cerevisiae* contains three characterized phosphatidate phosphatases, one of which is a soluble, non-integral membrane protein, Pah1p (YMR165C). Pah1 plays a major role in the synthesis of TAGs and phospholipids in *S. cerevisiae*. The Pah1 nucleotide sequence was synthesized and codon optimized for *S. elongatus* PCC 7942 expression using DNA2.0, received in a plasmid, subcloned using established molecular biology techniques into the IPTG-inducible vector pAM2991trc, and recombined into neutral site 1 (NS1) of *S. elongatus* PCC 7942. Colonies were selected from BG11-spec/strep plates, restreaked for isolation, and tested by PCR for positive colonies.

A *S. elongatus* PCC 7942 strain expressing both the ADP1-DGAT and Pah1 genes described above was generated by transforming an ADP1-DGAT expressing strain (ADP1-DGAT subcloned into IPTG-inducible vector pAM1579trc-kanamycin, which recombined in NS2) with the construct carrying Pah1 from NS1 (described above) and selecting transformants on plates containing kanamycin, streptomycin and spectinomycin. Inducible transcription of these genes was verified by real-time PCR.

Example 2

Generation of DGAT and ACCase-Expressing Cyanobacteria

*Synechococcus* sp. PCC 7002 contains fours genes encoding the four subunits of bacterial acetyl coenzyme A carboxylase (7002 acc). These genes (accA, accB, accC, and accD) were PCR amplified and two synthetic two-gene operons were constructed using splicing by overlap extenstion PCR techniques. Synthetic operon 1 contains accAD and synthetic operon 2 contains accBC. The two synthetic operons were cloned into vector pTG2087 (pAM2314Ftrc3.) The vector pTG2087 contains regions of homology for recombination into neutral site 1 (NS1) of *S. elongatus* PCC 7942, sequences encoding the lacI transcriptional repressor, and the pTrc promoter which is repressed by LacI. Synthetic 7002 acc operons 1 and 2 were cloned into pTG2087, in two separate sites, under control of the pTrc promoter to generate plasmid pTG2087-7002acc. Clone candidates were sequenced to confirm that there were no PCR-induced mutations in the coding sequence of any of the 7002 acc genes.

pTG2087-7002acc was transformed into *S. elongatus* PCC 7942 and recombinants into NS1 were selected by plating on BG11 media containing spectinomycin and streptomycin. Transformants that grew out in the presence of antibiotic were streaked for isolated colonies and single colonies were tested for the presence of the 7002 acc genes in NS1 by PCR. Inducible transcription of the 7002 acc genes was verified by real-time PCR.

Functional expression of the 7002 acc genes was tested by the ability to complement a deletion of the endogenous *S. elongatus* PCC 7942 accD gene. *S. elongatus* PCC 7942 with synthetic operon 1 (7002 accAD) recombined into NS1 was tested for the ability to complement loss of the native *S. elongatus* accD gene. Successful complementation indicated that the 7002 acc genes were functionally expressed in *S. elongatus* PCC 7942.

Figure 6:
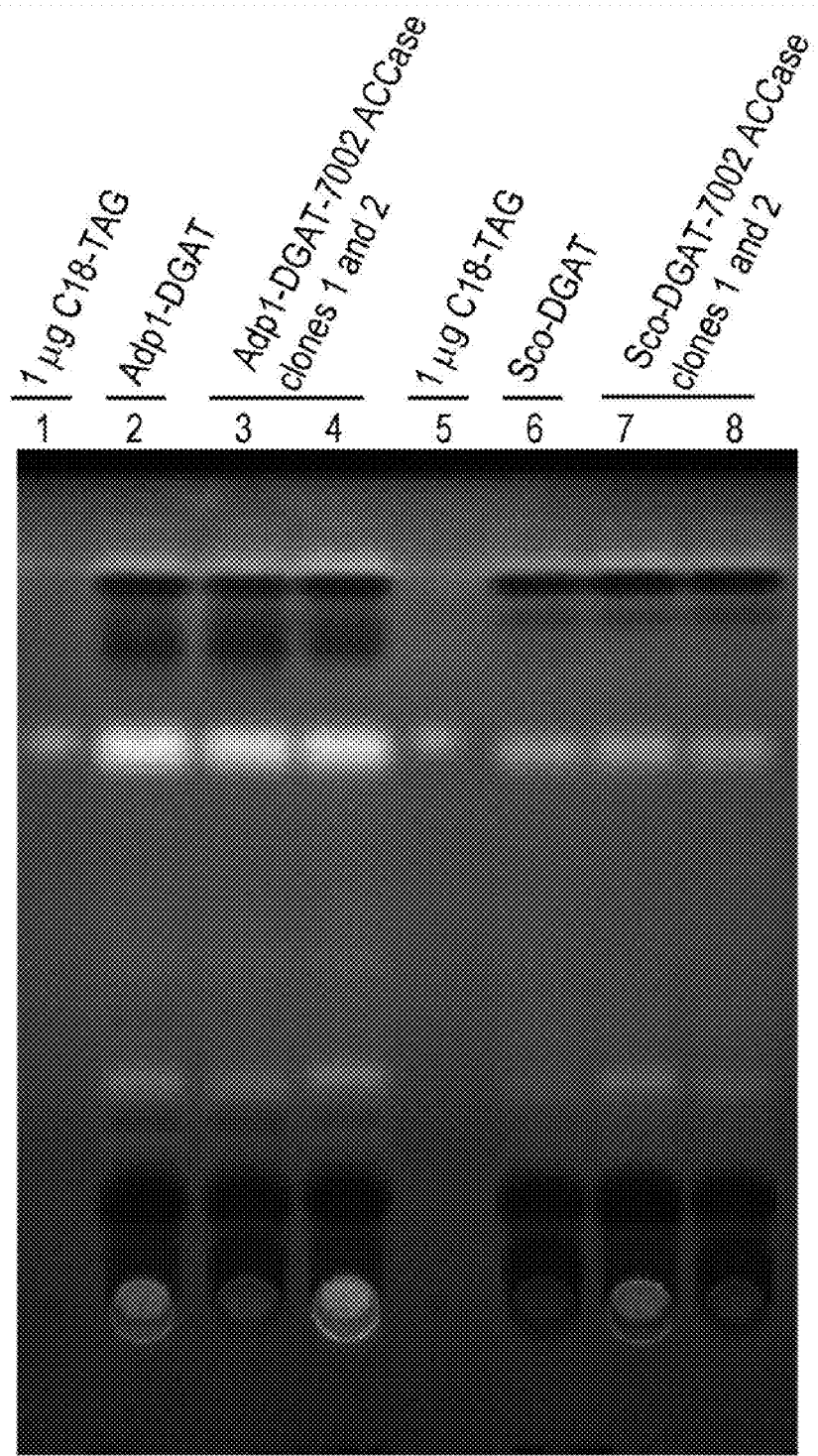
FIG. 6 shows a thin layer chromatography assay of triacylglceride (TAG) present in extracts obtained from *S. elongatus* PCC 7942 strains that over-expressed either Adp1-DGAT or Sco-DGAT, alone or in combination with a *Synechococcus* sp. PCC 7002 ACCase. A control TAG standard is shown.

The *S. elongatus* PCC 7942-7002 accADBC strain was transformed with vectors containing one of two DGAT genes (either ADP1-DGAT or ScoDGAT from Examples 1 and 7) for recombination into NS2. Transformants were selected by plating on media containing kanamycin. The recombination of ADP1-DGAT or ScoDGAT into NS2 was confirmed by PCR. These strains were tested for triglyceride production using the methods described in Examples 3 and 4. As shown in FIG. 6, Cyanobacteria induced to express both DGAT and ACCase produced comparable levels of TAGs as Cyanobacteria induced to express DGAT.

Example 3

Increased Fatty Acid Production in Cyanobacteria

ADP1-DGAT-expressing Cyanobacteria from Example 1 was tested for the ability to produce increased levels of fatty acids. Induction of ADP1-DGAT positive clones was carried out by the addition of 1 mM IPTG when culture reached an OD750=0.2. Samples were taken at 24 hours after induction, and analyzed for lipid content by gas chromatography (GC).

As seen in FIG. 1, GC results showed a 2-fold increase in lipid content for IPTG-induced DGAT compared to un-induced vector control.

Example 4

Triglyceride Production in Cyanobacteria and TLC Analysis of DGATs

Several enzymes with acylCoA: diacylglycerol acyltransferase activity have been described in the literature, and a number of homologs were identified by conducting homology searches of publicly available DNA and protein databases. Several DGAT homologs were synthesized, optimized for expression in *S. elongatus* PCC 7942, and integrated into its genome via homologous recombination as described in Example 1.

A modified version of ADP1-DGAT from Example 1 was cloned into vector pTG2087 (pAM2314Ftrc3.), a neutral site 1 expression vector described in Example 2. In this version, the 6 bases immediately following the ATG start codon of the ADP1-DGAT gene from Example 1 were deleted. This strain was named ADP1-DGATn.

*Streptomyces coelicolor* is a gram-positive TAG forming prokaryote that contains a well-characterized DGAT. The *Streptomyces*-DGAT (ScoDGAT) nucleotide sequence was synthesized and codon optimized for *S. elongatus* PCC 7942 expression using DNA2.0. The gene was received in a plasmid, subcloned using established molecular biology techniques into pTG2087 (pAM2314Ftrc3.), a neutral site 1 expression vector described in Example 2, and recombined into neutral site 1 (NS1) of *S. elongatus* PCC 7942. Colonies were selected from BG11-spec/strep plates, restreaked for isolation and tested by PCR for positive colonies. Inducible transcription of this gene was verified by real-time PCR.

*Alcanivorax borkumensis* is a marine protobacteria gamma TAG forming prokaryote that contains a well-characterized DGAT (atfA1). The *Alcanivorax*-DGAT (AboDGAT) nucleotide sequence was synthesized and codon optimized for *S. elongatus* PCC 7942 expression using DNA2.0. The gene was received in a plasmid, subcloned using established molecular biology techniques into pTG2087 (pAM2314Ftrc3.), a neutral site 1 expression vector described in Example 2, and recombined into neutral site 1 (NS1) of *S. elongatus* PCC 7942. Colonies were selected from BG11-spec/strep plates, restreaked for isolation and tested by PCR for positive colonies. Inducible transcription of this gene was verified by real-time PCR.

Induction experiments for ADP1-DGAT, ADP1-DGATn, ScoDGAT and AboDGAT were performed as described in Example 3. Samples were collected at 24 hours post-induction, and total lipid extracts were prepared for TLC analysis as follows. Pellets were resuspended in 100 ul of water, to which 375 ul of a 1:2 mixture of chloroform to methanol was added. Cells were extracted with frequent vortexing for 10 minutes. To this was added 125 ul of chloroform, and the extract was vortexed for another minute. Finally, phase separation was produced by adding 125 ul of 1M NaCl, with another 1 minute of vortexing. To speed separation, the samples were centrifuged in a clinical centrifuge for 10 minutes at an rcf of 1930. The organic phase was removed to a new tube and dried down in a vacuum dryer. The dry lipid extract was resuspended in 40 ul of a 2:1 chloroform:methanol mixture, and either a 6 ul aliquot or the entire volume was applied to TLC plates (200-um thick silica plates). Chromatography was run using a mobile phase comprised of 75% n-hexane, 25% diethylether acidified with 1 ml of glacial acetic acid per 100 ml solvent mixture. Completed runs were dried, and the lipids were imaged with primuline (50 mg/L dissolved in an 80% acetone solution). Images were recorded digitally using a hand-held UV lamp to excite the primuline stained plate.

Figure 2:
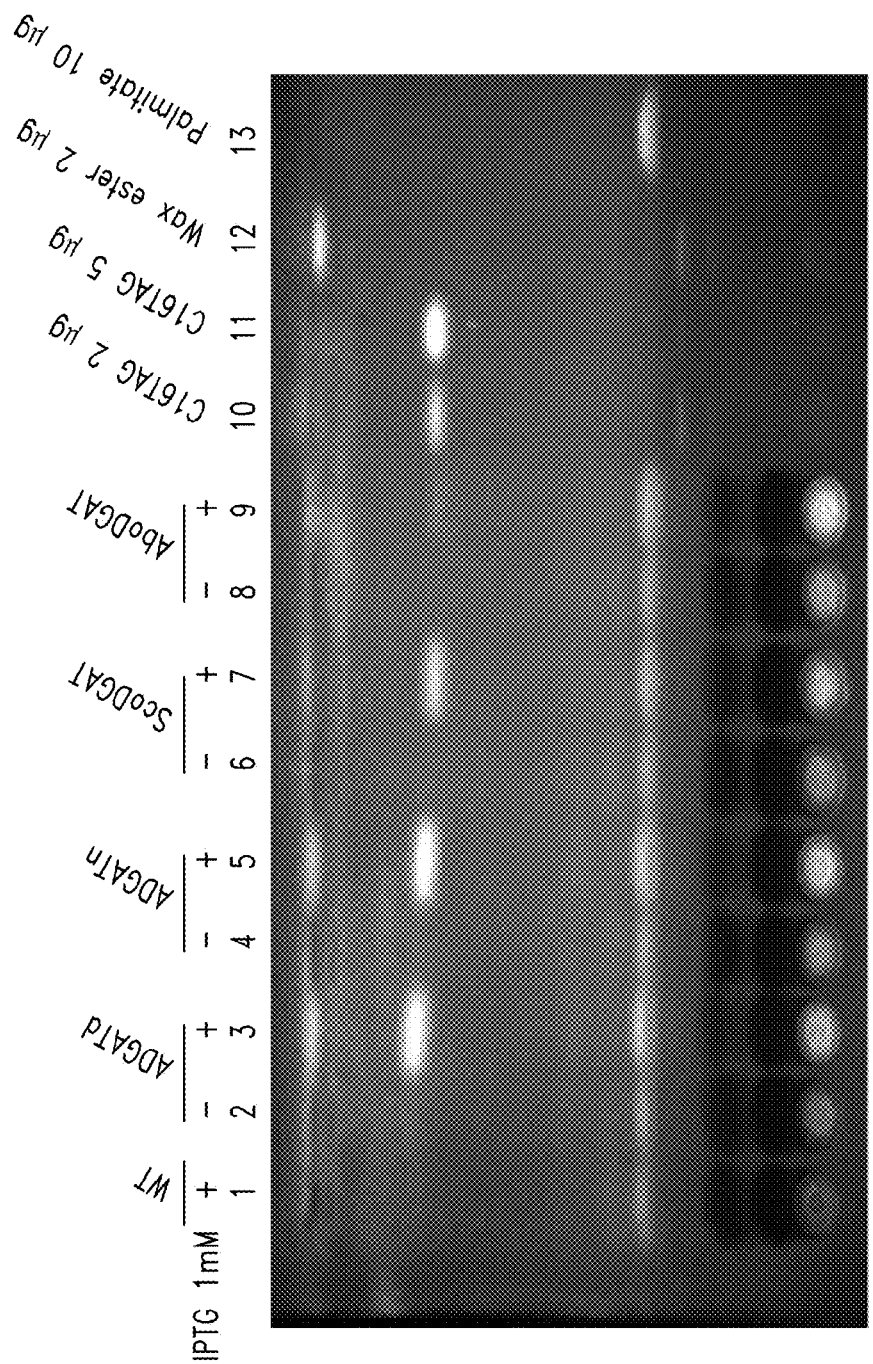
FIG. 2 shows a thin layer chromatography assay of triacylglceride (TAG) and fatty acids present in extracts obtained from *S. elongatus* PCC 7942 strains that carried one of four different DGAT genes (ADGATd, ADGATn, ScoDGAT, or AboDGA7) or a vector control, either uninduced or induced with IPTG. Control TAG (C16TAG) and fatty acid (palmitate) standards are also shown.

As shown in FIG. 2, all four DGAT genes resulted in TAG production when expressed in Cyanobacteria. Moreover, increases in fatty acids were observed in ADP1-DGAT, ADP1-DGATn, and AboDGAT expressing strains but not in ScoDGAT. These results demonstrate that heterologous expression of several DGATs in Cyanobacteria results in TAG formation.

Example 5

Triacylglceride and Free Fatty Acid Accumulation in *S. elongatus*

Figure 3:
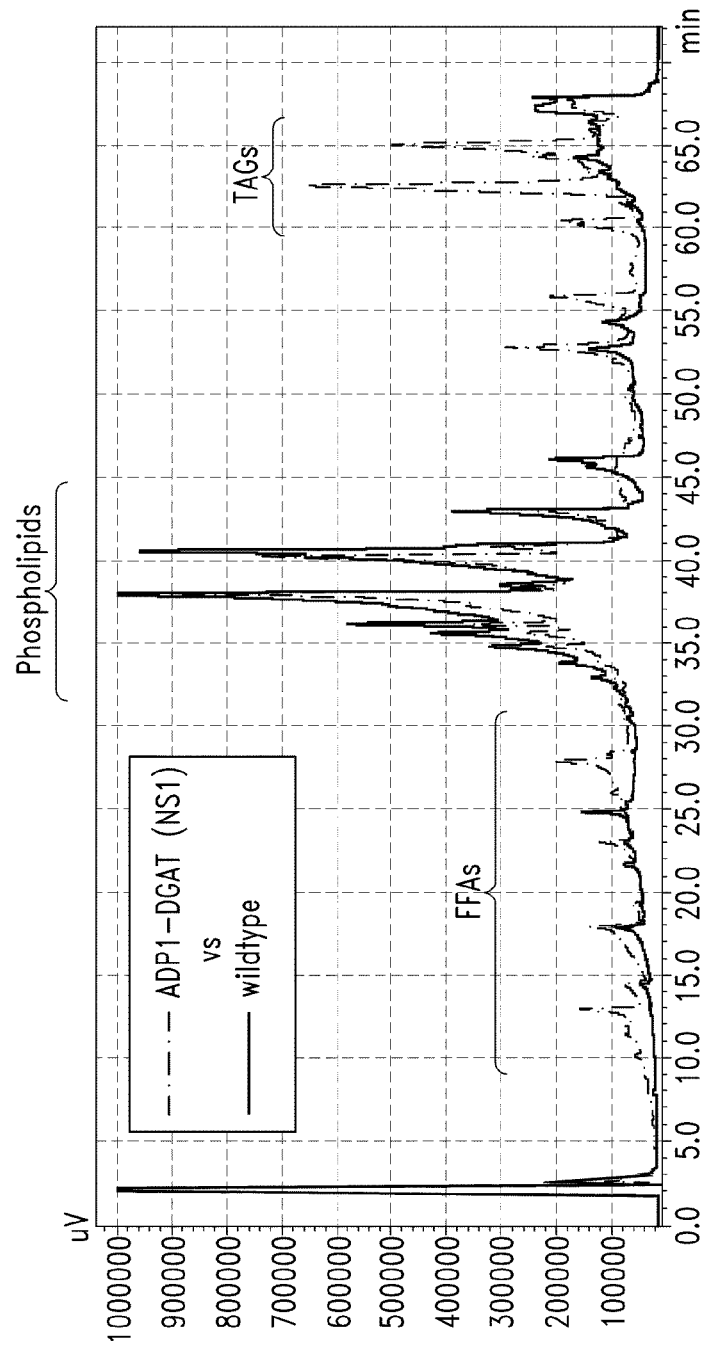
FIG. 3 is a graph showing the results of HPLC analysis of lipid extracts from *S. elongatus* PCC 7942 expressing ADGATd (dashed line) as compared to wild type *S. elongatus* (solid line) following induction. The y-axis indicates the intensity of the peaks for the different lipid species, free fatty acids (FFAs), phospholipids, and TAGs, and the x-axis indicates the corresponding retention time.

The *S. elongatus* PCC 7942 ADP1-DGAT expressing strain described in Example 1 was grown under induction conditions as described in Example 3, and total lipid extracts prepared as described in Example 4 were subjected to HPLC analysis. 40 microL of total lipid extracts were analyzed on a Shimadzu Prominence UFLC (Ultra Fast Liquid Chromatograph) connected to an ESA Bioscience Corona CAD Plus detector (Charged Aerosol Detector). A Hypersil Gold C8 3 μm 150×4.6 mm column at 0.8 mL/min flow rate was used. A binary gradient system with mobile phase A: methanol/water/acetic acid (750:250:4) and mobile phase B: acetonitrile/methanol/THF/acetic acid (500:375:125:4) was used. The results of a typical run are shown in FIG. 3, in which the y axis indicates the intensity of the peaks for the different lipid species, and the x axis indicates the corresponding retention time. Three major lipid groups, free fatty acids (FFAs), phospholipids, and TAGs are shown, as indentified using representative standards of these lipid species (not shown). As can be seen, the induced strain produced TAGs. In the un-induced strain, these were undetectable. Thus, exogenous expression of DGAT in Cyanobacteria results in TAG formation, as shown by TLC.

Example 6

Acyl Chain Composition of TAGs

Figure 4B:
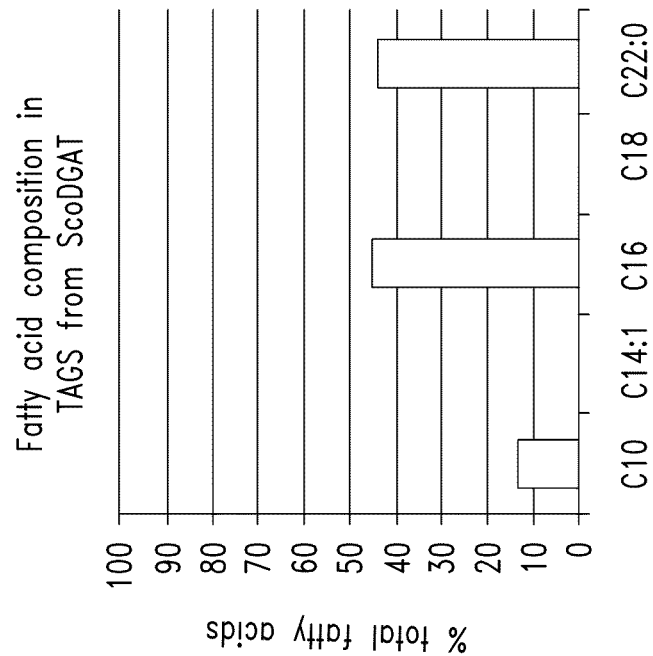
FIGS. 4A-4B provide graphs showing the acyl chain composition of TAGs produced by *S. elongatus* PCC 7942 expressing ADP1-DGAT or ScoDGAT following induction, as determined by gas chromatography of TAGs isolated by TLC.
Figure 4A:
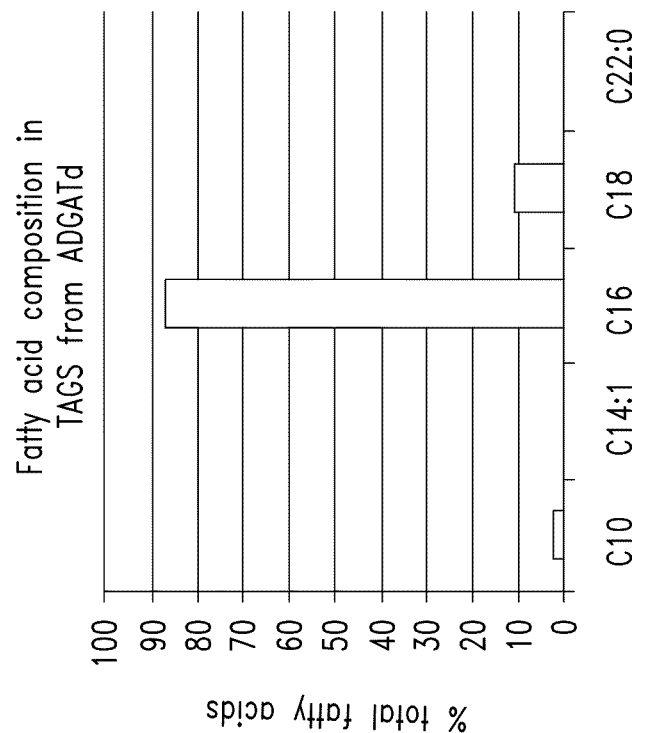

The ADP1-DGAT and ScoDGAT strains described in Example 1 and 4 were induced for TAG production as described in Example 3. Lipid extracts were prepared, and the non polar lipids were separated on a TLC as per the method described in Example 4. The spots on the TLC plate corresponding to TAGs, as determined by their co-migration with corresponding standards, were extracted from the TLC plates by cutting out a rectangular area encompassing each spot. This material was then subjected to transesterification and GC analysis. As can be seen in FIG. 4, the fatty acid composition of the TAGs produced by these two strains differed in that the TAGs produced by the ADP1-DGAT strain consisted of mixtures of C18 and C16 acyl chains (FIG. 4A), whereas the TAGs from the ScoDGAT strain consisted of mixtures of C16 and C22 acyl chains (FIG. 4B). This highlights the different acyl change specificities of these two DGAT enzymes and supports the introduction of two or more different DGATs into modified Cyanobacteria to generate multiple different TAGs.

Example 7

Triacylglyceride Production in Cyanobacteria

A gene encoding a DGAT was introduced into a different strain, *Synechcocystis* sp. strain PCC 6803 (hereafter referred to as PCC 6803), to determine if DGAT expression correlated with TAG production outside of *S. elongatus* PCC 7942. Two mutants were constructed in *Synechocystis* sp. strain PCC 6803. The first mutant carried a gene encoding ADP1-DGAT under control of the Ptrc promoter, a locus encoding kanamycin resistance (nptA) and the lactose repressor (lacI). As a negative control, a strain was constructed that carried nptA and lacI, but not the ADP1-DGAT gene. Both constructs were built in a neutral site vector devised for use in PCC 6803.

This vector directs recombination into a neutral site in PCC 6803, a region between two convergently transcribed native genes that have been described in the literature as non-essential. The mutagenesis generally followed the protocols of Eaton-Rye (Methods in Molecular Biology, Vol 24, p 309-323), except that transformants were plated on plain BG-11 plates and subjected to increasing kanamycin concentrations by injecting concentrated kanamycin under the agar pad at 12 and 36 hours. Successful incorporation of the ADP1-DGAT gene was demonstrated using colony PCR. The plates used for mutagenesis were comprised of 1×BG-11 (Pasteur formulation), 1.25% Bactoagar, and sodium thiosulfate to 3 g/L.

Transformants confirmed to have the correct insertions were grown to late exponential phase, aliquots of the cultures were centrifuged, washed in BG-11, re-pelleted, and resuspended to 50 ml of BG-11 with kanamycin. Half the cultures were induced with IPTG at a final concentration of 1 mM. Typically, samples were taken at 0, 3 and 6 days of induction. Pelleted samples were stored at −80° C.

Figures 5A, 5B:
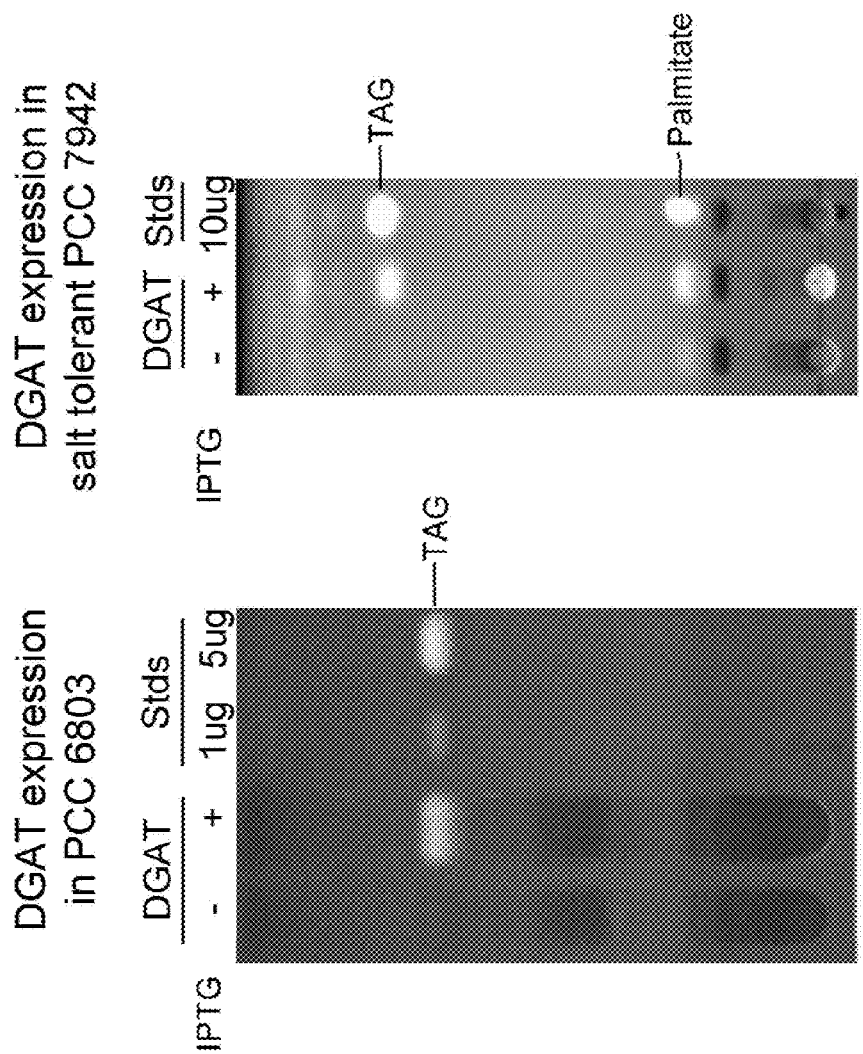
FIGS. 5A-5B show thin layer chromatography assays of triacylglceride (TAG) obtained from two different strains that carried ADP1-DGAT.

Methods similar to those described in Example 4 were used to perform TLC and determine how the expression of ADP1-DGAT affected the TAG content in PCC 6803. As shown in FIG. 5A, strains that did not carry ADP1-DGAT did not exhibit TAGs on TLC, while strains that did carry ADP1-DGAT produced TAGs. These experiments demonstrated that the engineered DGAT-dependent production of TAGs first seen in S. elongatus PCC 7942 is not unique to that strain, but instead is a general property of cyanobacteria engineered to contain a diacyl-glycerol acyltransferase activity.

Example 8

Generation of a Salt-Tolerant *Synechococcus elongatus* PCC 7942 Strain

S. elongatus PCC 7942 is a freshwater, Cyanobacterium that does not ordinarily grow well in high salts. This example describes the generation of a Cyanobacterium S. elongatus PCC 7942 mutant that grows in salt or brackish water and can produce TAGs. In addition to being able to grow in freshwater media (BG11), this strain can grow in salt concentrations of up to 3% (in BG11 media).

The mutant S. elongatus PCC 7942 strain was selected through several rounds of growth and dilution in high salt (1.5% NaCl) liquid media. Once a salt tolerant strain emerged (after several months of selection), it was tested for its ability to retain salt tolerance after several rounds of growth on BG11 plates made from freshwater. The resulting salt tolerant strain grew to equal density in either BG11 or 1.5% NaCl-BG11 for up to 14 days. The salt tolerant strain grew indistinguishably from wildtype in BG11, but showed a sharp increase in growth compared to wildtype PCC 7942 in media containing NaCl.

An ADP1-DGAT expressing salt tolerant strain of S. elongatus PCC 7942 was generated by transforming the salt strain described above with the ADP1-DGAT construct described in Example 1. This ADP1-DGAT salt tolerant strain showed a growth advantage over the ADP1-DGAT non-salt tolerant strain in media containing up to 3% salt and produced similar amounts of TAGs as the ADP1-DGAT parental non salt tolerant strain (FIG. 5B). This strain could be useful in production settings where it may be advantageous to use brackish water or seawater.

Example 9

Construction of Glycogen Pathway Deletion Strains

To test whether the carbon flow from the wild-type storage of carbon as glycogen into other potential carbon-based products could be diverted, glycogen biosynthetic enzymes in the glycogen pathway of *Synechococcus* were disabled. In particular, the phosphate adenylyltransferase gene (Synpcc7942_0603, glgC) and phosphoglucomutase gene (Synpcc7942_0156, pgm) genes in the S. elongatus PCC 7942 strain were individually inactivated by deletion to generate two different modified S. elongatus strains, Δpgm and ΔglgC.

The Δpgm and ΔglgC deletion strains were constructed as follows. Polymerase chain reaction was used to amplify genomic DNA regions flanking the pgm and glgC genes. Amplified upstream and downstream flanking regions were sequentially cloned upstream and downstream of the gentamicin resistance marker in plasmid pCRG. The pCRG plasmid is not capable of autonomous replication in *Synechococcus*.

Figure 7:
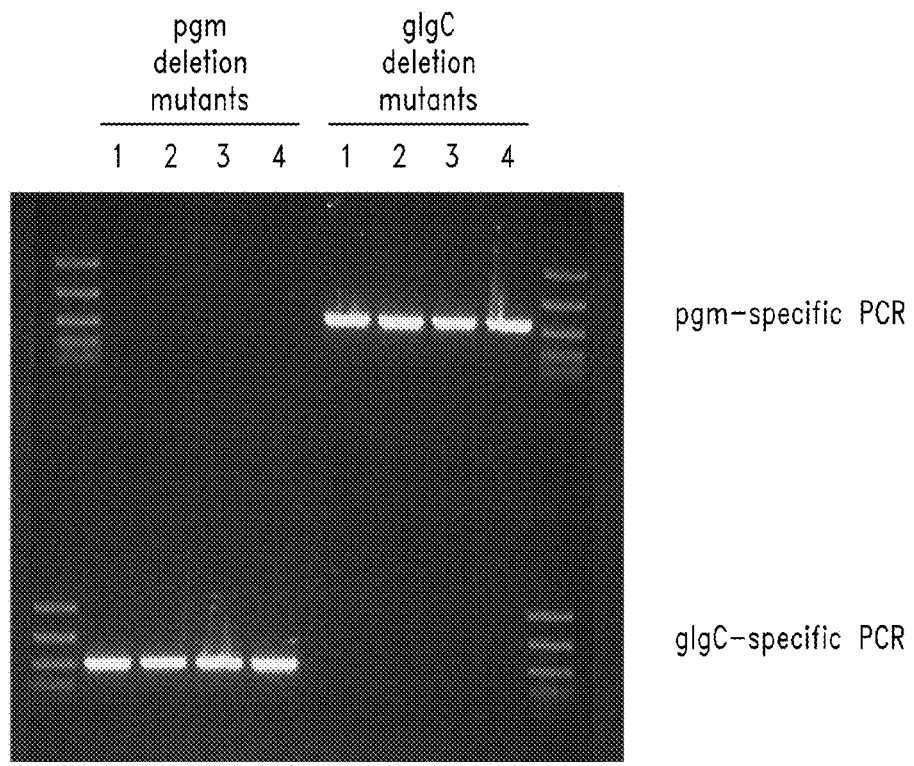
FIG. 7 shows the genomic DNA analysis by polymerase chain reaction (PCR) of pgm and glgC deletion mutants of *S. elongatus* PCC 7942. Pgm and glgC specific primers confirm the deletion of these genes in their respective Δpgm and ΔglgC *S. elongatus* PCC 7942 clones.

The resulting plasmids were individually transformed into S. elongatus PCC 7942 using established methods. Following selection on gentamicin-containing medium, recombinant strains were propagated and their genomic DNA analyzed by PCR to verify deletion of the targeted gene in the respective Δpgm and ΔglgC deletion strains (see FIG. 7).

Example 10

Reduced Glycogen Production by Glycogen Pathway Deletion Strains

Growth of S. elongatus PCC 7942 under conditions of nitrogen limitation has been shown to lead to glycogen accumulation (see, e.g., Goerl et al. *Microbiology* 144:2449-2458, 1998). The generated Δpgm and ΔglgC deletion strains of S. elongates PCC 7942, described in Example 9, were analyzed for their glycogen content versus wild type S. elongatus PCC 7942 after growth under nitrogen limiting conditions.

Figure 8A:
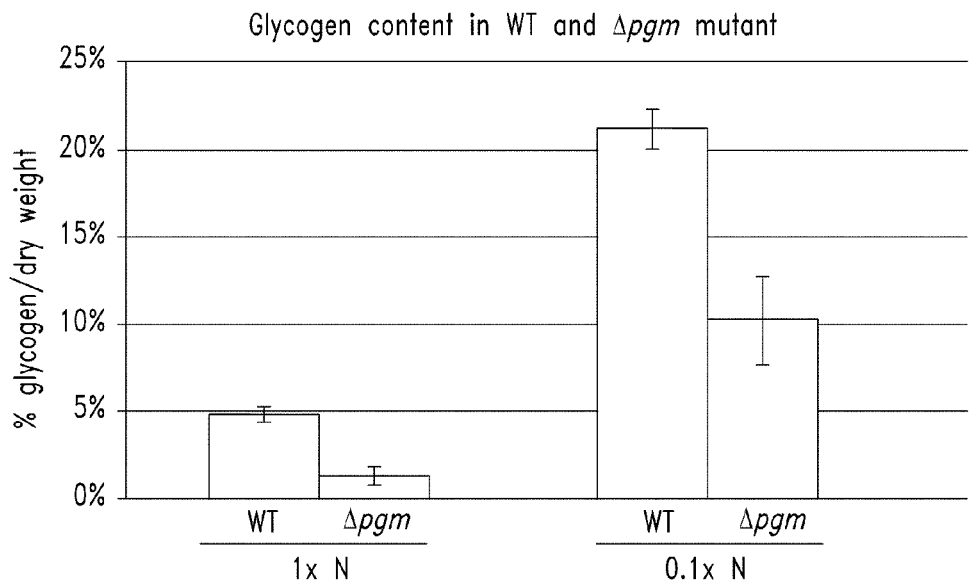
FIGS. 8A-8B show the glycogen content in wild type (WT), Δpgm (FIG. 8A), and ΔglgC (FIG. 8B) *S. elongatus* PCC 7942 strains after growth in 1×N or 0.1×N for 5-days.
Figure 8B:
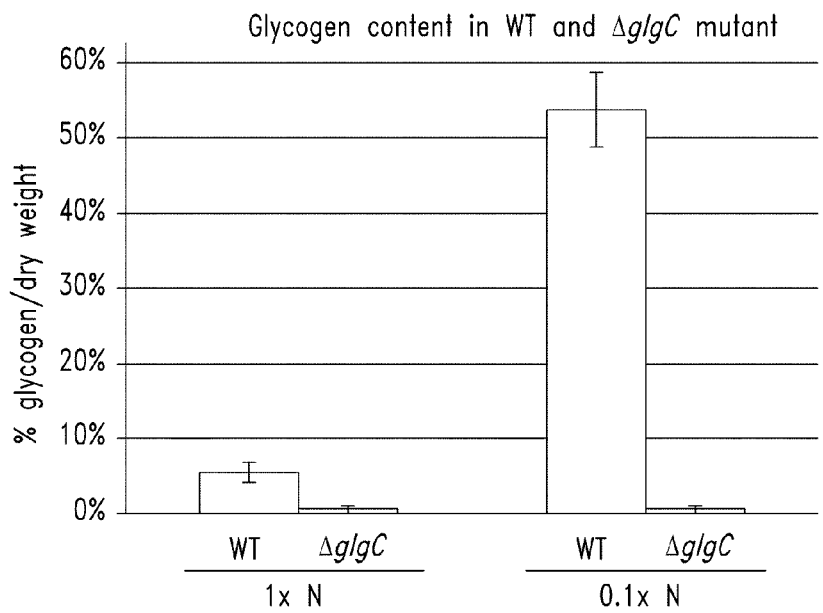

Wild type (WT) and deletion strains were cultured in either nitrogen replete BG11 medium (1×N) or BG11 media containing 1/10 the standard nitrogen concentration (0.1×N) for 5-days. A biochemical assay of glycogen content was performed as described in Suzuki et al. (*Biochimica et Biophysica Acta* 1770:763-773, 2007). The data from this experiment is displayed in FIG. 8 as % glycogen/dry weight. This data confirms that the Δpgm strain of S. elongatus PCC 7942 exhibits significantly reduced glycogen content, and also confirms that the ΔglgC strain of S. elongatus PCC 7942 exhibits undetectable levels of glycogen.

Example 11

Increased Lipid Production by Glycogen Pathway Deletion Mutants

The lipid production of S. elongatus PCC 7942 deletion strains Δpgm and ΔglgC, described in Example 9, was measured to demonstrate that when cells are unable to store carbon as glycogen, due to deletions of biosynthetic enzymes in their glycogen pathway, they divert the carbon into other biosynthetic pathways.

Figure 9A:
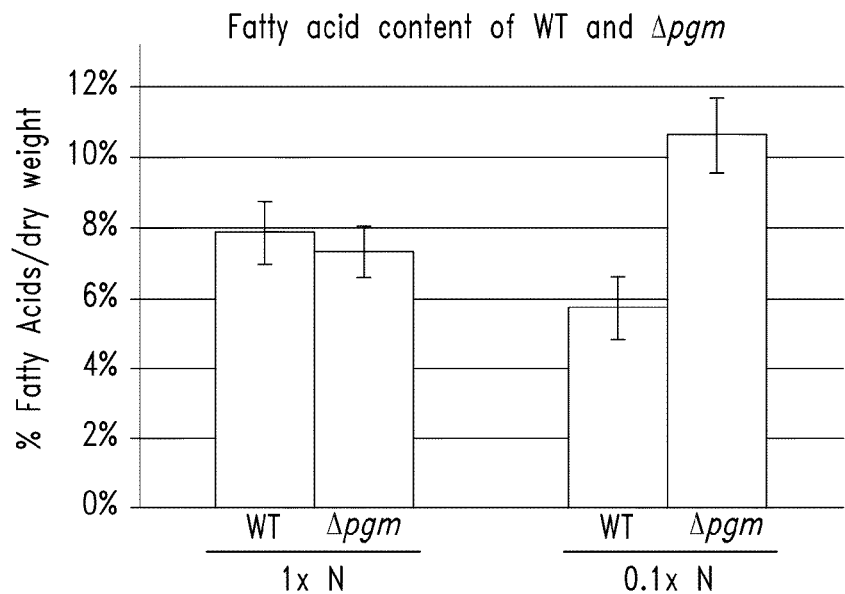
FIGS. 9A-9B show the fatty acid (lipid) content in WT and Δpgm *S. elongatus* PCC 7942 strains after growth in 1×N or 0.1×N for 5-days, as represented by % FAMES/dry weight (FIG. 9A) or the fatty acid (lipid) content in WT and ΔglgC strains after growth in 1×N or 0.1×N for 5-days (FIG. 9B).
Figure 9B:
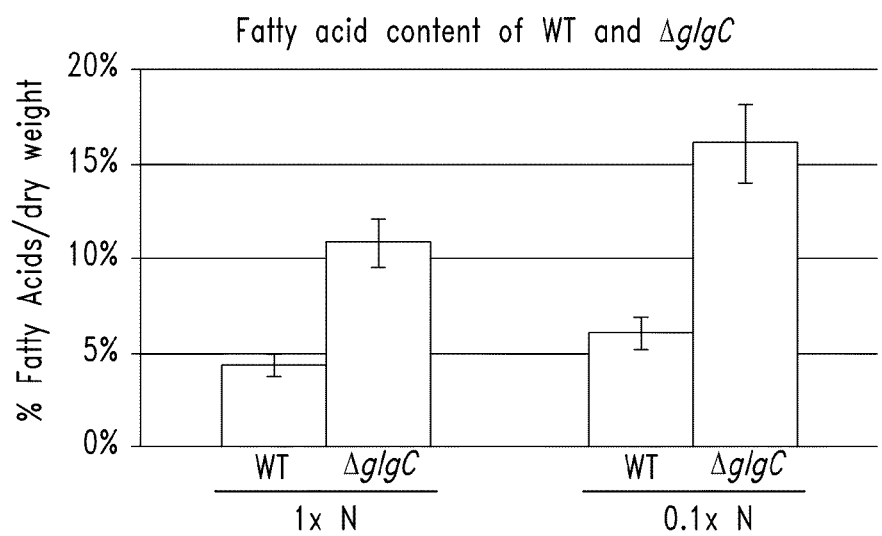

Wild type (WT) and deletion strains were cultured in either nitrogen replete BG11 medium (1×N) or BG11 media containing 1/10 the standard nitrogen concentration (0.1×N) for 5-days. Samples were taken at 5 days and tested by gas chromatography (GC) and Nile Red staining for lipid concentration. FIG. 9 shows the GC measurements represented as % FAMES/dry weight for the deletion strains as compared to WT. FIG. 9A shows the GC results for Δpgm strain, and FIG. 9B shows the GC results for ΔglgC strain. Comparable results were obtained for a ΔglgC strain of a salt tolerant S. elongatus PCC 7942 under reduced nitrogen conditions (o.1× N) (data not shown).

These results confirm that deletion of biosynthetic enzymes in the glycogen synthesis pathway of *Synechococcus* diverts carbon into other biosynthetic pathways, especially lipid biosynthetic pathways.

Example 12

Increased Lipid Production by Glycogen Pathway Deletion Mutants in *Synechococcus* PCC 7002 and *Synechocystis* PCC 6803

As described above, Δpgm and ΔglgC deletion strains of S. elongatus PCC 7942 produced increased amounts of lipids.

To demonstrate that glycogen pathway mutants of other strains also produced increased amounts of lipids, a glgC knockout strain was generated in *Synechococcus* sp. PCC 7002, and glgC-merodiploids were generated in *Synechocystis* sp. PCC 6803. Full glgC knockouts were unable to be generated in *Synechocystis* sp. PCC 6803. Merodiploids, containing both mutated and wild type copies of glgC, were readily obtained. *Synechococcus* sp. PCC 7002 and *Synechocystis* sp. PCC 6803 knockout strains were generated as described for *S. elongatus* PCC 7942 in Example 9. With respect to the merodiploids obtained with *Synechocystis* sp. PCC 6803, the mutated and wild type copies of the glgC gene were both detected by PCR analysis of the genomic DNA of multiple transformants.

Figure 10:
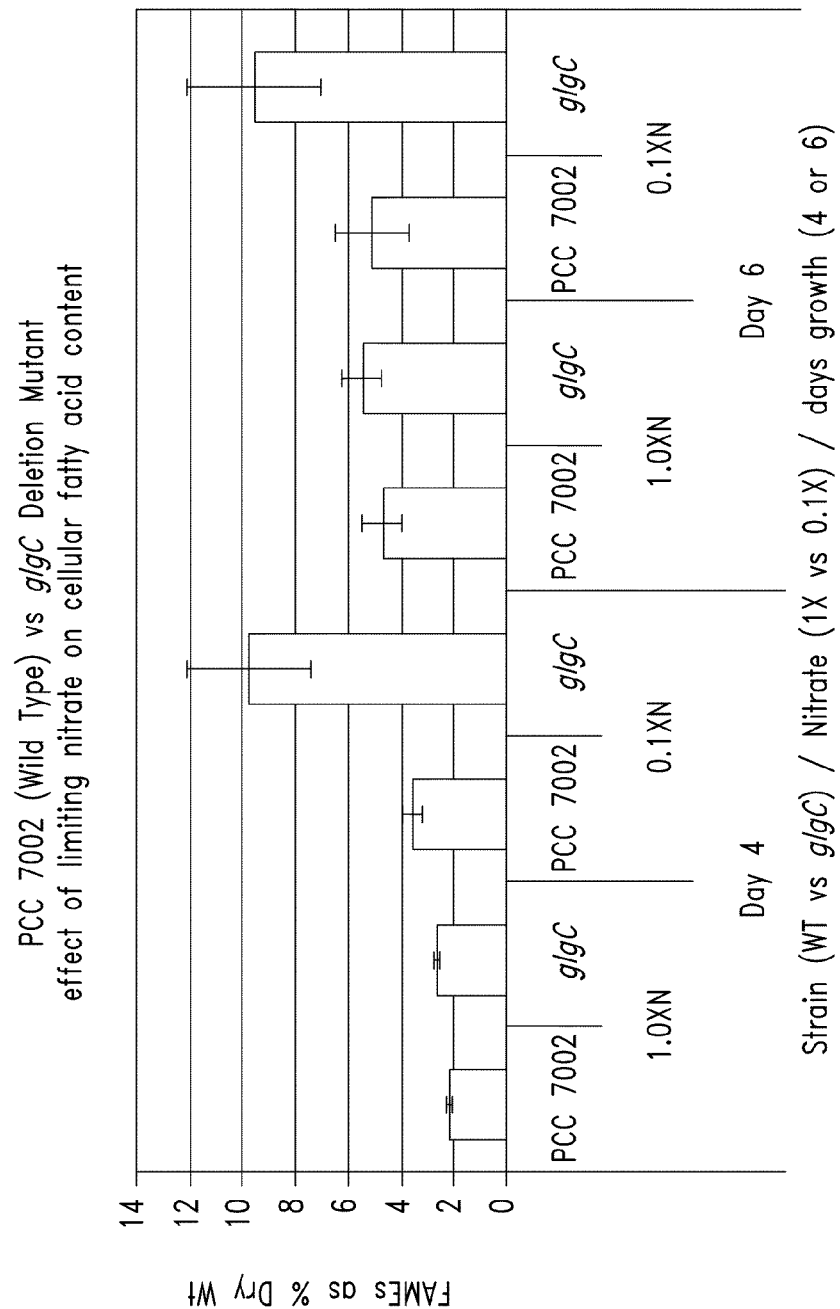
FIG. 10 is a graph showing gas chromatography analysis of total FAMES in *Synechococcus* sp. PCC 7002 and a glgC knockout mutant (strain 176-56, labeled "glgC").

Wild type *Synechococcus* sp. PCC 7002 and the glgC knockout mutant were grown in either nitrogen replete BG11 medium (1×N) or BG11 media containing 1/10 the standard nitrogen concentration (0.1×N) for 6 days. Samples were taken at 4 and 6 days and tested by gas chromatography (GC) for lipid concentration. There was no significant difference in lipid content between wild-type and the glgC knockout in *Synechococcus* sp.7002 when the strains are grown in nitrate replete media (1×) (FIG. 10). In contrast, the mutant showed a significant increase in lipid content on Day 4 when grown in nitrate limited media (0.1×) (FIG. 10). This difference persists at least until Day 6 (FIG. 10). The error bars reflect the variance in measured lipid content between biological replicates.

Figure 11:
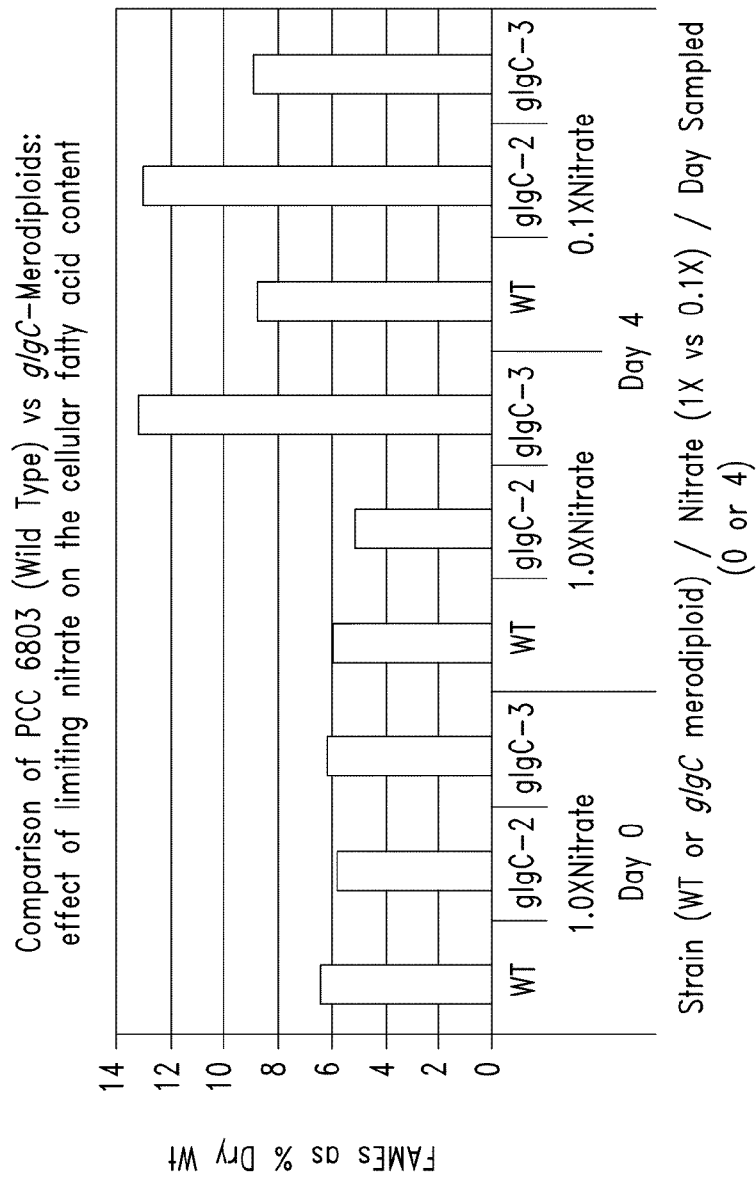
FIG. 11 is a graph showing gas chromatography analysis of total FAMEs content in *Synechocystis* sp. PCC 6803 wild-type and in two glgC merodiploids (glgC-2 and glgC-3) under various nitrogen conditions.

*Synechocystis* sp. PCC 6803 wild-type and two independent glgC merodiploid mutants were grown in normal media and then pelleted and resuspended as described above for the *Synechococcus* sp. PCC 7002 wild type and glgC knockout mutant. One glgC merodiploid, identified as glgC-3, funneled large amounts of carbon into the production of fatty acids under normal-nitrate (1.0×) conditions (FIG. 11). In contrast, under low nitrate (0.1×) conditions, a second merodiploid, glgC-2, showed a 1.5 fold increase in lipid content (FIG. 11).

The invention claimed is:

1. A modified photosynthetic microorganism that accumulates a reduced amount of glycogen as compared to the wild type photosynthetic microorganism,
wherein said modified photosynthetic microorganism has reduced expression, reduced activity, or mutation of a glucose-1-phosphate adenyltransferase (glgC) gene as compared to the wild type photosynthetic microorganism, wherein said glgC gene comprises one or more mutations or complete or partial gene deletions,
wherein said modified photosynthetic microorganism comprises one or more introduced polynucleotides encoding diacylglycerol acyltransferase (DGAT),
wherein said modified photosynthetic microorganism accumulates an increased amount of triglycerides, wax esters, or both as compared to a photosynthetic microorganism having the introduced polynucleotide(s) encoding DGAT without reduced expression or mutation of the glgC gene, and
wherein said photosynthetic microorganism is a Cyanobacterium.

2. The modified photosynthetic microorganism of claim 1, wherein said modified photosynthetic microorganism accumulates a reduced amount of glycogen under stress conditions as compared to the wild type photosynthetic microorganism.

3. The modified photosynthetic microorganism of claim 1, wherein said Cyanobacterium is a *Synechococcus elongatus*.

4. The modified Cyanobacterium of claim 3, wherein the *Synechococcus elongatus* is strain PCC 7942.

5. The modified Cyanobacterium of claim 4, wherein the Cyanobacterium is a salt tolerant variant of *Synechococcus elongatus* strain PCC 7942.

6. The modified photosynthetic microorganism of claim 1, wherein said Cyanobacterium is *Synechococcus* sp. PCC 7002 or *Synechocystis* sp. PCC 6803.

7. The modified photosynthetic microorganism of claim 1, wherein said one or more polynucleotides encoding DGAT are present in one or more expression vectors.

8. The modified photosynthetic microorganism of claim 1, wherein said glgC gene is an endogenous glgC gene that hybridizes to at least one of SEQ ID NOs: 59, 61, 63, 65, 67, 69, 71 or 73 under low stringency conditions.

9. A method of producing a modified photosynthetic microorganism that accumulates a reduced amount of glycogen as compared to the wild type photosynthetic microorganism, comprising,
modifying a photosynthetic microorganism to have a reduced level of expression, reduced activity, or mutation of a glucose-1-phosphate adenyltransferase (glgC) gene as compared to the level of expression of the glgC gene in a wild type photosynthetic microorganism by introducing one or more mutations or complete or partial gene deletions into said glgC gene, and
modifying the photosynthetic microorganism to include one or more introduced polynucleotides encoding diacylglycerol acyltransferase (DGAT),
wherein said modified photosynthetic microorganism accumulates an increased amount of triglycerides, wax esters, or both as compared to a photosynthetic microorganism having the introduced polynucleotide(s) encoding DGAT without reduced expression or mutation of the glgC gene, and
wherein said photosynthetic microorganism is a Cyanobacterium.

10. The method of claim 9, wherein said glgC gene is an endogenous glgC gene that hybridizes to at least one of SEQ ID NOs: 59, 61, 63, 65, 67, 69, 71 or 73 under low stringency conditions.

11. A method of producing a triglyceride, a wax ester, or both, comprising cultivating a modified photosynthetic microorganism in a suitable media to produce said triglyceride, wax ester, or both, said modified photosynthetic microorganism having:
reduced expression, reduced activity, or mutation of a glucose-1-phosphate adenyltransferase (glgC) gene wherein said glgC gene comprises one or more mutations or complete or partial gene deletions,
wherein said modified photosynthetic microorganism comprises one or more introduced polynucleotides encoding diacylglycerol acyltransferase (DGAT),
wherein said modified photosynthetic microorganism accumulates an increased amount of triglycerides, wax esters, or both as compared to a photosynthetic microorganism having the introduced polynucleotide(s) encoding DGAT without reduced expression or mutation of said glgC gene, and
wherein said photosynthetic microorganism is a Cyanobacterium.

12. The method of claim 11, wherein said glgC gene is an endogenous glgC gene that hybridizes to at least one of SEQ ID NOs: 59, 61, 63, 65, 67, 69, 71 or 73 under low stringency conditions.

* * * * *